(12) United States Patent
Erickson et al.

(10) Patent No.: US 11,974,988 B2
(45) Date of Patent: May 7, 2024

(54) NEUROPROTECTIVE COMPOSITIONS AND METHODS OF USING THE SAME

(71) Applicants: The Board of Supervisors of Louisiana State Univer University and Agricultural and Mechanical College, Baton Rouge, LA (US); The Regents of the University of California, Oakland, CA (US)

(72) Inventors: Jeffrey Erickson, New Orleans, LA (US); Heike Wulff, Davis, CA (US); Heesung Shim, Davis, CA (US); Vikrant Singh, Davis, CA (US); Latika Singh, Davis, CA (US)

(73) Assignees: BOARD OF SUPERVISORS OF LOUISIANA STATE UNIVERSITY AND AGRICULTURAL AND MECHANICAL COLLEGE, Baton Rouge, LA (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 22 days.

(21) Appl. No.: 17/099,031

(22) Filed: Nov. 16, 2020

(65) Prior Publication Data
US 2021/0205275 A1    Jul. 8, 2021

Related U.S. Application Data

(63) Continuation-in-part of application No. PCT/US2019/032477, filed on May 15, 2019.

(60) Provisional application No. 62/671,636, filed on May 15, 2018.

(51) Int. Cl.
| | |
|---|---|
| *A61K 31/426* | (2006.01) |
| *A61K 31/13* | (2006.01) |
| *A61K 31/427* | (2006.01) |
| *A61K 31/4439* | (2006.01) |
| *A61P 25/28* | (2006.01) |
| *C07D 277/40* | (2006.01) |
| *C07D 401/12* | (2006.01) |
| *C07D 417/10* | (2006.01) |

(52) U.S. Cl.
CPC ............ *A61K 31/426* (2013.01); *A61K 31/13* (2013.01); *A61K 31/427* (2013.01); *A61K 31/4439* (2013.01); *A61P 25/28* (2018.01); *C07D 277/40* (2013.01); *C07D 401/12* (2013.01); *C07D 417/10* (2013.01)

(58) Field of Classification Search
CPC ............................ C07D 277/40; A61K 31/426
See application file for complete search history.

(56) References Cited

U.S. PATENT DOCUMENTS

| | | |
|---|---|---|
| 2006/0035944 A1 | 2/2006 | Muto et al. |
| 2006/0135575 A1 | 6/2006 | Carayon et al. |

OTHER PUBLICATIONS

Sankaranarayanan et al. Mol Pharmacol 75:281-295, 2009.*
Nath et al, Indian Journal of Chemistry, Section B: Organic Chemistry Including Medicinal Chemistry (1981), 20B(7), 606-7.( CAS Abstract Only) 1981.*
Afenjar et al., Brain & Development 29 (2007) 547-552.
Ahlgren, H., Henjm, K. Ottersen, O. & Ruden-Pran, E. Validation of organotypical hippocampal slice cultures as an ex vivo model of brain ischemia: different roles of NMDA receptors in cell death signaling after exposure to NMDA or oxygen and glucose deprivation. Cell & Tiss. Res. 345, 329-341 (2011).
Ai, J. and A. Baker, Long-term potentiation of evoked presynaptic response at CA3-CA1 synapses by transient oxygen-glucose deprivation in rat brain slices. Exp. Brain Res., 2006. 169: p. 126-129.
Ali, R. & Siddiqui, N. Biological aspects of emerging benzothiazoles: a short review. J. chem. Article ID 345198, 12 pages (2013).
Ammir, M. & Hassan, M.Z. Functional roles of benzothiazole motif in antiepileptic drug research. Mini Rev. Med. Chem. 13, 2060-2075 (2013).
Antonic, A., et al., Hypothermia protects human neurons Int. J. Stroke, 2014. 9: p. 544-552.
Arias, C., Arrieta, I. & Tapia, R. β-amyloid peptide fragment 25-35 potentiates the calcium-dependent release of excitatory amino acids from depolarized hippocampal slices. J. Neurosci. Res. 41, 561-566 (1995).
Armano, S., et al., Localization and functional relevance of system. A neutral amino acid transporters in cultured hippocampal neurons. J. Biol Chem, 2002. 277(12): p. 10467-73.
Ashe, K.H. & Zahs, K.R. Probing the biology of Alzheimer's disease in mice. Neuron 66, 631-645 (2010).
Ates, O., et al., Do sodium channel blockers have neuroprotective effect after onset of ischemic insult? Neurol. Res., 2013 . 29: p. 317-323.
Bacci, A., et al., Block of glutamate-glutamine cycle between astrocytes and neurons inhibits epileptiform activity in hippocampus. J.. Neurophysiol, 2002. 88(5): p. 2302-10.
Bae, H.J., et al., Neuroprotective effect of low dose riluzole in gerbil model of transient global ischemia. Neurosci Lett, 2000. 294: p. 29-32.

(Continued)

*Primary Examiner* — Kamal A Saeed
(74) *Attorney, Agent, or Firm* — Baker, Donelson, Bearman, Caldwell & Berkowitz, P.C.

(57) ABSTRACT

This invention is directed to neuroprotective compositions and methods of using the same to treat neurodegenerative diseases.

18 Claims, 28 Drawing Sheets
Specification includes a Sequence Listing.

(56) References Cited

OTHER PUBLICATIONS

Belayev, L., Saul, I., Huh, P.W., Finotti, N., Zhao, W., Busto, R., and Ginsberg, M.D., Neuroprotective effect of high-dose albumin therapy against global ischemic brain injury in rats. Brain Res, 1999. 845: p. 107-111.

Bell, F.K.S., Bennett, D.A. & Cuello, A.C. Paradoxical upregulation of glutamatergic presynaptic boutons during mild cognitive impairment. J. Neurosci. 27, 10810-10817 (2007).

Bellingham, M.C., A review of the neural mechanisms of action and clinical efficiency of riluzole in treating Amyotrophic ateral Sclerosis: What we have learned in the last decade? CNS Neurosci & Ther., 2011. 17: p. 4-31.

Ben-Ari, Y. Limbic seizure and brain damage produced by kainic acid: mechanisms and relevance to human temporal lobe epilepsy. Neuroscience 14, 375-403 (1985).

Benoit, E. and D. Escande, Riluzole specifically blocks inactivated Na channels in myelinated nerve fibre. Pflugers Arch. European Journal of Physiology, 1991. 419: p. 603-609.

Benveniste, H., Drejer, J., Schousboe, A. & Diemer, N.A. Elevation of the extracellular concentrations of glutamate and aspartate in rat hippocampus during transient cerebral ischemia monitored by intracerebral microdialysis. J. Neurochem. 43, 1369-1374 (1984).

Benveniste, H., et al., Ischemic damage in hippocampal CA1 is dependent on glutamate release and intact innervation from CA3. J. Cereb. Blood Flow Metab., 1989. 9: p. 629-639.

Berge, S.M. et al., J. Pharm. Sci. 1977, 66, 2.

Bero, A.W., et al. Neuronal activity regulates the regional vulnerability to amyloid-beta deposition. Nat. Neurosci. 14, 750-756 (2011).

Bittigau, P. & Ikonomidou, C. Glutamate in neurologic diseases. J. Child Neurol. 12, 471-485 (1997).

Block, F., Global ischemia and behavioral deficits. Prog Neurobiol, 1999. 58: p. 279-295.

Bolshakov, V.Y. and S.A. Siegelbaum, Regulation of hippocampal transmitter release during development and long-term potentiation. Science, 1995. 269(5231): p. 1730-4.

Bonanomi, D., F. Benfenati, and F. Valtorta, Protein sorting in the synaptic vesicle life cycle. Prog Neurobiol, 2006 80 (4) p. 177-217.

Bordji, K., Becerril-Ortega, J. & Buisson, A. Synapses, NMDA receptor activity and neuronal Aβ production in Alzheimer's disease. Rev. Neurosci. 22, 285-294 (2011).

Boxer, P.A., et al., Comparison of phenytoin with noncompetitive N-methyl-D-aspartate antagonists in a model of focal brain ischemia in rat. Stroke, 1990. 21: p. 47-51.

Boza-Serrano, A., Yang, Y., Paulus, A. & Deieborg, R. Innate immune alterations are elicited in microglial cells before plaque deposition in the Alzheimer's disease mouse model 5xFAD. Sci. Rep. 8, 1550 (2018).

Broer, S., The SLC38 family of sodium-amino acid co-transporters. Pflugers Arch., 2014(466): . 155-172.

Brothers, H.M., et al. Riluzole partially rescues age-associated, but not LPS-induced, loss of glutamate transporters and spatial memory. J. Neuroimmune Pharmacol. 8, 1098-1105 (2013).

Bryson, H.M., B. Fulton, and P. Benefield, Riluzole. A review of its pharmacodynamic and pharmacokinetic properties and therapeutic potential in amyotrophic lateral sclerosis. Drugs, 1996. 52: p. 549-563.

Busche, M.A. & Konnerth, A. Neuronal hyperactivity—A key defect in Alzheimer's disease? BioEssays 37, 624-632 (2015).

Cacciamani, Fl., et al. Low cognitive awareness, but not compliance, is a good marker of preclinical Alzheimer's disease. J. Alzheimers Dis. 59, 753-762 (2017).

Carbone, M., Duty, S. & Rattray, M. Riluzole elevates GLT-1 activity and levels in striatal astrocytes. Neurochem. Int. 60, 31-38 (2012).

Celone, K.A., et al. Alterations in memory networks in mild cognitive impairment and Alzheimer's disease: an Independent component analysis. J. Neurosci. 26, 10222-10231 (2006).

Chan, S.A., et al., Fosphenytoin reduced hippocampal neuronal damage in rat following transient global ischemia. Acta Neurochirurgica, 1998. 140: p. 175-180.

Chaudhry, F.A., R. J. Reimer, and R.H. Edwards, The glutamine commute: take the N line and transfer to the A. J. Cell Biol., 2002. 157(3): p. 349-355.

Chen, R., et al. Monoacylglycerol lipase is a therapeutic target for Alzheimer's disease. Cell Rep. 2, 1329-1339 (2012).

Chew, B., Ryu, J.R., Ng,T., Ma, D., Dasgupta, A., Neo, S.H., Zhao, J., Zong, Z., Bichler, Z., Sajikumar, S., and Goh, E. L.K., Lentiviral silencing of GSK-3B in adult dentate gyrus impairs contextual fear memory and synaptic plasticity. Front. Behav. Neurosci., 2015. 9: p. 158-172.

Chin, J.H., Ma, L., MacTavish, D. & Jhamandas, J.H. Amyloid beta protein modulates glutamate-mediated neurotransmission in the rat basal forebrain: involvement of presynaptic neuronal nicotinic acetylcholine and metabotropic glutamate receptors. J. Neeurosci. 27, 9262-9269 (2007).

Choi, D.W., Excitotixic cell death. J. Neurobiol., 1992. 23: p. 1261-1276.

Choi, D.W., The role of glutamate neurotoxicity in hypoxic-ischemic neuronal death. Annu. Rev. Neurosci., 1990. 13: p. 171-182.

Chowdhury, G.M., et al., Glutamatergic and GABAergic neurotransmitter cycling and energy metabolism in rat cerebral cortex during postnatal development. J. Cereb. Blood Flow Metab., 2007. 27: p. 1895-1907.

Christensen, H.N. Role of amino acid transport and countertransport in nutrition and metabolism. Physiol. Rev. 70, 43-77 (1990).

Cirrito, J.R., et al. Synaptic activity regulates interstitial fluid amyloid-beta levels in vivo. Neuron 48, 913-922 (2005).

Citon, M. Alzheimer's disease: strategies for disease modification. Nat. Rev. Drug Discov. 9, 387-398 (2010).

Coleman et al., Mol Pharmacol. Sep. 2014;86(3):342-57. doi: 10.1124/mol.114.093286. Epub Jun. 23, 2014.

Coleman, N., et al., The riluzole derivative 2-amino-6-trifluoromethylthiobenzothiazole (SKA-19), a mixed KCa2 activator and Na V blocker, is a potent novel anticonvulsant. Neurotherapeutics, 2015. 12: p. 234-249.

Colie, S., et al. Neuronal p38a mediates synaptic and cognitive dysfunction in an Alzheimer's mouse mdel by controlling β-amyloid production. Sci. Rep. 7, 45306 (2017).

Colovic, M., Zennaro, E. & Caccia, S. Liquid chromatographic assay for riluzole in mouse plasma and central nervous system tissues. J. Chromatography B 803, 305-309 (2004).

Conti, F. and M. Melone, The glutamine commute: lost in the tube? Neurochem Int, 2006. 48(6-7): p. 459-64.

Cummings, J.L. Biomarkers in Alzheimer's disease drug development. Alzheimer's & Dementia 7, e13-e44 (2011).

Danysz, W., Parsons, C.G., Stoffler, H.J. & G., Q. Neuroprotective and symptomological action of memantine relevant for Alzheimer's disease—a unified glutamatergic hypothesis on mechanism of action. Neurotoxicity Res. 2, 85-97 (2000).

Das et al. 'Recent developments of 2-aminothiazoles in medicinal chemistry', European Journal of Medicinal Chemistry, Dec. 23, 2015 (Dec. 23, 2015), vol. 109, pp. 89-98; p. 96.

Dave, K.R., et al., Ischemic preconditioning ameliorates excitotoxicity by shifting glutamate/gamma-aminobutyric acid release and biosynthesis. J. Neurosci Res, 2005. 85(5): p. 665-73.

De Gois, S., et al, Homeostatic scaling of vesicular glutamate and GABA transporter expression in rat neocortical circuits. J. Neurosci, 2005.25(31): p. 7121-33.

De Haan, W., van Straaten, E.C.W., Gouw, A.A. & Stam, C.J. Altering neuronal excitability to preserve network connectivity in a computational model of Alzheimer's disease. PLoS Comput. Biol. 13, e1005707 (2017).

DeFazio, R.A., et al., GABA synapses mediate neuroprotection after ischemic and epsilonPKC preconditioning in rat hippocampal slice cultures. J. Cereb Blood Flow Metab, 2009. 29: p. 375-384.

Devi, L. & Ohno, M. Cognitive benefits of memantine in Alzheimer's 5XFAD model mice decline during advanced disease stages. Pharmacol. Biochem. Behav. 144, 60-66 (2016).

(56) References Cited

OTHER PUBLICATIONS

Dickerson, B.C., et al. Increased hippocampal activation in mild cognitive impairment compared to normal aging and AD. Neurology 65, 404-411 (2005).

Dickerson, B.C., Wolk, D.A. & Initiative, A.s.D.N. MRI cortical thickness biomarker predicts AD-like CSF and cognitive decline in normal adults. Neurology 78, 84-90 (2012).

Doble, A., The pharmacology and mechanism of action of riluzole. Neurology, 1996. 47 (6 Suppl 4): p. S233-S241.

Dodd, P.R., Excited to death: different ways to lose your neurons. Biogerontology, 2002. 3: p. 51-56.

Dudek, F.E. & Sutula, T.P. Epileptogenesis in the dentate gyrus: a critical perspective. Prog. Brain Res. 163, 755-773 (2007).

Duprat, F., et al., The neuroprotective agent riluzole activates the two P domain K(+) channels TREK-1 and TRAAK. Mol. Pharmacol., 2000. 57: p. 906-912.

Edmonds, E.C., Delano-Wood, L., Galasko, D.R., Salmon, D.P. & Bondi, M.W. Subtle cognitive decine and biomarker staging in preclinical Alzheimer's disease. J. Alzheimers Dis. 47, 231-242 (2015).

Edmonds, H.L., et al., Topiramate as a neuroprotectant in a rat model of global ischemia-induced neurodegeneration. Life Sci., 2001. 69: p. 2265-2277.

Erecinska, M.E. and I.A. Silver, Metabolism and role of glutamate in mammalian brain. Prog. Neurobiol., 1990. 35: p. 245-296.

Erickson, J.D., Functional identification of activity- regulated, high-affinity glutamine transport in hippocampal neurons inhibited by riluzole. J. Neurochem., 2017. 142: p. 29-40.

Falcao de Campos, C. & de Carvalho, M. Riluzole-induced recurrent pancreatitis. J. Clin. Neurosci. 45, 153-154 (2017).

Festing, M.F. & Alltman, D.G. Guidelines for the design and statistical analysis of experiments using laboratory animals. ILAR J. 43, 244-258 (2002).

Fisher, M., S. Jonas, and R.L. Sacco, Prophylactic neuroprotection for cerebral ischemia. Stroke, 1994. 25: p. 1075-1080.

Folch, J., et al. Memantine for the treatment of dementia: a review on its current and future applications. J. Alzheimers Dis. 62, 1223-1240 (2018).

Francis, P.T., Parson, C.G. & Jones, R.W. Rationale for combining glutamatergic and cholinergic approaches in the symptomatic treatment of Alzheimer's disease. Expert Rev. Neurotherapeutics 12, 1351-1365 (2014 ).

Frankiewicz, T. & Parson, C.G. Memantine restores long term potentiation impaired by tonic Nmethyl-D-aspartate (NMDA) receptor activation following reduction of Mg2+ in hippocampal slices. Neuropharmacology 38, 1253-1259 (1999).

Fremeau et al., Molecular Cloning and Expression of a High Affinity L-Proline Transporter Expressed in Putative Glutamatergic Pathways of Rat Brain, Neuron, vol. 8, pp. 915-926, May 1992.

Fujimoto, S., et al.,, Mechanisms of oxygen glucose deprivation-induced glutamate release from cerebrocortical slice cultures. Neurosci Res, 2004. 50: p. 179-187.

Fumagalli, E., Funicello, M., rauen, T., Gobbi, M. & Mennini, T. Riluzole enhances the activity of glutamate transporters GLAST, GLT1 and EAAC1. Eur. J. Pharmacol. 578, 171-176 (2008).

Gagoria, J., Verma, P.K. & Khatkar, A. Anticonvulsant and neurological profile of benzothiazoles: a mini-review. CNS Agents in Med. Chem. 15, 11-16 (2015).

Gidday, J.M., Cerebral preconditioning and I schaemic tolerance. Nat. Rev. Neurosci., 2006. 7: p. 437-448.

Gjessing, L.R., et al. "The free amino acids in human cerebrospinal fluid", Journal of Neurochemistry 19.7 (1972): 1807-1808.

Godyn, J., Jonczyk, J., Panek, D. & Malawska, B. Therapeutic strategies for Alzheimer's disease in clinical trials. Pharmacol. Rep. 68, 127-138 (2016).

Gould, P.L., "Salt selection for basic drugs", Int. J. Pharmaceutics 1986, 33, 201-217.

Grabb, M.C., et al., Preconditioned resistance to oxygen-glucose deprivation-induced cortical neuronal death: alterations in vesicular GABA and glutamate release. Neuroscience, 2002. 115(1): p. 173-83.

Groeneveld, G.J., et al. Inter-and intraindividual variability of riluzole serum concentrations in patients with ALS. J. Neurol. Sci. 191, 121-125 (2001).

Groeneveld, G.J., et al. Riluzole serum concentrations in patients with ALS: associations with side effects and symptoms. Neurology, 61, 1141-1143 (2003).

Grunnet, M., et al., Pharmacological modulation of SK3 channels. Neuropharmacology, 2001. 40: p. 879-887.

Guastella et al., Proc. Natl. Acad. Aci. USA, vol. 89, pp. 7189-7193, Aug. 1992 Neurobiology.

Gutierrez, R. and U. Heinemann, Synaptic reorganization is explanted cultures of rat hippocampus. Brain Res., 1999. 815: p. 304-316.

Hagglund, M.G., et al., Transport of L-glutamine, L-alanine, L-arginine and L-histidine by the neuron-specific Slc38a8 in CNS. J. Mol. Biol., 2015.427: p. 1495-1512.

Hamberger, A.C., et al., Glutamate as a CNS transmitter. I. Evaluation of glucose and glutamine as precursors for the synthesis of preferentially released glutamate. Brain Res., 1979. 168: p. 513-530.

Hamberger, A.C., et al., Glutamate as a CNS transmitter. II. Regulation of synthesis in the releasable pool. Brain Res, 1979. 168: p. 531-541.

Han et al. 'Exploration of Novel Ureidobenzothiazole Library Against Neuroinflammation', Bulletin of the Korean Chemical Society, Oct. 20, 2011 (Oct. 30, 2011), vol. 32, pp. 3805-3808; p. 3805.

Handoko, Mr., et al.Correlation of specific amyloid-β oligomers with tau in cerebrospinal fluid from cognitively normal older adults. JAMA Neurol. 70, 594-599 (2013).

Hascup, K.N. & Hascup, E.R. Soluble amyloid-β42 stimulates glutamate release through activation of the α7 nicotinic acetylcholine receptor. J. Alzheimers Dis. 53, 337-347 (2016).

Hassel, B. & Brathe, A. Neuronal pyruvate carboxylation supports formation of transmitter glutamate. J. Neurosci. 20, 1342-1347 (2000).

Hassen, G.W., D. Tian, and P.J. Bergold, A new model of ischemic preconditioning using young adult hippocampal slice cultures. Brain Res. Protocols, 2004. 13: p. 135-140.

Herbert, T., et al., Block of the rat brain IIA sodium channel alpha subunit by the neuroprotective drug riluzole. Mol Pharmacol, 1994. 45: p. 1055-1060.

Hertz, L., The glutamate-glutamine (GABA) cycle: importance of late postnatal development and potential reciprocal interactions between biosynthesis and degradation. Front Endocrinol, 2013. 4: p. 1-16.

Heurteaux, C., et al., Alpha-linolenic acid and riluzole treatment confer cerebral protection and improve survival after focal brain ischemia. Neuroscience, 2006. 137: p. 241-251.

Hogins, J., Crawford, D.C., Jiang, X., and Mennerick, S., Presynaptic silencing is an endogenous neuroprotectant during excitotoxic insults. Neurobiol. Dis., 2001. 43: p. 516-525.

Holmes, G.L. Seizure-induced neuronal injury: animal data. Neurology 59, S3-6 (2002).

Hong, S.H., et al., Docosahexaenoic acid confers enduring neuroprotection in experimental stroke. J. Neurol. Sci., 2014. 338: p. 135-141.

Huang, C.S., et al., Effects of the neuroprotective agent riluzole on the high voltage-activated calcium channels of rat dorsal root ganglion neurons. J. Pharmacol. Exp. Therp., 1997. 282: p. 1280-1290.

Hung, S.Y. & Fu, W.M. Drug candidates in clinical trials for Alzheimer's disease. J. Biomed. Sci. 24, 47 (2017).

Hunsberger, H.C., et al., Riluzole rescues glutamate alterations, cognitive deficits, and tau pathology associated with P201L tau expression. J. Neurochem., 2015. 135: p. 381-394.

Hunsberger, H.C., Kickman, J.E. & Reed, M.N. Riluzole rescues alterations in rapid glutamate transients in the hippocampus of rTg4510 mice. Metab. Brain Dis. 31, 711-715 (2016).

(56) References Cited

OTHER PUBLICATIONS

Hunsberger, H.C., Rudy, C.C., Batten, S.R., Gerhardt, G.A. & Reed, M.N. P301L tau expression affects glutamate release and clearance in the hippocampal trisynaptic pathway. J. Neurochem. 132, 169-182 (2014).

Huynh, r.A. & Mohan, C. Alzheimer's Disease: biomarkers in the genome, blood, and cerebrospinal fluid. Front. Neurol. 8, 102 (2017).

International Search Report for PCT/US2019/032477 dated Aug. 12, 2019.

Jack, C.R.J. & Holtzman, D.M. Biomarker modeling of Alzheimer's disease. Neuron 80, 1347-1358 (2013).

Janas, J., J. Skowronski, and L. Van Aeist, Lentiviral delivery of RNAi in hippocampal neurons. Methods Enzymol, 2006. 406: p. 593-605.

Jimenez-Mateos, E.M. and D.C. Henshall, Seizure preconditioning and epileptic tolerance: models and mechanisms. Int. J. Physiol. Pahophysiol. Pharmacol., 2009. 1: p. 180-191.

Jonas, S., Prophylactic pharmacologic neuroprotection against focal cerebral ischemia. Ann NY Acad Sci, 1995. 765: p. 21-25.

Jones, D.T., et al. Cascading network failure across the Alzheimer's disease spectrum. Brain 139, 547-562 (2016).

Kabogo, D., Rauw, G., Amritraj, A., Baker, G. & Kar, S. β-amyloid-related peptides potentiate K+ evoked glutamate release from adult rat hippocampal slices. Neurobiol. Aging 31, 1164-1172 (2010).

Kam, K. and R. Nicoll, Excitatory synaptic transmission persists independently of the glutamate-glutamine cycle. J. Neurosci, 2007. 27(34): p. 9192-200.

Kanamori, K. and B.D. Ross, Quantitative determination of extracellular glutamine concentration in rat brain, and its elevation in vivo by system. A transport inhibitor, alpha-(methylamino) isobutyrate. J. Neurochem, 2004. 90(1): p. 203-10.

Kanomori, K. and B.D. Ross, Electrographic seizures are significantly reduced by in vivo inhibition off neuronal uptake of extracellular glutamine in rat hippocampus. Elipesy Res., 2013. 107: p. 20-36.

Kavalali, E.T. and E. M. Jorgensen, Visualizing presynaptic function. Nat Neurosci, 2014. 17: p. 10-16.

Kazim, S.F, et al. Disease modifying effect of chronic oral treatment with a neurotrophic peptidergic compound in a triple transgenic mouse model of Alzheimer's disease. Neurobiol. Dis. 71, 110-130 (2014).

Kim, S.H., et al. Group II metabotropic glutamate receptor stimulation triggers production and release of Alzheimer's amyloid β42 from isolated intact nerve erminals. J. Neurosci. 30, 3870-3875 (2010).

Kostandy, B.. B. Tole role of glutamate in neuronal ischemic injury: the role of spark in fire. Neurol. Sci. 33, 223-237 (2012).

Kretschmer, B.D., Kratzer, U. & Schmidt, W.J. Riluzole, a glutamate release inhibitor, and motor behavior. Nauyn Schmiedebergs Arch. Pharmacol. 358, 181-190 (1998).

Lao, K., et al. Drug development for Alzheimer's disease: review. J. Drug Target 20, 1-10 (2018) 2019 27(2):164-173.

Legos, J.J. and F.C. Barone, Update on pharmacological strategies for stroke: prevention, acute intervention and regeneration. Curr Opin Investig Drugs, 2003. 4: p. 847-858.

Lesne, S., et al. NMDA receptor activation inhibits alpha-secretase and promotes neuronal amyloid-beta production. J. Neurosci. 25, 9367-9377 (2005).

Leung et al. 'Voltage-gated K+ channel modulators as neuroprotective agents', Life Sciences, Apr. 10, 2010 (Apr. 10, 2010), vol. 86, pp. 775-780; p. 777, p. 778.

Liang, S.L., G.C. Carlson, and D.A. Coulter, Dynamic regulation of synaptic GABA release by the glutamate-glutamine cycle in hippocampal area CA1. J. Neurosci, 2006. 26(33): p. 8537-48.

Lin, C.L.G., Kong, Q., Cuny, G.D. & Glicksman, M.A. Glutamate transporter EAAT2: a new target for the treatment of neurodegenerative diseases. Future Med. Chem. 4, 1689-1700 (2012).

Lingamaneni, R. and H.C. Hemmings, Effects of Anticonvulants on Veratridine and KCl-evoked glutamate release from rat cortical synaptosomes. Neurosci Lett, 1999. 276: p. 127-130.

Lipton, S.A. Failures and successes of NMDA receptor antagonists: molecular basis for the use of open-channel blockers like memantine in the treatment of acute and chronic neurologic insults. NexroRx 1, 101-110 (2004).

Lista, S., et al. Evolving evidence for the value of neuroimaging methods and biological markers in subjects categorized with subjective cognitive decline. J. Alzheimers Dis. 48, Suppl 1:S171-191 (2015).

Mackenzie, B. and J.D. Erickson, Sodium-coupled neutral amino acid (System N/A) transporters of the SLC38 gene family. Pflugers Arch, 2004. 447(5): p. 784-95.

Mackenzie, B., et al., Functional properties and cellular distribution of the system A glutamine transporter SNAT1 support specialized roles in central neurons. J Biol Chem, 2003. 278(26): p. 23720-30.

Maestu, F., et al. A multicenter study of the early detection of synaptic dysfunction in Mild Cognitive Impairment using Magnetoencephalography-derived functional connectivity. Neuroimage Clin. 9, 103-109 (2015).

Malgouris, C., et al., Riluzole, a novel antiglutamate, prevents memory loss and hippocampal neuronal damage in ischemic gerbils. J. Neurosci., 1989. 9: p. 3720-3727.

Martin, D., Thompson, M.A. & Nadler, J.V. The neuroprotective agent riluzole inhibits release of glutamate and aspartate from slices of hippocampal area Ca1. Eur. J. Pharmacol. 250, 473-476 (1993).

Martinez-Coria, H., et al. Memantine improves cognition and reduces Alzheimer's-like neuropathology in transgenic mice. Am. J. Pathol. 176, 870-880 (2010).

Marx, M.C, D. Billups, and B. Billups, Maintaining the presynaptic glutamate supply for excitatory neurotransmission. J. Neurosci. Res., 2015. 93: p. 1031-1044.

Masson, J., et al. Mice lacking brain/kidney phosphate-activated glutaminase (GLS1) have impaired glutamatergic synaptic transmission, altered breathing, disorganized goal-directed behavior and die shortly after birth. J. Neurosci. 26, 4660-4671 (2006).

McDonnell, M.E., et al. Riluzole prodrugs for melanoma and ALS: design, synthesis, and in vitro metabolic profiling. Bioorg. Med. Chem. 20, 5642-5648 (2012).

McGale, E. H. F. et al., "Studies of the inter-relationship between cerebrospinal fluid and plasma amino acid concentrations in normal individuals", Journal of neurochemistry 29.2 (1977): 291-297.

McIntosh, T.K., Smith, D.H., Voddi, M. Perri, B.R. & Stutzmann, J.M. Riluzole, a noval neuroprotective agent, attenuates both neurologic motor and cognitive dysfunction following experimental brain injury in the rat. J. Neurotrauma 13, 767-780 (1996).

Melikian, H.E., Neurotransmitter transporter trafficking: endocytosis, recycling and regulation. Pharmacol. Ther., 2004. 104: p. 17-27.

Melone, M., et al., Localization of the glutamine transporter SNAT1 in rat cerebral cortex and neighboring structures, with a note on its localization in human cortex. Cereb Cortex, 2004. 14(5): p. 562-74.

Miguel-Hidalgo, J.J., Alvarez, X.A., Cacabelos, R. & Quack, G. Neuroprotection by memantine against neurodegeneration induced by beta-amyloid (1-40). Brain Res. 958, 210-221 (2002).

Milane, A., et al Minocycline and riluzole brain disposition: interactions with p-glycoprotein at the blood-brain barrier. J. Neurochem. 103, 164-173 (2007).

Minkeviciene, R., Benerjee, P. & TTanila, H. Memantine improves spatial learning in a transgenic mouse model of Alzheimer's disease. J. Pharmacol. Exp. Ther. 311, 677-682 (2004).

Mitani, A., et al., Origin of ischemia-induced glutamate efflux in the CA1 field of the gerbil hippocampus: an in vivo brain microdialysis study. J. Neurochem., 1994. 63: p. 2152-2164.

Mokhtari, Z., Baluchnejadmojarad, T., Nikbakht, F., Mansouri, M. & Roghani, M. Riluzole ameliorates learning and memory deficits in Aβ25-35-induced rat model of Alzheimer's disease and is independent of cholinoceptor activation. Biomed. Pharmacother. 87, 135-144 (2016).

Moskowitz, M.A., E.H. Lo, and C. Ladecola, The science of stroke: mechanisms in search of treatments. Neuron, 2010.67: p. 181-198.

(56) References Cited

OTHER PUBLICATIONS

Mota, S.I., Ferreira, I.L. & Rego, A.C. Dysfunctional synapse in Alzheimer's disease—A focus on NMDA receptors. Neuropharmacology 76, 16-26 (2014).
Moulder, K.L., Cormier, R. J., Shute, A.A., Zormuski, C.F., and Mennerick, S., Homeostatic effects of depolarization on Ca2+ influx, synaptic signaling, and survival. J. Neurosci., 2003. 23: p. 1825-1831.
Nadler, J.V. Minireview. Kainic acid as a tool for the study of temporal lobe epilepsy. Life Sci. 29, 2031-2042 (1981).
Nadler, J.V. & Cuthbertson, G.J. Kainic acid neurotoxicity toward hippocampal formation: dependence on specific excitatory pathways. Brain Res. 195, 47-56 (1980).
Nagakura, A., Shitaka, Y., Yarimizy, Jr. & Matsuoka, N. Characterization of cognitive deficits in a transgenic mouse model of Alzheimer's disease and effects of donepezil and memantine. Eur. J. Pharmacol. 703, 53-61 (2013).
Nagoshi, N., H. Nakashima, and M.G. Fehlings, Riluzole as a neuroprotective drug for spinal cord injury: from bench to bedside. Molecules, 2015. 20: p. 7775-7789.
Noh, K.M., Hwang, J.Y., Shin, H.C. & Koh, J. Y. A novel neuroprotective mechanism of riluzole: direct inhibition of protein kinase C. Neurobiol. Dis. 7, 35-383 (2000).
Norenberg, M.D. and A. Martinez-Hernandez, Fine structural localization of glutamine synthetase in astrocytes of rat prain. Brain Res, 1979. 161: p. 303-310.
Oakley, H., et al. Intraneuronal beta-amyloid aggregates, neurodegeneration, and neuron loss in transgenic mice with five familial Alzheimer's disease mutations: potential factors in amyloid plaque formation. J. Neurosci. 26, 10129-10140 (2006).
Obrenovitch, T.P. and J. Urenjak, Altered glutamatergic transmission in neurological disorders: From high extracellular glutamate to excessive synaptic efficacy. Prog Neurobiol, 1997. 51: p. 39-87.
Okamoto, M., et al. Riluzole reduces amyloid beta pathology, improves memory, and restores gene expression changes in a transgenic mouse model of early-onset Alzheimer's disease. Translational Psychiatry 8, 153 (2018).
Olivares, D., et al., N-methyl D-aspartate (NMDA) receptor antagonists and memantine treatment for Alzheimer's disease, vascular dementia and Parkinson's disease. Curr. Alxheimer Res., 2012. 9: p. 746-758.
Olsen, T.S., U.J. Weber, and L.P. Kammersgaard, Therapeutic hypothermia for acute stroke. Lancet Neurol., 2003. 2: p. 410-416.
Pallo, S.P., diMaio, J., Cook, A., Nilsson, B. & Johnson, G.V.W. Mechanisms of tau and Aβ-induced excitotoxocity. Brain Res. 1634, 119-131 (2016).
Parsons, C.G., Danysz, W. & Quack, G. Memantine is a clinically well tolerated N-methyl-Daspartate (NMDA) receptor antagonist—a review of preclinical data. Neuropharmacology 38, 735-767 (1999).
Parsons, C.G., Danysz, W., Dekundy, A. & Pulte, I. Memantine and cholinesterase inhibitors: complementary mechanisms in the treatment of Alzheimer's disease. Neurotox. Res. 24, 358-369 (2013).
Parsons, M.P. & Raymond, L.A. Extrasynaptic NMDA receptor involvement in central nervous system disorders. Neuron 82, 279-293 (2014).
Paulson, J.B., et al. Amyloid plaque and neurofibrillary tangle pathology in a regulatable mouse model of Alzheimer's disease. Am. J. Pathol. 173, 762-772 (2008).
Pelletier, J.C., et al. Dipeptide prodrugs of the glutamate modulator riluzole. ACS Med. Chem. Lett. 9, 752-756 (2018).
Pereira, A.C., et al. Glutamatergic regulation prevents hippocampal-dependent age-related cognitive decline through dendritic spine clustering. Proc. Natl. Acad. Sci. 111, 18733-18738 (2014).
Pereira, A.C., et al., Age and Alzheimer's disease gene expression profiles reversed by the glutamate modulator riluzole. Mol. Psychiatry, 2017 . 22: p. 296-305.
Petito, C.K. and W.A. Pulsinelli, Delayed neuronal recovery and neuronal death in rat hippocampus following severe cerebral ischemia: possible relationship to abnormalities in neuronal processes. J. Cereb. Blood Flow Metab., 1984. 4: p. 194-205.
Petito, C.K., et al., Delayed hippocampal damage in humans following cardiorespiratory arrest. Neurology, 1987. 37: p. 1281-1286.
Pittenger, C., et al. Riluzole in the treatment of mood and anxiety disorders. CNS Drugs 22, 761-786 (2008).
Prakriya, M. and S. Mennerick, Selective depression of low-release probability excitatory synapses by sodium channel blockers. Neuron, 2000. 26: p. 671-682.
Pratt, J., et al., Neuroprotective actions of riluzoole in rodent models of global and focal cerebral ischaemia. Neurosci Lett, 1992. 140: p. 225-230.
Price, J.L. & Morris, J.C., Tangles and plaques in nondemented aging and "preclinical" Alzheimer's disease. Ann. Neurol. 45, 358-368 (1999).
Priyanka, S.N.K. & Jha, K.K. Benzothiazole; the molecule of diverse biological activities. Int. J. Curr. Pharm. Res. 2, 1-6 (2010).
Pulsinelli, W.A., et al., Ischemic brain injury and the therapeutic window. Ann NY Acad Sci, 1997. 835: p. 187-193.
Pulsinelli, W.A., J.B. Brierley, and F. Plum, Temporal profile of neuronal damage in a model of transient forebreain ischemia. Ann Neurol., 1982. 11: p. 491-498.
Reulecke, B.C., Denecke, J. (2009). Hyperprolinemia. In: Lang, F. (eds) Encyclopedia of Molecular Mechanisms of Disease. Springer, Berlin, Heidelberg. https://doi.org/10.1007/978-3-540-29676-8_3422.
Revett, T.J., Baker, G.B., Jhamandas, J. & Kar, S. Glutamate system, amyloid β peptides and tau protein: functional Interrelationships and relevance to Alzheimer disease pathology. J. Psychiatry Neurosci. 38, 6-23 (2013).
Robinson, M.B., Acute regulation of sodium-dependent glutamate transporters: a focus on constitutive and regulated trafficking. Hanb. Exp. Pharmacol., 2006. 175: p. .251-275.
Rothstein, J.D., et al. Localization of neuronal and glial glutamate transporters. Neuron 13, 713-725 (1994).
Rudy, C.C., Hunsberger, H.C., Weitzner, D.S. & Reed, M.N. The role of the tripartite glutamatergic synapse in the pathophysiology of Alzheimer's disease. Aging Dis. 6, 131-148 (2015).
Ruel, J., et al., Neuroprotective effect of riluzole in acute noise-induced hearing loss. Neuroreport, 2005. 16: p. 1087-1090.
Salameh, J.S., R.H. Brown, and J.D. Berry, Amyotrophic Lateral Sclerosis: Review. Semin Neurol., 2015. 35: p. 469-476.
Sanderink, G.J., Bournique, B., Stevens, J., Petry, M. & Martinet, M. Involvement of human CYP1A isoenzymes in the metabolism and drug interactions of riluzole in vitro. J. Pharmacol. Exp. Ther. 282, 1465-1472 (1997).
Sankaranarayanan et al. 'Naphtho[1,2-d]thiazol-2-ylamine (SKA-31 ), a New Activator of KCa2 and KCa3.1 Potassium Channels, Potentiates the Endothelium-Derived Hyperpolarizing Factor Response and Lowers Blood Pressure', Molecular Pharmacology, Feb. 1, 2009 (Feb. 1, 2009), vol. 75, pp. 281-295; p. 282, p. 287.
Santacruz, K., et al. Tau suppression in a neurodegenerative mouse model improves memory function. Science, 476-481 (2005).
Savitz, S.I. and M. Fisher, Prophylactic neuroprotection. Curr Drug Targets, 2007. 8: p. 846-849.
Schaffer, C., et al. Biomarkers in the diagnosis and prognosis of Alzheimer's disease. JALA 20, 589-600 (2015).
Seal, J.B., B. N. Buch, and J.D. Marks, New variability in cerebrovascular anatomy determines severity of hippocampal injury following forebrain ischemia in the Mongolian gerbil. Brain Res, 2006. 1074: p. 451-459.
Shank, R.P. and M.H. Aprison, Present status and significance of the glutamine cycle in neural tissues. Life Sci., 1981. 28: p. 837-842.
Sharma, P.C., Sinhmar, A., Sharma, A., Rajak, H. & Pathak, D.P. Medicinal significance of benzothiazole scaffold: an insight view. J. Enz. Inhib. Med. Chem. 28, 240-266 (2012).
Shen, Hai-Ying et al. "Sarcosine Suppresses Epileptogenesis in Rats With Effects on Hippocampal DNA Methylation." Frontiers in molecular neuroscience vol. 13 97. Jun. 5, 2020, doi:10.3389/fnmol.2020.00097.

(56) References Cited

OTHER PUBLICATIONS

Sibson, N.R., et al., In vivo (13)C NMR measurement of neurotransmitter glutamate cycling, anaplerosis and TCA cycle flux in rat brain during [2-13C] glucose infusion. J. Neurochem., 2001. 76: p. 975-989.
Small, G.W. Early diagnosis of Alzheimer's disease: update on combining genetic and brain-imaging measures. Dialogues Clin. Neurosci. 2, 241-246 (2000).
Smith, M.L., et al., Models for studying long-term recovery following forebrain ischemia in the rat: 2. A 2-vessel occlusion model. Acta Neurol. Scand., 1984. 69: p. 385-401.
Song, J.H., et al., Differential action of riluzole on tetrodotoxin-sensitive and tetrodotoxin-resistant sodium channels. J. Pharmacol. Exp. Ther., 1997. 282: p. 707-714.
Spadoni, F., et al., Lamotrigine derivatives and riluzole inhibit Ina2P in cortical neurons. Neuroeport, 2002. 13: p. 1167-1170.
Sperling, R.A., et al. Functional alterations in memory networks in early Alzheimer's Disease. Neuromolecular Med. 12, 27-43 (2010).
Stanton, P.K. and J.R. Moskal, Diphenylhydantoin protects against hypoxia-induced impairment of hippocampal synaptic transmission. Brain Res, 1991. 546: p. 351-354.
Stargardt, A., Swaab, D.F. & Bossers, K. The storm before the quiet: neuronal hyperactivity and Aβ in the presymptomatic stages of Alzheimer's disease. Neurobiol. Aging 36, 1-11 (2015).
Stefani, A., F. Spadoni, and G. Bernardi, Differential inhibition by riluzole, lamotrigine, and phenytoin of sodium and calcium currents in cortical neurons: implications for neuroprotective strategies. Exp. Neurol, 1997. 147: p. 115-122.
Stoppini, L., P.A. Buchs, and D. Muller, A simple method for organotypic cultures of nervous tissue. J. Neurosci Methods, 1991. 37(2): p. 173-82.
Stuzmann, J.M., Wahl, F., Pratt, J., Mary, V., Reibaud, M., Tecoult, E., and Rataud, J., Neuroprotective profile of riluzole in vivo models of acute neurodegenerative diseases. CNS Drug Reviews, 1997. 3: p. 83-101.
Szatkowski, M. and D. Attwell, Triggering and execution of neuronal death in brain ischaemia: two phases of glutamate release by different mechanisms. Trenda Neurosci, 1994. 17(9): p. 359-65.
Taft, W.C., et al., Phenytoin protects against ischemia-produced neuronal cell death. Brain Res, 1989. 483: p. 143-148.
Takahashi, K., et al. Restored glial glutamate transporter EAAT2 function as a potential therapeutic approach for Alzheimer's disease. J. Exp. Med. 212, 319-332 (2015).
Takeda, K., et al., Synaptic vesicles are capable of synthesizing the VGLUT substrate glutamate from a-ketoglutarate for vesicular loading. J. Neurochem, 2012. 121: p. 184-196.
Takeshima, S., et al. Riluzole-induced interstitial pneumonia in a case with amyotrophic lateral sclerosis. Rinsho Shinkeigaku 55, 840-843 (2015).
Tampellini, D. Synaptic activity and Alzheimer's disease: a critical update. Front. Neurosci. 9, Article 9 (2015).
Tanaka, R., et al., Neurogenesis after transient global ischemia in the adult hippocampus visualized by improved retroviral vector. Stroke, 2004. 35: p. 1454-1459.
Tani, H., Dulla, C.G., Huguenard, J.R. & Reimer, R.J. Glutamin is required for persistent epileptiform activity in the disinhibited neocortical brain slice. J. Neurosci. 30, 1288-1300 (2010).
Tani, H., et al. Modulation of epileptoform activity by glutamine and system A transport in a model of post-traumatic epilepsy. Neurobiol. Dis. 25, 230-238 (2007).
Tani, H., et al. A local glutamate-glutamine cycle sustains synaptic excitatory transmitter release. Neuron 81, 888-900 (2014).
Tauskela, J.S., et al., Preconditioning induces tolerance by suppressing glutamate release in neuron culture ischemia models. J. Neurochem., 2012. 122: p. 470-481.
Trotman, M., et al., The dichotomy of memantine treatment for ischemic stroke; dose-dependent protective and detrimental effects. J. Cereb. Blood Flow Metab., 2015.
Ugale, V.G., et al. Quinazolino-benzothiazoles: fused pharmacophores as anticonvulsant agents. Eur. J. Med. Chem. 53, 107-113 (2012).
Van der Worp., H.B., et al., Hypothermia in animal models of acute ischaemic stroke: A systematic review and meta-analysis. Brain, 2007. 130: p. 3063-3074.
Van Kan, H.J., et al. Association between CYP1A2 activity and riluzole clearance in patients with amyotrophic lateral sclerosis. Br. J. Clin. Pharmacol. 59, 310-313 (2005).
Varoqui, H., et al., Cloning and functional identification of a neuronal glutamine transporter. J Biol Chem, 2000. 276(6): p. 4049-54.
Vered, M., et al., Anti-ischemia activity of HU-211, a non-psychotropic synthetic cannabinoid. Acta Neurochir., 1994. 60: 335-337.
Verma, S.K., et al., Enhancement in the neuroprotective power of riluzole against cerebral ischemia using a brain targeted drug delivery vehicle. ACS Appl Mater Interfaces, 2016. 8: p. 19716-19723.
Wahl, F., et al., Neurological and behavioral outcomes of focal cerebral ischemia in rats. Stroke, 1992. 23: p. 267-272.
Wang, M.J., et al. Oligomeric forms of amyloid-β protein in plasma as a potential blood-based biomarker for Alzheimer's disease. Alzheimer's Res & Ther. 9, 98 (2017).
Wang, R. & Reddy, P.H. Role of glutamate and NMDA receptors in Alzheimer's disease. J. Alzheimers Dis. 57, 1041-1048 (2017).
Wang, S.J., K.Y. Wang, and W.C. Wang, Mechanisms underlying the riluzole inhibition of glutamate release from rat cerebral cortex nerve terminals (synaptosomes). Neuroscience, 2004. 125: p. 191-201.
Wasling, P.,E. Hanse, and B.Gustafsson, Developmental changes in release properties of the CA3-CA1 glutamate synapse in rat hippocampus. J. Neurophysiol, 2004. 92(5): p. 2714-24.
Webster, S., Bachstetter, A.D., Nelson, P.T., Schmitt, F.A. & Van Eldik, L.J. Using mice to model Alzheimer's dementia: an overview of the clinical disease and the preclinical behavioral changes in 10 mouse models. Fron. Genet. 5, 88 (2014).
Weng, Y.C. and J. Kriz, Differential neuroprotective effects of a minocycline-based drug cocktail in transient and permanent focal cerebral ischemia. Exp. Neurol., 2007. 204: p. 433-442.
Wilson, N.R., et al., Presynaptic regulation of quantal size by the vesicular glutamate transporter VGLUT1. J. Neurosci, 2005. 25(26): p. 6221-34.
Winblad, B. & Poritis, N. Memantine in severe dementia: results of the 9M-best study (benefit and efficacy in severely demented patients during treatment with memantine) Int. J. Geriat. Psychiatry 14,135-146 (1999).
Written Opinion for PCT/US2019/032477 dated Aug. 12, 2019.
Xiang, Z., et al., Long-term maintenance of mature hippocampal slices in vitro. J. Neurosci, Meth., 2000. 98: p. 145-154.
Yao, D., et al., A novel system A isoform mediating Na+/neutral amino acid cotransport. J. Biol Chem, 2000. 275(30): p. 22790-7.
Zahs, K.R. & Ashe, K.H. β-amyloid oligomers in aging and Alzheimer's disease. Front. Aging Neurosci. 5, 28 (2013).
Zhang, J., et al., Synaptic and cognitive improvements by inhibition of −2AG metabolism are through upregulation of microRNA-188-3p in a mouse model of Alzheimer's disease. J. Neurosci., 2014. 34: p. 14919-14933.
Zhou et al. 'Glutamate as a neurotransmitter in the healthy brain', Journal of Neural Transmission, Mar. 1, 2014 (Mar. 1, 2014), vol. 121, pp. 799-817; Abstract, p. 807.

* cited by examiner 1 2 3 4 5 6 7 8 9 10 11

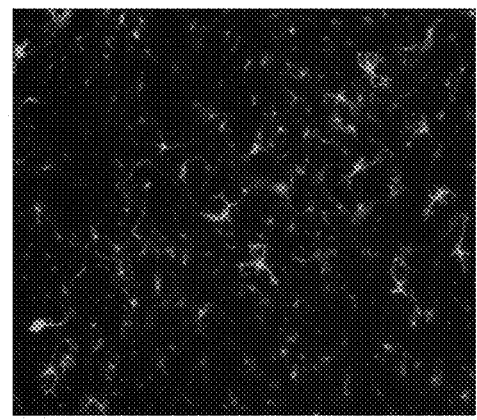
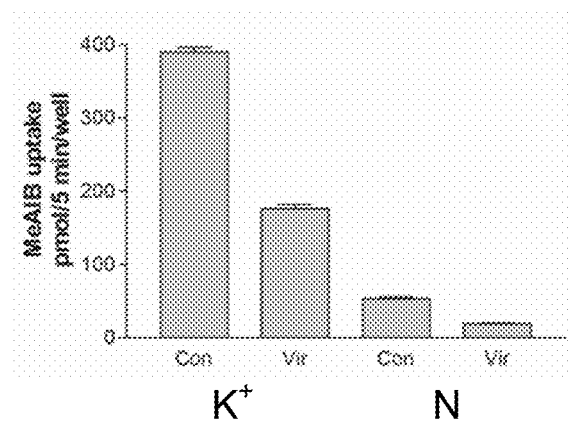
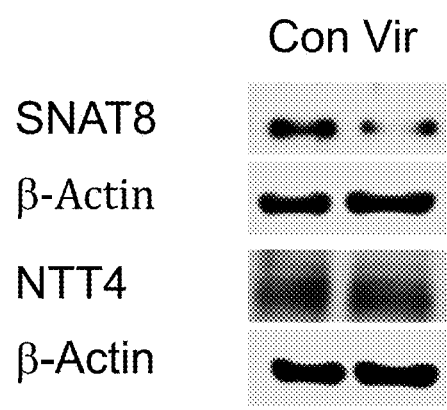
*FIG. 6*

| SKA41 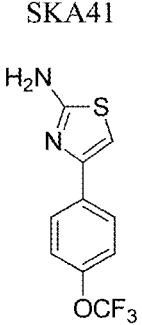 M.W: 260.24 Amount: 4.5mg Max solubility: 50μM | SKA75 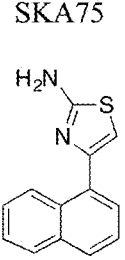 M.W: 226.30 5.0mg 25 μM | SKA76 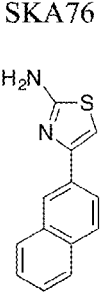 M.W: 226.30 5.1mg 25 μM | SKA77 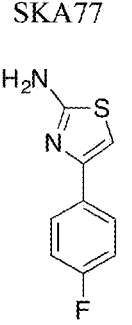 M.W: 194.23 5.2mg 100μM |
|---|---|---|---|
| SKA78 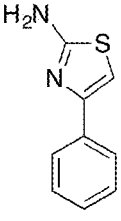 M.W: 176.24 6.0mg 100μM | SKA79 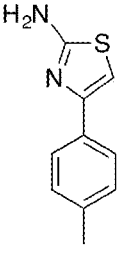 M.W: 190.26 5.9mg 100μM | SKA80 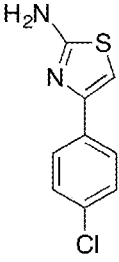 M.W: 210.68 5.4mg 50μM | SKA82 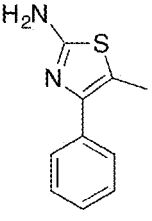 M.W: 190.26 5.7mg 100μM |
| SKA88 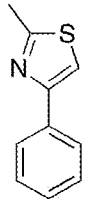 M.W: 175.25 4.2mg 100μM | SKA89 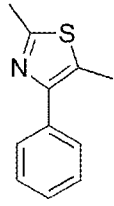 M.W: 189.28 13mg (liquid) 100μM | SKA94 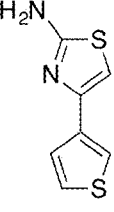 M.W: 182.26 6.2mg 100μM | SKA190 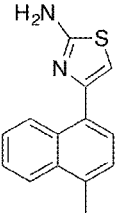 M.W: 240.32 4.4mg 50μM |
FIG. 9 CON'T

| SKA193 | SKA198 | SKA219 | SKA220 |
|---|---|---|---|
| 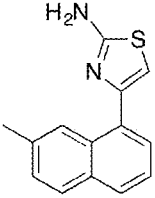 | 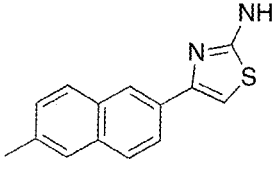 | 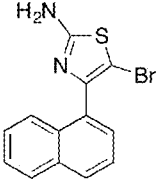 | 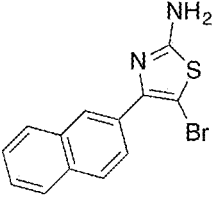 |
| M.W: 240.32<br>3.7mg<br>50μM | M.W: 240.32<br>4.8mg<br>50μM | M.W: 305.19<br>3.8mg<br>25μM | M.W: 305.19<br>3.4mg<br>25 μM |
| SKA230 | SKA232 | SKA247 | SKA251 |
| 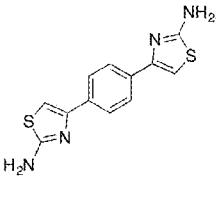 | 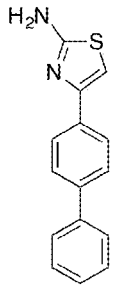 | 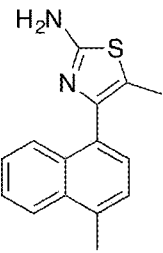 | 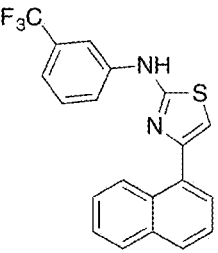 |
| M.W: 274.36<br>3.1mg<br>50μM | M.W: 252.34<br>5.4mg<br>50μM | M.W:254.35<br>3.0mg<br>50μM | M.W: 370.39<br>3.1mg<br>10μM |
| SKA255 | SKA257 | SKA258 | SKA260 |
| 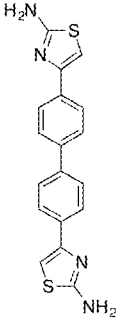 |  | 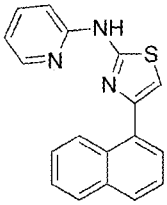 | 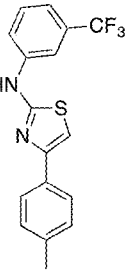 |
| M.W: 350.46<br>5.1mg<br>10μM | M.W: 371.28<br>4.4mg<br>10μM | M.W: 303.38<br>5.1mg<br>10μM | M.W: 334.36<br>5.8mg<br>10μM |
FIG. 9 CON'T

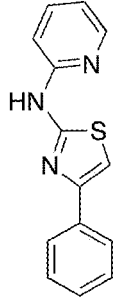
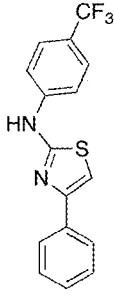
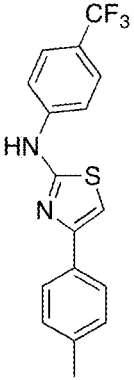
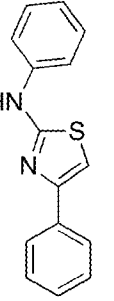
*FIG. 9 CON'T*

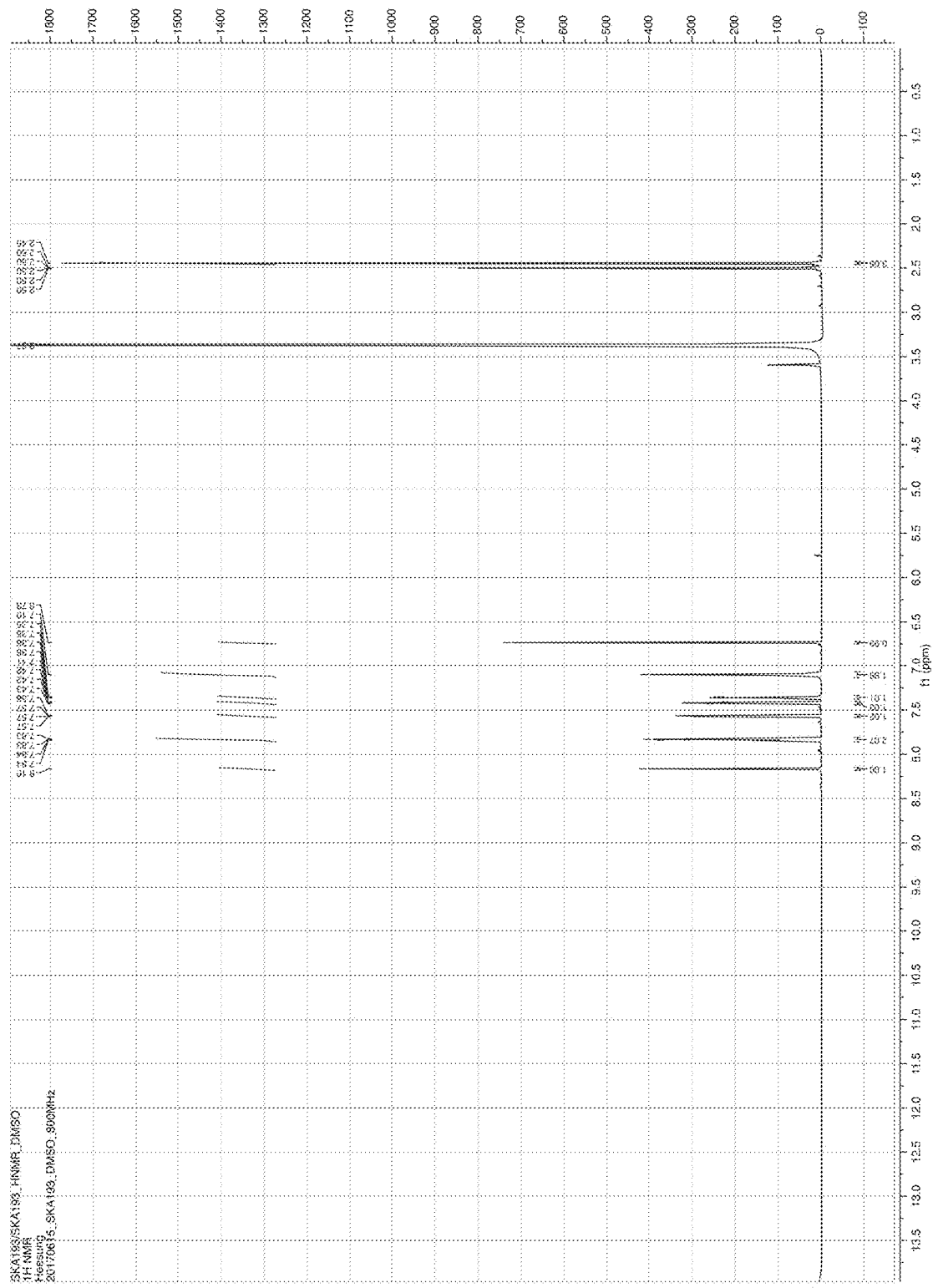
FIG. 11 CON'T

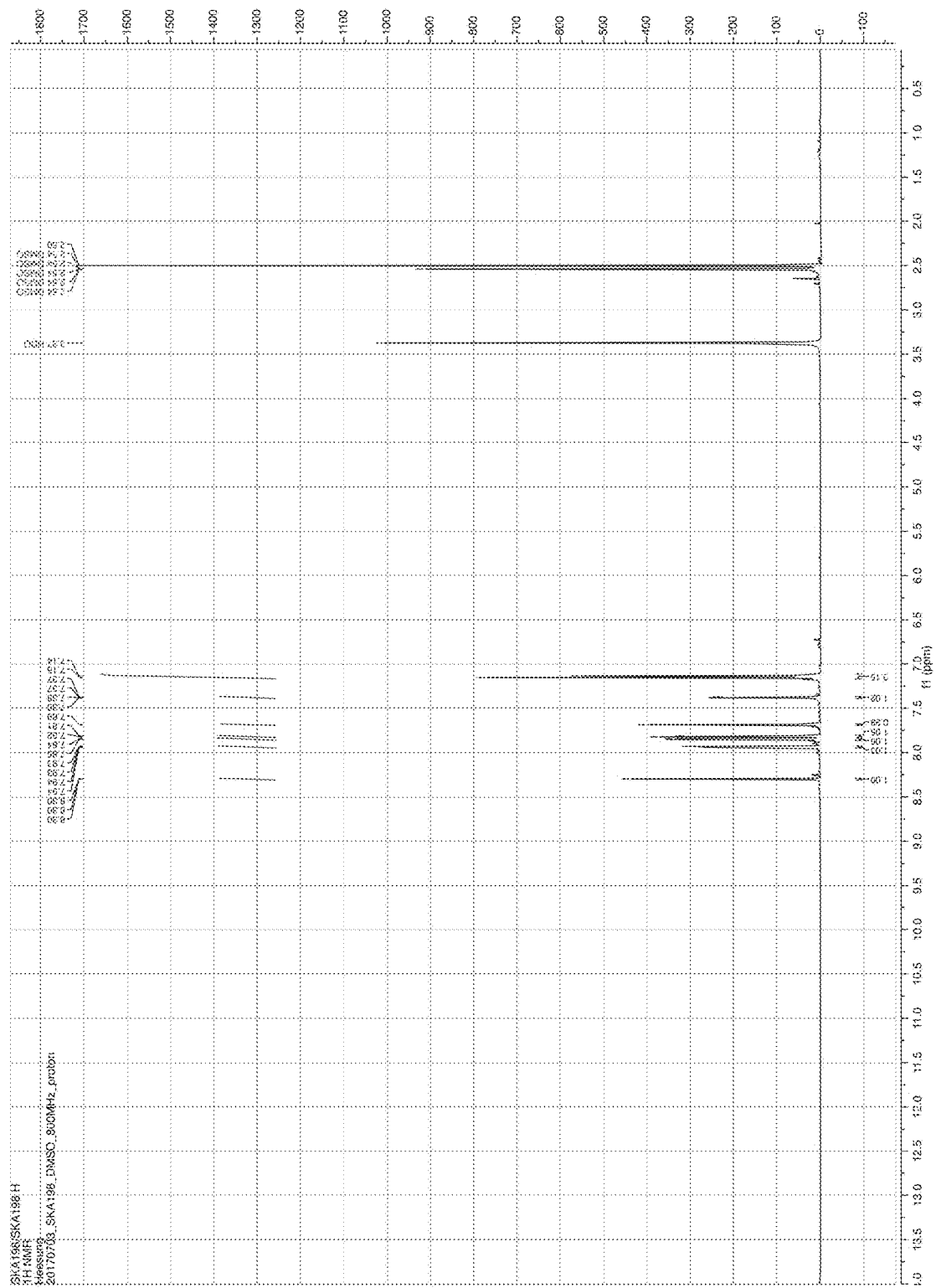
FIG. 12 CON'T

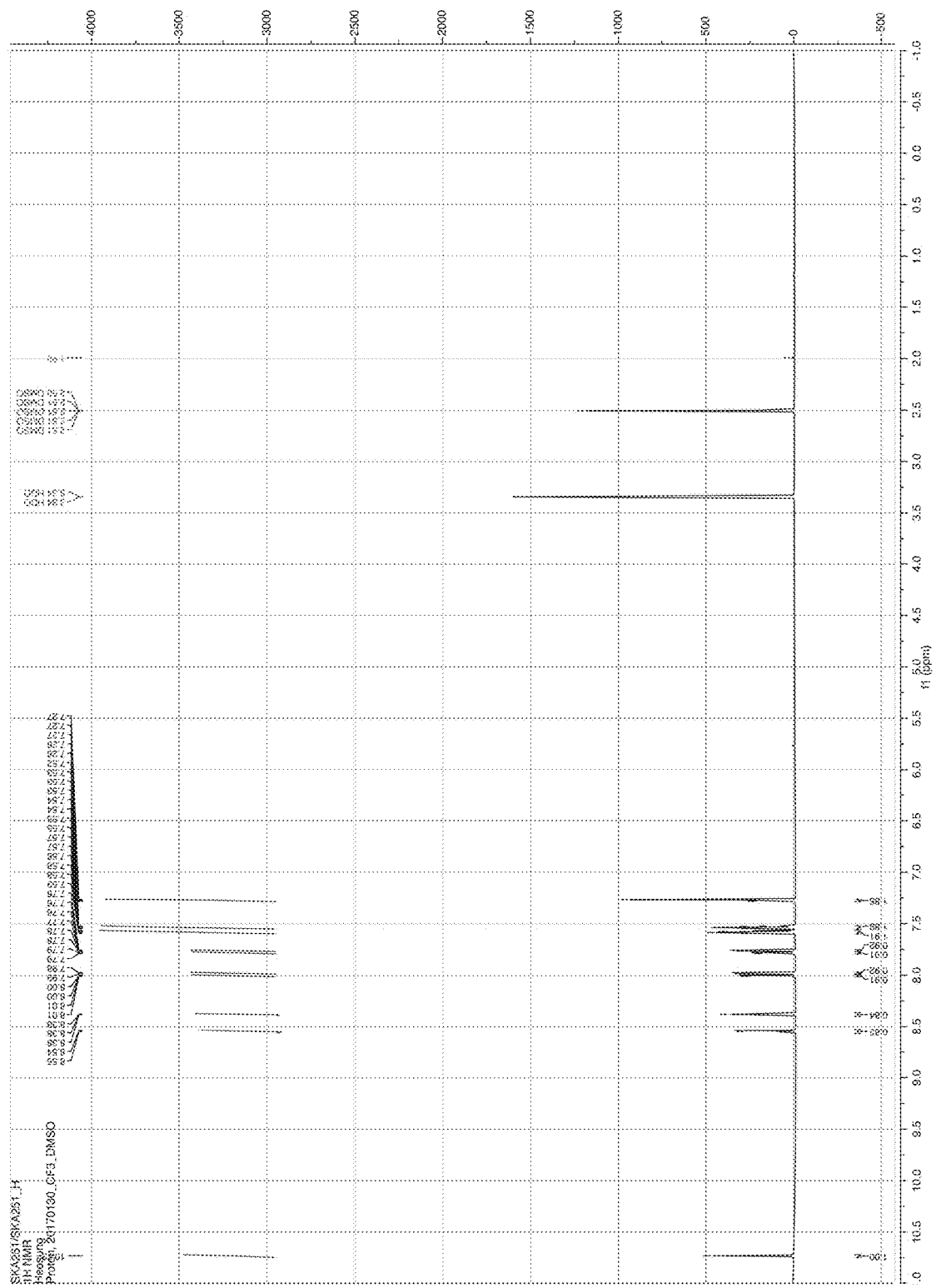
FIG. 13 CON'T

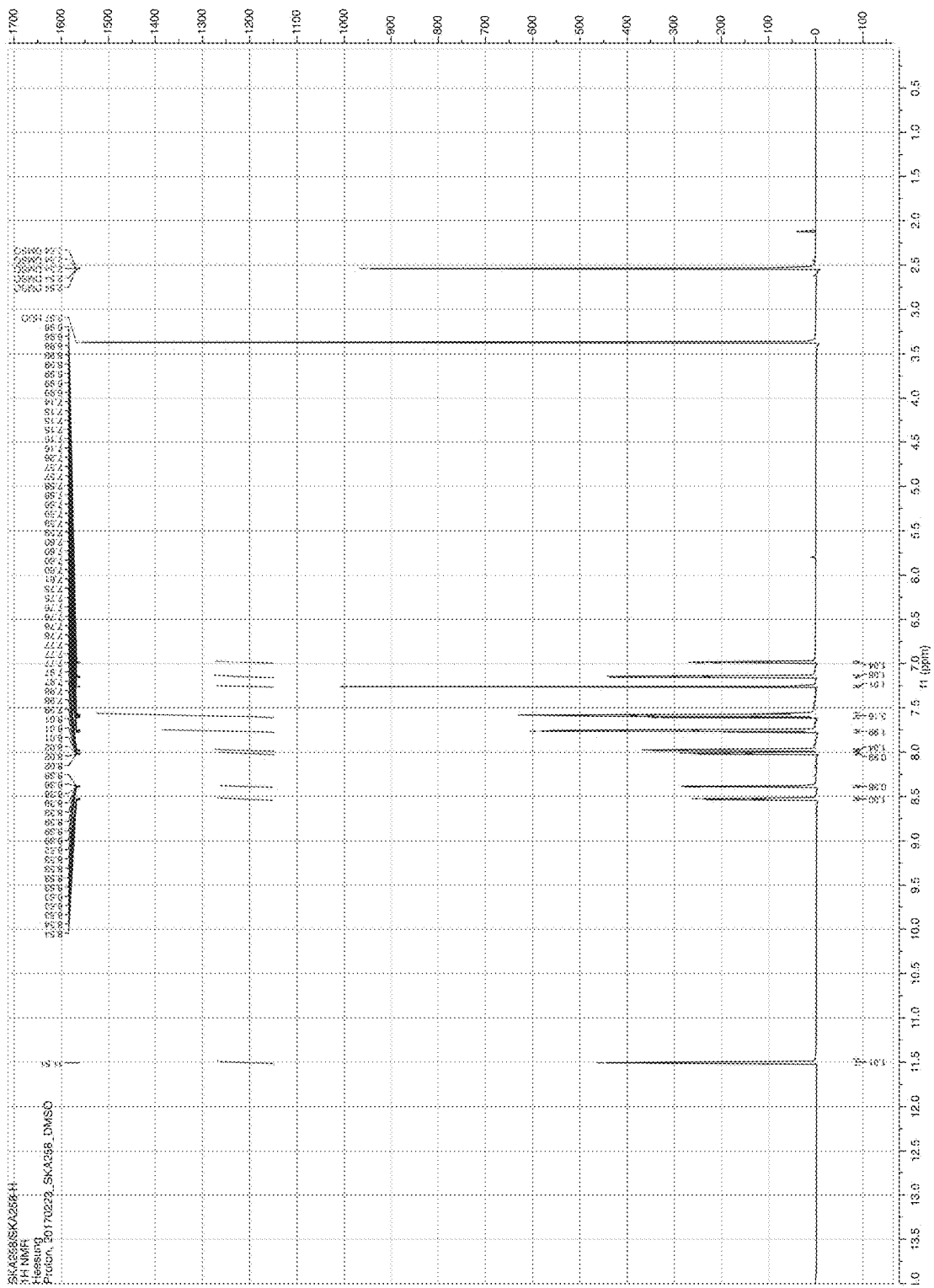
FIG. 14 CON'T

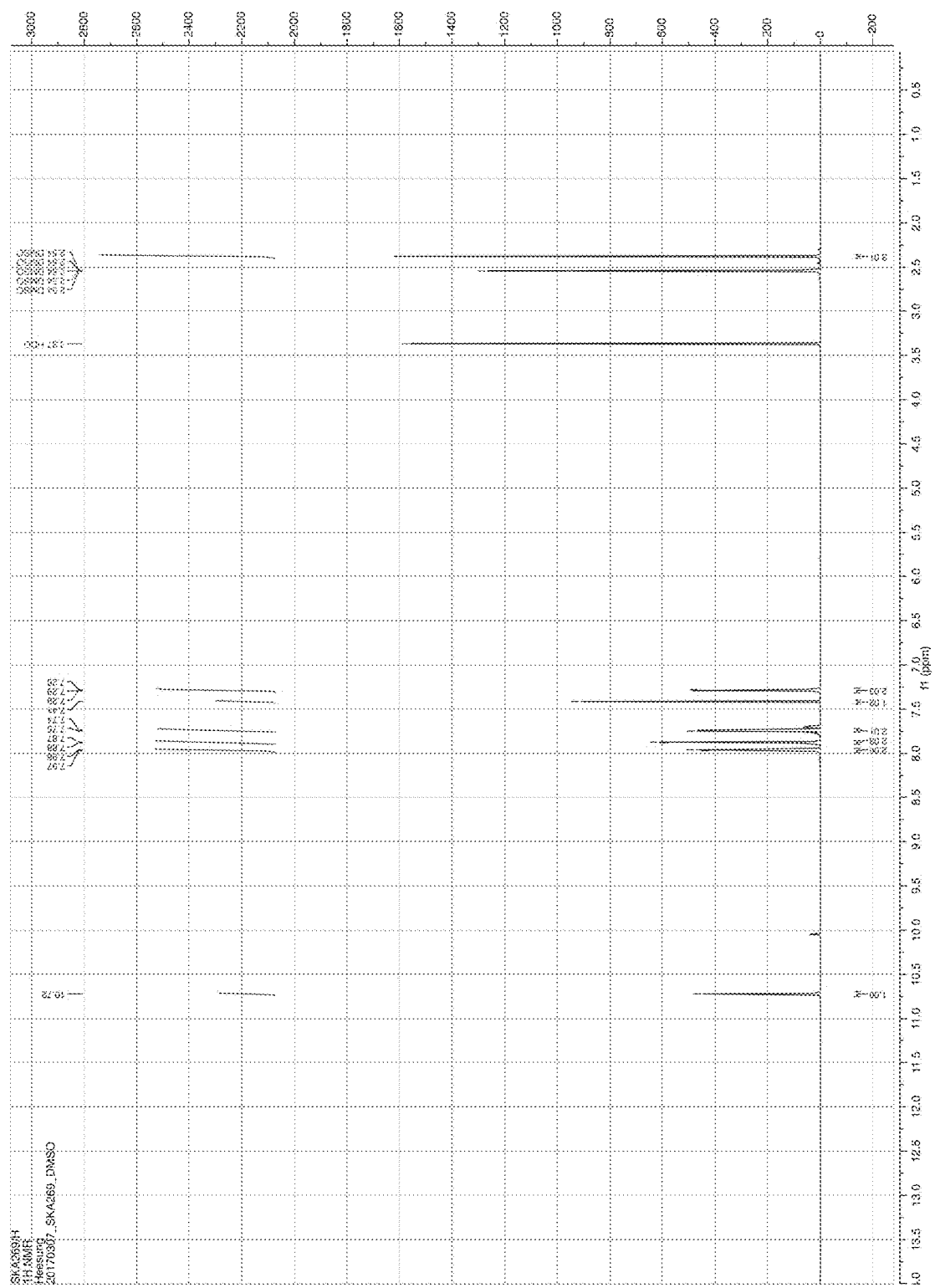
FIG. 15 CON'T

SEQUENCE LISTING

<160> NUMBER OF SEQ ID NOS: 3

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgaatgacac agccatcatt gtctcttgaa caagatggct gtgtcattgc         50

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggtcatcacg gtgcaatact atctcttgaa tagtattgca ccgtgatgac c        51

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctaaggtta agtcgccctc gtctcttgaa cgagggcgac ttaaccttag g        51

NEUROPROTECTIVE COMPOSITIONS AND METHODS OF USING THE SAME

This application is a continuation-in-part of International Application No. PCT/US2019/32477, filed May 15, 2019, which claims priority to U.S. Provisional Patent Application Ser. No. 62/671,636, filed May 15, 2018, the contents of each of which are incorporated herein by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT INTERESTS

This invention was made with government support under R21MH101612, R21NS101876, R21NS112788, R21NS109668, and R01NS113955 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 2, 2021, is named 2932719-018US2_SL.txt and is 1,173 bytes in size.

FIELD OF THE INVENTION

This invention is directed to neuroprotective compositions and methods of using the same to treat neurodegenerative diseases.

BACKGROUND OF THE INVENTION

Excitotoxicity is the pathological process by which nerve cells are damaged and killed by excessive stimulation by the neurotransmitter glutamate (Glu). Cerebral global ischemia induces excitotoxic neuronal death as a result of excessive presynaptic Glu release. Global cerebral ischemia is frequently encountered in cardiac arrest, profound hypotension, or during vascular occlusion in the course of perioperative neuro/cardiac surgical procedures. Patients surviving such episodes of cerebral ischemia often show neurobehavioral deficits and neuronal necrosis in vulnerable brain regions.

SUMMARY OF THE INVENTION

Aspects of the invention are directed towards a neuroprotective compound of formula (I):

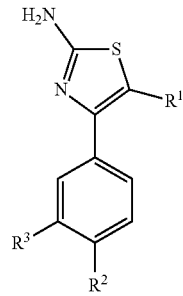

In embodiments of formula (I), $R^1$ is $CH_3$, H or Br; $R^2$ is H, or $CH_3$ or $CF_3$; and $R^3$ is H, benzene, or methyl-benzene; or a pharmaceutically acceptable salt thereof, or any combination thereof.

Further, the invention provides a neuroprotective compound having the chemical structure according to Table 1.

In embodiments, the neuroprotective compound comprises SKA-41, SKA-41(a), SKA-75, SKA-76, SKA-77, SKA-78, SKA-79, SKA-80, SKA-82, SKA-88, SKA-89, SKA-94, SKA-190, SKA-193, SKA-198, SKA-219, SKA-220, SKA-230, SKA-232, SKA-247, SKA-251, SKA-255, SKA-257, SKA-258, SKA-260, SKA-265, SKA-268, SKA-269, SKA-292, or any combination thereof. For example, the neuroprotective compound comprises SKA-41, SKA-190, SKA-193, SKA-219, or SKA-247.

Embodiments can comprise a composition comprising a therapeutically effective amount of the neuroprotective compound as described herein and/or a pharmaceutically acceptable carrier. Non-limiting examples of pharmaceutically acceptable carriers comprise solid or liquid fillers, diluents, and encapsulating substances, including but not limited to lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

In embodiments, the compound is provided in an acceptable pharmaceutical form for administration to a subject. For example, routes of administration include parenteral, e.g., intravenous, intradermal, subcutaneous, oral (e.g., inhalation), transdermal (topical), transmucosal, intraosseous, and rectal administration.

In embodiments, the neuroprotective compound has an $EC_{50}$ value of 0.01-50 micromolar in vitro, such as 0.1-10 micromolar in vitro. For example, the neuroprotective compound has an $EC_{50}$ value of 1-3 micromolar in vitro.

In embodiments, the neuroprotective compound decreases Glu-induced excitotoxicity. For example, embodiments reduce or eliminate Gln-derived excessive Glu release from synapses and thus decrease excitoxicity without interrupting basal glutamatergic synaptic transmission.

In embodiments, the neuroprotective compound modulates Gln import into glutamatergic synapses and Glu/Gln cycling between astrocytes and neurons.

The invention is further directed towards a method for preventing, treating, and/or reducing the severity of a neurodegenerative disease and/or condition in a subject. For example, the neurodegenerative diseases comprises Alzheimer's disease, cerebral ischemia (such as focal cerebral ischemia and/or global cerebral ischemia), amyotrophic lateral sclerosis traumatic brain injury-induced epileptogenesis peri-operative neuronal and/or cardiac stress, epilepsy, noise-induced hearing loss, or a combination thereof. In embodiments, the condition comprises cognitive impairment, neurodegeneration, neuronal cell death, excitotoxic cell death, or a combination thereof.

Aspects of the invention are further directed towards a method for effective prophylactic and management strategy to suppress neuronal death and cognitive impairment, the method comprising administering to said subject in need thereof a therapeutically effective amount of the neuroprotective compound herein.

In embodiments, the method comprises administering to said subject in need thereof a therapeutically effective amount of the neuroprotective compound or composition comprising the same. For example, a therapeutically effective amount of a neuroprotective compound of formula (I), such as SKA-41, SKA-41(a), SKA-75, SKA-76, SKA-77, SKA-78, SKA-79, SKA-80, SKA-82, SKA-88, SKA-89, SKA-94, SKA-190, SKA-193, SKA-198, SKA-219, SKA-220, SKA-230, SKA-232, SKA-247, SKA-251, SKA-255, SKA-257, SKA-258, SKA-260, SKA-265, SKA-268, SKA-269, SKA-292, or any combination thereof, is administered to the subject.

The invention is still further directed towards a method for preventing, treating, and/or reducing the severity of a disease and/or condition associated with glutamate-induced excitotoxicity in a subject. For example, the diseases comprises Alzheimer's disease, cerebral ischemia, amyotrophic lateral sclerosis traumatic brain injury, peri-operative neuronal and/or cardiac stress, epilepsy, noise-induced hearing loss, or a combination thereof. In embodiments, the condition comprises cognitive impairment, neurodegeneration, neuronal cell death, excitotoxic cell death, or a combination thereof.

In embodiments, the method comprises administering to said subject in need thereof a therapeutically effective amount of the neuroprotective compound. For example, a therapeutically effective amount of a neuroprotective compound of formula (I), such as SKA-41, SKA-41(a), SKA-75, SKA-76, SKA-77, SKA-78, SKA-79, SKA-80, SKA-82, SKA-88, SKA-89, SKA-94, SKA-190, SKA-193, SKA-198, SKA-219, SKA-220, SKA-230, SKA-232, SKA-247, SKA-251, SKA-255, SKA-257, SKA-258, SKA-260, SKA-265, SKA-268, SKA-269, SKA-292, or any combination thereof, is administered to the subject. Embodiments can further comprise administering concurrently or subsequently a therapeutically effective amount of an open-channel N-methyl-D-aspartate (NMDA) receptor blocker to the subject, such as memantine, as a complementary approach.

Still further, the invention is directed towards a medical kit for the treatment of a neurodegenerative disease.

In embodiments, the medical kit comprises printed instructions for administering the compound to the subject afflicted with or at risk of excessive Glu release from synapses, Glu-induced neurodegenerative disease or Glu-induced excitotoxicity. In other embodiments, the medical kit can comprise printed instructions for administering a neuroprotective compound as described herein, or a pharmaceutical composition comprising a compound as described herein and a pharmaceutically acceptable carrier. For example, the neuroprotective compound comprises a compound of formula (I), such as SKA-41, SKA-41(a), SKA-75, SKA-76, SKA-77, SKA-78, SKA-79, SKA-80, SKA-82, SKA-88, SKA-89, SKA-94, SKA-190, SKA-193, SKA-198, SKA-219, SKA-220, SKA-230, SKA-232, SKA-247, SKA-251, SKA-255, SKA-257, SKA-258, SKA-260, SKA-265, SKA-268, SKA-269, SKA-292, or any combination thereof.

Other objects and advantages of this invention will become readily apparent from the ensuing description.

Aspects of the invention are drawn towards a neuroprotective compound of formula (I):

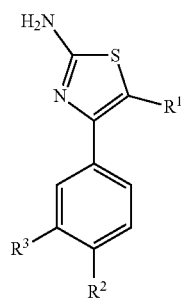

wherein, $R^1$ is $CH_3$, H, Br, Cl, F, I, D, $NH_2$, $OCH_3$, $CH_2CH_3$, $CH_2CH_2CH_3$, $CF_3$, alkyl group, or alkoxy group; $R^2$ is H, $CH_3$, $CF_3$, Cl, F, $OCF_3$, Br, I, $NH_2$, $OCH_3$, $CH_2CH_3$, $CH_2CH_2CH_3$, alkyl group, alkoxy group, or $SCF_3$; and $R^3$ is H, benzene, pyridine, imidazole, pyrrole, pyrimidine, pyridine, pyridazine, pyrimidine, pyrazine, a quinolone, an isoquinoline or methyl-benzene; or a pharmaceutically acceptable salt thereof. In embodiments, said compound has an $EC_{50}$ value of 1-3 micromolar in vitro. In embodiments, said compound decreases glutamate-induced excitotoxicity. In embodiments, glutamine-derived excessive glutamate release from synapses is reduced and excitoxicity is decreased without interrupting basal glutamatergic synaptic transmission. In embodiments, said compound modulates glutamine import into glutamatergic synapses and glutamate/glutamine cycling between astrocytes and neurons. In embodiments, said compound is provided in an acceptable pharmaceutical form for administration to a subject.

Aspects of the invention are drawn towards a neuroprotective compound of formula (II):

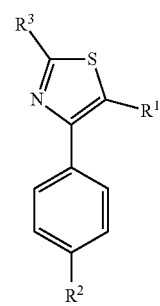

wherein $R^1$ is $CH_3$, H, Br, Cl, F, I, D, $NH_2$, $OCH_3$, $CH_2CH_3$, $CH_2CH_2CH_3$, alkyl group, alkoxy group, or $CF_3$; $R^2$ is H, $CH_3$ $CF_3$, Cl, F, Br, I, $OCF_3$, pyridine, imidazole, pyrrole, pyrimidine, pyridine, pyridazine, pyrimidine, pyrazine, a quinolone, an isoquinoline, or $SCF_3$; and $R^3$ is $NH_2$, $C_6H_6N$, $C_7H_5F_3N$, $C_5H_5N_2$, $C_6H_4Cl_2N$; or a pharmaceutically acceptable salt thereof. In embodiments, $R^1$ is Cl, $R^2$ is $OCF_3$, and $R^3$ is $NH_2$. In embodiments, the compound comprises SKA-41, SKA-190, SKA-193, SKA-219, SKA-220, SKA-247, SKA-375, SKA-376, SKA-377, SKA-378, SKA-379, SKA-380, SKA-381, SKA-382, SKA-383, SKA-384, SKA-385, SKA-386, SKA-387, SKA-388. In embodiments, the compound comprises SKA-376, SKA-377, SKA-378, SKA-381, or SKA-380. In embodiments, said compound has an $EC_{50}$ value of 1-3 micromolar in vitro. In embodiments, said compound decreases glutamate-induced excitotoxicity. In embodiments, glutamine-derived excessive glutamate release from synapses is reduced and excitoxicity is decreased without interrupting basal glutamatergic synaptic transmission. In embodiments, said compound modulates glutamine import into glutamatergic synapses and glutamate/glutamine cycling between astrocytes and neurons. In embodiments, said compound is provided in an acceptable pharmaceutical form for administration to a subject.

Aspects of the invention are drawn towards a neuroprotective compound of formula (III):

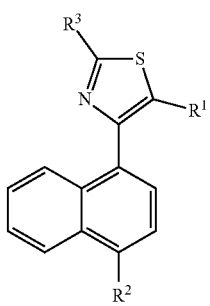

wherein $R^1$ is $CH_3$, H, Br, Cl, F, I, D, $NH_2$, $OCH_3$, $CH_2CH_3$, $CH_2CH_2CH_3$, alkyl group, alkoxy group or $CF_3$; $R^2$ is H, $CH_3$ $CF_3$, Cl, F, Br, I, $OCF_3$, pyridine, imidazole, pyrrole, pyrimidine, pyridine, pyridazine, pyrimidine, pyrazine, a quinolone, an isoquinoline, or $SCF_3$; and $R^3$ is $NH_2$, $C_6H_6N$, $C_7H_5F_3N$, $C_5H_5N_2$, $C_6H_4Cl_2N$; or a pharmaceutically acceptable salt thereof. In embodiments, $R^1$ is Cl, $R^2$ is $CH_3$, and $R^3$ is $NH_2$. In embodiments, $R^1$ is Cl, $R^2$ is H, and $R^3$ is $NH_2$. In embodiments, the compound comprises SKA-379 or SKA-382. In embodiments, said compound has an $EC_{50}$ value of 1-3 micromolar in vitro. In embodiments, said compound decreases glutamate-induced excitotoxicity. In embodiments, glutamine-derived excessive glutamate release from synapses is reduced and excitoxicity is decreased without interrupting basal glutamatergic synaptic transmission. In embodiments, said compound modulates glutamine import into glutamatergic synapses and glutamate/glutamine cycling between astrocytes and neurons. In embodiments, said compound is provided in an acceptable pharmaceutical form for administration to a subject.

Aspects of the invention are drawn towards a neuroprotective compound of formula (IV):

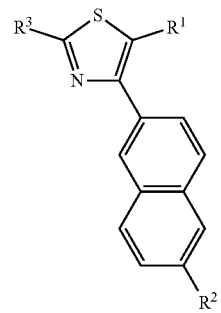

wherein, $R^1$ is $CH_3$, H, Br, Cl, F, I, D, $NH_2$, $OCH_3$, $CH_2CH_3$, $CH_2CH_2CH_3$, alkyl group, alkoxy group, or $CF_3$; $R^2$ is H, $CH_3$ $CF_3$, Cl, F, Br, I, $OCF_3$, pyridine, imidazole, pyrrole, pyrimidine, pyridine, pyridazine, pyrimidine, pyrazine, a quinolone, an isoquinoline, or $SCF_3$; and $R^3$ is $NH_2$, $C_6H_6N$, $C_7H_5F_3N$, $C_5H_5N_2$, $C_6H_4Cl_2N$; or a pharmaceutically acceptable salt thereof. In embodiments, $R^1$ is Cl, $R^2$ is H, and $R^3$ is $NH_2$. In embodiments, said compound has an $EC_{50}$ value of 1-3 micromolar in vitro. In embodiments, said compound decreases glutamate-induced excitotoxicity. In embodiments, glutamine-derived excessive glutamate release from synapses is reduced and excitoxicity is decreased without interrupting basal glutamatergic synaptic transmission. In embodiments, said compound modulates glutamine import into glutamatergic synapses and glutamate/glutamine cycling between astrocytes and neurons. In embodiments, said compound is provided in an acceptable pharmaceutical form for administration to a subject.

Aspects of the invention are drawn towards a neuroprotective compound having the chemical structure according to FIG. 9.

Aspects of the invention are drawn towards a method for preventing, treating, and/or reducing the severity of a neurodegenerative disease in a subject, comprising administering to said subject in need thereof a therapeutically effective amount of the neuroprotective compound of any one of the compounds described herein. In an embodiment, the neurodegenerative diseases comprises Alzheimer's disease, global cerebral ischemia, amyotrophic lateral sclerosis, traumatic brain injury-induced epileptogenesis peri-operative neuronal and/or cardiac stress, epilepsy, noise-induced hearing loss, or a combination thereof. In embodiments, the method further comprises administering concurrently or subsequently a therapeutically effective amount of an open-channel N-methyl-D-aspartate (NMDA) receptor blocker to the subject. In embodiments, the NMDA receptor blocker comprises memantine. In embodiments, the neuroprotective compound comprises SKA41, SKA190, SKA193, SKA219, SKA-220, SKA247, SKA-375, SKA-376, SKA-377, SKA-378, SKA-379, SKA-380, SKA-381, SKA-382, SKA-383, SKA-384, SKA-385, SKA-386, SKA-387, SKA-388. In embodiments, the neuroprotective compound is a compound of Formula (II). In embodiments, the neuroprotective compound is a compound of Formula (III). In embodiments, the neuroprotective compound is a compound of Formula (IV).

Aspects of the invention are drawn towards a method for preventing, treating, and/or reducing the severity of a disease and/or condition associated with glutamate-induced excitotoxicity in a subject, the method comprising administering to said subject in need thereof a therapeutically effective amount of the neuroprotective compound of any one of the compounds described herein. In embodiments, the method further comprises administering concurrently or subsequently a therapeutically effective amount of an open-channel N-methyl-D-aspartate (NMDA) receptor blocker to the subject. In embodiments, the NMDA receptor blocker comprises memantine. In embodiments, the neuroprotective compound comprises SKA41, SKA190, SKA193, SKA219, SKA-220, SKA247, SKA-375, SKA-376, SKA-377, SKA-378, SKA-379, SKA-380, SKA-381, SKA-382, SKA-383, SKA-384, SKA-385, SKA-386, SKA-387, SKA-388. In embodiments, the neuroprotective compound is a compound of Formula (II). In embodiments, the neuroprotective compound is a compound of Formula (III). In embodiments, the neuroprotective compound is a compound of Formula (IV).

Aspects of the invention are drawn towards a method for effective prophylactic and management strategy to suppress neuronal death and cognitive impairment, the method comprising administering to said subject in need thereof a therapeutically effective amount of the neuroprotective compound of any one of the compounds described herein. In embodiments, the diseases comprises Alzheimer's disease, cerebral ischemia, amyotrophic lateral sclerosis, traumatic brain injury, peri-operative neuronal and/or cardiac stress, epilepsy, noise-induced hearing loss, or a combination thereof. In embodiments, the condition comprises cognitive impairment, neurodegeneration, neuronal cell death, excitotoxic cell death, or a combination thereof. In embodiments, the method further comprises administering concurrently or subsequently a therapeutically effective amount of an open-channel N-methyl-D-aspartate (NMDA) receptor blocker to the subject. In embodiments, the NMDA receptor blocker comprises memantine. In embodiments, the neuroprotective compound comprises SKA41, SKA190, SKA193, SKA219, SKA-220, SKA247, SKA-375, SKA-376, SKA-377, SKA-378, SKA-379, SKA-380, SKA-381, SKA-382, SKA-383, SKA-384, SKA-385, SKA-386, SKA-387, SKA-388. In embodiments, the neuroprotective compound is a compound of Formula (II). In embodiments, the neuroprotective compound is a compound of Formula (III). In embodiments, the neuroprotective compound is a compound of Formula (IV).

Aspects of the invention are drawn towards a pharmaceutical composition comprising a neuroprotective compound according to anyone of the compounds described herein.

Aspects of the invention are drawn towards a medical kit for the treatment of a neurodegenerative disease comprising printed instructions for administering the compound to the subject afflicted with or at risk of a neurodegenerative disease; and a neuroprotective compound according to any one of the compounds described herein, or a pharmaceutical composition comprising a compound according to any one of compounds described herein and a pharmaceutically acceptable carrier.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1 shows a cartoon of the Glu/Gln cycle between neurons and astrocytes. Glu is released from synapses by $Ca^{2+}$-dependent exocytosis of synaptic vesicles where it can activate Glu receptors. Glu is rapidly cleared from the synaptic cleft by Glu transporters (EAAT1/EAAT2) located on surrounding astrocytes. Glu is then converted to Gln by the astrocyte-specific enzyme Gln synthetase. Gln then can exit the astrocyte by a 'system N type' Gln transporter. We have discovered a neuronal, activity-regulated, $K^+$-stimulated, $Ca^{2+}$-dependent Gln transport system that can be inhibited by the anti-glutamatergic compound riluzole in primary rat hippocampal cultures in vitro. Without wishing to be bound by theory, this high-affinity 'system A-type' transporter cycles between an intracellular pool of vesicles and the plasma membrane in synapses in an activity-dependent manner.

FIG. 6 shows SNAT 8 knockdown reduces activity-regulated Gln transport activity. (Top panel) lentivirus infection of hippocampal neurons in vitro (5 µl; 8-d post-infection) as monitored by EGFP expression. Middle panel, Lentiviral-mediated knockdown of $K^+$ depolarization induced and spontaneous (N) $Ca^{2+}$-dependent [$^{14}C$]-MeAIB transport (20 MeAIB, 5 min) in hippocampal neuronal culture by SNAT8 shRNA. 4° C. background (32 pmol) was subtracted. Values are from n=2 independent experiments. Bottom panel, Western blot analysis of crude synaptosomes (12,000×g) prepared from duplicate wells showing reduced SNAT8 protein levels with shRNA treatment. NTT4 levels are not affected by SNAT8 shRNA expression. Blots were stripped and re-probed with β-actin (30 µg protein/lane). While the NTT4 blots are overexposed it is clear that SNAT8 bands are reduced by SNAT8 shRNA compared to β-actin.

FIG. 9 shows SKA-41 and active and inactive SKA-41 derivatives.

DETAILED DESCRIPTION OF THE INVENTION

Figure 1:
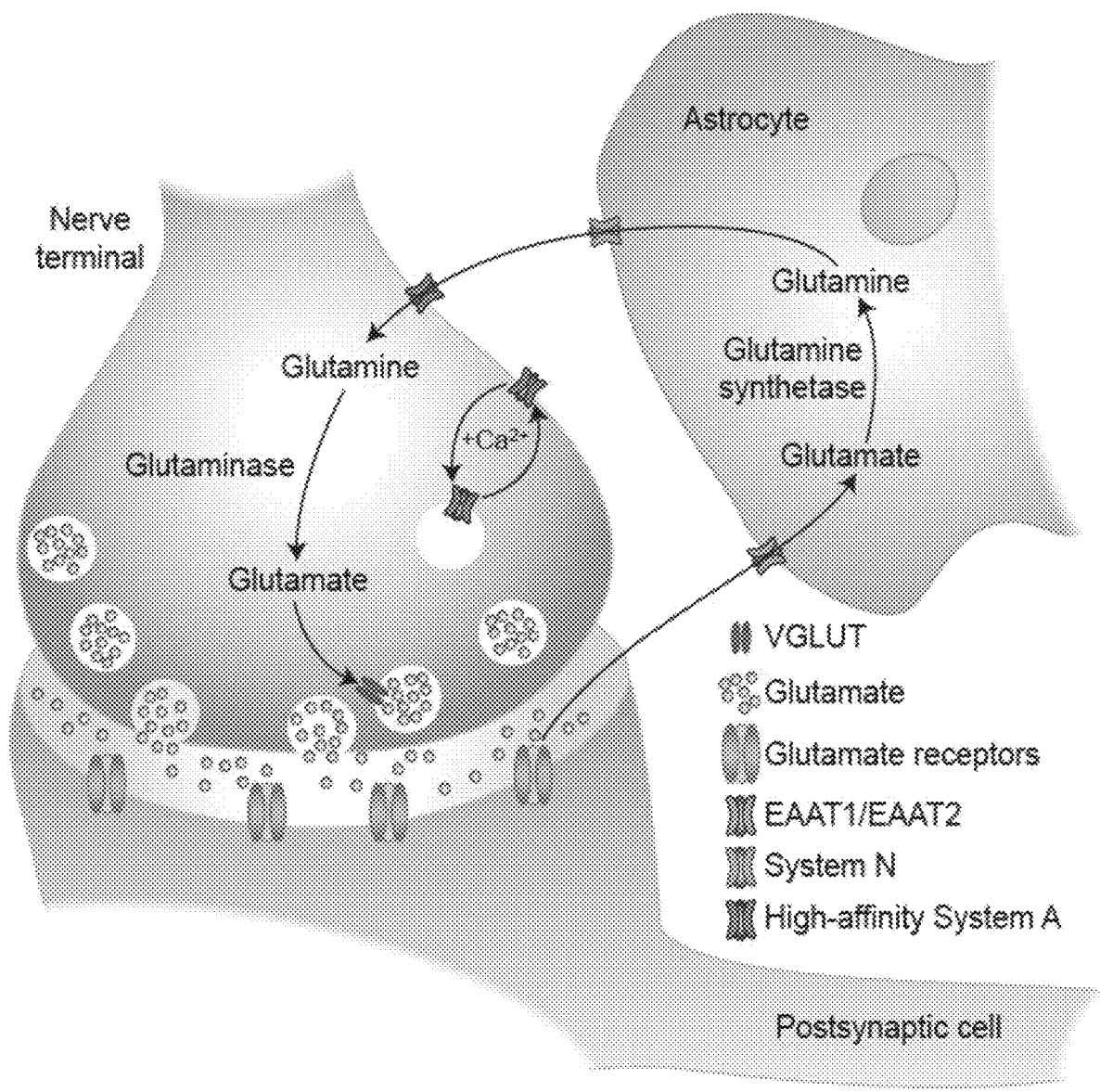
FIG. 1 shows the novel high-affinity System A transporter which may have physiological and pathological implications in understanding the neurobiology of excitotoxic synaptic Glu release in acute and chronic neurodegenerative diseases. Specifically.

Excessive and sustained release of Glu from pyramidal neurons in the cerebral cortex and hippocampus is an initial event that triggers calcium-dependent excitotoxicity in post-synaptic neurons in several acute and chronic neurodegenerative diseases. Thus, mechanisms to reduce excessive synaptic Glu release could potentially prevent excitotoxic damage to neurons, where treatment options are quite limited and postsynaptic interventions have proven disappointing in human studies because of poor efficacy or unacceptable side effects. It is believed that Glu transmission requires import of glutamine (Gln) into axon terminals from astrocytes to replenish cytoplasmic Glu levels and vesicular Glu stores lost following excessive synaptic Glu release. Thus, blocking synaptic import of Gln into synapses represents a novel therapeutic strategy to limit continued Glu release under conditions of excitotoxicity.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Excessive and sustained release of Glu from pyramidal neurons in the cerebral cortex and hippocampus is an initial event that triggers calcium-dependent excitotoxicity in postsynaptic neurons in several acute and chronic neurodegenerative diseases (Benveniste et al., 1984; Bittigau and Ikonomidou, 1997; Obrenovitch and Urenjak, 1997; Dodd, 2002; Holmes, 2002; Fujimoto et al., 2004; Dudek and Sutula, 2007; Kostandy, 2012). Thus, without wishing to be bound by theory, mechanisms to reduce excessive synaptic Glu release can prevent excitotoxic damage to neurons, where treatment options are quite limited and postsynaptic interventions have proven disappointing in human studies because of poor efficacy or unacceptable side effects. Glu transmission requires import of glutamine (Gln) into axon terminals from astrocytes to replenish cytoplasmic Glu levels and vesicular Glu stores lost following excessive synaptic Glu release. Thus, blocking synaptic import of Gln into synapses represents a novel therapeutic strategy to limit continued Glu release under conditions of excitotoxicity.

An in vitro assay in rat hippocampal neurons has been used to identify a novel neuronal activity-regulated Gln transport system and that is potently inhibited by the anti-glutamatergic drug riluzole. Riluzole can block excessive Glu release and can prevent neuronal damage that occurs in conditions of excessive presynaptic Glu release in many acute and chronic neurodegenerative diseases including Alzheimer's disease, global cerebral ischemia, traumatic brain injury, peri-operative neuronal and/or cardiac stress, epilepsy, and noise-induced hearing loss among others (Malgouris et al., 1989; Pratt et al., 1992; Bae et al., 2000; Ruel et al., 2005; Heurteaux et al., 2006; Hunsberger et al, 2015; Pereira et al., 2016; Verma et al., 2016). Riluzole can act on a wide range of molecular targets to inhibit synaptic Glu release including blocking $Na^+$ channels ($Na_V$) [Benoit and Escande, 1991; Herbert et al., 1994; Song et al., 1997; Stefani et al., 1997; Prakriya and Mennerik, 2000; Spadoni et al., 2002], stimulating $Ca^{2+}$-activated $K^+$ channels (Kv) [Grennet et al., 2001], and inhibiting N- and P/Q type $Ca^{2+}$ channels [Huang et al., 1997]. Riluzole may be most potent to inhibit activity-regulated Gln transport in neurons [1]. While riluzole has a broad activity, it is not very brain penetrant (Verma et al., 2016) and has reportedly caused recurrent acute pancreatitis (Falcao de Campos and de Carvalho, 2017).

Embodiments as described herein challenge the current research paradigms that neuronal Gln transporters SNAT1 and SNAT2 are involved in supplying Gln for glutamatergic transmission (Chaudhry et al., 2002; Mackenzie and Erickson, 2004; Conti and Melone, 2006). These Gln transporters are selectively inhibited by α-methylaminoisobutyric acid (MeAIB). Activity-induced modulation of synaptic efficacy and glutamatergic epileptiform activity are also significantly reduced by application of MeAIB [2]. SNAT1 and SNAT2 have been cloned and functionally identified. These two low affinity Gln/MeAIB transporters are excluded from axon terminals, suggesting that an unidentified neuronal Gln/MeAIB transporters expressed in excitatory synapses supports activity-regulated glutamatergic transmission.

Critical barriers to progress in understanding mechanisms involved in excessive Glu release from synapses and excitotoxicity in the brain are 1) the molecular identity of the neuronal activity-regulated Gln transporter in synapses is not known, 2) riluzole derivatives that preferentially block neuronal activity-regulated Gln transport over $Na^+$ or $Ca^{2+}$ channel blockade are not available, 3) lipophilic and more brain penetrant active riluzole derivatives are not available, and 4) the role of the neuronal activity-regulated Gln transporter in vitro or in vivo has not been determined.

Neuroprotective Compositions

The invention is directed to various neuroprotective compounds, for example those listed in Table 1. In some embodiments, the neuroprotective compound is formula (I):

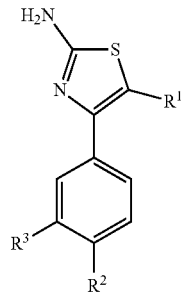

wherein $R^1$ is $CH_3$, H, Br, Cl, F, I, D, $NH_2$, $OCH_3$, $CH_2CH_3$, $CH_2CH_2CH_3$, $CF_3$, alkyl group, or alkoxy group; $R^2$ is H, $CH_3$, $CF_3$, Cl, F, $OCF_3$, Br, I, $NH_2$, $OCH_3$, $CH_2CH_3$, $CH_2CH_2CH_3$, alkyl group, alkoxy group, or $SCF_3$; and $R^3$ is H, benzene, pyridine, imidazole, pyrrole, pyrimidine, pyridine, pyridazine, pyrimidine, pyrazine, a quinolone, an isoquinoline or methyl-benzene; or a pharmaceutically acceptable salt thereof.

In some embodiments, $R^1$ is H, $R^2$ is C—$R^{2a}$ wherein $R^{2a}$ $F_3$, and $R^3$ is H. In some embodiments, $R^1$ is H, $R^2$ is C—$R^{2a}$ wherein $R^{2a}$ $H_3$, and $R^3$ is benzene. In some embodiments, $R^1$ is H, $R^2$ is H, and $R^3$ is methyl-benzene. In some embodiments, $R^1$ is Br, $R^2$ is H, and $R^3$ is benzene. In some embodiments, $R^1$ is $CH_3$, $R^2$ is C—$R^{2a}$ wherein $R^{2a}$ $H_3$, and $R^3$ is benzene. In other embodiments, the neuroprotective compound has a structure depicted in Table 1. All compounds listed herein were synthesized but are also commercially available by the provider indicated in parentheses ( ).

TABLE 1 shows SKA-41, and active (BOLD) and inactive derivatives:

| Compound Name | Structure | Molecular Weight (MW) | Amount (mg) | Max. Solubility (μM) |
|---|---|---|---|---|
| SKA-41 | 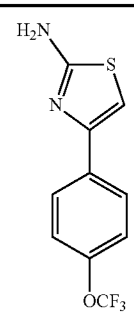 | 260.24 | 4.5 | 50 |

TABLE 1-continued shows SKA-41, and active (BOLD) and inactive derivatives:

| Compound Name | Structure | Molecular Weight (MW) | Amount (mg) | Max. Solubility (μM) |
| --- | --- | --- | --- | --- |
| SKA-75 CAS no. 56503-96-9 (Alfa Aesar) | 2-amino-4-(1-naphthyl)thiazole | 226.30 | 5.0 | 25 |
| SKA-76 CAS no. 21331-43-1 (Alfa Aesar) | 2-amino-4-(2-naphthyl)thiazole | 226.30 | 5.1 | 25 |
| SKA-77 CAS no. 77815-14-6 (Alfa Aesar) | 2-amino-4-(4-fluorophenyl)thiazole | 194.23 | 5.2 | 100 |
| SKA-78 CAS no. 2010-06-2 (Acros Organics) | 2-amino-4-phenylthiazole | 176.24 | 6.0 | 100 |
| SKA-79 CAS no. 2103-91-5 (Sigma-Aldrich) | 2-amino-4-(4-methylphenyl)thiazole | 190.26 | 5.9 | 100 |

TABLE 1-continued
shows SKA-41, and active (BOLD) and inactive derivatives:
| Compound Name | Structure | Molecular Weight (MW) | Amount (mg) | Max. Solubility (μM) |
| --- | --- | --- | --- | --- |
| SKA-80 CAS no. 2103-99-3 (Sigma-Aldrich) | 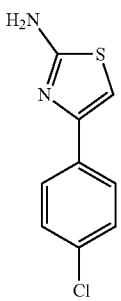 | 210.68 | 5.4 | 50 |
| SKA-82 CAS no. 30709-67-2 (Sigma-Aldrich) | 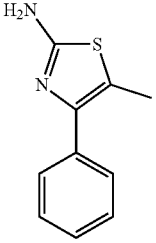 | 190.26 | 5.7 | 100 |
| SKA-88 CAS no. 1826-16-0 (Alfa Aesar) | 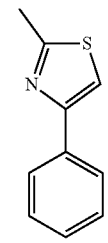 | 175.25 | 4.2 | 100 |
| SKA-89 CAS no. 19968-59-3 (Alfa Aesar) | 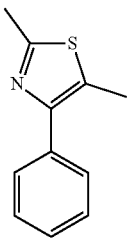 | 189.28 | 13.0 | 100 |
| SKA-94 CAS no. 28989-50-6 (Alfa Aesar) | 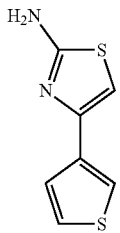 | 182.26 | 6.2 | 100 |

TABLE 1-continued shows SKA-41, and active (BOLD) and inactive derivatives:

| Compound Name | Structure | Molecular Weight (MW) | Amount (mg) | Max. Solubility (μM) |
|---|---|---|---|---|
| SKA-190 Active | 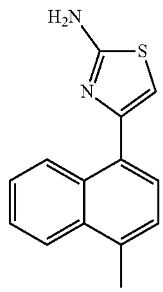 [SMILES: Cc1ccc(-c2csc(N)n2)c2ccccc12] | 240.32 | 4.4 | 50 |
| SKA-193 Active | 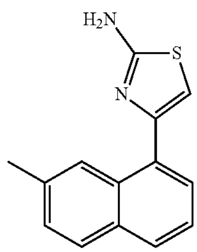 [SMILES: Cc1ccc2cccc(-c3csc(N)n3)c2c1] | 240.32 g/M | 3.7 | 50 |
| SKA-198 | 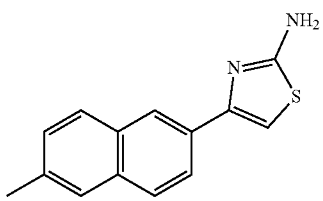 [SMILES: Cc1ccc2cc(-c3csc(N)n3)ccc2c1] | 240.32 | 4.8 | 50 |
| SKA-219 Active | 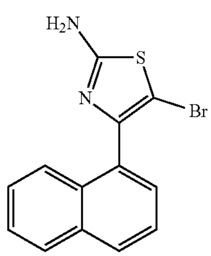 [SMILES: Nc1nc(-c2cccc3ccccc23)c(Br)s1] | 305.19 g/M | 3.8 | 25 |
| SKA-220 Active | 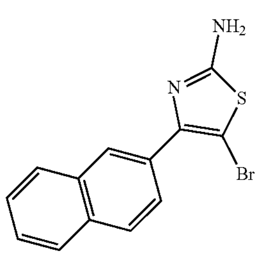 [SMILES: Nc1nc(-c2ccc3ccccc3c2)c(Br)s1] | 305.19 g/M | 3.4 | 25 |
| SKA-230 | 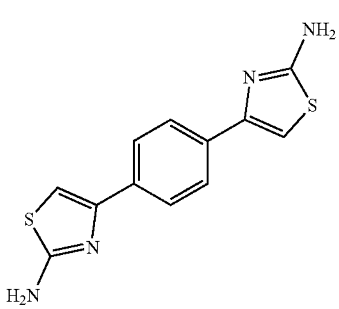 [SMILES: Nc1nc(-c2ccc(-c3csc(N)n3)cc2)cs1] | 274.36 | 3.1 | 50 |

TABLE 1-continued shows SKA-41, and active (BOLD) and inactive derivatives:

| Compound Name | Structure | Molecular Weight (MW) | Amount (mg) | Max. Solubility (μM) |
| --- | --- | --- | --- | --- |
| SKA-232 CAS no. 2834-79-9 (Sigma-Aldrich) | 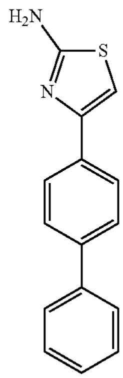 [SMILES: Nc1nc(-c2ccc(-c3ccccc3)cc2)cs1] | 252.34 | 5.4 | 50 |
| SKA-247 Active | 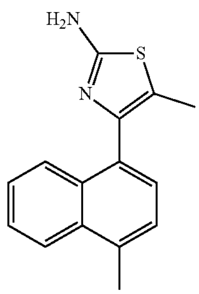 [SMILES: Cc1sc(N)nc1-c1ccc(C)c2ccccc12] | 254.35 g/M | 3.0 | 50 |
| SKA-251 | 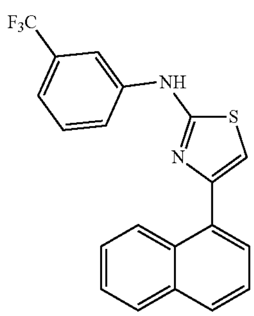 [SMILES: FC(F)(F)c1cccc(Nc2nc(-c3cccc4ccccc34)cs2)c1] | 370.39 | 3.1 | 10 |
| SKA-255 CAS no. 438233-93-3 (Oakwood Chemical) | 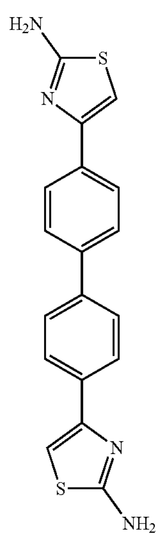 [SMILES: Nc1nc(-c2ccc(-c3ccc(-c4csc(N)n4)cc3)cc2)cs1] | 350.46 | 5.1 | 10 |

TABLE 1-continued shows SKA-41, and active (BOLD) and inactive derivatives:

| Compound Name | Structure | Molecular Weight (MW) | Amount (mg) | Max. Solubility (μM) |
| --- | --- | --- | --- | --- |
| SKA-257 | 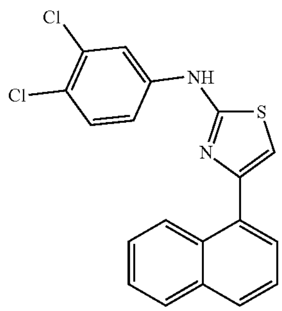 [SMILES: Clc1ccc(Nc2nc(-c3cccc4ccccc34)cs2)cc1Cl] | 371.28 | 4.4 | 10 |
| SKA-258 | 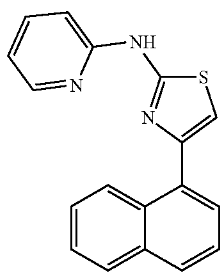 [SMILES: c1ccc(Nc2nc(-c3cccc4ccccc34)cs2)nc1] | 303.38 | 5.1 | 10 |
| SKA-260 | 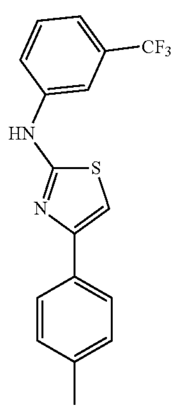 [SMILES: Cc1ccc(-c2csc(Nc3cccc(C(F)(F)F)c3)n2)cc1] | 334.36 | 5.8 | 10 |
| SKA-265 | 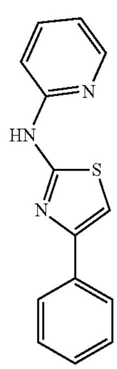 [SMILES: c1ccc(-c2csc(Nc3ccccn3)n2)cc1] | 253.32 | 4.2 | 50 |

TABLE 1-continued
shows SKA-41, and active (BOLD) and inactive derivatives:
| Compound Name | Structure | Molecular Weight (MW) | Amount (mg) | Max. Solubility (μM) |
| --- | --- | --- | --- | --- |
| SKA-268 | 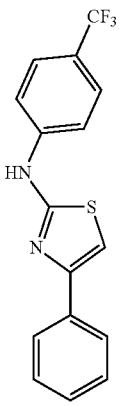 [SMILES: FC(F)(F)c1ccc(Nc2nc(-c3ccccc3)cs2)cc1] | 320.33 | 5.4 | 10 |
| SKA-269 | 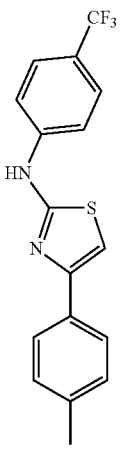 [SMILES: Cc1ccc(-c2csc(Nc3ccc(C(F)(F)F)cc3)n2)cc1] | 334.36 | 4.1 | 10 |
| SKA-292 | 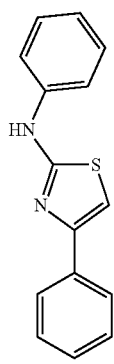 | 252.34 | 6.1 | 25 |
| SKA-41 Active CAS no. 436151-95-0 (Oakwood Chemical) | 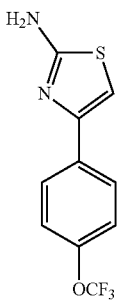 | 260.24 | | |

In some embodiments, the neuroprotective compound is formula (II):

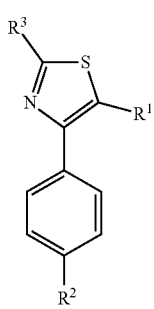

wherein $R^1$ is $CH_3$, H, Br, Cl, F, I, D, $NH_2$, $OCH_3$, $CH_2CH_3$, $CH_2CH_2CH_3$, alkyl group, alkoxy group or $CF_3$; $R^2$ is H, $CH_3$ $CF_3$, Cl, F, Br, I, $OCF_3$, pyridine, imidazole, pyrrole, pyrimidine, pyridine, pyridazine, pyrimidine, pyrazine, a quinolone, an isoquinoline or $SCF_3$; and $R^3$ is $NH_2$, $C_6H_6N$, $C_7H_5F_3N$, $C_5H_5N_2$, or $C_6H_4Cl_2N$; or a pharmaceutically acceptable salt thereof. In some embodiments, $R^1$ is Cl, $R^2$ is $OCF_3$, and $R^3$ is $NH_2$.

In some embodiments, the neuroprotective compound is formula (III):

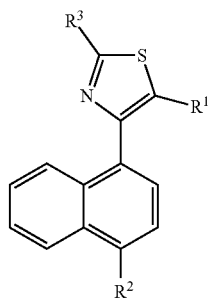

wherein $R^1$ is $CH_3$, H, Br, Cl, F, I, D, $NH_2$, $OCH_3$, $CH_2CH_3$, $CH_2CH_2CH_3$, alkyl group, alkoxy group, or $CF_3$; $R^2$ is H, $CH_3$ $CF_3$, Cl, F, Br, I, $OCF_3$, pyridine, imidazole, pyrrole, pyrimidine, pyridine, pyridazine, pyrimidine, pyrazine, a quinolone, an isoquinoline or $SCF_3$; and $R^3$ is $NH_2$, $C_6H_6N$, $C_7H_5F_3N$, $C_5H_5N_2$, or $C_6H_4Cl_2N$; or a pharmaceutically acceptable salt thereof. In some embodiments, $R^1$ is Cl, $R^2$ is $CH_3$, and $R^3$ is $NH_2$. In some embodiments, $R^1$ is F, $R^2$ is $CH_3$, and $R^3$ is $NH_2$. In some embodiments, $R^1$ is Cl, $R^2$ is H, and $R^3$ is $NH_2$. In some embodiments, $R^1$ is F, $R^2$ is H, and $R^3$ is $NH_2$.

In some embodiments, the neuroprotective compound is formula (IV):

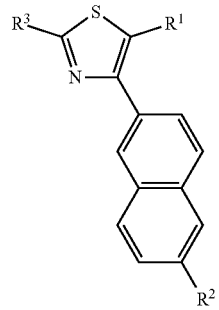

wherein $R^1$ is $CH_3$, H, Br, Cl, F, I, D, $NH_2$, $OCH_3$, $CH_2CH_3$, $CH_2CH_2CH_3$, alkyl group, alkoxy group, or $CF_3$; $R^2$ is H, $CH_3$ $CF_3$, Cl, F, Br, I, $OCF_3$, pyridine, imidazole, pyrrole, pyrimidine, pyridine, pyridazine, pyrimidine, pyrazine, a quinolone, an isoquinoline, or $SCF_3$; and $R^3$ is $NH_2$, $C_6H_6N$, $C_7H_5F_3N$, $C_5H_5N_2$, $C_6H_4Cl_2N$; or a pharmaceutically acceptable salt thereof; and $R^3$ is $NH_2$, $C_6H_6N$, $C_7H_5F_3N$, $C_5H_5N_2$, or $C_6H_4Cl_2N$. In some embodiments, $R^1$ is Cl, $R^2$ is H, and $R^3$ is $NH_2$. In some embodiments, $R^1$ is F, $R^2$ is H, and $R^3$ is $NH_2$.

In some embodiments, the neuroprotective compound is formula (V):

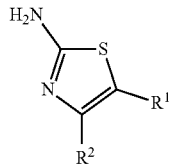

wherein $R^1$ is $CH_3$, H, Br, Cl, F, I, D, $NH_2$, $OCH_3$, $CH_2CH_3$, $CH_2CH_2CH_3$, alkyl group, alkoxy group, or $CF_3$ and $R^2$ is a quinolone, an isoquinolone, a cyclic group, or a polycyclic system. In some embodiments the cyclic group or polycyclic system contains heteroatoms. In some embodiments, the heteroatoms comprise oxygen (O), nitrogen (N), and sulfur (S).

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, and Gould, P. L., *Int. J. Pharmaceutics* 1986, 33, 201-217; the contents of each are hereby incorporated by reference.

In some embodiments, a pharmaceutically acceptable salt of a compound of formula (I) is an acid addition salt, for example a hydrohalide (such as hydrochloride or hydrobromide), sulfate, or phosphate salt. In some embodiments, a pharmaceutically acceptable salt of a compound of formula (I) is a hydrochloride salt. In some embodiments, a pharmaceutically acceptable salt of a compound of formula (I) is a base addition salt, for example a sodium, potassium, calcium, or ammonium salt. In some embodiments, the base addition salt is a tetrafluoroboro salt.

In embodiments, the neuroprotective compound comprises SKA-41, SKA-41(a), SKA-75, SKA-76, SKA-77, SKA-78, SKA-79, SKA-80, SKA-82, SKA-88, SKA-89, SKA-94, SKA-190, SKA-193, SKA-198, SKA-219, SKA-220, SKA-230, SKA-232, SKA-247, SKA-251, SKA-255, SKA-257, SKA-258, SKA-260, SKA-265, SKA-268, SKA-269, SKA-292 SKA-375, SKA-376, SKA-377, SKA-378, SKA-379, SKA-380, SKA-381, SKA-382, SKA-383, SKA-384, SKA-385, SKA-386, SKA-387, SKA-388.

The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

The compound or composition comprising the compound can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. It can also be administered once or twice daily to a subject for a period of years or until the death of the subject, such as can be the case for a subject suffering from a chronic neurodegenerative disorder.

Compounds can be incorporated into pharmaceutical compositions suitable for administration. Such compositions can comprise a compound and a pharmaceutically acceptable carrier. Thus, in some embodiments, the compounds of the invention are present in a pharmaceutical composition.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Non-limiting examples of pharmaceutically acceptable carriers comprise solid or liquid fillers, diluents, and encapsulating substances, including but not limited to lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat or human. In some embodiments, the subject is a mouse. In some embodiments, the subject is a rat. In some embodiments, the subject is a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For example, the parenteral preparation can be intraosseous infusion (IO). For example, the intraosseous infusion is performed with an intraosseous infusion gun.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™

(BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Neurodegenerative Diseases

The term "treating" can refer to partially or completely alleviating, ameliorating, improving, relieving, delaying onset of, inhibiting progression of, reducing severity of, and/or reducing incidence of one or more symptoms, features, or clinical manifestations of a particular disease, disorder, and/or condition. Treatment can be administered to a subject who does not exhibit signs of a disease, disorder, and/or condition (e.g., prior to an identifiable disease, disorder, and/or condition), and/or to a subject who exhibits only early signs of a disease, disorder, and/or condition for the purpose of decreasing the risk of developing pathology associated with the disease, disorder, and/or condition.

The term "subject" or "patient" can refer to any organism to which aspects of the invention can be administered, e.g., for experimental, diagnostic, prophylactic, and/or therapeutic purposes. Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

As used herein, "changed as compared to a control" sample or subject is understood as having a level of an analyte or diagnostic or therapeutic indicator (e.g., marker) to be detected at a level that is statistically different than a sample from a normal, untreated, or abnormal state control sample. The diagnostic or therapeutic indicator can be a behavioral or neurological symptoms, such as cognitive impairment, movement, or coordination. Determination of statistical significance is within the ability of those skilled in the art, e.g., the number of standard deviations from the mean that constitute a positive or negative result.

Kits

Neuroprotective compounds as described herein can also be provided in a kit. In one embodiment, the kit includes (a) a container that contains a composition that includes a composition as described herein, and optionally (b) informational material. The informational material can be descriptive, instructional, marketing or other material that relates to the methods described herein and/or the use of the compound for therapeutic benefit. In an embodiment, the kit includes also includes a second agent for treating a neurodegenerative disease or condition. For example, the kit includes a first container that contains a composition that includes a compound as described herein, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the compound, e.g., in a suitable dose, dosage form, or mode of administration (e.g., a dose, dosage form, or mode of administration described herein), to treat a subject who has a neurodegenerative disorder. The information can be provided in a variety of formats, include printed text, computer readable material, video recording, or audio recording, or an information that provides a link or address to substantive material.

In addition to a neuroprotective compound as described herein, the composition in the kit can include other ingredients, such as a solvent or buffer, a stabilizer, or a preservative. The compound can be provided in any form, e.g., liquid, dried or lyophilized form, preferably substantially pure and/or sterile. When the compounds are provided in a liquid solution, the liquid solution preferably is an aqueous solution. When the compounds are provided as a dried form, reconstitution generally is by the addition of a suitable solvent. The solvent, e.g., sterile water or buffer, can optionally be provided in the kit.

The kit can include one or more containers for the composition or compositions containing the neuroprotective compounds. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the compounds. The containers can include a combination unit dosage, e.g., a unit that includes both the neuroprotective compound and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight. The kit optionally includes a device suitable for administration of the composition, e.g., a syringe or other suitable delivery device. The device can be provided pre-loaded with one or both of the agents or can be empty, but suitable for loading.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Our results suggest a central role for an activity-regulated, neuronal Gln transporter in excitatory axon terminals that supports continued release of Glu under excitotoxic conditions. Targeting this Gln/MeAIB transporter in synapses provides a potential novel therapeutic preventative strategy to prevent excessive Glu release, protect vulnerable neurons, and prevent neurologic and cognitive dysfunction in patients who are at risk for global cerebral ischemia.

Global cerebral ischemia is frequently encountered in cardiac arrest, profound hypotension, or during vascular occlusion in the course of peri-operative neuro/cardiac surgical procedures [3]. Patents surviving such episodes of cerebral ischemia often show neurobehavioral deficits and neuronal necrosis in vulnerable brain regions. The region most vulnerable to global cerebral ischemia in both animals and humans is the CA1 pyramidal layer of the hippocampus [3-5]. We have recently discovered a neuronal activity-regulated, $K^+$ depolarization-stimulated, $Ca^{2+}$-dependent, high-affinity Gln transport system in hippocampal neurons that is potently inhibited by the anti-glutamatergic compound riluzole [1] and by riluzole derivatives SKA-41, SKA-190, SKA-193, SKA-219 and SKA-247. Described herein is an approach to molecularly identify a new target for riluzole, which is a drug that can prevent global cerebral ischemia-induced damage to CA1 neurons in vivo [6-14]. Riluzole is safe and has very few side effects and currently is in phase II clinical trials for mild AD [15]. Our discovery of neuronal activity-regulated Gln/MeAIB transport has important implications in advancing basic understanding of the neurobiology of excessive synaptic release of Glu, Glu/Gln cycling between neurons and glia, and Glu-induced neuronal excitotoxicity [15-20].

The scientific premise is that Gln is considered to be the preferred precursor for neurotransmitter Glu synthesis and must be imported into axon terminals from glia where it is synthesized [21-26]. While this 'so called' Glu/Gln cycle is an accepted model of neurotransmitter Glu recycling, the neuronal Gln transporter that mediates Gln transport for excitatory transmission has not been identified. A critical barrier to progress in this field has been the lack of direct functional evidence for activity-regulated and $Ca^{2+}$-dependent Gln transport activity in hippocampal neurons, until now.

Described herein is an activity-regulated Gln/MeAIB transporter that displays relative high affinity ($K_m$=30 μM) and operates maximally ($V_{max}$ at 200 μM) following $Ca^{2+}$-dependent exocytosis of this transporter to the plasma membrane that contributes to sustained excessive synaptic Glu release.

We have developed new compounds such as the riluzole-derivative SKA-41 and SKA-41 derivatives that are also potent inhibitors of activity-regulated Gln/MeAIB transport, but display reduced inhibition of $Na^+$ channels (i.e., Nav), and are more brain penetrant and selective, compared to riluzole.

Without wishing to be bound by theory, SKA-41 and SKA-41 derivatives can prevent neuronal CA1 damage and cognitive impairment resulting from global cerebral ischemia.

Statistical methods, sample sizes and power analysis: For in vitro work, two-tailed Student's t-tests are used and values are presented as means±SEM. All values are obtained from n>3 independent cultures. A value of p<0.05 is regarded as statistically significant. For in vivo work, rats are randomly allocated to groups, and data acquisition and analysis performed in a blinded manner. Repeated measures analysis of variance (ANOVA), followed by Bonferroni procedures to correct for multiple comparisons, are used for intergroup comparisons. Post-hoc comparisons between means are conducted using Tukey's tests with alpha level adjustment done by a method of simulation based on the number of planned comparisons. Differences are considered significant at an alpha level of 0.05. Power analyses of previous work suggests that 10-12 animals/group will be required to achieve a power of 0.85-0.90 in experiments involving neurological/behavioral scores, lesion areas and cell numbers as outcomes. Our extensive experience with analyses of these types suggests that all of these outcome variables may be dealt with under the assumption of asymptotic normality where sample sizes are adequate.

Figure 3:
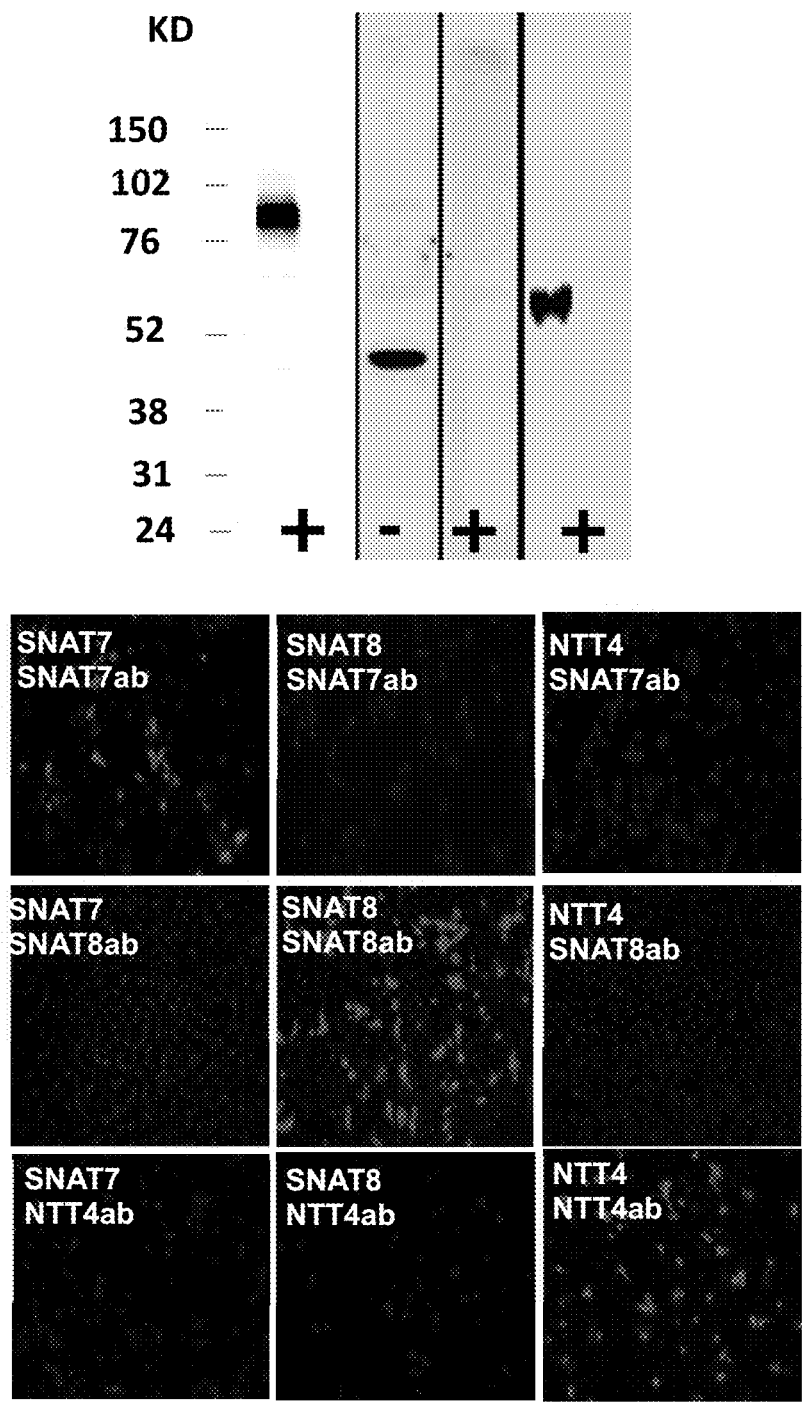
FIG. 3 shows (top panel) antibodies against NTT4 (left, 1:2000), SNAT8 (middle, 2 µg/ml), and SNAT7 (right, 2 µg/ml) recognize single mono-specific immunoreactive bands in hippocampal postnuclear extracts that can be blocked by adsorption with antigen used to produce the antibody (+). Bottom panel, CV-1 fibroblasts were transfected with SNAT7, SNAT8 or NTT4 (columns) and then immunocytochemistry was performed using antibodies (ab) against SNAT7 (upper), SNAT8 (middle), or NTT4 (lower). DAPI nuclear staining (blue).
Figure 4:
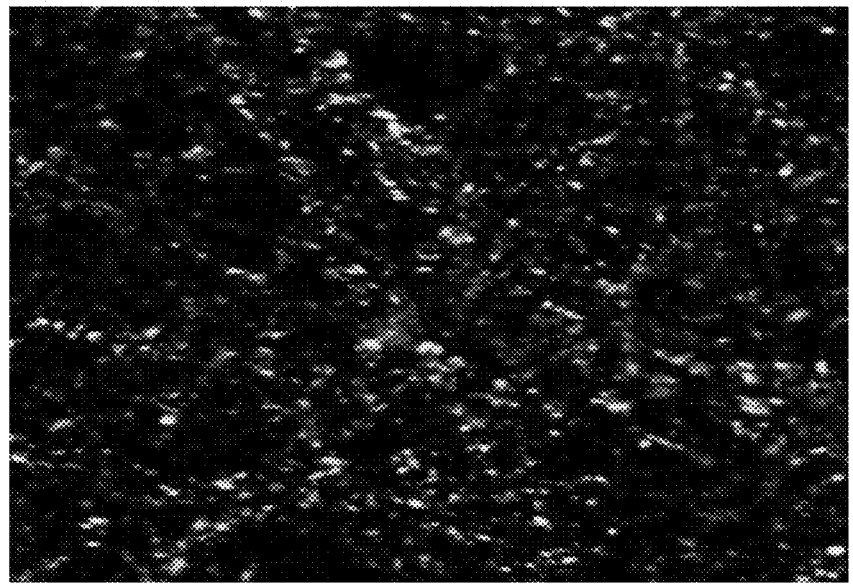
FIG. 4 shows SNAT8 is expressed in synapses. Hippocampal cultures (DIV16) stained with antibodies against VGLUT1 (red) and SNAT8 (green). Note numerous yellow puncta indicating that SNAT8 is present in VGLUT1-encoded synapses.
Figure 5:
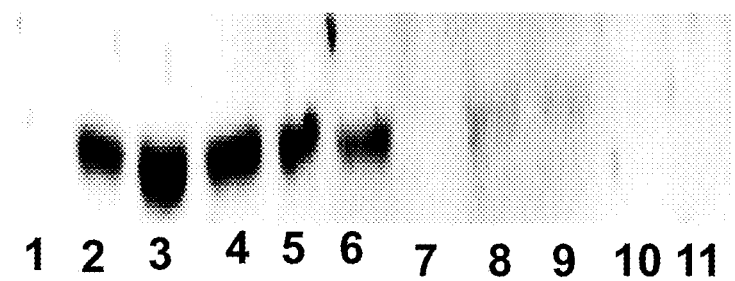
FIG. 5 shows protein distribution in synaptosome-enriched fractions from rat brain regions, specifically SNAT8 is enriched in rat forebrain regions. 30 µg protein from olfactory bulb (1), cortex (2), hippocampus (3), striatum (4), thalamus (5), hypothalamus (6), pituitary (7), cerebellum (8), medulla/pons (9), spinal cord (10), and liver (111).

We have validated antibodies that we have made and have confirmed that the transporter cDNA clones express proteins of correct size and are recognized by our selective antibodies. Described herein are polyclonal antibodies specific for SNAT1, SNAT2, SNAT7, SNAT8, and NTT4. SDS page analysis of hippocampal total extracts from adult rat brain reveal prominent bands of 55 Kd, 45 Kd and 75 Kd for SNAT7, SNAT8 and NTT4, respectively, which are blocked by the peptide or fusion protein (10 µM) used as the immunogen (FIG. 3). We have also isolated cDNA clones for these five transporters that have been sequenced verified and express protein recognized by our antibodies (FIG. 3). SNAT8 is also expressed in synapses (FIG. 4) and enriched in hippocampal synaptosomes (FIG. 5).

We have recently discovered an activity-regulated Gln/MeAIB transporter in hippocampal neuron in culture and its functional characteristics have been described [1]. This high-affinity and $Ca^{2+}$-regulated 'system A' glutamine transport system in hippocampal that is dependent on neural activity in mature synapses is upregulated during the critical postnatal period of functional maturation of the Glu/Gln cycle between astrocytes and neurons and synaptic Glu release. This novel Gln transport system may have physiological and pathological implications in understanding the neurobiology of excitotoxic synaptic Glu release in many acute and chronic neurodegenerative disorders.

Furthermore, this novel transport system is potently inhibited by riluzole, an anti-glutamatergic agent that is known to block Glu release from synapses. Riluzole is also the only FDA approved drug to treat amyotrophic lateral sclerosis (ALS). When given prophylactically riluzole can prevent hippocampal neuronal damage in the CA1 pyramidal neurons (the most vulnerable region) following global cerebral ischemia. Riluzole is also an anti-convulsant agent and is currently in clinical trials for patients with mild Alzheimer's disease.

Riluzole may act on a wide range of molecular targets to inhibit synaptic Glu release: riluzole inhibits $Na_V$ channels ($IC_{50S}$~1-500 µM) [27-32], activates small-conductance $Ca^{2+}$-activated $K^+$ channels ($EC_{50S}$~10-200 µM) [33], inhibits delayed-rectifier $K^+$ channels and activates two-pore $K^+$ channels (30 to 100 µM) [34], blocks N- and P/Q-type $Ca^{2+}$-channels ($IC_{50}$>40 µM) [35]. Riluzole, with its broad activity, may be most potent to inhibit activity regulated Gln/MeAIB transport ($IC_{50}$=1 µM) [1]. SKA41 and several active SKA41 derivatives are nearly equally potent as riluzole in vitro ($IC_{50}$~2 µM) but may be more selective, brain penetrant, and therefore more potent in vivo, and useful to support the notion that SNAT8 is involved in excitotoxic Glu release.

Figure 2:
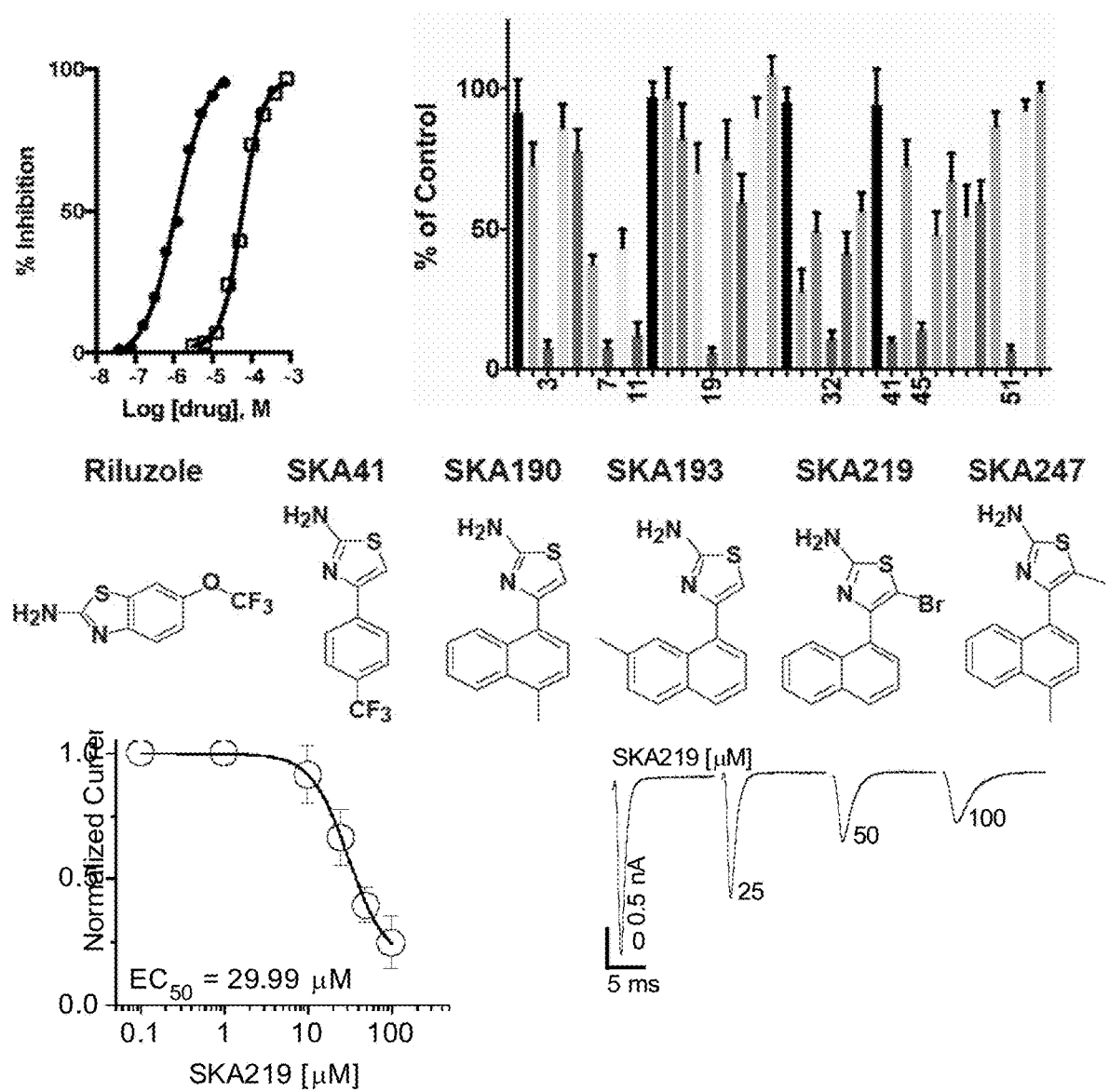
FIG. 2 shows the chemical structures and pharmacological properties of SKA-41 and four active SKA-41 derivatives on activity-regulated Gln/MeAIB transport and $Na_V$ currents. Top left, Riluzole (bold circles) is 50× more potent than phenytoin (clear squares) to inhibit activity-regulated Gln/MeAIB transport. Top right, Select riluzole derivatives retain potency to inhibit activity-regulated Gln/MeAIB transport (n=3). Middle, Chemical structures of SKA-41 and SKA-41 derivatives are distinct from riluzole. SKA-190, SKA-193, SKA-219, SKA-220 and SKA-247 are distinct from riluzole. Bottom left, SKA-219 is >10× less potent to inhibit $Na^+$ channel $Na_V1.2$ than to inhibit activity-regulated Gln/MeAIB transport (n=12). Bottom right, Sample traces showing concentration-dependent inhibition of $Na_V$ currents by SKA-219. Cells were held at −80 mV and current elicited by a 0 mV depolarization stepped from a −120 mV conditioning pulse at 0.1 Hz.

Riluzole's short half-life, limited brain penetration, sedative effects at high concentration, and recent studies reporting pancreatitis and respiratory symptoms poses limitations to its use as a therapeutic agent. It is therefore possible that derivatives of riluzole that are more selective against one target and more brain penetrant can be developed. Initially, 36 chemical derivatives of riluzole have been tested to determine if any are potent inhibitors of activity-regulated glutamine transport, and active compounds have been identified to be potent blockers of activity-regulated glutamine transport (FIG. 2). For example, see chemical derivatives of riluzole in Sankaranarayanan, Ananthakrishnan, et al. Molecular pharmacology 75.2 (2009): 281-295, the entirety of which is incorporated herein by reference. Several of these active compounds have previously been shown to block $Na_V$ channels while others are active at both $Na_V$ and KCa channels. SKA-41 was the only structurally unique compound that inhibited activity-regulated Gln transport. SKA-41 has no effect on KCa channels (see Sankaranarayanan A, et al. Mol Pharmacol. 2009 February; 75(2):281-95, the entire contents of which are incorporated herein by reference in its entirety).

We identified SKA-41 as a potent blocker of Gln transport (FIG. 2) and which is unlikely to interact with $Na_V$ or KCa channels. Twenty eight derivatives of SKA-41 have been synthesized and tested, and some of these compounds (for example, SKA-190, SKA-193, SKA-219, SKA-220 and SKA-247) were found to be nearly as potent as riluzole to inhibit activity regulated Gln/MeAIB transport in hippocampal neurons in vitro.

The identification of an activity-regulated, $Ca^i$-dependent, high-affinity Gln transport system in hippocampal neurons that is up-regulated during the critical period of the development of presynaptic excitatory strength and is potently inhibited by riluzole has important ramifications in the neurobiology of activity-stimulated presynaptic Glu release, the Glu/Gln cycle between astrocytes and neurons, and neuronal Glu-induced excitotoxicity in the brain.

Excessive and sustained presynaptic release of Glu is an initial event that triggers $Ca^{2+}$-dependent cell death in post-synaptic neurons in various conditions including traumatic brain injury, peri-operative neuronal and cardiac stress, epilepsy, global and focal ischemic stroke, mild Alzheimer's disease, noise-induced hearing loss, and others. Riluzole is neuroprotective in all of these conditions.

More selective riluzole derivatives may have better translational value. Without wishing to be bound by theory, pre-treatment with SKA-41 and any active SKA-41 derivatives will prevent hippocampal neuronal damage in the CA1 area following global cerebral ischemia. Brain and tissue contents of all the drugs will be measured, and compared to that of riluzole, to assess whether higher brain concentrations can be attained with more lipophilic compounds.

SKA-41 is as potent as riluzole to block activity-regulated glutamine transport but is more lipophilic, which would improve brain penetration and brain retention. SKA-41 and SKA-41 derivatives may also be more selective than riluzole to directly inhibit activity-regulated glutamine transport, and not interact with ion channels such as $Na_V$ or KCa channels.

Safety and toxicity studies will be performed, and neuroprotection in vivo will be demonstrated.

Example 2

Our objectives are to molecularly identify this neuronal activity-regulated Gln transporter and show that it represents a new therapeutic target to prevent Glu-induced excitotoxicity in conditions of excessive presynaptic Glu release. Without being bound by theory, SCHEME A) selective knock down of SNAT8 will reduce activity-regulated Gln/MeAIB transport in vitro, SCHEME B) SKA-41, and select SKA-41 derivatives, are potent and select inhibitors of the neuronal activity-regulated Gln transporter in vitro, and are more brain penetrant than riluzole in vivo, SCHEME C) selective knock down of SNAT8 expression in vivo is neuroprotective against Glu-induced excitotoxicity, and SCHEME D) administration of SKA-41 (and select derivatives) in vivo and in vitro is neuroprotective against Glu-induced excitotoxicity.

SCHEME A: Activity-regulated, $Ca^{2+}$-dependent Gln/MeAIB transport in hippocampal neurons is mediated by the Slc38 gene family member SNAT8 and is selectively blocked by select riluzole-derivatives.

We will molecularly identify the activity-regulated Gln/MeAIB transporter by selective lentiviruses expressing shRNA against Gln transporters SNAT1, SNAT2, SNAT7, SNAT8, NTT4, or with a scrambled shRNA, and neuronal activity-regulated $^{14}$C-MeAIB transport will be measured. Rescue experiments will utilize shRNA-resistant cDNAs.

We will determine the potency of SKA-41 and active SKA-41 derivatives (SKA-190, SKA-193, SKA-219, SKA-220 and SKA-247) to block neuronal activity-regulated Gln/MeAIB transport and whether they interact with Na$^+$ (Na$_V$) or Ca$^{2+}$-activated (KCa) channels electrophysiologically.

We use low concentrations of $^{14}$C-MeAIB as substrate to characterize this Gln transporter to limit the involvement of known neuronal Gln/MeAIB transporters SNAT1 or SNAT2, which display low affinity for MeAIB (>0.5 mM) and are not expressed in synapses. The neuronal activity-regulated Gln/MeAIB transport system discovered here displays high affinity (K$_m$=30+/−4 μM) for MeAIB [46].

To molecularly identify the activity regulated Gln/MeAIB transporter lentiviruses expressing shRNA against SNAT1, SNAT2, SNAT7, SNAT8, NTT4, or scrambled shRNA sequences are generated to knockdown transporter expression in cultures of hippocampal neurons. Neurons will be infected at DIV8 and Ca$^{2+}$-dependent, high-affinity [$^{14}$C]-MeAIB transport will be performed 10 days later. Knockdown of specific transporter proteins will be confirmed by Western blot.

Lentiviruses expressing shRNA-resistant cDNAs for any Slc transporter identified that inhibits transport will be generated to rescue activity-regulated Gln/MeAIB transport. The CMV-EGFP reporter cassette that is included in the vector will be excised and replaced with shRNA-resistant transporter (+/−EGFP-tagged) for rescue experiments. Cultures will be infected at DIV8 and Ca$^{2+}$-dependent, high-affinity $^{14}$C-MeAIB transport will be performed 10 days later. Transporter protein expression will be examined by Western blot.

Lentivirus-mediated gene delivery of shRNA is an effective way to selectively knockdown gene products in vitro. This synaptic Gln/MeAIB transporter may represent a novel therapeutic target for numerous disorders of excessive synaptic Glu release in the CNS. Identifying novel selective blockers of activity regulated Gln/MeAIB transport mediated by SNAT8 may have therapeutic value.

SCHEME B: SKA-41, and select SKA-41 derivatives (for example, SKA-190, SKA-193, SKA-219, SKA-220 and SKA-247) are potent and select inhibitors of the neuronal activity-regulated Gln transport in vitro.

Riluzole potently inhibits activity-regulated Gln/MeAIB transport (IC$_{50}$=1.3+/−0.1 μM, n=4), compared to phenytoin (IC$_{50}$=57+/−4 μM, n=3), a well-established Na$_V$ blocker (FIG. 2); most other anti-epileptic drugs (20 μM) are inactive (n=3). We tested 36 riluzole derivatives to determine the structure/activity relationship of these compounds to block neuronal activity-regulated Gln/MeAIB transport and found 7 active compounds (FIG. 2). However, SKA-41 was the only structurally unique compound. We next tested 28 chemical derivatives of SKA-41. SKA-190, SKA-193, SKA-219, SKA-219 and SKA-247 block 90% of transport activity at 10 μM (n=2), similarly to SKA-41 and riluzole. SKA-75, SKA-76 and SKA-198 displayed >50% inhibition of activity-regulated Gln/MeAIB transport when present at 10 μM. The IC$_{50}$ values to inhibit activity regulated Gln/MeAIB transport for SKA-219 and SKA-247 are ~2 μM The IC$_{50}$ value for SKA-219 to inhibit Na$_V$1.2, the major neuronal Na$^+$ channel, is 30 μM (FIG. 2, bottom), demonstrating >10-fold selectivity over Na$_V$ channels. Na$_V$ currents were recorded from N1E-115 neuroblastoma cells expressing Na$_V$1.2 (n=12).

We will further characterize the ability of the novel riluzole-derivative SKA-41 and four active SKA-41 derivatives SKA-190, SKA-193, SKA-219, SKA-220 and SKA-247 to inhibit neuronal activity-regulated [$^{14}$C]-MeAIB (20 μM) transport. We will assess if these compounds reduce both spontaneous and K$^+$-stimulated transport. We will generate dose-response inhibition curves. We will determine whether the active blockers act competitively or non-competitively with the transport system identified here.

We will assess if SKA-41, and these five active SKA-41 derivatives interact with Na$_V$ or K$_V$-operated channels in vitro. Cells transiently (or stably) expressing voltage-gated Na$^+$ or K$^+$ channels will be subjected to electrophysiological recording using the whole-cell patch-clamp technique. We will use HEK-293 cell lines stably expressing hNa$_V$1.1, hNa$_V$1.5, hNa$_V$1/7, hNa$_V$1.4, and hK$_V$2.1. We will use neuroblastoma N1E-115 cells that stably express Na$_V$1.2. All cells will be voltage clamped to a holding potential of −90 mV, otherwise specified if held at −120 mV in the case of Na$_V$1.2 use-dependence recording. Na$^+$ currents will be elicited by 30-ms pulse to 0 mV from −90 mV applied every 10 s. K$_V$2.1 currents will be elicited by 200-ms voltage steps from −90 to 40 mV applied every 10 s.

SCHEME C: Knockdown of SNAT8 Gln/MeAIB neuronal transporter in the hippocampus in vivo will reduce CA1 neuronal loss seen following global cerebral ischemia in adult rats. Wistar rats (3-4 months) of both sexes are used. Animals are anesthetized with 3% isoflurane in a mixture of 70% nitrous oxide and 30% oxygen and placed in a stereotaxic frame. Lentivirus (SNAT8 shRNA, scrambled shRNA) or saline is injected (2 μl at 0.2 μl/min) in two positions on each side of the rat hippocampus (site 1: AP=−3.1, ML=+/−1.4, DV=−3.8; site 2: AP=−4.4, ML=+/−3.3, DV=−3.3). SNAT8 knockdown, against other control SNATs, is assessed at 4, 6, and 8 weeks after injection to achieve maximal effect and to achieve steady-state levels. Confirmation of SNAT8 knockdown is verified by Western blots of hippocampal synaptosomes and immunohistochemistry 4 weeks after injection.

In other rats we inject lentivirus expressing SNAT8 shRNA, scrambled shRNA) or saline controls as above but then after 4-8 weeks they are subjected to global cerebral ischemia. Rats are anesthetized and physiological monitoring (rectal and cranial temperatures, blood gases, blood pressure and plasma glucose) is conducted during and after ischemia. [36]. These animals also undergo bCCAo (10 min) with simultaneous reduction of mean arterial pressure to 50 mmHg by withdrawal of arterial blood from a femoral artery [37, 38]. Because hypothermia is neuroprotective body and head temperature are maintained at 37° C. with rectal and cranial thermistors and a heating lamp and mat during ischemic insult.

Cognitive function (Y-maze) is evaluated on weeks 1, 2, 3 and 4 after ischemia, [39, 40]. All animals are pre-trained before ischemia. In the Y-maze the number of entries, spontaneous alteration and % of alteration are recorded [41]. After completion of the behavioral tests, animals are perfused and the number of histologically normal appearing CA1 neurons in a 0.4-mm segment of the medial, middle, and lateral parts of the hippocampus are counted. NeuN fluorescence is also performed to confirm numbers of NeuN$^+$ neurons in the CA1 region. Viral-mediated GFP expression levels are assessed by IHC to assure high-levels of lentiviral GFP expression.

Without being bound by theory, reducing SNAT8 expression in the hippocampus by lentivirus-mediated delivery of specific shRNA will reduce neuronal damage in the CA1 region and improve hippocampal-dependent cognitive function following global cerebral ischemia.

SCHEME D: Administration of SKA-41 and active SKA-41 derivatives will reduce hippocampal CA1 neuronal damage induced by global cerebral ischemia in vivo and in vitro.

SKA-41 and SKA-41 derivatives is administered to male and female rats (10 mg/kg) to determine basic pharmacokinetic (PK) parameters such as half-life ($t_{1/2}$), volume of distribution (Va.) and brain penetration. A standard dose of riluzole (10 mg/kg) is given to a separate group of rats for comparison. Drugs are first administered intravenously in a vehicle consisting of Miglyol 812 neutral oil (1 μl/g body weight) and then blood samples (~100 μL) collected at 5, 10, and 20 min, and 1, 2, 4, 12 and 24 h and plasma concentrations determined by HPLC/MS. The data are used to determine $V_d$ and $t_{1/2}$. After a washout period of 10 days (which for a small molecule drug is sufficient to eliminate the compound from the body) rats then receive 10 mg/kg of the compounds intraperitoneally (ip) in Migyol 812 (1 μl/g body weight) and blood samples collected and plasma concentrations analyzed as above. After another washout period, rats again receive 10 mg/kg and after 2 h and samples taken from blood, brain, liver, spleen, heart and subcutaneous fat for analysis Another group of rats each receive oral doses of 10 mg/kg and blood samples collected and analyzed as above.

Riluzole, SKA-41 and active SKA-derivatives (SKA-190, SKA-193, SKA-219, SKA-220 and SKA-247) are administered at 10, 5, 2.5 and 1 mg/kg to rats 15 min before and 4 hr after bCCAo. Animals will also receive these compounds at the same dose twice daily thereafter. Vehicle groups receive only the solvent (Miglyol 812 neutral oil).

Figure 8:
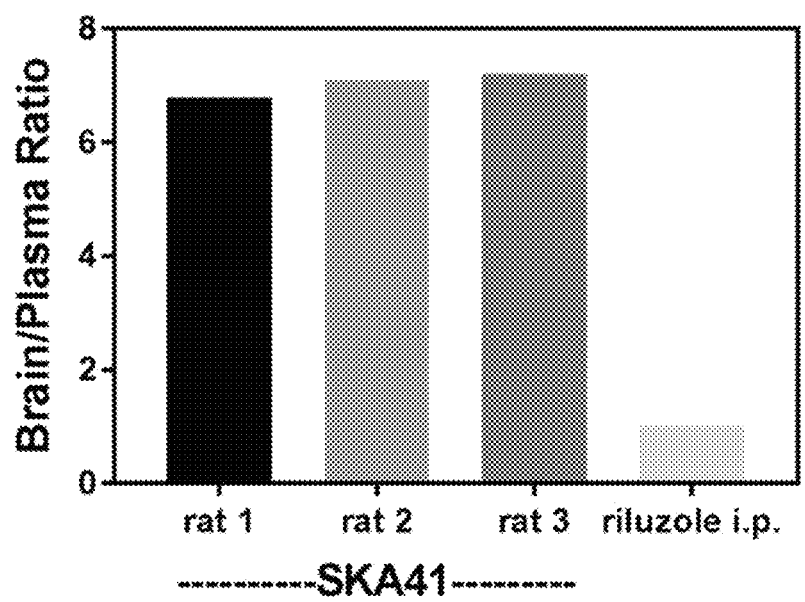
FIG. 8 shows the brain/plasma ratios for SKA-41, which is seven times higher than for riluzole. LC/MS analysis was performed with an Acquity UPLC GEH C-18 column. The mobile phase gradient used to elute SKA-41 from the UPLC column was as follows: 10% acetonitrile and 90% water both containing 0.1% formic acid (0-0.5 min) to 75% acetonitrile and 25% water (0.51-1.75 min) and back to 10% acetonitrile and 90% water (1.76-3.5 min) with a flow rate of 0.20 ml per minute. Under these conditions SKA-41 had a retention time of 1.88 minutes. The average values for plasma and brain concentrations of SKA-41 were 1.77 µM and 12.55 µM, respectively.
Figure 10:
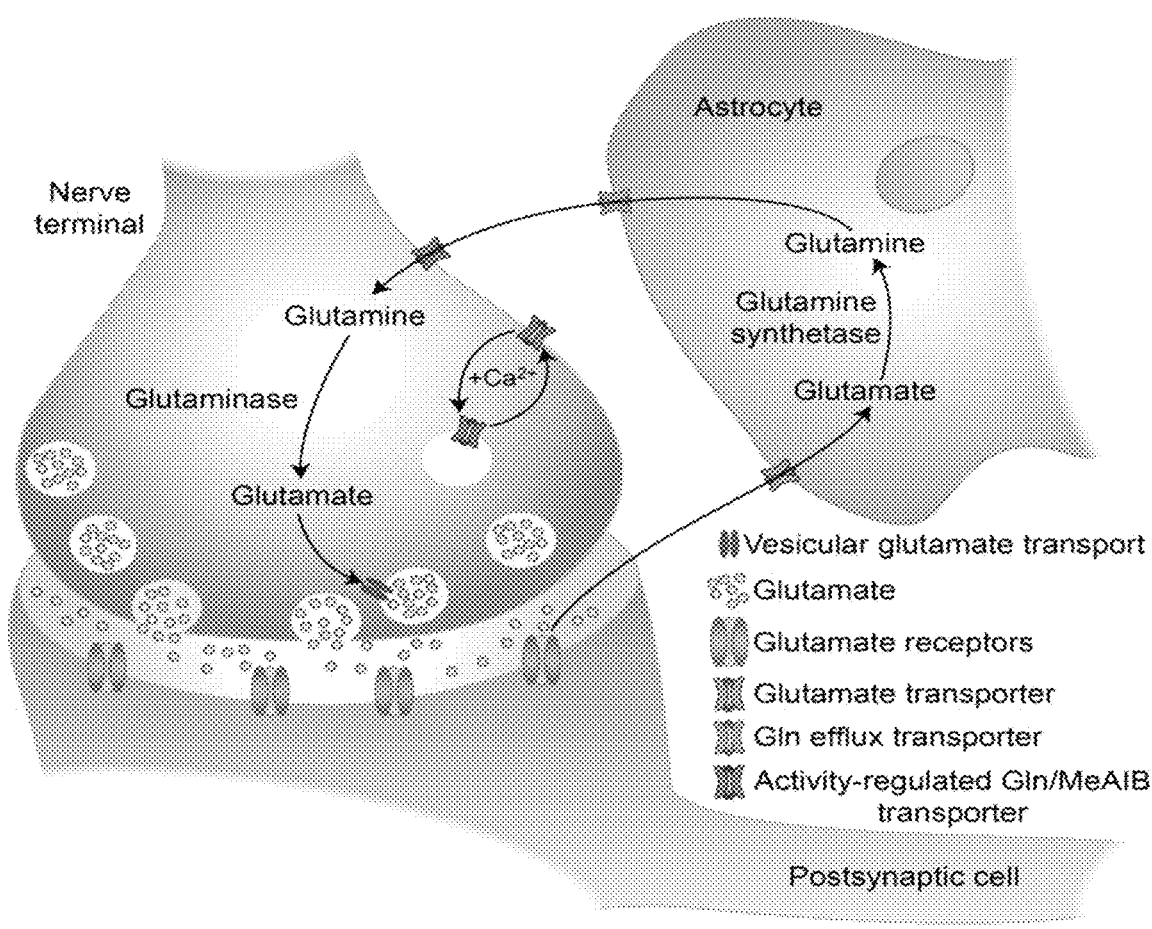
FIG. 10. shows the novel high-affinity activity-regulated Gln/MeAIB transporter described here may have physiological and pathological implications in understanding the neurobiology of excitotoxic synaptic glutamate release in acute and chronic neurodegenerative diseases.
Figure 11:
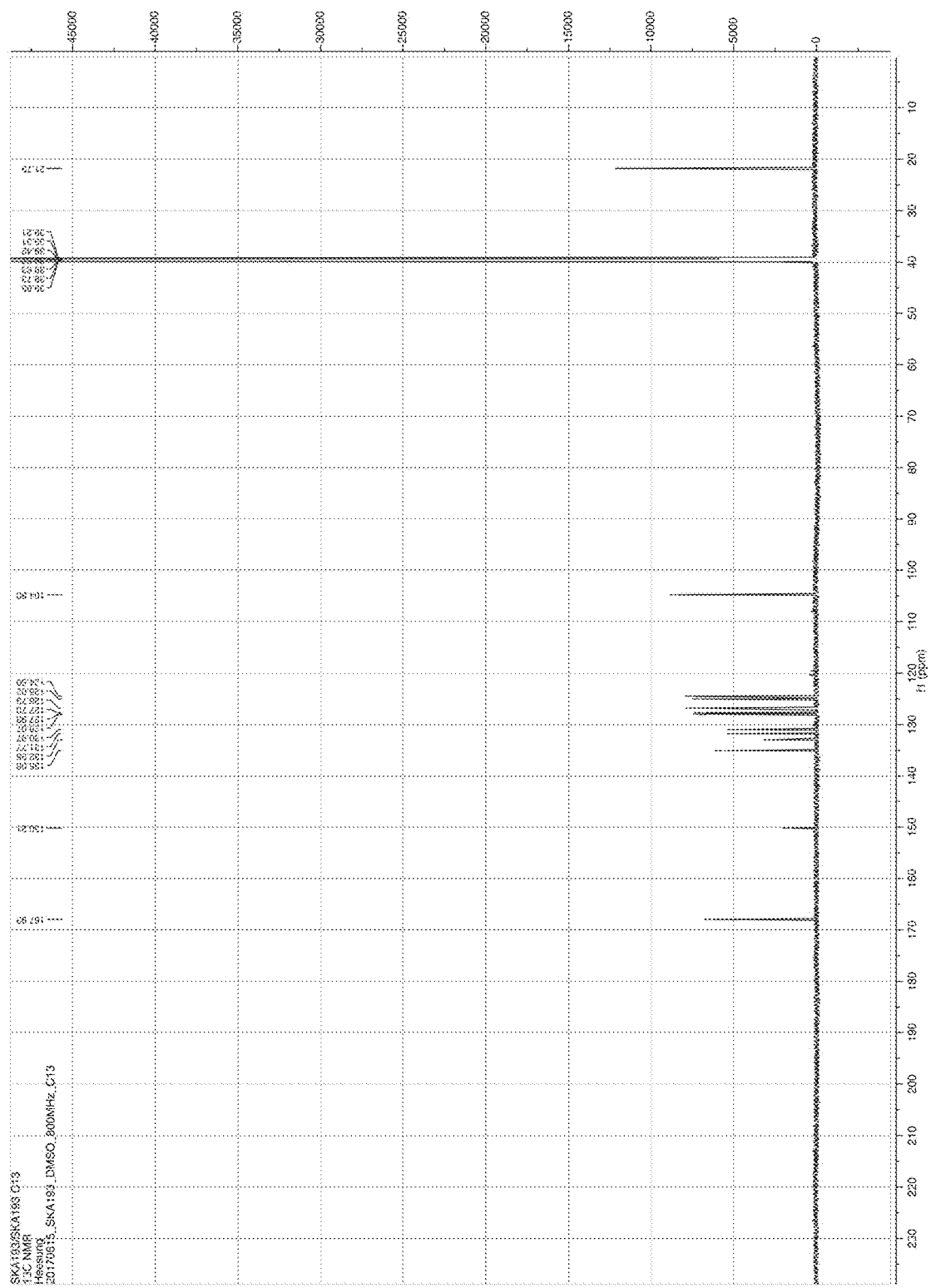
FIG. 11 shows $^1$H and $^{13}$C NMR for SKA-193.
Figure 12:
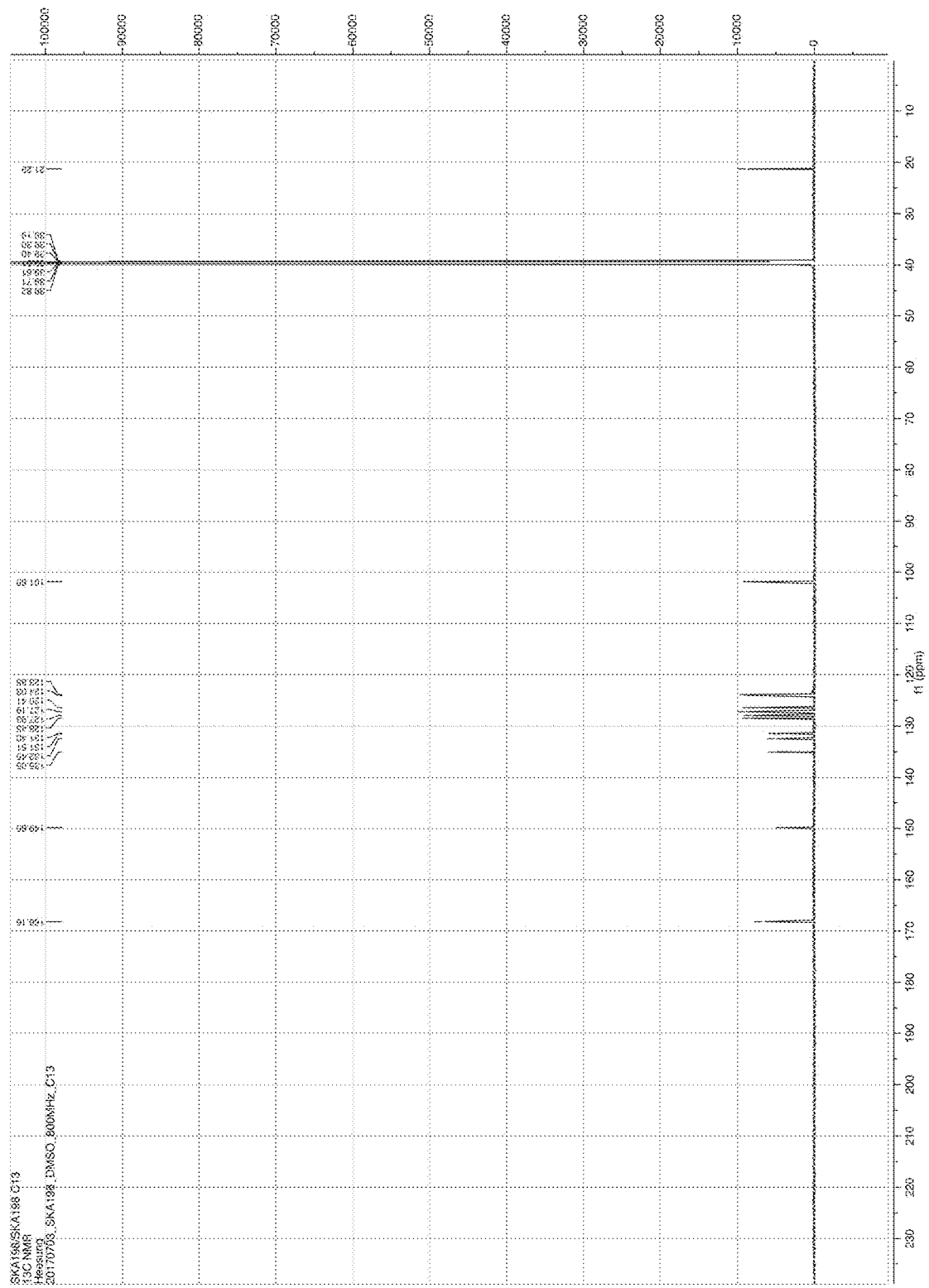
FIG. 12 shows $^1$H and $^{13}$C NMR for SKA-198.
Figure 13:
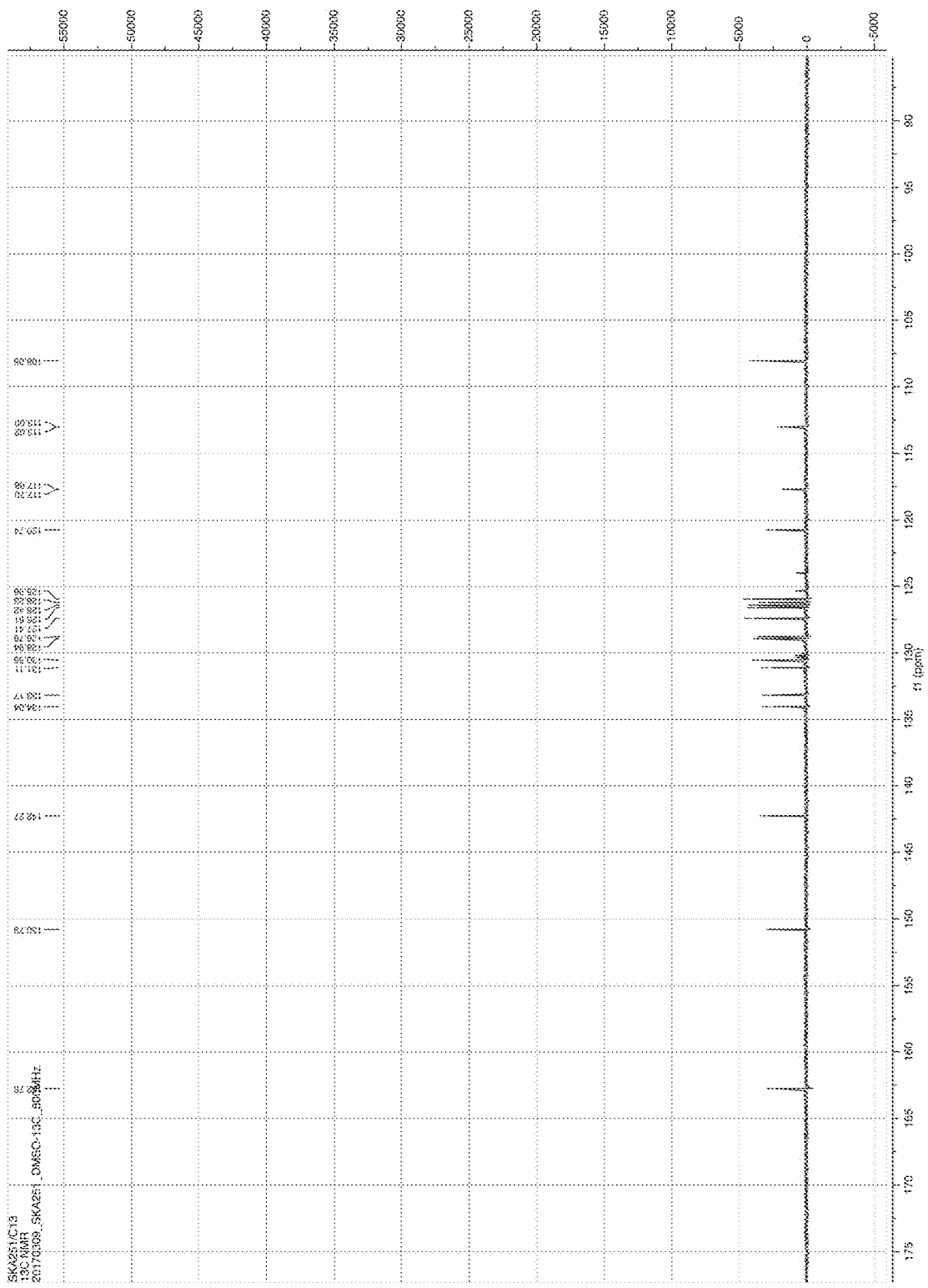
FIG. 13 shows $^1$H and $^{13}$C NMR for SKA-251.
Figure 14:
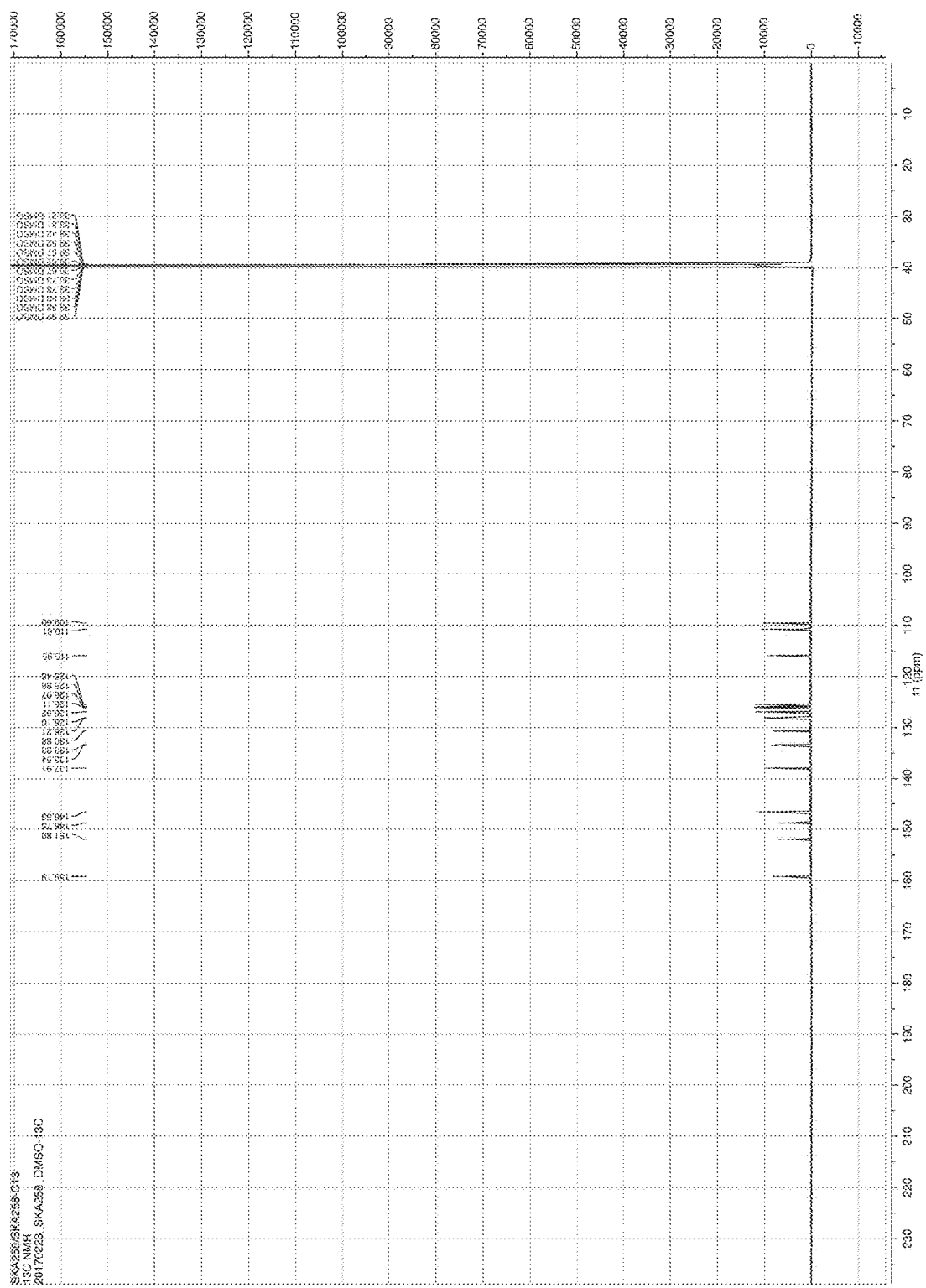
FIG. 14 shows $^1$H and $^{13}$C NMR for SKA-258.
Figure 15:
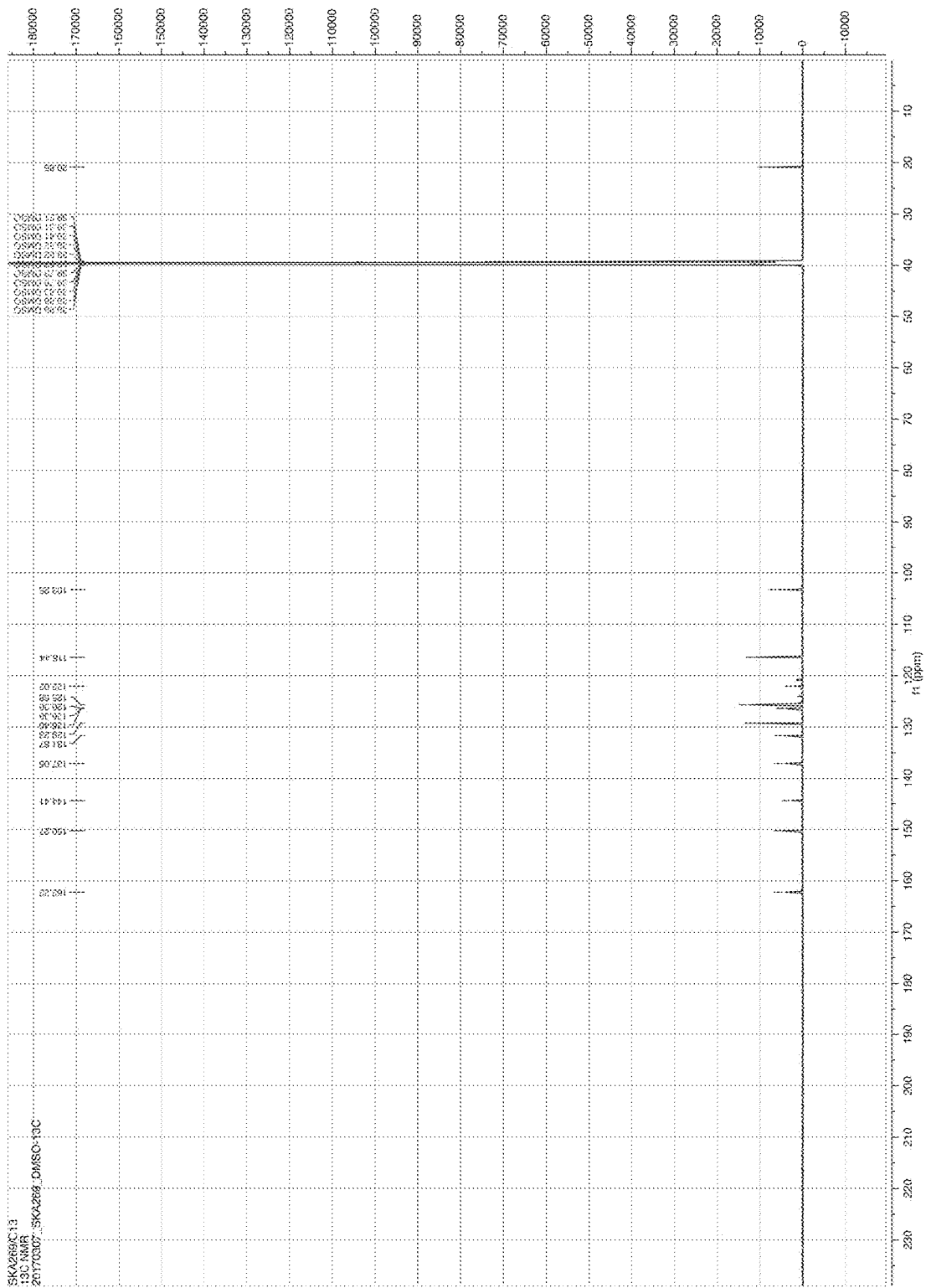
FIG. 15 shows $^1$H and $^{13}$C NMR for SKA-269.

FIG. 8 shows the brain/plasma ratios of SKA-41. We have developed a method to determine SKA-41 concentrations in brain and plasma. We injected 3 male rats (~300 g) with 10 mg/kg SKA-41 in Miglyol 812 i.p. and then sacrificed 1 h later. Brain plasma ratio is about 7 demonstrating that SKA-41 is highly brain penetrant. The brain/plasma ratio for riluzole is 1 [20]. SKA-41 was well tolerated with no overt toxicity or sedation at this dose.

Cognitive function (Y-maze) is evaluated on weeks 1, 2, 3 and 4 after ischemia. All animals are pre-trained before ischemia. In the Y-maze the number of entries, spontaneous alteration and % of alteration are recorded. After completion of the behavioral tests, animals are perfused and the number of histologically normal appearing CA1 neurons in a 0.4-mm segment of the medial, middle, and lateral parts of the hippocampus and pyramidal neurons in neocortical layers 3, 5, and 6 counted. NeuN fluorescence is performed to confirm numbers of NeuN+ neurons in the CA1 region. Viral-mediated GFP expression levels is also assessed by IHC to assure high-levels of lentiviral GFP expression.

Without being bound by theory, SKA-41 and active SKA-41 derivatives, are more potent than riluzole in vivo to block neuronal damage in vulnerable brain regions and improve cognitive function following global cerebral ischemia. These riluzole-derivatives likely display a more selective action on activity-regulated Gln/MeAIB transport activity compared to general cell soma and proximal dendrite $Na_V$ blockade. These riluzole-derivatives also likely will exhibit better brain penetration and brain retention than riluzole and therefore may be more potent, and selective. We do not anticipate any neurotoxicity (i.e., normal in the positional sense test, the muscle tone test, and the gait and stance test) at the dose we will be using.

The neuroprotective effects of SKA-41 and active SKA-41 derivatives SKA-190, SKA-193, SKA-219, SKA-220 SKA-247, riluzole, several inactive SKA-41 derivatives, phenytoin, and vehicle (DMSO) to prevent CA1 neuronal damage can also be examined following OGD/reperfusion injury in mature organotypic hippocampal slice cultures in vitro.

Organotypic hippocampal slice cultures are typically prepared from immature animals (postnatal [P] day 7) [42] and are cultured for two weeks prior to any experiments. Thus, these cultures develop in vitro during a critical period of in vivo process outgrowth, synaptogenesis and functional maturation of stable neural circuits. We have shown that activity-regulated Gln/MeAIB transport is coordinately up-regulated across development [1] during this period of development of Glu/Gln cycling between neurons and astrocytes [43, 44] and increased synaptic Glu release in pyramidal neurons in vitro and in vivo [45-48]. While the major excitatory synaptic connections in vivo are faithfully preserved in immature slice cultures, mossy fiber sprouting occurs and eventually spontaneous epileptiform activity is observed [49].

We use a novel organotypic hippocampal slice culture procedure where slices are prepared from more mature Sprague Dawley rats ages 20-30 days [50, 51] such that maturation of hippocampal circuits during this critical period ($2^{nd}$ and $3^{rd}$ postnatal weeks) occurs in vivo. These mature slice cultures retain hippocampal cytoarchitecture and synaptic connections up to 3 months in vitro. Spontaneous epileptiform activity is rarely observed suggesting long-term retention of normal neuronal excitability and intact and balanced excitatory and inhibitory synaptic networks [50, 51]. The brain dissection, removal, cooling to 4° C., and slicing (400 mM; McIllwain tissue chopper) of hippocampi, and plating onto Millicell CM filters are the same in both procedures. One critical aspect of the mature slice cultures is that rats are anesthetized with ketamine (100 mg/g) before sacrifice, which blocks NMDA receptor function and Glu-induced excitotoxicity during the dissection procedure [50, 51]. A second unique and critical aspect is that after the filters are placed into six-well dishes containing 1 ml of culture medium, the cultures are incubated at 32° C. in a 5% $CO_2$ atmosphere for at least two weeks prior to the beginning of all experiments [50, 51]. Pre-clinical studies have suggested that mild hypothermia affects a wide range of cell death mechanisms including energy depletion, free radical formation and glutamate-induced excitotoxicity [52]. Mild hypothermia provides neuroprotection after cardiac arrest, hypoxic-ischemic encephalopathy, and in animal models of ischemic stroke [53, 54].

One to three days before an experiment the cultures are shifted to a 37° C. incubator in 5% $CO_2$ atmosphere. Mature organotypic hippocampal slices are incubated in deoxygenated, glucose-free medium for 10 min (to mimic the interruption of the supply of oxygen and nutrients to the brain parenchyma as seen in global cerebral ischemia) or normoxic, glucose-containing medium. Slices are randomly divided into control group, model group (vehicle), drug intervention group (low-, intermediate-, and high-dose). Riluzole, SKA-41, SKA-190, SKA-193, SKA-219, SKA-220, SKA-247 or phenytoin of different concentrations (1 μM, 504, 20 μM, and 60 μM) are added to the culture medium 30 min prior to OGD and are present throughout the experiment until the cultures are terminated. Controls include inactive riluzole-derivatives or DMSO (vehicle).

To quantify neuronal damage, the fluorescent marker propidium iodide (PI) is used. PI is a polar substance that enters only dead or dying cells with damaged cell membranes and binds to DNA with a bright red, intensified fluorescence (630 nm) when absorbing blue-green light (493 nm). One day before the addition of drugs, PI (5 mg/ml) is added to the culture medium to allow visualization and quantification of basal cell death ($T_0$). The following day the PI fluorescence in the CA1 subregion is quantified by image acquisition software. Immediately after image acquisition, the slices are treated with OGD (10 min) or normoxic conditions. These treatments are done in an apparatus that has been preheated to 37° C. containing modified Earles balanced salt solution (+/−glucose) bubbled with 95% $N_2$, 5% $CO_2$ or with 20% $O_2$, 75% $N_2$ and 5% $CO_2$. After 10 min treatment, the medium is replaced with fresh medium containing 5 mg/ml PI and the cultures returned to the 37° C. incubator under normoxic conditions. Images of PI fluorescence are obtained at daily intervals for three days. After the final image acquisition, the medium is changed, 10 μM NMDA (a glutamate receptor agonist) and 5 mg/ml PI are added, and the slices incubated overnight to achieve maximal neuronal death. The PI fluorescence of maximal neuronal death is defined as $T_{max}$. The percent cell death is as follows: ($T_{24, 48}$, or $_{72}-T_0/(T_{max}-T_0)$.

Glu release induced by OGD into the medium is measured at 1, 2 and 6 h using the Amplex Red Glutamic Acid/Glu Oxidase Assay Kit. The extracellular glutamate level is detected as an increase in the resorufin fluorescence value, which is normalized by subtracting the basal Glu level of the phenol red-free medium and plotted as the percentage of Glu released from the control groups.

Example 3

SNAT8 knock down in adult rat hippocampus in vivo via shRNA lentiviral infection will be neuroprotective against global cerebral ischemia, similarly to riluzole (an antiglutamatergic agent): We provide in vitro evidence that chemical 'preconditioning' by brief exposure to NMDA-dependent depolarization results in a down-regulation of $K^+$-stimulated and activity-regulated spontaneous transport activity. Brief exposure to preconditioning agents in vitro induces a neuroprotective response within 24 hr that involves modification of Glu synapses that includes reduction of synaptic Glu release to protect against subsequent Glu-induced excitotoxic injury onto principal Glu neurons.

An intervention to alleviate excitotoxicity without interrupting synaptic transmission; if this transporter were activated specifically to mediate a certain injury mechanism, then it would be more compelling: SNAT8-mediated Gln transport is low under normal conditions because other mechanisms can support synaptic Glu synthesis and release (i.e., α-ketoglutarate) under normal conditions. Rationale is provided for developing SNAT8-derived drugs to limit activity-driven Gln import in axon terminals to replenish cytoplasmic Glu levels required to sustain excitotoxic Glu release. Such an anti-glutamatergic drug is directed at a Gln transporter that can be induced by high activity (e.g. $K^+$-depolarization, $Ca^{2+}$-dependent exocytosis) and not a protein integral to vesicular Glu filling, or the release process, which would disrupt normal transmission.

Other neuronal Gln transporters could also be involved: The related neuronal Gln/MeAIB transporters SNAT1 nor SNAT2 are not activity regulated Gln transporters, and unlike SNAT8, neither is expressed in pre-synaptic terminals [2, 55]. We were the first to propose the concept [1] that a $K^+$-depolarization stimulated Gln/MeAIB transporter in glutamatergic synapses displays relatively high substrate affinity ($K_m$=30 μM); unlike SNAT1 and SNAT2 which are low affinity ($K_m$=0.5 mM) transporters that are only expressed in cell bodies and dendrites.

Riluzole can act on a wide range of molecular targets to inhibit synaptic Glu release and is already established to confer protection from excitotoxicity: Inhibition of activity regulated Gln/MeAIB transport in hippocampal cultures described here is one of the most potently inhibited effects by riluzole ($IC_{50}$~1 μM). We have identified several novel riluzole derivatives, for example SKA-41 related, that potently block transport (but are less potent on $Na_V$ channels) and these are also more lipophilic to allow greater brain permeation (FIG. 8).

Neuronal toxicity may non-selectively reduce activity-regulated MeAIB transport: Lentiviral infection of neurons is relatively non-toxic [56], but we can confirm cell viability using a commercial kit.

Verification that SNAT8 mediates activity-regulated Gln/MeAIB transport by heterologous expression is lacking: Gln/MeAIB uptake by SNAT8 in an oocyte expression system is only 2-fold above background {Hagglund, 2015 #6126, which could be due to intracellular sequestration of an activity inducible Gln transporter protein providing a potential regulatory mechanism.

The concentration of Gln in CSF and ventricular fluid is 400 μM {Gjessing, L. R., et al. *Journal of neurochemistry* 19.7 (1972): 1807-1808; McGale, E. H. F., et al. *Journal of neurochemistry* 29.2 (1977): 291-297.}, which is more in line with the relative affinity of SNAT1 and SNAT2 for Gln [2]: Gln levels in extrasynaptic space are low (~30 μM) as recently measured by microdialysis [57] in which case SNAT1 and SNAT2 activity would be quite low.

$Ca^{2+}$-dependent $^{14}C$-MeAIB transport is present under spontaneous conditions and increases following $K^+$-stimulation: This likely reflects differences in constitutive vs. regulated ($K^+$) cycling of SNAT8 between intracellular pools and the plasma membrane [58-60].

Riluzole inhibition of SNAT8 may not be competitive, but non-competitive and dependent on other known (or unknown) targets, such as specialized $Na^+$ channels: Inhibition of SNAT8 activity (directly or indirectly) may help explain riluzole's neuroprotective properties to limit excitotoxic Glu release, neuronal damage, and impaired cognition.

Advantages of this transporter over others in the Slc38 or the Slc1, 6, and 7 family of transporters: $Na^+$-dependent/uni-directional import of Gln is critical as it concentrates Gln in synapses instead of only exchanging Gln for other neutral amino acids. We provide evidence that $Ca^{2+}$-dependent, glutamatergic-regulated, high-affinity Gln/MeAIB transport in neurons is mediated by SNAT8. The only other Nat dependent Gln/MeAIB transporter in these families that is known to be restricted to axon terminals is NTT4. Identification of novel $Ca^{2+}$-regulated, high affinity Gln transport [1] reveals an innovative gateway to molecularly identify it using this expression assay to further understand its role in Glu-neurotransmission and excitotoxicity in vitro and in vivo.

Targeting Glu excitotoxicity as a neuroprotective strategy is an extremely well-worn path; very short time window in which Glu excitotoxicity can be safely and effectively targeted: Understanding presynaptic mechanisms, and the development of more specific drugs to reduce synaptic Glu synthesis and excitotoxic Glu release has been neglected, at the expense of disappointing glutamatergic postsynaptic efforts. Reducing excessive and sustained release of Glu from pyramidal neuron synapses to prevent $Ca^{2+}$-dependent excitotoxicity in postsynaptic neurons can be an effective prophylactic and management strategy to suppress neuronal death and cognitive impairment; especially in the event of on-going various clinical emergencies.

Animals exhibiting seizures following injections would confound the results: Animals exhibiting seizures are not included.

Adeno-associated viruses to knockdown SNAT8 in vivo could be used instead: CNS genes are routinely knocked down by hippocampal lentivirus injection. Lentiviral particles are also larger than AAV, which limits their spread to regions outside of the hippocampus.

Potential differences in transporter expression and function between cultures and in adult animals: DIV>16 cultures exhibit a mature VGLUT1-encoded presynaptic glutamatergic phenotype like in vivo [45-48].

May be difficult to detect reduction of SNAT proteins by Western blot: We always run NTT4 and β-actin controls and compare band intensity ratios.

Lentiviral constructs have no cellular specificity: SNAT8 knockdown by SNAT8 shRNA occurs only in SNAT8-expressing cells. Off target effects of shRNA in SNAT8-negative cells are minimal as we pre-screen all shRNA molecules in NCBI databases for uniqueness.

Other transporters may upregulate to compensate: Gln/MeAIB transporters SNAT1 and SNAT2 are not in axon terminals [55].

Excitatory transmission persists independently of Glu/Gln cycle [61]: That study utilized DIV 8-10 cultures or very young rats (postnatal day 12); activity-regulated Gln/MeAIB transport is low in immature neurons.

Blocking SNAT3 and SNAT5-mediated Gln release from glia is a better target to limit the availability of Gln to neurons: There are more than 14 Gln transporters in the brain that are differentially localized and regulated in neurons and glia that serve various cellular functions including DNA/protein synthesis glutathione production, metabolic (Glu) functions, in addition to supplying Gln for Glu biosynthesis in synaptic transmission. Targeting activity-regulated neuronal Gln/MeAIB transport in hippocampal synapses is a more selective approach to influence synaptic Glu transmission that does not interfere with other cellular functions of Gln.

Riluzole and phenytoin are both neuroprotective agents in animal models of global cerebral ischemia, but riluzole is more potent, and both are more effective when given before onset of the ischemia [13], which is hard to time precisely: Global cerebral ischemia often occurs following different surgical procedures that may lead to a reduction of blood flow to the brain. Prophylactic treatment of at-risk patients with SKA-41 derivative may be advantageous.

SNAT8 knockdown alone in vivo may impair cognition by itself: Riluzole has very few side effects and currently is in phase II clinical trials for mild AD; its likely target in the brain also includes inhibiting SNAT8 activity and suppression of excitotoxic glutamatergic neurotransmission.

Riluzole is known already to reduce neuronal damage after global cerebral ischemia; Riluzole is not very brain penetrant despite its great clinical potential in reducing Glu-induced excitotoxicity in neuronal disease states in vivo and in vitro models: Lipophilic SKA41-derivatives that selectively block activity-regulated Gln/MeIAB transport, and that are likely more brain penetrant, may be more selective prophylactic agents to reduce neuronal hippocampal CA1 damage in the event of global cerebral ischemia.

Example 4

Chemical Synthesis of SKA-41 Derivatives

General Method I. Preparation of Methyl Substituted 4-(naphthalenyl)thiazol-2-amine.

Acetylchloride (750 µl, 10 mmol) and $AlCl_3$ (1.33 g, 10 mmol) were added sequentially to 20 ml of chloroform at room temperature. 1-Methylnaphthalene (1 ml, 7 mmol) in 5 ml of chloroform was then added to the reaction mixture. After the addition was completed, the reaction mixture was stirred for 2 hours, and the progress of the reaction was monitored by TLC. The reaction mixture was quenched with sodium bicarbonate solution and washed with water and brine. The solvent was removed under reduced pressure to give a 1-(4-methylnaphthalen-1-yl)ethan-1-one. Next, trimethylphenyl ammonium tribromide (1.125 g, 3 mmol) was added to a solution of the resulting compound, 1-(4-methylnaphthalen-1-yl)ethan-1-one (460 mg, 2.5 mmol), in 20 ml of dichloromethane (DCM) and the reaction mixture was stirred at room temperature for 8 hours. Thiourea (228 mg, 3 mmol) was then added to reaction and the mixture was stirred for another 12 hours before quenching with 4N NaOH. The reaction mixture was washed with water and brine and the solvent was evaporated to give the crude product. The crude product was purified by flash-chromatography using ethyl acetate/petroleum ether (2:8 v/v).

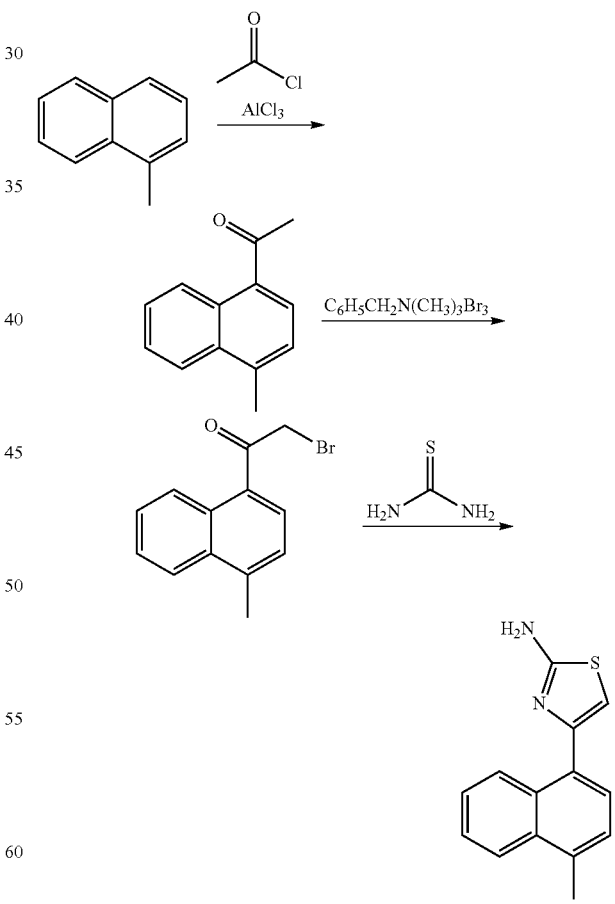

General Method II. Preparation of Substituted 4-Phenylthiazole or 4-Naphthalenyl Thiazoles.

Appropriately substituted acetophenones or naphthanones were dissolved in chloroform (20 ml) at room temperature.

Liquid bromine (1.2-1.5 equivalent) in chloroform (5 ml) was then added drop-wise. After the addition of bromine was completed, differently substituted thioureas (1.5 equivalent) were added to the reaction mixture and stirred for 2 hours. The progress of the reaction was monitored by TLC. The reaction mixture was quenched with saturated aqueous solution of sodium hydrogen carbonate and the pH of solution was adjusted to between 7 and 7.5. The organic phase was washed with water and brine and the solvent was removed under the vacuum. The residue was purified via flash chromatography (petroleum ether-ethyl acetate, 7:3).

General Scheme of General Method II

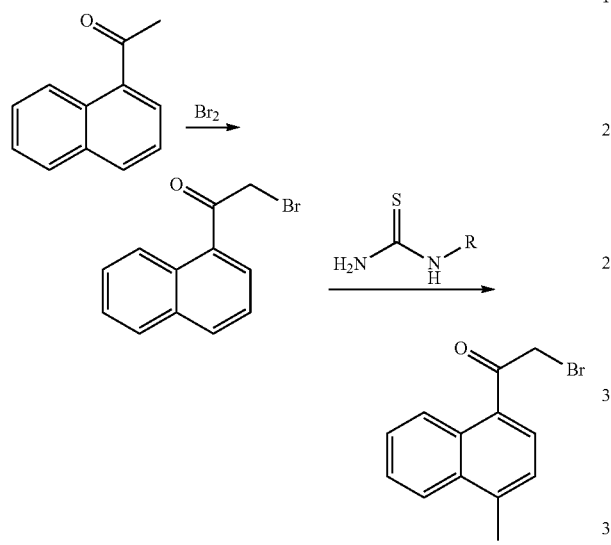

General Method III. Alternative Preparation of Substituted 4-phenylthiazole or 4-naphthalenyl thiazoles.

2-Bromo acetophenone was added to a solution of a substituted thiourea in 20 ml of absolute ethanol. The mixture was refluxed at 70° C. for 2 hours. After completion of the reaction, the ethanol was evaporated under vacuum. The dried reaction mixture was poured into dichloromethane and neutralized with saturated $NaHCO_3$. The organic phase was washed with water and brine, and then dried with anhydrous $Na_2SO_4$. Finally, the solvent was evaporated under vacuum. The crude product was reconstituted in a methanol-water mixture (99:1), treated with charcoal and recrystallized.

Scheme of General Method III

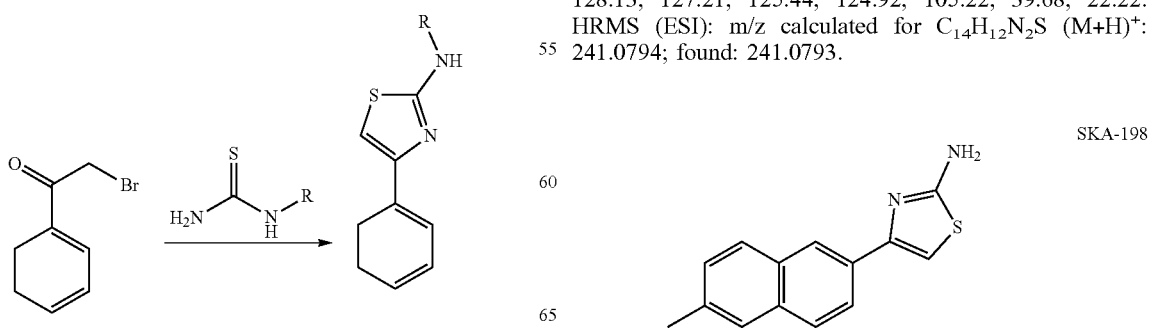

Chemical Compounds Synthesized

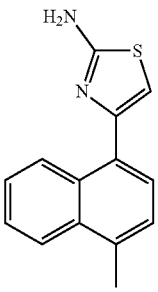

SKA-190

4-(4-Methylnaphthalen-1-yl)thiazol-2-amine (SKA-190). SKA-190 was prepared from 1-methylnaphthalene (1 ml, 7 mmol) according to General Method I. The product was obtained as golden crystals (355 mg, 20%); m.p=168-169° C. (CAS no. 332064-25-2). MW=240.32. $^1$H NMR (800 MHz, DMSO); δ=8.49 (dd, J=8.4, 1.3 Hz, 1H), 8.09-8.06 (m, 1H), 7.60 (ddd, J=8.3, 6.7, 1.4 Hz, 1H), 7.57-7.53 (m, 2H), 7.40 (dd, J=7.2, 1.1 Hz, 1H), 7.12 (s, 2H), 6.74 (s, 1H), 2.70 (d, J=1.0 Hz, 3H). $^{13}$C NMR (201 MHz, DMSO); δ=168.64, 150.32, 135.53, 132.93, 131.99, 131.88, 128.93, 128.41, 127.67, 126.88, 124.51, 124.33, 102.36, 21.77

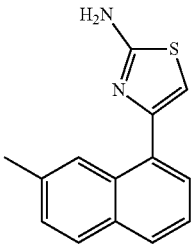

SKA-193

4-(7-Methylnaphthalen-1-yl)thiazol-2-amine (SKA-193). SKA-193 was prepared from 2-methylnaphthalene (1 ml, 7 mmol) according to General Method I. The product was isolated as light yellow powder (70 mg, 4%); m.p.=154-156° C. MW=240.32. $^1$H NMR (800 MHz, CDCl3-d6, δ) 8.08-8.05 (m, 10H), 7.84-7.78 (m, 17H), 7.74 (d, J=8.6 Hz, 1H), 7.61 (s, 7H), 7.61-7.52 (m, 2H), 7.44 (s, 6H), 7.42 (d, J=8.1 Hz, 1H), 7.37-7.35 (m, 6H), 7.28 (s, 3H), 6.66-6.63 (m, 12H), 3.88 (s, 2H), 2.30 (s, 2H). $^{13}$C NMR (201 MHz, DMSO); δ=168.36, 150.63, 135.49, 133.38, 132.20, 131.40, 128.49, 128.35, 128.13, 127.21, 125.44, 124.92, 105.22, 39.68, 22.22. $^{13}$C NMR (201 MHz, DMSO); δ=168.36, 150.63, 135.49, 133.38, 132.20, 131.40, 128.49, 128.35, 128.13, 127.21, 125.44, 124.92, 105.22, 39.68, 22.22. HRMS (ESI): m/z calculated for $C_{14}H_{12}N_2S$ (M+H)$^+$: 241.0794; found: 241.0793.

SKA-198

4-(6-Methylnaphthalen-2-yl)thiazol-2-amine (SKA-198). SKA-198 was prepared from 2-methylnaphthalene according to General Method I. The product was isolated as light yellow powder (110 mg, 15%); m.p.=178-179° C. MW=240.32. ¹H NMR (800 MHz, DMSO); δ=8.31-8.28 (m, 5H), 7.94 (dd, J=8.6, 1.7 Hz, 5H), 7.83 (dd, J=24.8, 8.5 Hz, 10H), 7.69 (s, 5H), 7.38 (dd, J=8.4, 1.7 Hz, 5H), 7.15 (d, J=14.1 Hz, 15H), 2.55 (s, 3H), 2.51 (d, J=9.1 Hz, 1H). ¹³C NMR (201 MHz, DMSO); δ=168.64, 150.32, 135.53, 132.93, 131.99, 131.88, 128.93, 128.41, 127.67, 126.88, 124.51, 124.33, 102.36, 21.77. HRMS (ESI): m/z calculated for $C_{14}H_{12}N_2S$ (M+H)⁺: 241.0794; found: 241.0792.

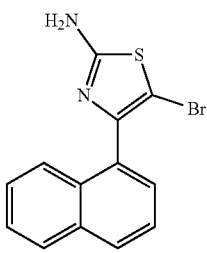

SKA-219

5-Bromo-4-(1-naphthalenyl)thiazol-2-amine (SKA-219). 2-Amino-4-(1-naphthyl) thiazole (106 mg, 0.46 mmol) was dissolved in 10 ml of chloroform. Liquid bromine (30 μl, 0.46 mmol) in chloroform (3 ml) was then added drop-wise. The reaction mixture was stirred at room temperature for 30 min. The progress of the reaction was monitored by TLC. The reaction mixture was quenched with 4N NaOH and washed with sodium thiosulfate, water and brine. The organic phase was dried with anhydrous sodium sulfate and the solvent was dried under vacuum. The crude product was recrystallized with methanol. The product was isolated as brown crystals (70 mg, 50%); m.p.=155° C. (CAS no. 99515-43-2). MW=305.19. ¹H NMR (800 MHz, DMSO); δ=7.99-7.95 (m, 2H), 7.85-7.81 (m, 1H), 7.58-7.49 (m, 4H), 7.36 (s, 2H). ¹³C NMR (201 MHz, DMSO); δ=167.72, 148.78, 133.72, 131.99, 131.52, 129.09, 128.62, 128.40, 126.61, 126.43, 125.65, 90.55.

SKA-220

5-Bromo-4-(naphthalen-2-yl)thiazol-2-amine (SKA-220). SKA-220 was prepared from 2-amino-4-(2-naphthy) thiazole (106 mg, 0.46 mmol) according to the method described for SKA-219. The product was isolated as light brown crystal (100 mg, 71%); m.p.=140-141° C. (CAS no. 99514-91-7). 305.19. MW=¹H NMR (800 MHz, DMSO-d₆); δ=8.35 (s, 1H), 7.96 (s, 3H), 7.99-7.91 (m, 2H), 7.56-7.52 (m, 2H), 7.38 (s, 2H), 3.31 (s, 4H), 3.17 (s, 4H), 2.89 (s, 2H), 2.07 (s, 1H). ¹³C NMR (200 MHz, DMSO); δ=167.48, 147.52, 133.04, 132.74, 131.70, 128.65, 128.01, 127.97, 127.52, 126.96, 126.92, 126.17, 88.06.

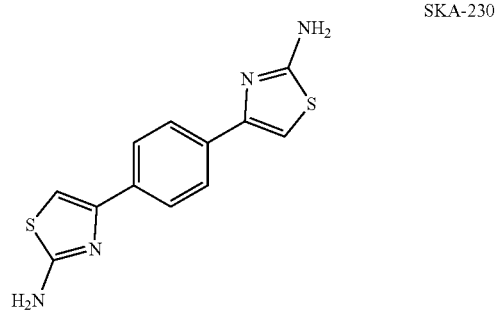 [SMILES: Nc1nc(-c2ccc(-c3csc(N)n3)cc2)cs1]

SKA-230

4,4'-(1,4-Phenylene)bis(thiazol-2-amine) (SKA-230). SKA-230 was prepared from 1,4 acetylbenzene (243 mg, 1.5 mmol) according to General Method II. The product was isolated as light yellow powder (197 mg, 47%); m.p.=350° C. (CAS no. 13355-22-1). MW=274.36. ¹H NMR (800 MHz, DMSO-d₆); δ=8.59 (s, 4H), 7.89 (s, 4H), 7.35 (s, 2H). ¹³C NMR (201 MHz, DMSO-d₆); δ=70.34, 126.60, 103.96.

SKA-247

5-Methyl-4-(4-methylnaphthalen-1-yl)thiazol-2-amine (SKA-247). SKA-247 was prepared from 1-methylnaphthalene (1 ml, 7 mmol) and propionyl chloride (950 ml, 10 mmol) according to General Method I. The product was isolated as white crystals (40 mg, 2%); m.p.=225-227° C. (CAS no. 1541829-10-0). MW=254.35. ¹H NMR (800 MHz, DMSO-d₆); δ=8.08 (dd, J=8.5, 1.1 Hz, 1H), 7.93 (dd, J=8.4, 1.2 Hz, 1H), 7.59 (m, 1H), 7.53 (m, 1H), 7.42 (d, J=7.1 Hz, 1H), 7.34 (d, J=7.0 Hz, 1H), 6.83 (s, 2H), 2.72 (s, 3H), 2.08 (s, 3H). ¹³C NMR (201 MHz, DMSO-d₆); δ=165.10, 145.69, 134.21, 132.25, 131.84, 127.65, 127.34, 126.39, 126.14, 125.91, 124.69, 116.46, 40.23, 39.60, 12.19.

SKA-251

4-(Naphthalen-1-yl)-N-(3-(trifluoromethyl)phenyl)thiazol-2-amine (SKA-251). SKA-251 was prepared from 1-acetonaphthone (500 mg, 2.94 mmol) and 3-(trifluoromethyl)phenylthiourea according to General Method II. The product was isolated as white crystals (50 mg, 46%); m.p.=135° C. MW=370.39. ¹HNMR (800 MHz, DMSO-d₆); δ=10.73 (s, 1H), 8.55 (d, J=8.5 Hz, 1H), 8.38 (d, J=2.1 Hz, 1H), 8.01 (m, 2H), 7.77 (ddd, J=16.4, 7.6, 1.7 Hz, 2H), 7.56 (m, 4H), 7.27 (m, 2H). ¹³C NMR (201 MHz, DMSO-d₆); δ 162.76, 150.79, 142.27, 134.04, 130.55, 128.94, 128.78, 127.41, 126.60, 126.42, 126.23, 125.95, 120.74, 108.05, 39.66. HRMS (ESI): m/z calculated for $C_{20}H_{13}F_3N_2S$ (M+H)⁺: 371.0825; found: 371.0832.

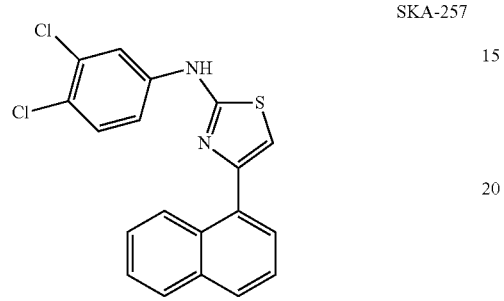

SKA-257

N-(3,4-Dichlorophenyl)-4-(naphthalen-1-yl)thiazol-2-amine (SKA-257). SKA-257 was prepared from 1-acetonaphthone (500 mg, 2.94 mmol) and 3,4-dichlorophenyl-thiourea according to General Method II. The product was isolated as white powder (340 mg, 31%); m.p.=243-244° C. (CAS no. 879445-31-5). MW=372.28. ¹H NMR (800 MHz, DMSO-d₆); δ=10.73 (s, 1H), 8.47 (m, 1H), 8.23 (d, J=2.4 Hz, 1H), 8.03 (m, 2H), 7.74 (dd, J=7.0, 1.1 Hz, 1H), 7.58 (m, 3H), 7.53 (m, 2H), 7.26 (s, 1H). ¹³C NMR (201 MHz, DMSO-d₆); δ=131.19, 128.94, 128.79, 127.44, 126.70, 126.44, 126.21, 125.95, 118.24, 117.44, 108.20, 40.44.

SKA-258

4-(Naphthalen-1-yl)-N-(pyridin-2-yl)thiazol-2-amine (SKA-258). SKA-258 was prepared from 1-acetonaphthone and 2-pyridylthiourea according to General Method II. The product was isolated as white powder (436 mg, 35%); m.p.=225° C. MW=303.38. ¹H NMR (800 MHz, DMSO-d₆); δ=11.51 (s, 1H), 8.53 (m, 1H), 8.39 (ddd, J=5.0, 1.9, 0.9 Hz, 1H), 7.99 (m, 1H), 7.96 (m, 1H), 7.75 (m, 2H), 7.59 (m, 3H), 7.26 (s, 1H), 7.15 (dt, J=8.3, 1.0 Hz, 1H), 6.99 (ddd, J=7.2, 5.0, 1.0 Hz, 1H). ¹³C NMR (201 MHz, DMSO-d₆); δ=159.65, 152.35, 149.22, 147.00, 138.38, 134.00, 133.79, 131.15, 128.67, 128.56, 127.39, 126.58, 126.54, 126.33, 125.94, 116.42, 111.28, 110.07. HRMS (ESI): m/z calculated for $C_{18}H_{13}N_3S$ (M+H)⁺: 304.0903; found: 304.0905.

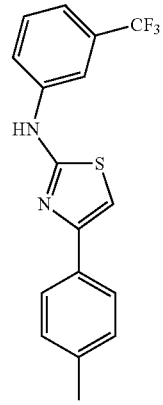

SKA-260

4-(p-Tolyl)-N-(3-(trifluoromethyl)phenyl)thiazol-2-amine (SKA-260). SKA-260 was prepared from 2-bromo-4'-methylacetophenone (500 mg, 2.34 mmol) and 3-(trifluoromethyl)phenylthiourea according to General Method III. The product was isolated as orange crystals (744 mg, 95%); m.p.=108° C. (CAS no. 778566-59-9). MW=350.46. ¹H NMR (800 MHz, DMSO-d₆) δ=10.68 (s, 1H), 8.42 (t, J=2.0 Hz, 1H), 7.89 (dd, J=8.2, 2.2 Hz, 1H), 7.85 (m, 2H), 7.61 (t, J=7.9 Hz, 1H), 7.39 (s, 1H), 7.33 (m, 1H), 7.29 (m, 2H), 2.37 (s, 3H). ¹³C NMR (200 MHz, DMSO-d₆) δ=162.90, 150.55, 142.24, 137.54, 132.16, 130.60, 130.26, 130.10, 129.74, 125.96, 125.44, 124.08, 120.67, 117.66, 117.64, 113.15, 113.13, 113.11, 103.39, 21.28.

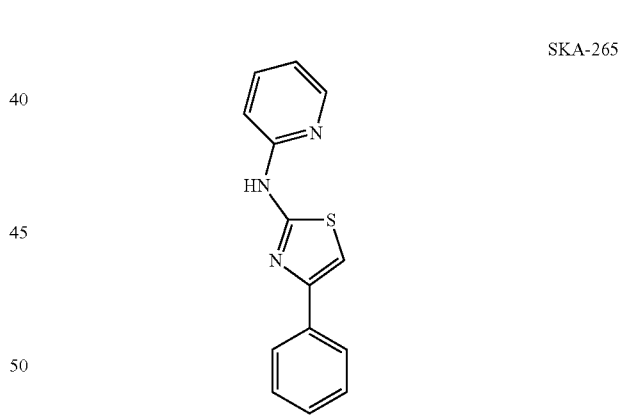

SKA-265

4-Phenyl-N-(pyridin-2-yl)thiazol-2-amine (SKA-265). SKA-265 was prepared from 2-bromoacetophenone (500 mg, 2.5 mmol) and 2-pyridylthiourea according to general method III. The product was isolated as white crystals (495 mg, 78%); m.p.=158° C. (CAS no. 92663-22-4). MW=253.32. ¹H NMR (800 MHz, DMSO-d₆); δ=11.41 (s, 1H), 8.32 (ddd, J=5.0, 1.9, 0.9 Hz, 1H), 7.92 (m, 2H), 7.72 (ddd, J=8.4, 7.1, 1.9 Hz, 1H), 7.43 (m, 3H), 7.31 (td, J=7.3, 1.3 Hz, 1H), 7.11 (dd, J=8.3, 1.0 Hz, 1H), 6.94 (ddd, J=7.2, 5.0, 1.0 Hz, 1H). ¹³C NMR (200 MHz, DMSO-d₆); δ=159.96, 152.31, 149.04, 146.94, 138.37, 129.09, 127.91, 126.04, 116.44, 111.27, 106.37, 40.28, 39.74.

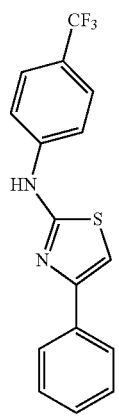

SKA-268

4-Phenyl-N-(4-(trifluoromethyl)phenyl)thiazol-2-amine (SKA-268). SKA-268 was prepared from 2-bromoacetophenone (500 mg, 2.5 mmol) and [4-(trifluoromethyl) phenyl] thiourea according to General Method III. The product was isolated as yellow crystals (530 mg, 66%); m.p.=153° C. (CAS no. 1303995-45-0). MW=320.33. $^1$H NMR (800 MHz, DMSO-$d_6$); δ=10.75 (s, 1H), 8.01 (m, 4H), 7.75 (d, J=8.5 Hz, 2H), 7.49 (m, 3H), 7.37 (m, 1H). $^{13}$C NMR (200 MHz, DMSO-$d_6$); δ=162.79, 150.65, 144.85, 134.77, 129.15, 128.22, 127.15, 126.87, 126.85, 126.84, 126.82, 126.21, 125.81, 124.46, 123.12, 121.59, 121.43, 121.27, 121.11, 116.95, 104.65.

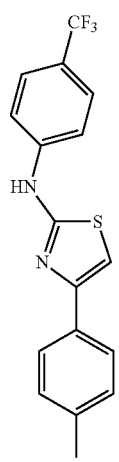

SKA-269

4-(p-Tolyl)-N-(4-(trifluoromethyl)phenyl)thiazol-2-amine (SKA-269). SKA-269 was prepared from 2-bromo-4'-methylacetophnone and [4-(trifluoromethyl)phenyl]thiourea according to General Method III. The product was isolated as yellow crystal (446 mg, 53%); m.p.=155° C. MW=334.36. $^1$H NMR (800 MHz, DMSO-$d_6$); δ=10.72 (s, 1H), 7.96 (d, J=8.5 Hz, 2H), 7.89-7.86 (m, 2H), 7.75 (t, J=9.8 Hz, 2H), 7.41 (s, 1H), 7.29 (m, 2H), 2.38 (s, 3H). $^{13}$C NMR (200 MHz, DMSO-$d_6$); δ=162.69, 150.73, 144.88, 137.52, 132.14, 129.70, 126.85, 126.83, 126.81, 126.14, 125.81, 122.49, 121.37, 121.22, 116.90, 103.71, 21.32. HRMS (ESI): m/z calculated for $C_{17}H_{13}F_3N_2S$ (M+H)$^+$: 335.0824; found: 335.0826.

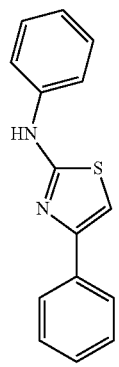

SKA-292

N,4-Diphenylthiazol-2-amine (SKA-292). SKA-292 was prepared from 2-bromo-acetophenone (500 mg, 2.5 mmol) and N-phenylthiourea according to General Method III. The product was isolated as yellow crystal (550 mg, 90%); m.p.=135-137° C. (CAS no. 1843-16-9). MW=252.34. $^1$H NMR (800 MHz, DMSO-$d_6$); δ=10.31 (s, 1H), 7.96 (m, 2H), 7.73 (m, 2H), 7.47 (t, J=7.7 Hz, 2H), 7.38 (m, 3H), 7.35 (m, 1H), 7.00 (tt, J=7.3, 1.1 Hz, 1H). $^{13}$C NMR (200 MHz, DMSO-$d_6$); δ=163.51, 150.54, 141.68, 134.99, 129.48, 129.11, 128.04, 126.12, 121.65, 117.25, 103.38.

Example 5

Market Need/Value Proposition. The notion of 'successful aging' means the achievement of living into old age with healthy and disease-free brains (and bodies). Acute and chronic neurodegenerative conditions can lead to intractable brain diseases with no known cure that significantly affect human health. To date, the pathogenesis of brain diseases is still poorly understood and effective disease-modifying therapies that can prevent (and delay) the progression of neurodegeneration have not been firmly established. Expensive strategies that treat individuals who have already been diagnosed with neurodegenerative brain disease are not available. Therapeutic measures that prevent (or delay) the progression of neurodegeneration is a valuable option for successful aging. Indeed, effective prophylactic and management strategies to suppress and prevent neuronal death and cognitive impairment resulting from acute and chronic neurodegenerative conditions are needed.

Excessive and sustained release of glutamate, the major excitatory neurotransmitter in the brain, from excitatory neurons can be an initial event that triggers $Ca^{2+}$-dependent cell death (excitotoxicity) in postsynaptic neurons in various deleterious conditions, such as traumatic brain injury, perioperative neuronal and cardiac stress, epilepsy, global and focal cerebral ischemia, Alzheimer's disease (AD), noise-induced hearing loss, and in several in vitro models of neurodegenerative diseases including oxygen-glucose/reperfusion (OGD) injury [1-8], a model of global cerebral ischemia. Mechanisms to reduce synaptic glutamate release could therefore potentially prevent excitotoxicity and glutamate-induced neurodegenerative disease [9-12]. For ischemic stroke and AD, in particular, treatment options are quite limited because postsynaptic interventions have proven disappointing in human studies due to poor efficacy or unacceptable side effects [11, 13, 14]; although memantine, an FDA approved drug for AD as an activity-dependent glutamate/NMDA receptor antagonist provides a moderate decrease in clinical deterioration [15-17]. Riluzole, a drug that reduces glutamate release from synapses [18-21], is neuroprotective in all of the above mentioned acute and chronic neurodegenerative conditions when given prophylactically [22-29]. While riluzole is quite well known for its neuroprotective activity in animal models of acute and chronic neurodegenerative disease its short half-life, with side-effects such as sedation at higher concentration, limited brain penetrance [29], and the fact that it may act on a wide range of other molecular targets poses a limitation to its use as a therapeutic agent in humans. Today, riluzole is registered under the trade name Rilutek and its only clinical use is for the treatment of amyotrophic lateral sclerosis (ALS; aka, Lou Gehrig's disease); although it is currently in phase II clinical trials for mild AD [28].

Without wishing to be bound by theory, activity-regulated glutamine (Gln) import into excitatory neurons from astrocytes to regulate and replenish synaptic cytoplasmic glutamate stores, vesicular accumulation and synaptic release can be a target to regulate glutamate release from synapses under conditions where excessive glutamate release and excitotoxicity exist [30]. Keeping up with excessive glutamate release requires that synaptically released glutamate is rapidly cleared by astrocytes, converted to Gln by an enzyme (Gln synthetase) that is only found in astrocytes, and then Gln is returned to neurons via an activity-regulated (and methylaminoisobutyric acid [MeAIB]-sensitive) Gln transporter for glutamate synthesis and continued exocytotic release [31]. Riluzole derivatives that specifically block activity-regulated Gln transport into excitatory synapses may prevent synaptic glutamate synthesis that is required for excessive glutamate release and subsequent excitotoxic neuronal damage in patients at risk for stroke, in early-stage neurodegenerative diseases such as AD, and in other acute and chronic conditions that lead to dementia.

Market Size/Societal Need. Death and disability following global and focal cerebral ischemia and the costs associated with AD represents a sizeable market, particularly among the elderly. Heart disease is $1^{st}$, stroke is $5^{th}$, and AD is the $6^{th}$ leading cause of death in the U.S. The global market for AD treatment will more than double in value from $4.9 billion in 2013 to reach an estimated $13.3 billion by 2023, according to the research and consulting firm GlobalData. According to the World Health Organization (WHO), ischemic stroke accounts for around 17 million deaths annually. As per the Centers for Disease Control and Prevention (CDC), ischemic stroke leads to 1 out of every 20 deaths costing around $34 billion each year in the U.S. The large patient pool has accelerated the ischemic stroke and AD therapeutics market with a rising aging population, especially in western countries. Hence, there is an impending need for early therapeutics to prevent neuronal damage, disability, and deaths from ischemic stroke, epileptogenesis resulting from traumatic brain injury, impaired cognition in AD, and morbidity in other Glu-induced neurodegenerative diseases, in general.

Without wishing to be bound by theory, the prevention of neuronal damage to the most vulnerable neurons of the brain, such as the CA1 pyramidal neurons of the hippocampus, following transient ischemia can be obtained by prophylactic treatment with novel riluzole-derived drugs that are more selectively target the activity-regulated Gln transporter in synapses. Global cerebral ischemia is frequently encountered in clinical settings of cardiac arrest, profound hypotension, or during vascular occlusion in the course of peri-operative neuro/cardiac surgical procedures. Hypertension, atrial fibrillation, and coronary heart diseases are supporting factors, which also promote the growth of ischemic stroke therapeutics market. Reducing excessive and sustained release of glutamate from pyramidal neuron synapses to prevent $Ca^{2+}$-dependent excitotoxicity in postsynaptic neurons in the hippocampus can be an effective prophylactic and management strategy to suppress neuronal death and cognitive impairment; especially early in the event of on-going various clinical emergencies and in acute and chronic neurodegenerative brain disease.

Competitive Advantage. A problem with riluzole as a therapeutic drug in humans is that it acts on a wide range of molecular targets that may contribute to inhibit synaptic release of neurotransmitters, but which occur over a large dose range (1-500 mM) [62]. Riluzole is reported to inhibit $Na^+$ channels [27-32], $Ca^{2+}$-channels [35], and delayed-rectifier $K^+$ channels, and activates small-conductance $Ca^{2+}$-activated $K^+$ channels and two-pore $K^+$ channels [33, 34]. Despite riluzole's many targets one of its most potent actions is to inhibit activity-regulated Gln/MeAIB transport into neurons ($IC_{50}$~1 mM) [1]. Inhibition of $Na^+$ or $Ca^{2+}$ channels would reduce synaptic chemical transmission in all neurons of the brain and therefore would not preferentially reduce glutamate transmission.

An intervention to alleviate excitotoxicity without interrupting synaptic transmission in general, and glutamate transmission under normal conditions, in particular, would be ideal. Activity-regulated Gln transport is low under normal conditions [1] because other mechanisms likely support synaptic glutamate synthesis and release (i.e., α-ketoglutarate) under normal conditions. Under conditions of excessive glutamate release that occurs during cerebral ischemia, activity-regulated Gln transport in synapses via glutamate/Gln cycling may be more important. Developing drugs to limit activity-driven Gln import in axon terminals to replenish cytoplasmic glutamate levels required to sustain excitotoxic glutamate release is described herein. Such an anti-glutamatergic drug could be directed at Gln transport activity that can be induced by high activity (e.g., $K^+$-depolarization, $Ca^{2+}$-dependent exocytosis) and not a protein integral to vesicular glutamate filling, the release process itself, or $Na^+/Ca^{2+}$ channel activity, which would disrupt normal transmission of all neurotransmitters.

Example 6

Exemplary Method to Quantitate SKA41 Levels in Tissues, Such as Brain Sample and Plasma Twelve week-old male Sprague-Dawley rats were purchased from Charles River Laboratories (Wilmington, Mass.) and housed in microisolator cages with rodent chow and autoclaved water ad libitum. All experiments were in accordance with National Institutes of Health guidelines and approved by the University of California, Davis Institutional Animal Care and Use Committee.

SKA-41 is dissolved in Miglyol 812 neutral oil (caprylic/capric triglyceride; Trade name Neobee M5, Spectrum Chemicals, Gardena, Calif., USA) at 1 mg/mL and injected intraperitoneally at 10 mg/kg. After 1 hour, rats (n=3) are subjected to cardiac puncture under deep isoflurane anesthesia and then sacrificed before removing the brain. Blood is collected into EDTA blood sample collection tubes. Plasma is separated by centrifugation and samples stored at −80° C. pending analysis.

Sample Preparation: SKA-41

Commercial SPE cartridges (Hypersep C18, 100 mg, 1 mL) are purchased from Thermo Scientific (Houston, Tex., U.S.A). Before the extraction, cartridges are conditioned with acetonitrile, 2×1 mL, followed by water 2×1 mL. After loading the SPE cartridges with plasma samples, they are washed with 2×1 mL of 20% acetonitrile in water followed by elution with a 2×1 mL of acetonitrile. Elute fractions are collected and evaporated to dryness. The residues are reconstituted to solution using appropriate volume of acetonitrile and used for LC-MS analysis.

Brain samples are treated as following: 4.0 mL of acetonitrile is added to 200 mg of tissue sample and homogenized thoroughly using a T25 digital ULTRA-TURRAX® homogenizer (IKA® Works Inc., NC, USA). The homogenized samples are centrifuged for 10 min at 4000 rpm, the supernatant is separated and evaporated under a constant air flow as described above. The residues are reconstituted using appropriate volume of acetonitrile. The reconstituted material is loaded onto the preconditioned SPE cartridges it is then eluted with 2 mL of acetonitrile. Load and elute fractions are collected and evaporated to dryness. The residues are reconstituted to solution with 200 µL acetonitrile and used for LC-MS analysis.

LC/MS analysis LC/MS analysis is performed with a Waters Acquity UPLC (Waters, N.Y., USA) equipped with a Acquity UPLC BEH C-18 column 1.7 µM, 2.1×50 mM (Waters, N.Y., USA) interfaced to a TSQ Quantum Access Max mass spectrometer (MS) (Thermo Fisher Scientific, Waltham, Mass., USA). The mobile phase gradient used to elute SKA-41 from the UPLC column is as follows: 10% acetonitrile and 90% water both containing 0.1% formic acid (0-0.5 min) to 75% acetonitrile and 25% water (0.51-1.75 min) and back to 10% acetonitrile and 90% water (1.76-3.5 min) with a flow rate of 0.20 ml per minute. Under these conditions SKA-41 has a retention time of 1.88 minutes.

Using Heated electrospray ionization source (HESI II) in positive ion mode, capillary temperature 300° C., vaporizer temperature: 250° C., spray voltage 3000 V, sheath gas pressure (N2) 30 units, auxiliary gas pressure (N2) 5 units, ion sweep gas pressure (N2) 1 unit, SKA-41 was analyzed by the selective reaction monitoring (SRM) transition of its molecular ion peak 261.0 $(M+1)^+$ into 175.0 and 133.0 m/z. An 8-point calibration curve spanning a concentration range from 50 nM to 10 µM range was developed for quantification.

Three (3) male rats (~300 g) were injected with 10 mg/kg SKA-41 in Miglyol 812 neutral oil i.p. and then sacrificed 1 h later. The brain/plasma ratio for SKA-41 is about 7, demonstrating that SKA-41 is highly brain penetrant. (See FIG. 8). The brain/plasma ratio for riluzole is 1. Further, SKA-41 was well tolerated. As with riluzole, the animals were a little quiet but no overt toxicity or sedation at this dose.

Referring to FIG. 8, brain/plasma ratios of SKA-41 are shown. Commercial SPE cartridges were loaded with plasma or brain samples in acetonitrile. LC/MS analysis was performed with an Acquity UPLC GEH C-18 column. The mobile phase gradient used to elute SKA41 from the UPLC column was as follows: 10% acetonitrile and 90% water both containing 0.1% formic acid (0-0.5 min) to 75% acetonitrile and 25% water (0.51-1.75 min) and back to 10% acetonitrile and 90% water (1.76-3.5 min) with a flow rate of 0.20 ml per minute. Under these conditions SKA41 had a retention time of 1.88 minutes. The average values for plasma and brain concentrations of SKA-41 were 1770 nM and 12,550 nM, respectively.

References Included in this Example, Each of Which Are Incorporated by Reference Herein in Each of Their Entireties 1. Erickson, J. D., *Functional identification of activity-regulated, high-affinity glutamine transport in hippocampal neurons inhibited by riluzole.* J. Neurochem., 2017. 142: p. 29-40.
2. Mackenzie, B. and J. D. Erickson, *Sodium-coupled neutral amino acid (System N/A) transporters of the SLC38 gene family.* Pflugers Arch, 2004. 447(5): p. 784-95.
3. Pulsinelli, W. A., et al., *Ischemic brain injury and the therapeutic window.* Ann NY Acad Sci, 1997. 835: p. 187-193.
4. Petito, C. K. and W. A. Pulsinelli, *Delayed neuronal recovery and neuronal death in rat hippocampus following severe cerebral ischemia: possible relationship to abnormalities in neuronal processes.* J. Cereb. Blood Flow Metab., 1984. 4: p. 194-205.
5. Pulsinelli, W. A., J. B. Brierley, and F. Plum, *Temporal profile of neuronal damage in a model of transient forebrain ischemia.* Ann Neurol., 1982. 11: p. 491-498.
6. Malgouris C., et al., *Riluzole, a novel antiglutamate, prevents memory loss and hippocampal neuronal damage in ischemic gerbils.* J. Neurosci., 1989. 9: p. 3720-3727.
7. Pratt, J., et al., *Neuroprotective actions of riluzole in rodent models of global and focal cerebral ischaemia.* Neurosci Lett, 1992. 140: p. 225-230.
8. Doble, A., *The pharmacology and mechanism of action of riluzole.* Neurology, 1996. 47 (6 Suppl 4): p. S233-S241.
9. Stutzmann, J. M., Wahl, F., Pratt, J., Mary, V., Reibaud, M., Tecoult, E., and Rataud, J., *Neuroprotective profile of riluzole in in vivo models of acute neurodegenerative diseases.* CNS Drug Reviews, 1997. 3: p. 83-101.
10. Bae, H.-J., et al., *Neuroprotective effect of low dose riluzole in gerbil model of transient global ischemia.* Neurosci Lett, 2000. 294: p. 29-32.
11. Heurteaux, C., et al., *Alpha-linolenic acid and riluzole treatment confer cerebral protection and improve survival after focal brain ischemia.* Neuroscience, 2006. 137: p. 241-251.
12. Weng, Y. C. and J. Kriz, *Differential neuroprotective effects of a minocycline-based drug cocktail in transient and permanent focal cerebral ischemia.* Exp. Neurol., 2007. 204: p. 433-442.
13. Ates, O., et al., *Do sodium channel blockers have neuroprotective effect after onset of ischemic insult?* Neurol. Res., 2013. 29: p. 317-323.
14. Verma, S. K., et al., *Enhancement in the neuroprotective power of riluzole against cerebral ischemia using a brain targeted drug delivery vehicle.* ACS Appl Mater Interfaces, 2016. 8: p. 19716-19723.
15. Pereira, A. C., et al., *Age and Alzheimer's disease gene expression profiles reversed by the glutamate modulator riluzole.* Mol. Psychiatry, 2016. 22: p. 296-305.
16. Ruel, J., et al., *Neuroprotective effect of riluzole in acute noise-induced hearing loss.* Neuroreport, 2005. 16: p. 1087-1090.
17. Salameh, J. S., R. H. Brown, and J. D. Berry, *Amyotrophic Lateral Sclerosis: Review.* Semin Neurol., 2015. 35: p. 469-476.
18. Hunsberger, H. C., et al., *Riluzole rescues glutamate alterations, cognitive deficits, and tau pathology associated with P30IL tau expression.* J. Neurochem., 2015. 135: p. 381-394.
19. Nagoshi, N., H. Nakashima, and M. G. Fehlings, *Riluzole as a neuroprotective drug for spinal cord injury: from bench to bedside.* Molecules, 2015. 20: p. 7775-7789.
20. Coleman, N., et al., *The riluzole derivative 2-amino-6-trifluoromethylthio-benzothiazole (SKA-19), a mixed*

KCa2 activator and Na V blocker, is a potent novel anticonvulsant. Neurotherapeutics, 2015. 12: p. 234-249.
21. Hamberger, A. C., et al., *Glutamate as a CNS transmitter. I. Evaluation of glucose and glutamine as precursors for the synthesis of preferentially released glutamate.* Brain Res, 1979. 168: p. 513-530.
22. Hamberger, A. C., et al., *Glutamate as a CNS transmitter. II. Regulation of synthesis in the releasable pool.* Brain Res, 1979. 168: p. 531-541.
23. Norenberg, M. D. and A. Martinez-Hernandez, *Fine structural localization of glutamine synthetase in astrocytes of rat brain.* Brain Res, 1979. 161: p. 303-310.
24. Shank, R. P. and M. H. Aprison, *Present status and significance of the glutamine cycle in neural tissues.* Life Sci., 1981. 28: p. 837-842.
25. Erecinska, M. E. and I. A. Silver, *Metabolism and role of glutamate in mammalian brain.* Prog. Neurobiol., 1990. 35: p. 245-296.
26. Sibson, N. R., et al., *In vivo (13)C NMR measurement of neurotransmitter glutamate cycling, anaplerosis and TCA cycle flux in rat brain during [2-13C]glucose infusion.* J. Neurochem., 2001. 76: p. 975-989.
27. Benoit, E. and D. Escande, *Riluzole specifically blocks inactivated Na channels in myelinated nerve fibre.* Pflugers Arch., 1991. 419: p. 603-609.
28. Herbert, T., et al., *Block of the rat brain IIA sodium channel alpha subunit by the neuroprotective drug riluzole.* Mol Pharmacol, 1994. 45: p. 1055-1060.
29. Song, J. H., et al., *Differential action of riluzole on tetrodotoxin-sensitive and tetrodotoxin-resistant sodium channels.* J. Pharmacol. Exp. Ther., 1997. 282: p. 707-714.
30. Stefani, A., F. Spadoni, and G. Bernardi, *Differential inhibition by riluzole, lamotrigine, and phenytoin of sodium and calcium currents in cortical neurons: implications for neuroprotective strategies.* Exp Neurol, 1997. 147: p. 115-122.
31. Prakriya, M. and S. Mennerick, *Selective depression of low-release probability excitatory synapses by sodium channel blockers.* Neuron, 2000. 26: p. 671-682.
32. Spadoni, F., et al., *Lamotrigine derivatives and riluzole inhibit INa2P in cortical neurons.* Neuroreport, 2002. 13: p. 1167-1170.
33. Grennet, M., et al., *Pharmacological modulation of SK3 channels.* Neuropharmacology, 2001. 40: p. 879-887.
34. Duprat, F., et al., *The neuroprotective agent riluzole activates the two P domain K(+) channels TREK-1 and TRAAK.* Mol. Pharmacol., 2000. 57: p. 906-912.
35. Huang, C. S., et al., *Effects of the neuroprotective agent riluzole on the high voltage-activated calcium channels of rat dorsal root ganglion neurons.* J. Pharmacol. Exp. Ther., 1997. 282: p. 1280-1290.
36. Vered, M., et al., *Anti-ischemia activity of HU-211, a non psychotropic synthetic cannabinoid.* Acta Neurochir., 1994. 60: p. 335-337.
37. Smith, M. L., et al., *Models for studying long-term recovery following forebrain ischemia in the rat: 2. A 2-vessel occlusion model.* Acta Neurol. Scand., 1984. 69: p. 385-401.
38. Belayev, L., Saul, I., Huh, P. W., Finotti, N., Zhao, W., Busto, R., and Ginsberg, M. D., *Neuroprotective effect of high-dose albumin therapy against global ischemic brain injury in rats.* Brain Res, 1999. 845: p. 107-111.
39. Block, F., *Global ischemia and behavioral deficits.* Prog Neurobiol, 1999. 58: p. 279-295.
40. Hong, S.-H., et al., *Docosahexaenoic acid confers enduring neuroprotection in experimental stroke.* J. Neurol. Sci., 2014. 338: p. 135-141.
41. Wahl, F., et al., *Neurological and behavioral outcomes of focal cerebral ischemia in rats.* Stroke, 1992. 23: p. 267-272.
42. Stoppini, L., P. A. Buchs, and D. Muller, *A simple method for organotypic cultures of nervous tissue.* J Neurosci Methods, 1991. 37(2): p. 173-82.
43. Chowdhury, G. M., et al., *Glutamatergic and GABAergic neurotransmitter cycling and energy metabolism in rat cerebral cortex during postnatal development.* J. Cereb. Blood Flow Metab., 2007. 27: p. 1895-1907.
44. Hertz, L., *The glutamate-glutamine (GABA) cycle: importance of late postnatal development and potential reciprocal interactions between biosynthesis and degradation.* Front Endocrinol, 2013. 4: p. 1-16.
45. Bolshakov, V. Y. and S. A. Siegelbaum, *Regulation of hippocampal transmitter release during development and long-term potentiation.* Science, 1995. 269(5231): p. 1730-4.
46. Wasling, P., E. Hanse, and B. Gustafsson, *Developmental changes in release properties of the CA3-CA1 glutamate synapse in rat hippocampus.* J Neurophysiol, 2004. 92(5): p. 2714-24.
47. De Gois S., et al., *Homeostatic scaling of vesicular glutamate and GABA transporter expression in rat neocortical circuits.* J Neurosci, 2005. 25(31): p. 7121-33.
48. Wilson, N. R., et al., *Presynaptic regulation of quantal size by the vesicular glutamate transporter VGLUT1.* J Neurosci, 2005. 25(26): p. 6221-34.
49. Gutierrezabc, R. and U. Heinemanna, *Synaptic reorganiation in explanted cultures of rat hippocampus.* Brain Res., 1999. 815: p. 304-316.
50. Xiang, Z., et al., *Long-term maintenance of mature hippocampal slices in vitro.* J. Neurosci. Meth., 2000. 98: p. 145-154.
51. Hassen, G. W., D. Tian, and P. J. Bergold, *A new model of ischemic preconditioning using young adult hippocampal slice cultures.* Brain Res Protocols, 2004. 13: p. 135-140.
52. Olsen, T. S., U. J. Weber, and L. P. Kammersgaard, *Therapeutic hypothermia for acute stroke.* Lancet Neurol., 2003. 2: p. 410-416.
53. Antonic, A., et al., *Hypothermia protects human neurons.* Int. J. Stroke, 2014. 9: p. 544-552.
54. Van der Worp, H. B., et al., *Hypothermia in animal models of acute ischaemic stroke: a systematic review and meta-analysis.* Brain, 2007. 130: p. 3063-3074.
55. Conti, F. and M. Melone, *The glutamine commute: lost in the tube?* Neurochem Int, 2006. 48(6-7): p. 459-64.
56. Janas, J., J. Skowronski, and L. Van Aeist, *Lentiviral delivery of RNA1 in hippocampal neurons.* Methods Enzymol, 2006. 406: p. 593-605.
57. Kanomori, K. and B. D. Ross, *Electrographic seizures are significantly reduced by in vivo inhibition of neuronal uptake of extracellular glutamine in rat hippocampus.* Epilepsy Res, 2013. 107: p. 20-36.
58. Melikian, H. E., *Neurotransmitter transporter trafficking: endocytosis, recycling and regulation.* Pharmacol. Ther., 2004. 104: p. 17-27.
59. Bonanomi, D., F. Benfenati, and F. Valtorta, *Protein sorting in the synaptic vesicle life cycle.* Prog Neurobiol, 2006. 80(4): p. 177-217.

60. Robinson, M. B., *Acute regulation of sodium-dependent glutamate transporters: a focus on constitutive and regulated trafficking*. Handb. Exp. Pharmacol., 2006. 175: p. 251-275.
61. Kam, K. and R. Nicoll, *Excitatory synaptic transmission persists independently of the glutamate-glutamine cycle*. J Neurosci, 2007. 27(34): p. 9192-200.
62. Bellingham, M. C., *A review of the neural mechanisms of action and clinical efficiency of riluzole in treating Amyotrophic Lateral Sclerosis What we have learned in the last decade?* CNS Neurosci. & Ther., 2011. 17: p. 4-31.

Example 7

Excitotoxicity is the pathological process by which nerve cells are damaged and killed by excessive stimulation by the neurotransmitter glutamate (Glu). Cerebral global ischemia induces excitotoxic neuronal death as a result of excessive presynaptic Glu release. Without wishing to be bound by theory, Glu transmission requires import of glutamine (Gln) into axon terminals from astrocytes to replenish cytoplasmic Glu levels and vesicular stores lost following excessive synaptic Glu release. Thus, blocking import of Gln into synapses represents a new therapeutic strategy to limit continued Glu release under conditions of excitotoxicity. We have recently developed an in vitro assay in rat hippocampal neurons that identifies a novel neuronal activity-regulated Gln transport system, which is potently inhibited by the anti-glutamatergic drug riluzole. Critical barriers to progress in understanding mechanisms involved in excessive Glu release from synapses and excitotoxicity are 1) the molecular identity of the neuronal activity-regulated Gln transporter in synapses is not known, 2) riluzole derivatives that selectively block the neuronal activity-regulated Gln transporter are not available, and 3) the role of the neuronal activity-regulated Gln transporter in vivo has not been determined.

Riluzole blocks excessive synaptic Glu release and can prevent neuronal damage that occurs in conditions of excessive presynaptic Glu release including global cerebral ischemia in rodents. We have identified several more brain penetrant riluzole derivatives, for example SKA41 (and other derivatives), that potently block neuronal activity-regulated Gln transport, but these are not potent modulators of $Na^+$ (i.e., $Na_V$) or $K^+$ (i.e., KCa) channels, compared to riluzole. Molecular identification of riluzole-sensitive, Gln transport function in hippocampal neurons will provide new information about the neurobiology of regulated synaptic Glu release, the Glu/Gln cycle between astrocytes and neurons, and Glu-induced excitotoxicity.

Without wishing to be bound by theory, activity-regulated Gln transport is mediated by SNAT8, a member of the Slc38 gene family of transporters. Neuronal Gln transporters SNAT1 and SNAT2 are excluded from axon terminals, indicating that an unidentified neuronal Gln transporter is required to sustain synaptic glutamatergic transmission.

Objectives herein are to molecularly identify this neuronal activity-regulated Gln transporter and validate it as a new therapeutic target to prevent Glu-induced excitotoxicity in conditions of excessive presynaptic Glu release. Without wishing to be bound by theory, experiments herein will demonstrate 1) selective knock down of SNAT8 will reduce activity-regulated Gln/MeAIB transport in vitro, 2) SKA41, and selected SKA41 derivatives, are potent and specific inhibitors of the neuronal activity-regulated Gln transporter in vitro, and are more brain penetrant than riluzole in vivo, 3) selective knock down of SNAT8 expression in vivo is neuroprotective against Glu-induced excitotoxicity induced by global cerebral ischemia, and 4) in vivo administration of SKA41 (and selected derivatives) is neuroprotective against Glu-induced excitotoxicity induced by global cerebral ischemia.

Objective I: Validate that activity-regulated, $Ca^{2+}$-dependent Gln transport in hippocampal neurons is mediated by SNAT8 and is specifically blocked by selected riluzole-derivatives in vitro. We will molecularly identify the activity-regulated Gln transporter by selective lentiviruses expressing shRNA against SNAT1, SNAT2, SNAT8, NTT4, or with a scrambled shRNA, and neuronal activity-regulated Gln transport will be measured. Rescue experiments will utilize shRNA-resistant cDNAs. We will determine the potency of SKA41 and active SKA41 derivatives to block neuronal activity-regulated Gln/MeAIB transport and test their selectivity over $Na^+$ ($Na_V$) or $Ca^{2+}$-activated (KCa) channels electrophysiologically.

Objective II: Validate that knockdown of SNAT8 in the hippocampus, or administration of SKA41 and active SKA41-derivatives, will reduce pyramidal neuron damage induced by global cerebral ischemia in vivo. Rats will be injected with lentivirus expressing SNAT8 shRNA (or control shRNAs) bilaterally into the hippocampus. After 4 weeks, we will subject animals to bilateral common carotid artery occlusion (bCCAo) and severe hypotension (50 mmHg) for 10 min. A separate group of rats will be treated with SKA41 or the "best" of the active SKA41 derivatives before, during and after ischemia. Cognitive function will be assessed in these rats at weeks 1, 2, 3 and 4. Histopathological evaluation and counts of pyramidal neurons will be assessed using cresyl violet, NeuN staining, and lentiviral-derived EGFP fluorescence after 4 weeks.

Our results suggest a central role for an activity-regulated, neuronal Gln transporter in excitatory axon terminals that supports continued release of Glu under excitotoxic conditions. Targeting this Gln transporter in synapses provides a new therapeutic preventative strategy to limit excessive Glu release, protect vulnerable neurons, and prevent neurologic and cognitive dysfunction in patients who are at risk for global cerebral ischemia.

Significance—Global cerebral ischemia can be encountered in cardiac arrest, profound hypotension, or during vascular occlusion in the course of peri-operative neuro/cardiac surgical procedures [1]. Patients surviving such episodes of cerebral ischemia can show neurobehavioral deficits and neuronal necrosis in vulnerable brain regions. The region most vulnerable to global cerebral ischemia in both animals and humans is the CA1 pyramidal layer of the hippocampus [1-3]. We have recently discovered a neuronal activity-regulated, $K^+$ depolarization-stimulated, $Ca^{2+}$-dependent, high-affinity Gln transport system in hippocampal neurons that is potently inhibited by the anti-glutamatergic compound riluzole and by the riluzole derivatives SKA41, SKA190, SKA193, SKA219, and SKA-247. Our project incorporates a novel approach to molecularly identify this novel target for riluzole, which is a drug that can prevent global cerebral ischemia-induced damage to CA1 neurons in vivo [4-12]. Riluzole is FDA approved for the treatment of ALS and currently is in phase II clinical trials for mild AD [13]. Our discovery of neuronal activity-regulated Gln transport has important implications in advancing basic understanding of the neurobiology of excessive synaptic release of Glu, Glu/Gln cycling between neurons and glia, and Glu-induced neuronal excitotoxicity [12-18].

Without wishing to be bound by theory, Gln is considered to be the preferred precursor for synthesis of neurotransmitter Glu and must be imported into axon terminals from glia where it is synthesized [19-25]. While this 'so called' Glu/Gln cycle is an accepted model of neurotransmitter Glu recycling, the neuronal Gln transporter that mediates Gln transport for excitatory transmission has not been identified. A critical barrier to progress in this field has been the lack of direct functional evidence for activity-regulated and $Ca^{2+}$-dependent Gln transport activity in hippocampal neurons, until now.

Our research challenges the current research paradigms that the neuronal Gln/MeAIB transporters SNAT1 or SNAT2 are involved in supplying Gln for glutamatergic transmission [26-30]. Activity-induced modulation of synaptic efficacy [31-33] and glutamatergic epileptiform activity [34-37] are significantly reduced by application of α-methylaminoisobutyric acid (MeAIB), a competitive inhibitor of the $Na^+$-coupled Gln transporter (SNAT) subtypes 1 and 2 [27]. We were the first to clone and functionally identify the first neuronal Gln transporters SNAT1 and SNAT2 [38, 39], and we have since documented that these two low affinity Gln/MeAIB transporters are excluded from axon terminals [27, 40, 41], indicating that an unidentified neuronal Gln/MeAIB transporter expressed in excitatory synapses supports activity-regulated glutamatergic transmission.

Without wishing to be bound by theory, studies herein will demonstrate that 1) SNAT8 is the activity-regulated Gln/MeAIB transporter in glutamatergic synapses that is potently blocked by riluzole, which decreases Glu release from synapses [6, 42-45]; 2) selected riluzole derivatives (e.g., SKA41-related), are less potent on $Na^+$ or $K^+$ channels than riluzole, yet are potent blockers of activity-regulated Gln/MeAIB transport, more brain penetrant than riluzole, and are neuroprotective in vivo; and 3) selective knockdown of SNAT8 in hippocampal neurons in vivo provides protection against global cerebral ischemia-induced neuronal damage and impaired cognitive function. Additional experiments will validate the role of SNAT8 in excessive Glu release in other animal models of acute and chronic neurodegenerative diseases. When the objectives herein are validated, the concepts, treatments, and preventative interventions related to human disorders of excessive synaptic Glu release will be improved as a result of providing rationale for the development of SNAT8-targeted, riluzole-derived drugs to limit activity-driven Gln import in axon terminals and replenishment of cytoplasmic Glu levels that sustain excitotoxic release [12-18]. Such an anti-glutamatergic drug would be directed at a synaptic Gln/MeAIB transporter that can be induced by high activity (e.g., $K^+$-depolarization) and not a protein integral to vesicular Glu filling or the release process, which would disrupt normal transmission.

Innovation

We are the first to identify the concept that an activity-regulated Gln/MeAIB transporter that displays relative high affinity ($K_m$=30 μM) and operates maximally ($V_{max}$ at 200 μM) following $Ca^{2+}$-dependent exocytosis of this protein to the plasma membrane contributes to sustained and excessive synaptic Glu release.

We have developed new compounds, for example the riluzole-derivative SKA41 and related compounds, that are potent inhibitors of activity-regulated Gln/MeAIB transport, but also display reduced inhibition of $Na^+$ channels (i.e., $Na_V$), and can be more brain penetrant and selective, compared to riluzole.

Without wishing to be bound by theory, SKA41 and its active derivatives can prevent neuronal CA1 damage and cognitive impairment resulting from global cerebral ischemia.

We have developed a new assay to further functionally characterize and to molecularly identify this activity-regulated Gln/MeAIB transporter and will be the first to determine its contribution to neuronal damage in vulnerable brain regions and impaired cognition following cerebral ischemia.

Approach

Statistical methods, sample sizes and power analysis: For in vitro work, two-tailed Student's t-tests will be used and values will be presented as means±SEM. For in vivo work, rats will be randomly allocated to groups, and data acquisition and analysis performed in a blinded manner. Repeated measures analysis of variance (ANOVA), followed by Tukey's procedures to correct for multiple comparisons will be utilized. Differences are considered significant at an alpha level of 0.05. Power analyses of previous work suggests that 10-12 animals/group will be required to achieve a power of 0.85-0.90 in experiments involving neurological/behavioral scores, lesion areas and cell numbers as outcomes. All of these outcome variables will be dealt with under the assumption of asymptotic normality where sample sizes are adequate.

Rigor and Reproducibility. To increase scientific rigor and insure reproducibility of our results we have incorporated elements consistent with recently published NIH guidelines. 1) Preliminary data has been carefully analyzed and repeated to validate objectives herein, 2) We have used the same suppliers of reagents in generation of the preliminary data, 3) We have validated antibodies that we have made and have confirmed that the transporter cDNA clones express proteins of correct size and are recognized by our selective antibodies, 4) We include methods for rigorous statistical analyses and needed sample sizes, 5) We have carefully defined time points of post-ischemic neurodegeneration and associated behavioral changes based upon our extensive experience using these methods, and 6) We have included quantifiable endpoints relevant to each aspect of the project.

Objective I. Validate that Activity-Regulated, $Ca^{2+}$-Dependent Gln/MeAIB Transport in Hippocampal Neurons is Mediated by SNAT8 and is Specifically Blocked by Selected Riluzole-Derivatives In Vitro.

We have discovered a new, neuronal activity-regulated, $K^+$-stimulated, $Ca^{2+}$-dependent Gln transport system that is preferentially inhibited by the anti-glutamatergic compound riluzole in rat hippocampal cultures in vitro [46] (FIG. 1). We used low concentrations of [$^{14}$C]-MeAIB as substrate to characterize this Gln transporter to limit the involvement of the known neuronal Gln/MeAIB transporters SNAT1 or SNAT2, which display low affinity for MeAIB (>0.5 mM) and are not expressed in synapses. The neuronal activity-regulated Gln/MeAIB transport system discovered here displays high affinity ($K_m$=30+/−40 μM) for MeAIB [46]. We find that neuronal activity-regulated Gln/MeAIB transport is coordinately regulated across development [46] with known period of development of Glu/Gln cycling [47, 48] and increased synaptic Glu release in pyramidal neurons in vitro and in vivo [49-52]. Riluzole (left) potently inhibits activity-regulated Gln/MeAIB transport ($IC_{50}$=1.3+/−0.1 μM, n=4), compared to phenytoin ($IC_{50}$=57+/−40 μM, n=3), a well-established $Na_V$ blocker (FIG. 2, top left); most other antiepileptic drugs (20 μM) are inactive (n=3). We tested 36 riluzole derivatives to determine the structure/activity relationship of these compounds to block activity-regulated Gln/MeAIB transport and found 8 active compounds (FIG. 2, top right, SKA-3,7,11,19,32,41,45,51). However, SKA41 was the only structurally unique compound (FIG. 2, middle). The other active compounds were also either known KCa2 activators and/or $Na_V$ blockers [18, 53]. SKA41 has no effect on KCa channels [53] and may not be a potent $Na_V$ blocker. Data indicates that SKA190, SKA193, SKA219, and SKA247 block 90% of transport activity at 10 µM, similarly to SKA41 and riluzole. The $IC_{50}$ values for SKA219 and SKA247 are ~2 µM. The $IC_{50}$ value for SKA219 to inhibit $Na_V1.2$, the major neuronal Nay, is -30 µM (FIG. 2, bottom), demonstrating >10-fold selectivity over $Na_V$ channels.

Polyclonal antibodies have been made in rabbits specific for SNAT1, SNAT2, SNAT7, SNAT8, and NTT4. SDS page analysis of hippocampal total extracts from adult rat brain reveal prominent bands of 55 Kd, 45 Kd and 75 Kd for SNAT7, SNAT8 and NTT4, respectively, which are blocked by the peptide or fusion protein (10 µM) used as the immunogen (FIG. 3). We have also isolated cDNA clones for these five transporters that have been sequence verified and express protein recognized by our antibodies (FIG. 3). SNAT8 is also expressed in synapses (FIG. 4, 5).

Lentiviral SNAT8 shRNA expressing plasmids (pLL3.7) were made using the following shRNA sequences: (cgaatgacacagccatcattgTCTCTT-GAAcaagatggctgtgtcattgc (SEQ ID NO: 1) and ggtcatcacggtgcaatacta-TCTCTT-GAAtagtattgcaccgtgatgacc (SEQ ID NO: 2)) and have made a scrambled (SCRM) shRNA control (cctaaggttaagtcg-ccctcgTCTCTTGAAcgagggcgacttaaccttagg (SEQ ID NO: 3)). Efficiency of transfection is >90% (FIG. 6). Our data validate the use of our new in vitro assay, our reagents, and our methods to screen riluzole-derived compounds to identify more selective blockers of neuronal activity-regulated Gln/MeAIB transport, and to molecularly identify the cDNA that encodes this activity.

A. SNAT8 can be a new therapeutic target for numerous disorders of excessive synaptic Glu release in the CNS [12-18]. Identifying novel (SKA41 and SKA41 derivatives), selective, potent, and more brain-penetrant blockers of activity regulated Gln/MeAIB transport may have improved therapeutic value to prevent neuronal damage and cognitive impairment, compared to riluzole.

B. We will molecularly identify the neuronal transporter expressed in excitatory synapses that mediates activity-regulated Gln/MeAIB transport in vitro [46] and develop more selective blockers of activity-regulated Gln/MeAIB transport in hippocampal neurons.

Obj. 1-A: Lentiviruses expressing shRNA against SNAT1, SNAT2, SNAT7, SNAT8, NTT4, or scrambled shRNA sequences will be generated to knockdown transporter expression in hippocampal neurons in vitro. Neurons will be infected at DIV8 and $Ca^{2+}$-dependent, high-affinity [$^{14}C$]-MeAIB transport will be performed 10 days later. Knockdown of specific transporter proteins will be confirmed by Western blot. n=6 per shRNA; 2 unique shRNAs per transporter; Total=24 rats for 24 independent cultures.

Obj. 1B: Lentiviruses expressing shRNA-resistant cDNAs for any transporter identified in Exp. 1-A will be generated to rescue activity-regulated Gln/MeAIB transport in vitro. The CMV-EGFP reporter cassette in the vector will be excised and replaced with shRNA-resistant transporter (+/−EGFP-tagged) for rescue experiments. Cultures will be infected at DIV8 and Ktstimulated and spontaneous $^{14}C$-MeAIB transport will be performed 10 days later. Transporter expression will be examined by Western blot. Total=12 rats (for cultures).

Obj. 1C: We will further validate the ability of the novel riluzole-derivatives, such as SKA41 and four active SKA41-derivatives SKA190, SKA193, SKA219, and SKA-247 to inhibit neuronal activity-regulated [$^{14}C$]-MeAIB (20□M) transport in vitro. We will determine if these compounds reduce both spontaneous and $K^+$-stimulated transport. We will generate concentration-response inhibition curves. We will determine whether the active blockers act competitively or non-competitively with the transport system identified here. n=6; Total=24 rats (for cultures).

Obj. 1D: We will assess if SKA41 and the four active SKA41 derivatives interact with $Na^+$ or $K^+$-operated channels in vitro. HEK-293 cells transiently (or stably) expressing voltage-gated $Na^+$ or $K^+$ channels will be subjected to electrophysiological recording using the whole-cell patch-clamp technique as described previously [18, 53]. We will use HEK-293 cell lines stably expressing $hNa_V1.1$, $hNa_V1.5$, $hNa_V1.7$, $hNa_V1.4$, $hK_V2.1$ and $mKv3.1$. We will use neuroblastoma N1E-115 cells that stably express $Na_V1.2$. All cells will be voltage clamped to a holding potential of −90 mV, otherwise specified if held at −120 mV in the case of $Na_V1.2$ use-dependence recording. $Na^+$ currents will be elicited by 30-ms pulsed to 0 mV from −90 mV applied every 10 s. $K_V2.1$ and $K_V3.1$ currents will be elicited by 200-ms voltage steps from −90 to 40 mV applied every 10 s.

Without wishing to be bound by theory, the knock-down of spontaneous and $K^+$-stimulated, $Ca^{2+}$-dependent Gln/MeAIB transport activity in hippocampal neurons by SNAT8 shRNA can be rescued by expression of shRNA-resistant SNAT8 alone. SKA41 and several SKA41 derivatives will be competitive blockers of neuronal activity-regulated Gln/MeAIB transport. SKA41 and its active derivatives are inactive on KCa currents [18, 53]. Active SKA41 derivatives will selectively block activity regulated Gln/MeAIB transport and are >10 times less potent than riluzole to block $Na_V$ channels. n=12; (utilizing cell lines).

Alternative sub-objectives 1) Riluzole may act on a wide range of molecular targets to inhibit synaptic Glu release: riluzole inhibits $Na_V$ channels ($IC_{50S}$~1-50 µM) [54-59], activates small-conductance $Ca^{2+}$-activated $K^+$ channels ($EC_{50S}$~10-20 µM) [60], inhibits delayed-rectifier $K^+$ channels and activates two-pore $K^+$ channels (30 to 100 µM) [61], blocks N- and P/Q-type $Ca^{2+}$ channels ($IC_{50}$>40 µM) [62]. While riluzole may be most potent to inhibit activity regulated Gln/MeAIB transport ($IC_{50}$=1 µM) [46], SKA41 and several active SKA41 derivatives ($IC_{50}$~2 µM) may be more selective, brain penetrant, and therefore more potent in vivo. 2) Neuronal toxicity may non-selectively reduce activity-regulated MeAIB transport: Lentiviral infection of neurons is relatively non-toxic [63], but we will confirm cell viability using a commercial kit. 3) Other activity-regulated Gln/MeAIB transporters may exist: SNAT1 and SNAT2 are expressed in cell bodies and proximal dendritic regions [27, 28, 46], not in axon terminals like SNAT8 (FIG. 5, 6). 4) Gln/MeAIB uptake by SNAT8 in an oocyte expression system is only 2-fold above background [64]: This could be due to intracellular sequestration of an activity inducible Gln transporter protein providing a potential regulatory mechanism. 5) The concentration of Gln in CSF and ventricular fluid is 400 µM [65, 66], which is more in line with the relative affinity of SNAT1 and SNAT2 for Gln [27]. Gln levels in extrasynaptic space are low (~30 µM) as recently measured by microdialysis [67]. 6) $Ca^{2+}$-dependent $^{14}C$-MeAIB transport is present under spontaneous conditions and increases following $K^+$-stimulation: This likely reflects differences in constitutive vs. regulated ($K^+$) cycling of SNAT8 between intracellular pools and the plasma membrane [68-71]. 7) Riluzole inhibition of SNAT8 may not be competitive, but non-competitive and dependent on other known (or unknown) targets, such as specialized $Na^+$ channels [6, 18, 45, 57-59, 72]: Inhibition of SNAT8 activity (directly or indirectly) may help explain riluzole's neuroprotective properties to limit excitotoxic Glu release, neuronal damage, and impaired cognition [12-18].

Objective II. Validate that Knockdown of SNAT8 in the Hippocampus, or Administration of SKA41 and Active SKA41-Derivatives, Will Reduce Pyramidal Neuron Damage Induced by Global Cerebral Ischemia In Vivo.

Figure 7:
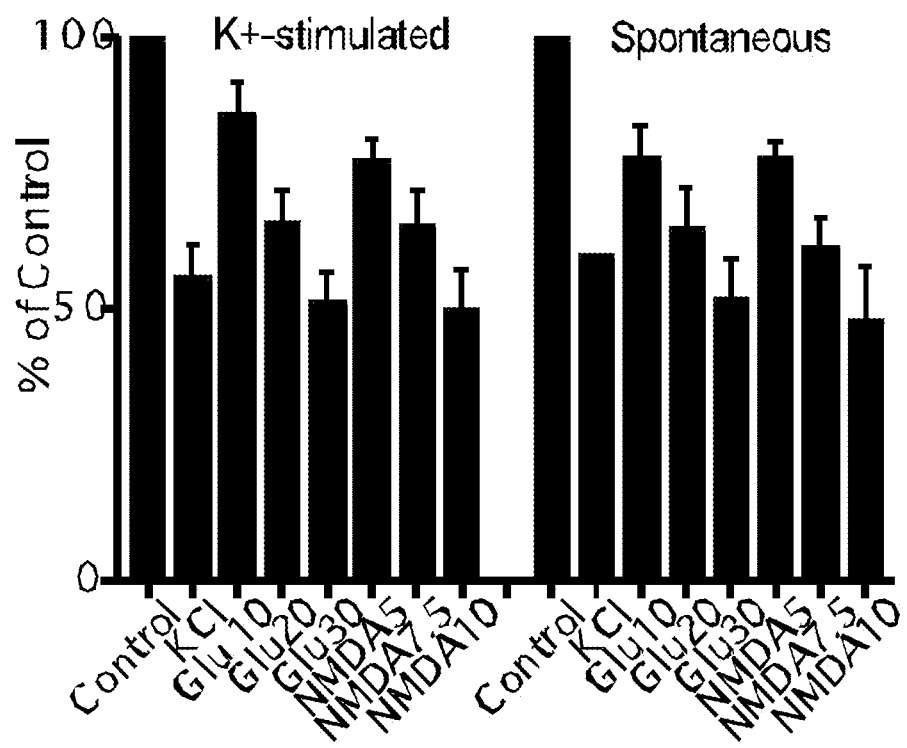
FIG. 7 shows chemical preconditioning reduces activity-regulates transport. Specifically, brief exposure to KCl, Glu, or NMDA (30 min) reduces K$^+$-stimulated and spontaneous MeAIB transport after 24 hr. 4° C. values subtracted. n=2, mean+/−S.D.

Brief neuronal activity (K$^+$ stimulation, Glu or NMDA exposure) induces homeostatic neuroprotective mechanisms (a.k.a., preconditioning [73]). We exposed mature neurons to Krebs buffer containing KCl (45 mM; replacing Na$^+$), Glu (10-3004) or NMDA (5-1004), the buffer was then replaced with conditioned media, and then K$^+$-stimulated and spontaneous Ca$^{2+}$ regulated MeAIB transport was measured after 24 hr (FIG. 7). Activity-regulated Gln/MeAIB transport is reduced (~50%) by these treatments.

Pharmacologic exploitation of mechanisms to reduce synaptic Glu release may treat excitotoxicity resulting from stroke, where treatment options are quite limited and post-synaptic interventions have proven disappointing in human studies because of poor efficacy or unacceptable side effects [74]. Brief exposure to preconditioning agents induces a neuroprotective response that involves modification of Glu synapses to protect against subsequent Glu-induced excitotoxic injury onto principal Glu neurons [75-78]. The neuroprotective property of riluzole (SKA41 and its active derivatives) may include their interaction with SNAT8 activity. Without wishing to be bound by theory, knockdown of SNAT8 in the hippocampus, or that SKA41 and active SKA41 derivatives, will greatly reduce pyramidal neuronal death and prevent cognitive dysfunction observed following global cerebral ischemia. Lentiviral shRNA delivery is safe, efficient, and effective to selectively knockdown gene products in the hippocampus in vivo [79, 80].

We will validate that knockdown of SNAT8 in the hippocampus in vivo reduces CA1 neuronal loss seen following global cerebral ischemia in adult rats. We will also validate that administration of SKA41 and active SKA41-related inhibitors of neuronal-activity regulated Gln transport prevent pyramidal neuron damage following global cerebral ischemia.

Figure 16:
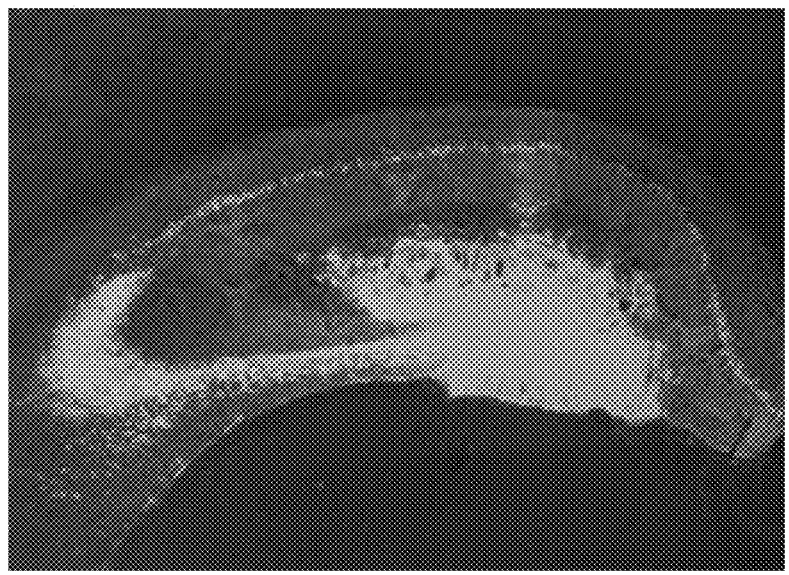
FIG. 16 shows Lentivirus (2 µL) expressing EGFP was injected into the rat dentate gyrus of the rat hippocampus. High levels of EGFP are observed; esp. in the DG and CA3 region.

Obj. 2-A: Wistar rats (3-4 months) of both sexes will be used. Animals will be anesthetized with 3% isoflurane in a mixture of 70% nitrous oxide and 30% 02 and placed in a stereotaxic frame. Lentivirus (transporter shRNA, scrambled shRNA) or saline will be injected (2 µl at 0.2 µl/min) in two positions on each side of the rat hippocampus (site 1: AP=−3.1, ML=+/−1.4, DV=−3.8; site 2: AP=−4.4, ML=+/−3.3, DV=−3.3) (FIG. 16) [81]. We will assess transporter knockdown at 4, 6, and 8 weeks after injection, to achieve maximal effect and achieve steady-state. SNAT8 knockdown will be verified by Westerns of hippocampal synaptosomes and immunohistochemistry 4 weeks after injection. n=6 per group; 3 shRNA treatments; 3 timepoints; both sexes; Total=108 rats.

Figure 17:
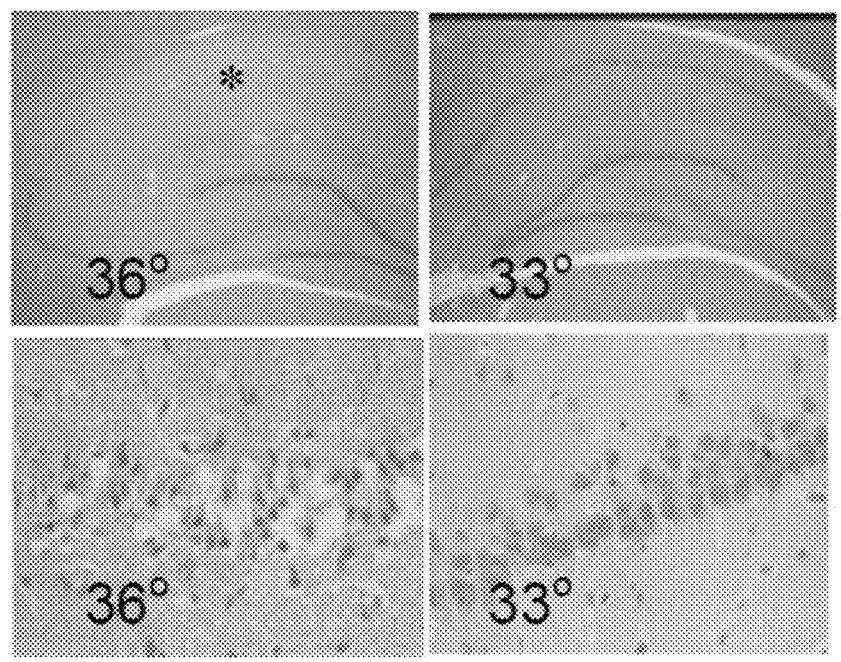
FIG. 17 shows Representative brain sections stained with hematoxylin and eosin from rats subjected to global ischemia under normothermia (left) vs hypothermia (right) followed by 3d of recirculation. CA1 (*) hippocampal necrosis is evident at 36° C. and higher magnification of CA1 region (lower) showing ischemic neurons. On the other hand, normal pyramidal cell staining is present throughout CA1 (*) region under hypothermic conditions (33° C.).

Obj. 2-B: Wistar rats (3-4 months) of both sexes will be injected with lentivirus (SNAT8 shRNA, scrambled shRNA) or saline controls as in Obj. 2-A and after 4-8 weeks will be subjected to global cerebral ischemia. Animals will be anesthetized, intubated and physiological monitoring (rectal/cranial temps, blood gases, blood pressure and plasma glucose) will be conducted during and after ischemia [82]. Animals will also undergo bCCAo (10 min) with simultaneous reduction of mean arterial pressure to 50 mmHg by withdrawal of arterial blood from a femoral artery [83, 84]. Hypothermia is neuroprotective (FIG. 17), so body and head temp will be maintained at 37° C. with rectal and cranial thermistors, a heating lamp and mat during ischemic insult. Cognitive function (Y-maze) will be evaluated on weeks 1, 2, 3 and 4 after ischemia [85, 86]. Animals will be pre-trained before bCCAo. The number of entries, spontaneous alteration and % of alteration will be recorded [87]. After completion of the behavioral tests, histopathological evaluation and counts of the medial, middle, and lateral parts of the hippocampal CA1 region and pyramidal neurons in neocortical layers 3,5, and 6 will be assessed using cresyl violet, NeuN staining, and lentiviral EGFP fluorescence after 4 weeks. n=12 per group; 3 treatments; both sexes; Total—72 rats Obj. 2-C: We will administer SKA41 and the four SKA41 derivatives to male and female rats (10 mg/kg) to determine basic pharmacokinetic (PK) parameters such as half-life ($t_{1/2}$), volume of distribution (Va.) and brain penetration. Drugs will first be administered intravenously in a vehicle consisting of 10% Cremohor E:90% PBS (1 µl/g body weight) and then blood samples (~100 µL) will be collected at 5, 10, and 20 min, and 1, 2, 4, 12 and 24 h and plasma concentrations determined by HPLC/MS. The data will be used to determine $V_d$ and $t_{1/2}$. After a washout period of 10 days (which for a small molecule drug is sufficient to eliminate the compound from the body) rats will then receive 10 mg/kg of the compounds (i.p.) in Migyol 812 (1 µl/g body wt.) and plasma concentrations analyzed as above. After another washout period, rats will again receive 10 mg/kg and after 2 h samples will be taken from blood, brain, liver, spleen, heart and subcutaneous fat for analysis Another group of 10 rats each will receive oral doses in drinking water (+1% saccharin) of 10 mg/kg and blood samples will be collected and analyzed as above. n=5 per group, 5 drugs, 2 treatments; both sexes; Total=100.

We have determined SKA41 concentrations in plasma and brain. We injected 3 male rats (~300 g) with 10 mg/kg SKA41 in Miglyol 812 neutral oil i.p., sacrificed 1 h later, and prepared acetonitrile extracts of plasma and whole brain. Data shows that the brain/plasma ratio is about 7 demonstrating that SKA41 is highly brain penetrant. The brain/plasma ratio for riluzole is 1 [18]. SKA41 was well tolerated with no overt toxicity or sedation at this dose.

Obj. 2D: We will validate the dose-response relationship between riluzole and SKA41 compounds for neuroprotection in vivo by administering riluzole, SKA41, and its "best" SKA41 derivative i.p. at 10, 5, 2.5 and 1 mg/kg to rats 15 min before and 4 hr after bCCAo. Animals will also receive these compounds at the same dose daily throughout the recovery period (4 weeks). Controls will receive only the solvent (Migyol 812). Cognitive function and histopathological evaluation will be evaluated as in Exp. 2B. n=12 per group; 4 treatments; 4 doses; both sexes; Total=384 rats Without wishing to be bound by theory, 1) selective reduction of SNAT8 gene expression in the hippocampus will reduce CA1 neuronal damage and improve cognitive function following global cerebral ischemia. 2) SKA41 and select SKA41-derivatives will be more potent than riluzole in vivo to protect cortical pyramidal neurons and pyramidal neurons in the CA1 region of the hippocampus and to retain cognitive function following global cerebral ischemia. SKA41 and its active derivatives will exhibit better brain penetration and brain retention than riluzole [12, 18]. We do not anticipate any profound sedation or neurotoxicity at these doses.

Alternative sub-objectives 1) Oral administration is the route riluzole is administered in humans: Prophylactic treatment of compounds in drinking water [16] may be a suitable alternative (see Obj.2C). 2) Drug toxicity of SKA41 and derivatives: Toxicity issues will be addressed once we establish the 'best' SKA41 derivative and effective dose. 3) Differences in transporter expression and function between cultures (used in Aim 1) and in adult animals (Aim 2): DIV>16 cultures exhibit a mature VGLUT1-encoded pre-synaptic glutamatergic phenotype like in vivo [49-52]. 4) Lentiviral constructs have no cellular specificity: SNAT8 knockdown by SNAT8 shRNA occurs only in SNAT8-expressing cells. Off target effects of shRNA in SNAT8-negative cells are minimal as we pre-screen all shRNA molecules in NCBI databases for uniqueness. 5) Excitatory transmission persists independently of Glu/Gln cycle [20]: That study utilized DIV 8-10 cultures; activity-regulated Gln/MeAIB transport is low in DIV 8-10 cultures [46]. 6) Blocking SNAT3 and SNAT5-mediated Gln release from glia is a better target to limit the availability of Gln to neurons: Targeting activity-regulated neuronal Gln/MeAIB transport in synapses is a more selective approach to influence synaptic Glu transmission that does not interfere with other cellular functions of Gln. 7) Riluzole is neuroprotective in animal models of global cerebral ischemia [5-8, 11, 12, 88-92], but is more effective when given before onset of the ischemia [11], which can be hard to time precisely: Global cerebral ischemia often occurs following different surgical procedures that may lead to a reduction of blood flow to the brain. Prophylactic treatment of at-risk patients with a SNAT8 inhibitor such as a SKA41 derivative may be advantageous [93, 941, 95-98]. 8) Reduction of SNAT8 activity alone may impair cognition by itself: Riluzole only produces mild sedation at higher doses. 9) Why not just use riluzole for neuroprotection: Riluzole is not very brain penetrant [12] and has reportedly caused recurrent acute pancreatitis [99]. Lipophilic SKA41 derivatives are likely also more brain penetrant and so may be more selective and potent prophylactic agents for neuroprotection.

References Cited in this Example

1. Pulsinelli, W. A., et al., Ischemic brain injury and the therapeutic window. Ann NY Acad Sci, 1997. 835: p. 187-193.
2. Petito, C. K. and W. A. Pulsinelli, Delayed neuronal recovery and neuronal death in rat hippocampus following severe cerebral ischemia: possible relationship to abnormalities in neuronal processes. J. Cereb. Blood Flow Metab., 1984. 4: p. 194-205.
3. Pulsinelli, W. A., J. B. Brierley, and F. Plum, Temporal profile of neuronal damage in a model of transient forebrain ischemia. Ann Neurol., 1982. 11: p. 491-498.
4. Malgouris C., et al., Riluzole, a novel antiglutamate, prevents memory loss and hippocampal neuronal damage in ischemic gerbils. J. Neurosci., 1989. 9: p. 3720-3727.
5. Pratt, J., et al., Neuroprotective actions of riluzole in rodent models of global and focal cerebral ischaemia. Neurosci Lett, 1992. 140: p. 225-230.
6. Doble, A., The pharmacology and mechanism of action of riluzole. Neurology, 1996. 47 (6 Suppl 4): p. S233-S241.
7. Stutzmann, J. M., Wahl, F., Pratt, J., Mary, V., Reibaud, M., Tecoult, E., and Rataud, J., Neuroprotective profile of riluzole in in vivo models of acute neurodegenerative diseases. CNS Drug Reviews, 1997. 3: p. 83-101.
8. Bae, H.-J., et al., Neuroprotective effect of low dose riluzole in gerbil model of transient global ischemia. Neurosci Lett, 2000. 294: p. 29-32.
9. Heurteaux, C., et al., Alpha-linolenic acid and riluzole treatment confer cerebral protection and improve survival after focal brain ischemia. Neuroscience, 2006. 137: p. 241-251.
10. Weng, Y. C. and J. Kriz, Differential neuroprotective effects of a minocycline-based drug cocktail in transient and permanent focal cerebral ischemia. Exp. Neurol., 2007. 204: p. 433-442.
11. Ates, O., et al., Do sodium channel blockers have neuroprotective effect after onset of ischemic insult? Neurol. Res., 2013. 29: p. 317-323.
12. Verma, S. K., et al., Enhancement in the neuroprotective power of riluzole against cerebral ischemia using a brain targeted drug delivery vehicle. ACS Appl Mater Interfaces, 2016. 8: p. 19716-19723.
13. Pereira, A. C., et al., Age and Alzheimer's disease gene expression profiles reversed by the glutamate modulator riluzole. Mol. Psychiatry, 2016. 22: p. 296-305.
14. Ruel, J., et al., Neuroprotective effect of riluzole in acute noise-induced hearing loss. Neuroreport, 2005. 16: p. 1087-1090.
15. Salameh, J. S., R. H. Brown, and J. D. Berry, Amyotrophic Lateral Sclerosis Review. Semin Neurol., 2015. 35: p. 469-476.
16. Hunsberger, H. C., et al., Riluzole rescues glutamate alterations, cognitive deficits, and tau pathology associated with P301L tau expression. J. Neurochem., 2015. 135: p. 381-394.
17. Nagoshi, N., H. Nakashima, and M. G. Fehlings, Riluzole as a neuroprotective drug for spinal cord injury: from bench to bedside. Molecules, 2015. 20: p. 7775-7789.
18. Coleman, N., et al., The riluzole derivative 2-amino-6-trifluoromethylthio-benzothiazole (SKA-19), a mixed KCa2 activator and Na V blocker, is a potent novel anticonvulsant. Neurotherapeutics, 2015. 12: p. 234-249.
19. Hamberger, A. C., et al., Glutamate as a CNS transmitter. II. Regulation of synthesis in the releasable pool. Brain Res, 1979. 168: p. 531-541.
20. Hamberger, A. C., et al., Glutamate as a CNS transmitter. I. Evaluation of glucose and glutamine as precursors for the synthesis of preferentially released glutamate. Brain Res, 1979. 168: p. 513-530.
21. Norenberg, M. D. and A. Martinez-Hernandez, Fine structural localization of glutamine synthetase in astrocytes of rat brain. Brain Res, 1979. 161: p. 303-310.
22. Shank, R. P. and M. H. Aprison, Present status and significance of the glutamine cycle in neural tissues. Life Sci., 1981. 28: p. 837-842.
23. Erecinska, M. E. and I. A. Silver, Metabolism and role of glutamate in mammalian brain. Prog. Neurobiol., 1990. 35: p. 245-296.
24. Sibson, N. R., et al., In vivo (13)C NMR measurement of neurotransmitter glutamate cycling, anaplerosis and TCA cycle flux in rat brain during [2-13C]glucose infusion. J Neurochem., 2001. 76: p. 975-989.
25. Kam, K. and R. Nicoll, Excitatory synaptic transmission persists independently of the glutamate-glutamine cycle. J Neurosci, 2007. 27(34): p. 9192-200.
26. Chaudhry, F. A., R. J. Reimer, and R. H. Edwards, The glutamine commute: take the N line and transfer to the A. J. Cell Biol., 2002. 157(3): p. 349-355.
27. Mackenzie, B. and J. D. Erickson, Sodium-coupled neutral amino acid (System N/A) transporters of the SLC38 gene family. Pflugers Arch, 2004. 447(5): p. 784-95.
28. Conti, F. and M. Melone, The glutamine commute: lost in the tube? Neurochem Int, 2006. 48(6-7): p. 459-64.
29. Broer, S., The SLC38 family of sodium-amino acid co-transporters. Pflugers Arch., 2014(466): p. 155-172.

30. Marx, M.-C., D. Billups, and B. Billups, Maintaining the presynaptic glutamate supply for excitatory neurotransmission. J. Neurosci. Res., 2015. 93: p. 1031-1044.
31. Bacci, A., et al., Block of glutamate-glutamine cycle between astrocytes and neurons inhibits epileptiform activity in hippocampus. J Neurophysiol, 2002. 88(5): p. 2302-10.
32. Armano, S., et al., Localization and functional relevance of system A neutral amino acid transporters in cultured hippocampal neurons. J Biol Chem, 2002. 277(12): p. 10467-73.
33. Liang, S. L., G. C. Carlson, and D. A. Coulter, Dynamic regulation of synaptic GABA release by the glutamate-glutamine cycle in hippocampal area CA1. J Neurosci, 2006. 26(33): p. 8537-48.
34. Kanamori, K. and B. D. Ross, Quantitative determination of extracellular glutamine concentration in rat brain, and its elevation in vivo by system A transport inhibitor, alpha-(methylamino)isobutyrate. J Neurochem, 2004. 90(1): p. 203-10.
35. Tani, H., et al., Modulation of epileptiform activity by glutamine and system A transport in a model of post-traumatic epilepsy. Neurobiol Dis 2007. 25(2): p. 230-8.
36. Tani, H., et al., Glutamine is required for persistent epileptiform activity in the disinhibited neocortical brain slice. J. Neurosci., 2010. 30: p. 1288-1300.
37. Kanamori, K. and B. D. Ross, Electrographic seizures are significantly reduced by in vivo inhibition of neuronal uptake of extracellular glutamine in rat hippocampus. Epilepsy Res, 2013. 107: p. 20-36.
38. Varoqui, H., et al., Cloning and functional identification of a neuronal glutamine transporter. J Biol Chem, 2000. 275(6): p. 4049-54.
39. Yao, D., et al., A novel system A isoform mediating Na+/neutral amino acid cotransport. J Biol Chem, 2000. 275(30): p. 22790-7.
40. Mackenzie, B., et al., Functional properties and cellular distribution of the system A glutamine transporter SNAT1 support specialized roles in central neurons. J Biol Chem, 2003. 278(26): p. 23720-30.
41. Melone, M., et al., Localization of the glutamine transporter SNAT1 in rat cerebral cortex and neighboring structures, with a note on its localization in human cortex. Cereb Cortex, 2004. 14(5): p. 562-74.
42. Bryson, H. M., B. Fulton, and P. Benfield, Riluzole. A review of its pharmacodynamic and pharmacokinetic properties and therapeutic potential in amyotrophic lateral sclerosis Drugs, 1996. 52: p. 549-563.
43. Kretschmer, B. D., U. Kratzer, and W. J. Schmidt, Riluzole, a glutamate release inhibitor, and motor behavior. N. S. Arch. Pharm., 1998. 358: p. 181-190.
44. Lingamaneni, R. and H. C. Hemmings, Effects of anticonvulsants on veratridine- and KCl-evoked glutamate release from rat cortical synaptosomes. Neurosci Lett, 1999. 276: p. 127-130.
45. Wang, S. J., K. Y. Wang, and W. C. Wang, Mechanisms underlying the riluzole inhibition of glutamate release from rat cerebral cortex nerve terminals (synaptosomes). Neuroscience, 2004. 125: p. 191-201.
46. Erickson, J. D., Functional identification of activity-regulated, high-affinity glutamine transport in hippocampal neurons inhibited by riluzole. J. Neurochem., 2017. 142: p. 29-40.
47. Chowdhury, G. M., et al., Glutamatergic and GABAergic neurotransmitter cycling and energy metabolism in rat cerebral cortex during postnatal development. J. Cereb. Blood Flow Metab., 2007. 27: p. 1895-1907.
48. Hertz, L., The glutamate-glutamine (GABA) cycle: importance of late postnatal development and potential reciprocal interactions between biosynthesis and degradation. Front Endocrinol, 2013. 4: p. 1-16.
49. Bolshakov, V. Y. and S. A. Siegelbaum, Regulation of hippocampal transmitter release during development and long-term potentiation. Science, 1995. 269(5231): p. 1730-4.
50. Wasling, P., E. Hanse, and B. Gustafsson, Developmental changes in release properties of the CA3-CA1 glutamate synapse in rat hippocampus. J Neurophysiol, 2004. 92(5): p. 2714-24.
51. De Gois S., et al., Homeostatic scaling of vesicular glutamate and GABA transporter expression in rat neocortical circuits. J Neurosci, 2005. 25(31): p. 7121-33.
52. Wilson, N. R., et al., Presynaptic regulation of quantal size by the vesicular glutamate transporter VGLUT1. J Neurosci, 2005. 25(26): p. 6221-34.
53. Sankaranarayanan, A., Raman, G., Busch, C., Schultz, T., Zimin, P. I., Hoyyer, J., Kohler, R., and Wulff, H., Naphtho[1,2-d]thiazol-2-ylamine (SLA-31, a new activator of KCa2 and KCa3.1 potassium channels, potentiates the endothelium-derived hyperpolarizing factor response and lowers blood pressure. Mol. Pharmacol., 2009. 75: p. 281-295.
54. Benoit, E. and D. Escande, Riluzole specifically blocks inactivated Na channels in myelinated nerve fibre. Pflugers Arch., 1991. 419: p. 603-609.
55. Herbert, T., et al., Block of the rat brain IIA sodium channel alpha subunit by the neuroprotective drug riluzole. Mol Pharmacol, 1994. 45: p. 1055-1060.
56. Song, J. H., et al., Differential action of riluzole on tetrodotoxin-sensitive and tetrodotoxin-resistant sodium channels. J. Pharmacol. Exp. Ther., 1997. 282: p. 707-714.
57. Stefani, A., F. Spadoni, and G. Bernardi, Differential inhibition by riluzole, lamotrigine, and phenytoin of sodium and calcium currents in cortical neurons: implications for neuroprotective strategies. Exp Neurol, 1997. 147: p. 115-122.
58. Prakriya, M. and S. Mennerick, Selective depression of low-release probability excitatory synapses by sodium channel blockers. Neuron, 2000. 26: p. 671-682.
59. Spadoni, F., et al., Lamotrigine derivatives and riluzole inhibit INa2P in cortical neurons. Neuroreport, 2002. 13: p. 1167-1170.
60. Grennet, M., et al., Pharmacological modulation of SK3 channels. Neuropharmacology, 2001. 40: p. 879-887.
61. Duprat, F., et al., The neuroprotective agent riluzole activates the two P domain K(+) channels TREK-1 and TRAAK. Mol. Pharmacol., 2000. 57: p. 906-912.
62. Huang, C. S., et al., Effects of the neuroprotective agent riluzole on the high voltage-activated calcium channels of rat dorsal root ganglion neurons. J. Pharmacol. Exp. Ther., 1997. 282: p. 1280-1290.
63. Janas, J., J. Skowronski, and L. Van Aeist, Lentiviral delivery of RNAi in hippocampal neurons. Methods Enzymol, 2006. 406: p. 593-605.
64. Hagglund, M. G., et al., Transport of L-glutamine, L-alanine, L-arginine and L-histidine by the neuron-specific Slc38a8 in CNS. J. Mol. Biol., 2015. 427: p. 1495-1512.
65. Gjessing, L. R., P. Gjesdahl, and O. Sjaastad, The free amino acids in human cerebrospinal fluid. J Neurochem, 1972. 19(7): p. 1807-8.

66. McGale, E. H., et al., Studies of the inter-relationship between cerebrospinal fluid and plasma amino acid concentrations in normal individuals. J Neurochem, 1977. 29(2): p. 291-7.
67. Kanomori, K. and B. D. Ross, Electrographic seizures are significantly reduced by in vivo inhibition of neuronal uptake of extracellular glutamine in rat hippocampus. Epilepsy Res, 2013. 107: p. 20-36.
68. Melikian, H. E., Neurotransmitter transporter trafficking: endocytosis recycling and regulation. Pharmacol. Ther., 2004. 104: p. 17-27.
69. Bonanomi, D., F. Benfenati, and F. Valtorta, Protein sorting in the synaptic vesicle life cycle. Prog Neurobiol, 2006. 80(4): p. 177-217.
70. Kavalali, E. T. and E. M. Jorgensen, Visualizing presynaptic function. Nat Neurosci, 2014. 17: p. 10-16.
71. Robinson, M. B., Acute regulation of sodium-dependent glutamate transporters: a focus on constitutive and regulated trafficking. Handb. Exp. Pharmacol., 2006. 175: p. 251-275.
72. Martin, D., M. A. Thompson, and J. D. Nadler, The neuroprotective agent riluzole inhibits release of glutamate and aspartate from slices of hippocampal area CA1. Eur. J. Pharmacol., 1993. 250: p. 473-476.
73. Jimenez-Mateos, E. M. and D. C. Henshall, Seizure preconditioning and epileptic tolerance: models and mechanisms. Int. J. Physiol. Pahophysiol. Pharmacol., 2009. 1: p. 180-191.
74. Hogins, J., Crawford, D. C., Jiang, X., and Mennerick, S., Presynaptic silencing is an endogenous neuroprotectant during excitotoxic insults. Neurobiol. Dis 2011. 43: p. 516-525.
75. Grabb, M. C., et al., Preconditioned resistance to oxygen-glucose deprivation-induced cortical neuronal death: alterations in vesicular GABA and glutamate release. Neuroscience, 2002. 115(1): p. 173-83.
76. Moulder, K. L., Cormier, R. J., Shute, A. A., Zormuski, C. F., and Mennerick, S., Homeostatic effects of depolarization on Ca2+ influx, synaptic signaling, and survival. J. Neurosci., 2003. 23: p. 1825-1831.
77. Dave, K. R., et al., Ischemic preconditioning ameliorates excitotoxicity by shifting glutamate/gamma-aminobutyric acid release and biosynthesis J Neurosci Res, 2005. 82(5): p. 665-73.
78. Tauskela, J. S., et al., Preconditioning induces tolerance by suppressing glutamate release in neuron culture ischemia models. J. Neurochem., 2012. 122: p. 470-481.
79. Chew, B., Ryu, J. R., Ng, T., Ma, D., Dasgupta, A., Neo, S. H., Zhao, J., Zong, Z., Bichler, Z., Sajikumar, S., and Goh, E. L. K., Lentiviral silencing of GSK-3B in adult dentate gyrus impairs contextual fear memory and synaptic plasticity. Front. Behav. Neurosci., 2015. 9: p. 158-172.
80. Zhang, J., et al., Synaptic and cognitive improvements by inhibition of 2-AG metabolism are through upregulation of microRNA-188-3p in a mouse model of Alzheimer's disease. J. Neurosci., 2014. 34: p. 14919-14933.
81. Tanaka, R., et al., Neurogenesis after transient global ischemia in the adult hippocampus visualized by improved retroviral vector. Stroke, 2004. 35: p. 1454-1459.
82. Vered, M., et al., Anti-ischemia activity of HU-211, a non-psychotropic synthetic cannabinoid. Acta Neurochir., 1994. 60: p. 335-337.
83. Smith, M. L., et al., Models for studying long-term recovery following forebrain ischemia in the rat: 2. A 2-vessel occlusion model. Acta Neurol. Scand., 1984. 69: p. 385-401.
84. Belayev, L., Saul, I., Huh, P. W., Finotti, N., Zhao, W., Busto, R., and Ginsberg, M. D., Neuroprotective effect of high-dose albumin therapy against global ischemic brain injury in rats. Brain Res, 1999. 845: p. 107-111.
85. Block, F., Global ischemia and behavioral deficits. Prog Neurobiol, 1999. 58: p. 279-295.
86. Hong, S.-H., et al., Docosahexaenoic acid confers enduring neuroprotection in experimental stroke. J. Neurol. Sci., 2014. 338: p. 135-141.
87. Wahl, F., et al., Neurological and behavioral outcomes of focal cerebral ischemia in rats. Stroke, 1992. 23: p. 267-272.
88. Taft, W. C., et al., Phenytoin protects against ischemia-produced neuronal cell death. Brain Res, 1989. 483: p. 143-148.
89. Boxer, P. A., et al., Comparison of phenytoin with noncompetitive N-methyl-D-aspartate antagonists in a model of focal brain ischemia in rat. Stroke, 1990. 21: p. 47-51.
90. Stanton, P. K. and J. R. Moskal, Diphenylhydantoin protects against hypoxia-induced impairment of hippocampal synaptic transmission. Brain Res, 1991. 546: p. 351-354.
91. Chan, S. A., et al., Fosphenytoin reduces hippocampal neuronal damage in rat following transient global ischemia. Acta Neurochirurgica, 1998. 140: p. 175-180.
92. Edmonds, H. L., et al., Topiramate as a neuroprotectant in a rat model of global ischemia-induced neurodegeneration. Life Sci., 2001. 69: p. 2265-2277.
93. Fisher, M., S. Jonas, and R. L. Sacco, Prophylactic neuroprotection for cerebral ischemia. Stroke, 1994. 25: p. 1075-1080.
94. Jonas, S., Prophylactic pharmacologic neuroprotection against focal cerebral ischemia. Ann NY Acad Sci, 1995. 765: p. 21-25.
95. Legos, J. J. and F. C. Barone, Update on pharmacological strategies for stroke: prevention, acute intervention and regeneration. Curr Opin Investig Drugs, 2003. 4: p. 847-858.
96. Savitz, S. I. and M. Fisher, Prophylactic neuroprotection. Curr Drug Targets, 2007. 8: p. 846-849.
97. Seal, J. B., B. N. Buch, and J. D. Marks, New variability in cerebrovascular anatomy determines severity of hippocampal injury following forebrain ischemia in the Mongolian gerbil. Brain Res, 2006. 1074: p. 451-459.
98. Takeda, K., et al., Synaptic vesicles are capable of synthesizing the VGLUT substrate glutamate from α-ketoglutarate for vesicular loading. J. Neurochem., 2012. 121: p. 184-196.
99. Falcao de Campos, C. and M. de Carvalho, Riluzole-induced recurrent pancreatitis J. Clin. Neurosci., 2017. 45: p. 153-154.

Example 8

The beauty of riluzole as a template for new chemistry is that it is what is called a "privileged" structure, meaning that it can exert multiple pharmacological activities when appropriately decorated. Therefore, it can be used as a template for the design of selective drugs for any of its multiple targets by altering its structure. This approach is very likely to result in a very drug-like and CNS penetrant compound. Several riluzole derivatives that I have identified (i.e., SKA-41 and several active SKA-41 derivatives) display excellent potency (IC$_{50}$~2 mM) to inhibit activity-regulated Gln/MeAIB transport in neurons, but may be more selective, brain penetrant, and therefore more potent in vivo than riluzole. We believe that these novel riluzole-derived compounds may be useful tools to support the notion that activity-regulated Gln transport in synapses is involved in excitotoxic glutamate release, and support the progression of these active SKA-41 derivatives to in vivo studies and clinical trials for neuroprotection against acute and chronic Glu-induced neurodegeneration and brain disease.

Ease/Cost of Proof-of-Concept. A novel in vitro assay has been developed that can be used to screen potential drugs for their ability to inhibit activity-regulated Gln/MeAIB transport in hippocampal neurons. For each rat used to prepare a dissociated neuronal culture over 50 data values can be examined that can represent individual compounds, dose-response curves, and various controls in a highly reproducible in vitro assay. Once the comparisons of SKA-41 and its active derivatives to riluzole have been completed in dissociated cultures, their ability to prevent the destruction of CA1 pyramidal neurons by OGD/reperfusion injury in a unique mature organotypic hippocampal slice culture preparation [42, 43] will be examined. Mature slice cultures will be utilized in vitro because they maintain the synaptic architecture, longevity and stability that is characteristic of the adult hippocampus in vivo. In vivo animal models have been shown to faithfully model ischemia-induced neuronal damage, while in vitro models have the potential to be important adjuncts to in vivo studies. In vitro models allow large numbers of samples to be treated and analyzed in one experiment. There is greater access to the neurons before and after ischemia, thus allowing for optical, biochemical and electrophysiological studies that would not be feasible in vivo. In vitro models provide a more controlled environment for the testing of potential neuroprotective drugs.

Research and Development Plan. Excessive presynaptic glutamate release causes the excitatory/inhibitory (E/I) imbalance that is believed to initiate acute and chronic neurodegeneration in many CNS disorders including global and focal ischemia, epileptogenesis and epilepsy, traumatic brain injury, noise-induced hearing loss and in AD, among others. A critical barrier to progress in understanding the mechanisms involved in sustaining excessive glutamate release that leads to excitotoxicity has been the lack of functional information about the transport system that mediates Gln import into excitatory synapses to support this activity, until now. Gln import into axon terminals from glia is required to replenish and maintain vesicular glutamate stores for continued release under high synaptic glutamate activity via a glutamate/Gln cycle between astrocytes and neurons (FIG. 1210). We have recently defined the functional properties of such an activity-regulated Gln transport system in hippocampal neurons and showed that it could be blocked by riluzole, a drug that blocks synaptic glutamate release, and by a-methylisoaminobutyric acid (MeAIB), which blocks Gln uptake into neurons [30]. A goal of this project is to determine whether this novel activity-regulated Gln transport system supports excessive glutamate release under conditions of glutamate-induced excitotoxocity. Without wishing to be bound by theory, activity-regulated Gln transport in hippocampal excitatory synapses can be specifically targeted by selective riluzole-derivatives to prevent excessive glutamate release and provide neuroprotection against OGD/reperfusion injury, an in vitro model of global cerebral ischemia.

Specific Aim 1: Identify selective riluzole-derivatives that preferentially block activity-regulated Gln/MeAIB transport compared to Na$^+$-channel (Na$_V$) blockade. In preliminary studies, we screened over 60 riluzole-derivatives in our novel in vitro assay and identified a class of riluzole-derived compounds that retain potency to block activity-regulated Gln transport but are 10× less potent to block Na$_V$ channels. In this aim, we will study our lead compounds, for example 5 lead compounds, to establish their relative affinity (IC$_{50}$) for the transport system and determine if they act competitively or non-competitively with the activity-regulated Gln/MeAIB transporter under spontaneous conditions and following high K$^+$-induced glutamate release.

Specific Aim 2: Test the prediction that blockade of activity-regulated Gln/MeAIB transport by selective riluzole-derivatives protects hippocampal CA$^1$ pyramidal neurons from OGD/reperfusion injury in vitro. We will use an in vitro model of global cerebral ischemia that involves OGD/reperfusion injury in a mature organotypic hippocampal slice preparation in vitro that leads to excessive presynaptic glutamate release and death of CA1 pyramidal neurons. Without wishing to be bound by theory, SKA-41 and its derivatives that block activity-regulated Gln transport are neuroprotective and will prevent CA1 neuronal damage following OGD/reperfusion injury.

Impact: The development of active riluzole derivatives that are not potent blockers of Na$_V$ channels in neurons as potential novel therapeutic drugs to reduce activity-regulated Gln transport and excitotoxic glutamate release from synapses is innovative. This project incorporates a novel theoretical concept in the discovery of a missing neuronal link in the glutamate/Gln cycle involved in supplying Gln to synapses for excitotoxic glutamate transmission. Resolution of this missing link in the role for activity-regulated Gln transport for synaptic glutamate synthesis that affects excitotoxic glutamate release in hippocampal neurons will provide the basis for future studies to molecularly identify this transporter, and to verify its physiological role in synapses in vivo to better understand the fundamental presynaptic mechanisms that lead to glutamate-induced acute and chronic neurodegenerative diseases.

Aim 1: Identify Selective Riluzole-Derivatives that Preferentially Block Activity-Regulated Gln/MeAIB Transport Compared to Na$^+$-Channel (Na$_V$) Blockade.

Data for Aim 1: We have discovered a novel, neuronal activity-regulated, K$^+$-stimulated, Ca$^{2+}$-dependent Gln transport system that is preferentially inhibited by the anti-glutamatergic compound riluzole in primary rat hippocampal cultures in vitro [30] (FIG. 1012). We used low concentrations of $^{14}$C-MeAIB as substrate to characterize this Gln transporter to limit the involvement of other known neuronal Gln/MeAIB transporters SNAT1 or SNAT2, which display low affinity for MeAIB (>0.5 mM) and are not expressed in synapses (see [44]). The neuronal activity-regulated Gln/MeAIB transport system discovered here displays high affinity (K$_m$=30+/-4 μM) for Gln/MeAIB [30], which matches extrasynaptic levels in vivo. Activity-regulated Gln transport is coordinately regulated across development [30], which occurs during the period of development of glutamate/Gln cycling [31, 45] and increased synaptic glutamate release pyramidal neurons in vitro and in vivo [46-49].

Riluzole is neuroprotective in conditions of excessive glutamate release because it inhibits glutamate release from synapses. Riluzole also inhibits activity-regulated Gln/MeAIB import into hippocampal neurons [30]. Neurons were pre-incubated with riluzole or other anti-glutamatergic agents for 2 min in Ca$^{2+}$-containing Krebs buffer and then incubated with same medium containing $^{14}$C-MeAIB (20 µM) for 15 min. Drugs examined include riluzole, lamotrigine, phenytoin, carbazepam, topiramate, ethosuximide, valproic acid, Gabapentin, zonasamide, and levetiracetam. The relative inhibitory constant ($IC_{50}$) for riluzole to inhibit activity-regulated MeAIB transport is 1.3+/−0.1 µM (FIG. 2, top left panel). Phenytoin, a well-established Na$^+$-channel blocker, displays an $IC_{50}$ value of 57+/−4 µM to block activity-regulated MeAIB transport (FIG. 2, top left panel), which is 50× less potent than riluzole. All other agents tested are ineffective at 20 µM concentration. The relative potency for riluzole and phenytoin described here are consistent with the reported differences between riluzole and phenytoin to provide neuroprotection against global cerebral ischemia [50].

We tested 36 riluzole derivatives to begin to sort out the structure/activity relationship of these compounds to block neuronal activity-regulated Gln/MeAIB transport. We found 8 active compounds that are potent blockers of activity-regulated MeAIB transport (FIG. 2, top right panel, red bars). However, SKA-41 was the only structurally unique compound (FIG. 2, middle panel). The other active compounds are either established Ca$^{2+}$-activated channel (KCa2) activators (SKA-3, SKA-45) or Na$^+$ channel (Na$_V$) blockers (SKA-7 and SKA-32). Riluzole, SKA-19, and SKA-11 are mixed Na$_V$ blockers and KCa activators [51, 52]. Additional chemical derivatives of SKA-41 were synthesized, which have been previously shown have no effect on KCa channels [51]. Preliminary data indicate that SKA-190, SKA-193, SKA-219, and SKA-247 block 90% of transport activity at 10 mM (n=2), similarly to SKA-41, riluzole and the other active compounds. The $IC_{50}$ values for SKA-219 and SKA-247 to inhibit activity-regulated Gln/MeAIB transport are ~2 mM. We tested if any of these SKA-41 derivatives (i.e., SKA-219) could block Na$_V$ channel activity using N1E-115 neuroblastoma cells that express Na$_V$1.2, which is the major neuronal Na$^+$ channel. The $EC_{50}$ concentration of SKA-219 to give half maximal response to inhibit Na$_V$1.2 is ~30 mM (FIG. 2, bottom panel), demonstrating 10-fold selectivity to inhibit activity-regulated Gln/MeAIB transport over Na$_V$ channels.

a. Rationale. Without wishing to be bound by theory, riluzole prevents neuronal damage in many acute and chronic neurodegenerative diseases by inhibiting the synaptic release of glutamate [18-21]. The design of selective riluzole-derived compounds that preferentially target activity-regulated Gln/MeAIB transport in synapses, and not Na$^+$ or KCa channels, may be useful and more selective research tools to support the notion that activity-regulated Gln transport in neurons is a potential new therapeutic target to prevent excitotoxic glutamate release and glutamate-induced neurodegeneration.

b. Design. We will further characterize the ability of the novel riluzole-derivative SKA-41 and four active SKA-41 derivatives SKA-190, SKA-193, SKA-219, and SKA-247 to inhibit activity-regulated $^{14}$C-MeAIB (20 µM) transport in mature (days in vitro [DIV]>16) hippocampal dissociated neuron-enriched cultures. We will assess if these compounds reduce both K$^+$-stimulated and spontaneous activity-regulated transport. We will generate dose-response inhibition curves (IC50) and will determine whether these potent blockers act competitively or non-competitively with the transport system identified here.

We will assess if SKA-41, and these four active SKA-41 derivatives interact with Na$_V$ or K$_V$-operated channels in vitro. Cells transiently (or stably) expressing voltage-gated Na$^+$ or K$^+$ channels will be subjected to electrophysiological recording using the whole-cell patch-clamp technique as described previously [51, 52]. We will use HEK-293 cell lines stably expressing hNa$_V$1.1, hNa$_V$1.5, hNa$_V$1/7, hNa$_V$1.4, and hK$_V$2.1. We will use neuroblastoma N1E-115 cells that natively express Na$_V$1.2. All cells will be voltage clamped to a holding potential of −90 mV, otherwise specified if held at −120 mV in the case of Na$_V$1.2 use-dependence recording. Na$^+$ currents will be elicited by 30-ms pulse to 0 mV from −90 mV applied every 10 s. K$_V$2.1 currents will be elicited by 200-ms voltage steps from −90 to 40 mV applied every 10 s.

Aim 2: Test Whether the Blockade of Activity-Regulated Gln/MeAIB Transport by Selective Riluzole-Derivatives Protects Hippocampal CA1 Pyramidal Neurons from OGD/Reperfusion Injury In Vitro.

Rationale. Patients surviving an episode of cerebral ischemia often show neurobehavioral deficits and neuronal necrosis in vulnerable brain regions. The region most vulnerable to global cerebral ischemia in both animals and humans is the CA1 pyramidal layer of the hippocampus [53-56]. OGD/reperfusion injury is an in vitro model of global ischemia widely used to study various mechanisms of glutamate-induced neuronal cell death and survival in the hippocampus. OGD results in general metabolic failure and increased extra-synaptic K$^+$ levels (>50 mM) that lead to increased excitotoxic release of glutamate from nerve terminals [57, 58]. Ischemia-induced presynaptic hyperexcitability contributes to prolonged excessive glutamate release at synapses that preferentially kills CA1 pyramidal neurons in the hippocampus [1, 59-62]. Pharmacologic exploitation of mechanisms to reduce synaptic glutamate release could potentially treat excitotoxicity resulting from OGD and global cerebral ischemia. We have identified several novel riluzole derivatives, for example SKA-41 (and 4 SKA-41 derivatives), that potently block neuronal activity-regulated Gln transport, but may not be potent modulators of Na$^+$ (i.e., Na$_V$) or K$^+$ (i.e., KCa) channels, compared to riluzole. The neuroprotective property of riluzole, SKA-41, and select SKA-41 derivatives may all include their selective interaction with activity-regulated Gln/MeAIB transport.

Design. We will determine the neuroprotective effects of SKA-41 and 'active' SKA-41 derivatives SKA-190, SKA-193, SKA-219, and SKA-247, compared to riluzole, several inactive derivatives, phenytoin, and vehicle (DMSO) to prevent CA1 neuronal damage following OGD/reperfusion injury in mature organotypic hippocampal slice cultures.

Organotypic hippocampal slice cultures are typically prepared from immature animals (postnatal [P] day 7) [63] and are cultured for two weeks prior to any experiments. Thus, these cultures develop in vitro during a critical period of in vivo process outgrowth, synaptogenesis and functional maturation of stable neural circuits. We have shown that activity-regulated Gln/MeAIB transport is coordinately up-regulated across development [30] during this period of development of glutamate/Gln cycling between neurons and astrocytes [31, 45] and increased synaptic glutamate release in pyramidal neurons in vitro and in vivo [46-49]. While the major excitatory synaptic connections in vivo are faithfully preserved in immature slice cultures, mossy fiber sprouting occurs and eventually spontaneous epileptiform activity is observed [64].

Thus, we will use a novel organotypic hippocampal slice culture procedure where slices are prepared from more mature Sprague Dawley rats ages 20-30 days [42, 43] such that maturation of hippocampal circuits during this critical period ($2^{nd}$ and $3^{rd}$ postnatal weeks) occurs in vivo. These mature slice cultures retain hippocampal cytoarchitecture and synaptic connections up to 3 months in vitro. Spontaneous epileptiform activity is rarely observed suggesting long-term retention of normal neuronal excitability and intact and balanced excitatory and inhibitory synaptic networks [42, 43]. The brain dissection, removal, cooling to 4° C., and slicing (400 mM; McIllwain tissue chopper) of hippocampi, and plating onto Millicell CM filters are the same in both procedures. One critical aspect of the mature slice cultures is that rats are anesthetized with ketamine (100 mg/g) before sacrifice, which blocks NMDA receptor function and glutamate-induced excitotoxicity during the dissection procedure [42, 43]. A second unique and critical aspect is that after the filters are placed into six-well dishes containing 1 ml of culture medium, the cultures are incubated at 32° C. in a 5% CO2 atmosphere for at least two weeks prior to the beginning of all experiments [42, 43]. Pre-clinical studies have suggested that mild hypothermia affects a wide range of cell death mechanisms including energy depletion, free radical formation and glutamate-induced excitotoxicity [65]. Mild hypothermia provides neuroprotection after cardiac arrest, hypoxic-ischemic encephalopathy, and in animal models of ischemic stroke [66, 67].

One to three days before an experiment the cultures will be shifted to a 37° C. incubator in 5% $CO_2$ atmosphere. Mature organotypic hippocampal slices will be incubated in deoxygenated, glucose-free medium for 10 min (to mimic the interruption of the supply of oxygen and nutrients to the brain parenchyma as seen in global cerebral ischemia) or normoxic, glucose-containing medium. Slices will be randomly divided into control group, model group (vehicle), drug intervention group (low-, intermediate-, and high-dose). Riluzole, SKA-41, SKA-190, SKA-193, SKA-219, SKA-247 or phenytoin of different concentrations (5 mM, 20 mM, and 60 mM) will be added to the culture medium 30 min prior to OGD and will be present throughout the experiment until the cultures are terminated. Controls will include an inactive riluzole-derivatives (SKA-89 and SKA-94) and DMSO (vehicle).

To quantify neuronal damage, the fluorescent marker propidium iodide (PI) will be used. PI is a polar substance that enters only dead or dying cells with damaged cell membranes and binds to DNA with a bright red, intensified fluorescence (630 nm) when absorbing blue-green light (493 nm). One day before the addition of drugs, PI (5 mg/ml) is added to the culture medium to allow visualization and quantification of basal cell death ($T_0$). The following day the PI fluorescence in the CA1 subregion will be quantified by image acquisition software. Immediately after image acquisition, the slices will be treated with OGD (10 min) or normoxic conditions. These treatments will be done in an apparatus that has been preheated to 37° C. containing modified Earles balanced salt solution (+/−glucose) bubbled with 95% $N_2$, 5% $CO_2$ or with 20% $O_2$, 75% $N_2$ and 5% $CO_2$. After 10 min treatment, the medium is replaced with fresh medium containing 5 mg/ml PI and the cultures returned to the 37° C. incubator under normoxic conditions. Images of PI fluorescence will be obtained at daily intervals for three days. After the final image acquisition, the medium will be changed, 10 mM NMDA (a glutamate receptor agonist) and 5 mg/ml PI will be added, and the slices will be incubated overnight to achieve maximal neuronal death. The PI fluorescence of maximal neuronal death is defined as $T_{max}$. The percent cell death is as follows: $(T_{24, 48}, or\ _{72}-T_0/(T_{max}-T_0))$.

Glutamate release induced by OGD into the medium will be measured at 1, 2 and 6 h using the Amplex Red Glutamic Acid/Glutamate Oxidase Assay Kit according to the manufacturer's instructions. The extracellular glutamate level is detected as an increase in the resorufin fluorescence value, which will be normalized by subtracting the basal glutamate level of the phenol red-free medium and plotted as the percentage of glutamate released from the control groups.

Scope of work, milestones and outcome that will be achieved within budget. Without wishing to be bound by theory, SKA-41 and selective SKA-41 derivatives (but not the $Na^+$-channel blocker phenytoin) are potent blockers of neuronal activity-regulated Gln/MeAIB transport, similar to riluzole. SKA-41 and SKA-41 derivatives are inactive on KCa currents [51, 52]. Without wishing to be bound by theory, all active SKA-41 derivatives are at least 10× less potent than riluzole to block $Na_V$ channels demonstrating selectivity. Further, SKA-41 and all four active SKA-41 derivatives will greatly reduce the loss of CA1 pyramidal neurons in the hippocampus following OGD/reperfusion injury in vitro. This work will lay the foundation for the continuation of this project to 1) synthesize additional SKA-41 derivatives with even greater selectivity to inhibit activity-regulated Gln transport in neurons with improved brain permeation and 2) further demonstrate neuroprotective properties of potent SKA-41 derivatives in vivo.

Embodiments as described herein will improve the treatments and preventative interventions related to human disorders of excessive synaptic glutamate release that result in glutamate-induced neurodegenerative diseases. This improvement results from the development of riluzole-derived drugs that more specifically limit activity-driven Gln import in axon terminals and replenishment of cytoplasmic glutamate levels that sustain excitotoxic release.

References Included in this Example, Each of Which Are Incorporated by Reference Herein in Each of Their Entireties 1. Benveniste, H., et al., *Elevation of the extracellular concentrations of glutamate and aspartate in rat hippocampus during transient cerebral ischemia monitored by intracerebral microdialysis.* J Neurochem, 1984. 43(5): p. 1369-74.
2. Bittigau, P. and C. Ikonomidou, *Glutamate in neurologic diseases.* J. Child Neurol., 1997. 12: p. 471-485.
3. Obrenovitch, T. P. and J. Urenjak, *Altered glutamatergic transmission in neurological disorders: From high extracellular glutamate to excessive synaptic efficacy.* Prog Neurobiol, 1997. 51: p. 39-87.
4. Dodd, P. R., *Excited to death: different ways to lose your neurons.* Biogerontology, 2002. 3: p. 51-56.
5. Holmes, G. L., *Seizure-induced neuronal injury: animal data.* Neurology, 2002. 59: p. S3-6.
6. Fujimoto, S., et al., *Mechanisms of oxygen glucose deprivation-induced glutamate release from cerebrocortical slice cultures.* Neurosci Res, 2004. 50: p. 179-187.
7. Dudek, F. E. and T. P. Sutula, *Epileptogenesis in the dentate gyrus: a critical perspective.* Prog. Brain Res., 2007. 163: p. 755-773.
8. Kostandy, B. B., *The role of glutamate in neuronal ischemic injury: the role of spark in fire.* Neurol Sci, 2012. 33: p. 223-237.
9. Grabb, M. C., et al., *Preconditioned resistance to oxygen-glucose deprivation-induced cortical neuronal death: alterations in vesicular GABA and glutamate release.* Neuroscience, 2002. 115(1): p. 173-83.
10. DeFazio, R. A., et al., *GABA synapses mediate neuroprotection after ischemic and epsilonPKC preconditioning in rat hippocampal slice cultures.* J Cereb Blood Flow Metab, 2009. 29: p. 375-384.

11. Hogins, J., Crawford, D. C., Jiang, X., and Mennerick, S., *Presynaptic silencing is an endogenous neuroprotectant during excitotoxic insults.* Neurobiol. Dis 2011. 43: p. 516-525.
12. Tauskela, J. S., et al., *Preconditioning induces tolerance by suppressing glutamate release in neuron culture ischemia models.* J. Neurochem., 2012. 122: p. 470-481.
13. Gidday, J. M., *Cerebral preconditioning and ischaemic tolerance.* Nat. Rev. Neurosci., 2006. 7: p. 437-448.
14. Moskowitz, M. A., E. H. Lo, and C. Ladecola, *The science of stroke: mechanisms in search of treatments.* Neuron, 2010. 67: p. 181-198.
15. Lipton, S. A., *Failures and successes of NMDA receptor antagonists: Molecular basis for the use of open-channel blockers like memantine in the treatment of acute and chronic neurologic insults.* NeuroRx, 2004. 1: p. 101-110.
16. Olivares, D., et al., *N-methyl D-aspartate (NMDA) receptor antagonists and memantine treatment for Alzheimer's disease, vascular dementia and Parkinson's disease.* Curr. Alzheimer Res., 2012. 9: p. 746-758.
17. Trotman, M., et al., *The dichotomy of memantine treatment for ischemic stroke; dose-dependent protective and detrimental effects.* J. Cereb. Blood Flow Metab., 2015. 35: p. 230-239.
18. Martin, D., M. A. Thompson, and J. D. Nadler, *The neuroprotective agent riluzole inhibits release of glutamate and aspartate from slices of hippocampal area CA1.* Eur. J. Pharmacol., 1993. 250: p. 473-476.
19. Kretschmer, B. D., U. Kratzer, and W. J. Schmidt, *Riluzole, a glutamate release inhibitor, and motor behavior.* N. S. Arch. Pharm., 1998. 358: p. 181-190.
20. Lingamaneni, R. and H. C. Hemmings, *Effects of anticonvulsants on veratridine-and KCl-evoked glutamate release from rat cortical synaptosomes.* Neurosci Lett, 1999. 276: p. 127-130.
21. Wang, S. J., K. Y. Wang, and W. C. Wang, *Mechanisms underlying the riluzole inhibition of glutamate release from rat cerebral cortex nerve terminals (synaptosomes).* Neuroscience, 2004. 125: p. 191-201.
22. Malgouris C., et al., *Riluzole, a novel antiglutamate, prevents memory loss and hippocampal neuronal damage in ischemic gerbils.* J. Neurosci., 1989. 9: p. 3720-3727.
23. Pratt, J., et al., *Neuroprotective actions of riluzole in rodent models of global and focal cerebral ischaemia.* Neurosci Lett, 1992. 140: p. 225-230.
24. Bae, H.-J., et al., *Neuroprotective effect of low dose riluzole in gerbil model of transient global ischemia.* Neurosci Lett, 2000. 294: p. 29-32.
25. Ruel, J., et al., *Neuroprotective effect of riluzole in acute noise-induced hearing loss.* Neuroreport, 2005. 16: p. 1087-1090.
26. Heurteaux, C., et al., *Alpha-linolenic acid and riluzole treatment confer cerebral protection and improve survival after focal brain ischemia.* Neuroscience, 2006. 137: p. 241-251.
27. Hunsberger, H. C., et al., *Riluzole rescues glutamate alterations, cognitive deficits, and tau pathology associated with P30IL tau expression.* J. Neurochem., 2015. 135: p. 381-394.
28. Pereira, A. C., et al., *Age and Alzheimer's disease gene expression profiles reversed by the glutamate modulator riluzole.* Mol. Psychiatry, 2016. 22: p. 296-305.
29. Verma, S. K., et al., *Enhancement in the neuroprotective power of riluzole against cerebral ischemia using a brain targeted drug delivery vehicle.* ACS Appl Mater Interfaces, 2016. 8: p. 19716-19723.
30. Erickson, J. D., *Functional identification of activity-regulated, high-affinity glutamine transport in hippocampal neurons inhibited by riluzole.* J. Neurochem., 2017. 142: p. 29-40.
31. Hertz, L., *The glutamate-glutamine (GABA) cycle: importance of late postnatal development and potential reciprocal interactions between biosynthesis and degradation.* Front Endocrinol, 2013. 4: p. 1-16.
32. Bellingham, M. C., *A review of the neural mechanisms of action and clinical efficiency of riluzole in treating Amyotrophic Lateral Sclerosis What we have learned in the last decade?* CNS Neurosci. & Ther., 2011. 17: p. 4-31.
33. Benoit, E. and D. Escande, *Riluzole specifically blocks inactivated Na channels in myelinated nerve fibre.* Pflugers Arch., 1991. 419: p. 603-609.
34. Herbert, T., et al., *Block of the rat brain HA sodium channel alpha subunit by the neuroprotective drug riluzole.* Mol Pharmacol, 1994. 45: p. 1055-1060.
35. Song, J. H., et al., *Differential action of riluzole on tetrodotoxin-sensitive and tetrodotoxin-resistant sodium channels.* J. Pharmacol. Exp. Ther., 1997. 282: p. 707-714.
36. Stefani, A., F. Spadoni, and G. Bernardi, *Differential inhibition by riluzole, lamotrigine, and phenytoin of sodium and calcium currents in cortical neurons: implications for neuroprotective strategies.* Exp Neurol, 1997. 147: p. 115-122.
37. Prakriya, M. and S. Mennerick, *Selective depression of low-release probability excitatory synapses by sodium channel blockers.* Neuron, 2000. 26: p. 671-682.
38. Spadoni, F., et al., *Lamotrigine derivatives and riluzole inhibit INa2P in cortical neurons.* Neuroreport, 2002. 13: p. 1167-1170.
39. Huang, C. S., et al., *Effects of the neuroprotective agent riluzole on the high voltage-activated calcium channels of rat dorsal root ganglion neurons.* J. Pharmacol. Exp. Ther., 1997. 282: p. 1280-1290.
40. Grennet, M., et al., *Pharmacological modulation of SK3 channels.* Neuropharmacology, 2001. 40: p. 879-887.
41. Duprat, F., et al., *The neuroprotective agent riluzole activates the two P domain K(+) channels TREK-I and TRAAK.* Mol. Pharmacol., 2000. 57: p. 906-912.
42. Xiang, Z., et al., *Long-term maintenance of mature hippocampal slices in vitro.* J. Neurosci. Meth., 2000. 98: p. 145-154.
43. Hassen, G. W., D. Tian, and P. J. Bergold, *A new model of ischemic preconditioning using young adult hippocampal slice cultures.* Brain Res Protocols, 2004. 13: p. 135-140.
44. Mackenzie, B. and J. D. Erickson, *Sodium-coupled neutral amino acid (System N/A) transporters of the SLC38 gene family.* Pflugers Arch, 2004. 447(5): p. 784-95.
45. Chowdhury, G. M., et al., *Glutamatergic and GABAergic neurotransmitter cycling and energy metabolism in rat cerebral cortex during postnatal development.* J. Cereb. Blood Flow Metab., 2007. 27: p. 1895-1907.
46. Bolshakov, V. Y. and S. A. Siegelbaum, *Regulation of hippocampal transmitter release during development and long-term potentiation.* Science, 1995. 269(5231): p. 1730-4.
47. Wasling, P., E. Hanse, and B. Gustafsson, *Developmental changes in release properties of the CA3-CA1 glutamate synapse in rat hippocampus.* J Neurophysiol, 2004. 92(5): p. 2714-24.

48. De Gois S., et al., *Homeostatic scaling of vesicular glutamate and GABA transporter expression in rat neocortical circuits.* J Neurosci, 2005. 25(31): p. 7121-33.
49. Wilson, N. R., et al., *Presynaptic regulation of quantal size by the vesicular glutamate transporter VGLUT1.* J Neurosci, 2005. 25(26): p. 6221-34.
50. Ates, O., et al., *Do sodium channel blockers have neuroprotective effect after onset of ischemic insult?* Neurol. Res., 2013. 29: p. 317-323.
51. Sankaranarayanan, A., Raman, G., Busch, C., Schultz, T., Zimin, P. I., Hoyyer, J., Kohler, R., and Wulff, H., *Naphtho[1,2-d]thiazol-2-ylamine (SLA-31, a new activator of KCa2 and KCa3.1 potassium channels, potentiates the endothelium-derived hyperpolarizing factor response and lowers blood pressure.* Mol. Pharmacol., 2009. 75: p. 281-295.
52. Coleman, N., et al., *The riluzole derivative 2-amino-6-trifluoromethylthio-benzothiazole (SKA-19), a mixed KCa2 activator and Na V blocker, is a potent novel anticonvulsant.* Neurotherapeutics, 2015. 12: p. 234-249.
53. Pulsinelli, W. A., J. B. Brierley, and F. Plum, *Temporal profile of neuronal damage in a model of transient forebrain ischemia.* Ann Neurol., 1982. 11: p. 491-498.
54. Petito, C. K. and W. A. Pulsinelli, *Delayed neuronal recovery and neuronal death in rat hippocampus following severe cerebral ischemia: possible relationship to abnormalities in neuronal processes.* J. Cereb. Blood Flow Metab., 1984. 4: p. 194-205.
55. Petito, C. K., et al., *Delayed hippocampal damage in humans following cardiorespiratory arrest.* Neurology, 1987. 37: p. 1281-1286.
56. Pulsinelli, W. A., et al., *Ischemic brain injury and the therapeutic window.* Ann NY Acad Sci, 1997. 835: p. 187-193.
57. Choi, D. W., *The role of glutamate neurotoxicity in hypoxic-ischemic neuronal death.* Annu. Rev. Neurosci., 1990. 13: p. 171-182.
58. Szatkowski, M. and D. Attwell, *Triggering and execution of neuronal death in brain ischaemia: two phases of glutamate release by different mechanisms.* Trends Neurosci, 1994. 17(9): p. 359-65.
59. Benveniste, H., et al., *Ischemic damage in hippocampal CA1 is dependent on glutamate release and intact innervation from CA3.* J. Cereb. Blood Flow Metab., 1989. 9: p. 629-639.
60. Choi, D. W., *Excitotoxic cell death.* J. Neurobiol., 1992. 23: p. 1261-1276.
61. Mitani, A., et al., *Origin of ischemia-induced glutamate efflux in the CA1 field of the gerbil hippocampus: an in vivo brain microdialysis study.* J. Neurochem., 1994. 63: p. 2152-2164.
62. Ai, J. and A. Baker, *Long-term potentiation of evoked presynaptic response at CA3-CA1 synapses by transient oxygen-glucose deprivation in rat brain slices.* Exp. Brain Res., 2006. 169: p. 126-129.
63. Stoppini, L., P. A. Buchs, and D. Muller, *A simple method for organotypic cultures of nervous tissue.* J Neurosci Methods, 1991. 37(2): p. 173-82.
64. Gutierrezabc, R. and U. Heinemanna, *Synaptic reorganiation in explanted cultures of rat hippocampus.* Brain Res., 1999. 815: p. 304-316.
65. Olsen, T. S., U. J. Weber, and L. P. Kammersgaard, *Therapeutic hypothermia for acute stroke.* Lancet Neurol., 2003. 2: p. 410-416.
66. Antonic, A., et al., *Hypothermia protects human neurons.* Int. J. Stroke, 2014. 9: p. 544-552.
67. Van der Worp, H. B., et al., *Hypothermia in animal models of acute ischaemic stroke: a systematic review and meta-analysis.* Brain, 2007. 130: p. 3063-3074.

Example 9

Alzheimer's disease (AD) is the most common neurodegenerative disorder, characterized by progressive memory loss and cognitive decline. Histopathologically, brains of AD patients exhibit an accumulation of amyloid plaques, composed of amyloid β (Aβ) peptides, and of neurofibrillary tangles made up of abnormally hyperphosphorylated tau protein. In the early stages of the disease, enhanced depolarization-stimulated release of glutamate (Glu) and accumulation of Aβ and aberrant tau triggers Glu-induced, NMDA receptor (NMDAR)-dependent excitotoxicity that leads to impaired cognition and eventual cell death. Riluzole (Rilotek®) is a medication approved for the treatment of amyotrophic lateral sclerosis (ALS), is an anticonvulsant, and is currently in Phase II clinical trials for AD. Recent work has revealed that riluzole prevents age-related cognitive decline in rats as well as in a transgenic mouse model of AD that expresses mutant human tau. Riluzole also attenuates the learning and memory deficits in an Aβ25-35-induced rat model of AD and attenuates production of toxic AP peptides, amyloid plaque deposition, and cognitive deficits in a mouse model of early-onset AD that harbors five AP precursor protein (APP) and presenilin (PSEN) mutations linked to familial forms of AD (5×FAD). The target of riluzole in AD models is not clear but it is thought to exert its effects, in part, by reducing activity-stimulated synaptic Glu release. The use of riluzole as a therapeutic agent in Glu-induced/NMDAR-dependent excitotoxicity, however, is limited because riluzole is not very brain penetrant, interacts with multiple pharmacologic targets, causes sedation at higher doses and has reportedly caused pancreatitis and interstitial lung disease.

Excessive and sustained Glu release from synapses triggers NMDA-dependent excitotoxicity in many acute and chronic neurodegenerative conditions. Glu release from synapses must be rapidly recycled to maintain the presynaptic Glu supply for excitatory neurotransmission under high neuronal activity. Glutamine (Gln) released from glia is thought to serve as a precursor for Glu in synaptic terminals under these conditions. We have discovered that neural activity stimulates Gln transport in neurons and that such activity-stimulated Gln transport is coordinately regulated with synaptic Glu release. Interestingly, activity-stimulated Gln transport in pyramidal neurons is one of the most potently inhibited targets of riluzole (IC50=1 µM). We have developed novel riluzole-derived drugs that are potent inhibitors of activity-stimulated Gln transport and are neuroprotective for this project. Importantly, these riluzole-derived drugs are more brain penetrant than riluzole, for example up to 10× more brain penetrant than riluzole, more selective against activity-stimulated Gln transport than other targets of riluzole (e.g., $Na^+$ channel blockade) and therefore are more selective, with potentially fewer side effects. Without wishing to be bound by theory, these studies will explore the improved neuroprotective value of these novel compounds in vivo using an early-onset transgenic mouse model of AD expressing APP and PSEN mutations (5×FAD mice).

Specific Aim 1: Validate that Novel Riluzole-Derivatives Preferentially Block Activity-Stimulated Gln Transport in Synapses and are More Brain Penetrant than Riluzole.

We will study our lead riluzole derivatives to establish their relative affinity (IC50) for the activity-stimulated Gln transport system and their kinetic properties, assess their ability to inhibit $Na^+$ or $K^+$ channels, and compare their brain penetrance/pharmacokinetics to that of riluzole. Without wishing to be bound by theory, a novel riluzole derivative (SKA-41) and several SKA-41 derivatives retain potency to block activity-stimulated Gln transport in hippocampal neurons, block the major $Na^+$ channel in neurons (NaV) less potently, and are more brain penetrant than riluzole.

Specific Aim 2: Validate that Novel Riluzole-Derivatives that Preferentially Block Activity-Stimulated Gln Transport in Synapses Reduce Amyloid β Pathology and Improve Learning and Memory in a Transgenic Mouse Model of Early-Onset AD.

The riluzole-derivative SKA-41 and the most potent and brain penetrant SKA-41 derivative will prevent cognitive decline in 5xFAD mice and reduce accumulation of Aβ42 and Aβ oligomer (all forms) plaques in the entorhinal cortex and hippocampus. AP load will be assessed by immunohistochemistry; full-length APP protein and soluble Aβ42 peptide levels will be determined by Western blot. Hippocampal-dependent spatial learning and memory will be evaluated using the Y-maze test.

Impact: Without wishing to be bound by theory, the results of these R21 studies will show that: 1) SKA-41 and its novel active derivatives more potently block activity-stimulated Gln/MeAIB transport than other targets of riluzole (for example, NaV), 2) the riluzole-derivatives SKA-41, SKA-190, SKA-193, SKA-219, SKA-200 and SKA-247 are more brain penetrant and have longer t1/2 than riluzole, and 3) SKA-41 and the most brain penetrant SKA-41 derivative are neuroprotective and prevent Aβ accumulation in neurons and cognitive decline in early-onset AD mice (5xFAD). More brain penetrant riluzole derivatives that selectively block activity-stimulated Gln transport and reduce NMDAR-dependent excitotoxicity and accumulation of Aβ deposits in hippocampal synapses may offer a more selective presynaptic therapeutic approach to AD and other related dementias that will complement existing FDA-approved medications against NMDA-mediated neurotoxicity. Significance.

Presently, an estimated 6 million Americans suffer from AD, and this number is expected to significantly increase in the coming decades as the population ages. Considerable data suggest that the disease process begins years before clinical diagnostic confirmation [1-3]. Novel biomarkers and cognitive tests for preclinical AD [4-15] may identify subjects at risk for development of AD in order to initiate early therapeutic intervention to prevent neuronal Glu-induced/NMDA-dependent excitotoxicity that leads to cognitive impairment. In human subjects with mild cognitive impairment (MCI) and in early stages in a tau animal model of AD an elevation in glutamatergic presynaptic bouton density [16], and increased VGLUT1 levels and Glu release [17] are observed in the hippocampus. Neuronal hyperactivity and increased functional connectivity has been confirmed in preclinical AD, MCI and early AD stages at various levels [18-24]. Increased Glu release and activation of extrasynaptic NMDA receptors leads to excitotoxicity that enhances production of β-amyloid and tau protein, which, in turn, exacerbates excitotoxicity, cell death and further deterioration of cognitive functions [25-34]. While the low affinity, uncompetitive NMDAR antagonist memantine provides some improvement in preventing Aβ production, aggregation and cognition in AD patients [2, 35-40] and in animal models of AD [41-44], development and testing of drugs to reduce excessive Glu release from synapses in animal models of AD has been neglected [45-47]. Our research offers a presynaptic, complementary therapeutic approach to AD and other related dementias.

The scientific premise for the project is that riluzole prevents age-related cognitive decline in rodents [48] and in three well-documented rodent models of AD: 1) a transgenic mouse model of AD expressing mutant human tau (rTg4510) [49, 50], 2) a Aβ25-35-induced rat model of AD 51 and 3) an early-onset AD mouse model that harbors five Aβ precursor protein (APP) and presenilin (PSEN) mutations linked to familial forms of AD (5xFAD mice) [52]. Riluzole also attenuates the production of toxic Aβ peptides and amyloid plaque deposition in 5xFAD mice [52]. The ability of riluzole to confer neuroprotection and prevent cognitive impairment in most neurological conditions characterized by excessive synaptic release of Glu is well-established [53-62]. However, there are limitations of riluzole as a therapeutic agent because it not very brain penetrant and has a short half-life [61, 63-65], has sedative properties [61, 66, 67] and has been reported to induce recurrent acute pancreatitis [68] and interstitial pneumonia [69].

Innovation. A great challenge for biomedical science today is to develop novel disease-modifying approaches for AD that complement approved therapies to delay/prevent NMDA-dependent excitotoxicity that leads to cognitive impairment. We have recently discovered a brain penetrant derivative of riluzole SKA-41 and five SKA-41 derivatives SKA-190, SKA-193, SKA-219, SKA-200 and SKA-247 that potently block activity-stimulated Gln transport activity in neurons. Our preliminary results show that SKA-41 is neuroprotective and an anti-convulsant in two models of excessive Glu release from synapses. Without wishing to be bound by theory, our novel, potent and more brain penetrant riluzole derivatives are superior therapeutic agents to attenuate accumulation of toxic Aβ peptides, amyloid plaque deposition, and memory deficits in an early-onset AD model (5xFAD mice). Reducing activity-stimulated Gln transport in synapses for neuroprotection incorporates a novel theoretical concept that the missing link in the Gln/Glu cycle that supplies Gln to synapses from glia to maintain excessive Glu release may be a novel therapeutic target to limit excitotoxic neural injury in early stage AD.

Statistical methods, sample sizes and power analysis Statistical analyses will be performed using GraphPad Prism software version 7.0 (GraphPad Software Inc). For in vitro work, values will be presented as means±SEM from at least n=3-6 independent cultures. A value of p<0.05 is regarded as statistically significant. Repeated measures analysis of variance (ANOVA), followed by Bonferroni procedures to correct for multiple comparisons, will be used for in vitro and in vivo intergroup comparisons. Post-hoc comparisons between means will be conducted with alpha level adjustment done by a method of simulation based on the number of planned comparisons. Differences are considered significant at an alpha level of 0.05. Our extensive experience with analyses of these types suggests that all of these outcome variables may be dealt with under the assumption of asymptotic normality where sample sizes are adequate. We have chosen sample sizes based on power analysis [70] and past literature utilizing these methodologies [52, 71-75] with the intention to minimize the number of animals to be used.

Rigor and Reproducibility. To increase scientific rigor and insure reproducibility of our results we have incorporated elements consistent with recently published NIH guidelines for r proposals. 1) Preliminary data for each aim have been carefully analyzed and repeated to validate our approach, 2) We have used the same suppliers of reagents in generation of the preliminary data, 3) We include methods for rigorous statistical analyses and needed sample sizes, 4) We have carefully defined time points for AP accumulation and cognitive decline in 5×FAD mice based on past literature utilizing these methodologies [52, 71-75], 5) We have included quantifiable endpoints relevant to each aspect of the project, and 6) We will use male and female rats in the in vivo experiments to determine if there are sex-related differences.

Aim 1. Validate that Novel Riluzole-Derivatives Preferentially Block Activity-Stimulated Gln Transport in Synapses and are More Brain Penetrant than Riluzole.

Preliminary Data for Aim 1. We have recently discovered a novel, neuronal, high-affinity, activity-regulated, $K^+$-stimulated, Gln transport system that is inhibited by the anti-glutamatergic compound 2-(methylamino)isobutyrate (MeAIB) in primary rat hippocampal cultures in vitro (FIG. 1). MeAIB reduces activity-induced modulation of synaptic Glu efficacy [76] and Glu epileptiform activity [77-79]. MeAIB is a transported substrate selective for the system A subpopulation of Gln transporters [80] and is not metabolized, which renders it more stable than Gln. Thus, we used 14C-MeAIB (20 µM) in a whole cell assay to identify and characterize a Gln/MeAIB transporter that relies on extracellular $Ca^{2+}$ ions for expression at the plasma membrane, that is stimulated by $K^+$-depolarization, and that is activity-regulated by glutamatergic transmission [81]. The neuronal activity-stimulated Gln/MeAIB transport system displays high affinity ($K_m$=30+/−4 µM) for MeAIB (and Gln) [81]. $K^+$-stimulated and activity-regulated, spontaneous Gln/MeAIB transport is coordinately regulated [81] with the known period of development (2nd and 3rd postnatal weeks) of increased Glu/Gln cycling between astrocytes and neurons [82, 83] and increased synaptic Glu release from pyramidal neurons in vitro and in vivo [84-87].

Importantly, we find that riluzole (left) potently inhibits activity-regulated Gln/MeAIB transport ($IC_{50}$=1.3+/−0.1 µM) in hippocampal neurons (FIG. 2, top left). Phenytoin, a NaV blocker, is less effective ($IC_{50}$=57+/−4 µM) and most other antiepileptic drugs (20 µM) are inactive, except lamotrigine ($IC_{50}$=20 µM). We tested 36 riluzole derivatives to define structure/activity relationships of these compounds to block neuronal activity-regulated Gln/MeAIB transport. We found 8 active compounds that are potent blockers (FIG. 2, top right panel, red bars): however, when compared to riluzole, SKA-41 was the only structurally unique compound (FIG. 2, middle panel). The other active compounds are also established KCa2 activators (SKA-3, SKA-45), NaV blockers (SKA-7, SKA-32) or are mixed NaV blockers and KCa activators (SKA-11, SKA-19) [61, 88]. We have synthesized 28 chemical derivatives of SKA-41 for this project. Of these, SKA-190, SKA-193, SKA-219, SKA-220, and SKA-247 block 90% of transport activity at 10 µM, similar to riluzole, SKA-19, SKA-41, and the other active riluzole-derived compounds. We tested to determine if any of these SKA-41 derivatives (e.g., SKA-219) could block NaV channel activity using N1E-115 cells that constitutively express NaV1.2, which is the major neural $Na^+$ channel. The $EC_{50}$ concentration of SKA-219 to inhibit NaV1.2 was ~30 µM (FIG. 2, bottom left), demonstrating ~15-fold selectivity to inhibit activity-regulated Gln/MeAIB transport over NaV channels.

We have also determined the concentrations of SKA-41 in plasma and brain (FIG. 8). We injected 3 male rats (~300 g) with 10 mg/kg SKA-41 in Miglyol 812 neutral oil, sacrificed then 1 h later, and prepared acetonitrile extracts of plasma and whole brain. The brain:plasma ratio was ~7 demonstrating that SKA-41 is highly brain penetrant compared to riluzole for which the brain:plasma ratio is ~1 [89, 90]. SKA-41 was well tolerated with no overt toxicity or sedation at this dose.

a. Rationale. Riluzole prevents neuronal damage, in part, by inhibiting the synaptic release of Glu [91-94]. Therefore, selective riluzole-derived compounds that preferentially target activity-regulated Gln transport in synapses, and not $Na^+$ or $K^+$ channels, are likely to be more useful and more selective research tools to support our concept that activity-regulated Gln transport in synapses is required to support excitotoxic Glu release in acute and chronic neurodegeneration.

b. Design. We will further characterize the selective riluzole-derivatives that we have synthesized to determine if they preferentially block activity-regulated Gln transport activity over $Na^+$ or $K^+$ channel blockade. We will also determine the pharmacokinetics and brain:plasma ratios of these compounds in mice.

Exp. 1-A. We will pharmacologically characterize the ability of riluzole, SKA-41 and five active SKA-41 derivatives SKA-190, SKA-193, SKA-219, SKA-220, and SKA-247 to inhibit activity-regulated $^{14}$C-MeAIB transport in dissociated hippocampal cultures. Cultures will be prepared from postnatal (P1) mouse pups (B6SJLF1/J mice; Jackson Laboratory) and transport assays will be performed in mature neurons (DIV16). We will determine if these compounds reduce both $K^+$-stimulated and spontaneous transport, generate concentration-response inhibition curves (IC50) and determine whether they act competitively or noncompetitively with the transport system. n=5 independent cultures per group, 7 drugs; 4 response treatments; Total=1 culture/month-2 years=24 mouse litters.

Exp. 1B. We will assess if SKA-41, and determine if these five active SKA-41 derivatives affect neuronal $Na_V$ or $K_V$ in vitro. Cells transiently (or stably) expressing voltage-gated Na+ or K+ channels will be subjected to electrophysiological recording using the whole-cell patch-clamp technique as described previously [61, 88]. These studies will use HEK-293 cell lines stably expressing h$Na_V$1.1, h$Na_V$1.5, h$Na_V$1.7, h$Na_V$1.4, h$K_V$2.1 and h$K_V$3.1. Neuroblastoma N1E-115 cells will be used for m$Na_V$1.2. All cells will be voltage clamped to a holding potential of −90 mV, otherwise specified if held at −120 mV in the case of NaV1.2 use-dependence recording. $Na^+$ currents will be elicited by 30-ms pulse to 0 mV from −90 mV applied every 10 s. $K_V$2.1 or $K_V$3.1 currents will be elicited by 200-ms voltage steps from −90 to 40 mV applied every 10 s. As an additional control, we will test SKA-41 and its active derivatives on $Na^+$ channel activity in hippocampal pyramidal neurons as described [61]. n=5 per group, 6 drugs; both sexes; Total=30 mice.

Exp. 1C. We will administer SKA-41 and the five SKA-41 derivatives to male and female B6SJLF1/J mice (10 mg/kg; 8 weeks of age) to determine basic pharmacokinetic (PK) parameters such as half-life ($t_{1/2}$), volume of distribution ($V_d$) and brain penetration. Riluzole is usually used at 4-12 mg/kg in rodents [17, 48-50, 53, 54, 56, 57, 59, 60, 62, 64, 66, 73, 95, 96]. Drugs will first be administered to two groups of 5 mice (males and females) intravenously in a vehicle consisting of 10% Cremophore EL/90% PBS (1 µl/g body weight) and then blood samples (~20 µL) will be collected at 5, 10, and 20 min, and 1, 2, 4, 12 and 24 h after injection. We will determine plasma concentrations by HPLC/MS. Results will be used to determine $V_d$ and $t_{1/2}$.

Separate groups of 5 mice will receive 10 mg/kg of the compounds intraperitoneally (i.p) in Migyol 812 (1 µl/g body wt.) and plasma concentrations will be analyzed as above. Blood samples will be collected and analyzed as above. A third group of mice will receive 10 mg/kg (i.p.) and after 2 h samples will be taken from blood, brain, liver, spleen, heart and subcutaneous fat for analysis Once peak plasma concentrations have been determined for SKA-41 and the 'best' SKA-41 derivative in B6SJLF1/J mice, we will measure plasma concentrations and brain:plasma levels following 10 mg/kg (i.p.) in 5×FAD mice to control for any possible differences between 5×FAD and control littermates (B6SJLF1/J). Controls: n=5 per group, 3 groups; 6 drugs; both sexes. 5×FAD mice: n=5 per group, 4 groups; both sexes. Total=220 mice.

Without wishing to be bound by theory, riluzole, SKA-41 and active SKA-41 derivatives (but not phenytoin) will be competitive blockers of neuronal activity-regulated Gln/MeAIB transport. We predict that SKA-41 and all five active SKA-41 derivatives will be inactive on voltage-gated K$^+$ currents. Without wishing to be bound by theory, SKA-41 and the novel, active SKA-41 derivatives will be at least >15× less potent than riluzole to block Nav channels. SKA-41 and all active SKA-41 derivatives will exhibit better brain penetration and brain retention than riluzole. Based on our preliminary studies, we do not anticipate any profound sedation or neurotoxicity at 10 mg/kg.

Other Considerations. 1) There are multiple targets of riluzole that could inhibit synaptic Glu release and provide neuroprotection: It is accepted that riluzole inhibits Nav channels ($IC_{50,S}$~1-50 µM) [98-103], activates small-conductance Ca2+-activated K+ channels ($EC_{50}$>20 µM) 104, inhibits delayed-rectifier K$^+$ channels and activates two-pore K+ channels ($IC_{50}$>30 µM) 105, blocks N- and P/Q-type Ca$^{2+}$ channels ($IC_{50}$>40 µM) 106, inhibits protein Kinase C ($IC_{50}$>30 µM) 107 and enhances the activity of glutamate transporters GLAST, GLT1 and EAAC1 ($EC_{50}$>100 µM) [108]. Despite riluzole's many targets one of its most potent actions is to inhibit activity-regulated Gln/MeAIB transport ($IC_{50}$~1 µM) (FIG. 2, top left). The attractiveness of riluzole as a template for new chemistry is that it is what is termed a "privileged" structure, meaning that it can exert multiple pharmacological activities when appropriately decorated. Therefore, riluzole can be used as a template for the design of selective drugs for any of its multiple targets by altering its structure [62, 109, 110]. SKA-41 and several active SKA41 derivatives are potent inhibitors of activity-stimulated Gln transport (FIG. 2, top left and bottom right) and may be more selective (FIG. 2, bottom left) with less sedation, more brain penetrant (FIG. 8) and therefore more potent in vivo. 2) An intervention to alleviate excitotoxicity without interrupting normal transmission would be ideal: We provide a rationale for developing anti-glutamatergic drugs directed at synaptic Gln transport that is induced by high activity (e.g., K$^+$-depolarization, Ca$^{2+}$-dependent exocytosis) and not a protein integral to vesicular Glu filling, the release process itself, Na$^+$ or Ca$^{2+}$ channel activity, or postsynaptic Glu receptors which would disrupt normal transmission. Activity-regulated Gln transport is low under normal conditions because other mechanisms support synaptic Glu synthesis and release (i.e α-ketoglutarate) under normal conditions [111-114]. Under increased activity the Glu/Gln cycle is more important. 3) In humans, high inter- and intraindividual variability of riluzole serum concentrations following oral administration are observed due to variable first pass effects by the liver [115-118]: Differences in hepatic P450 enzymes CYP1A2 or other CYP expression would be less significant in inbred mouse strains compared to outbred lines or humans. While variability in plasma levels following oral administration is seen with all small molecule drugs we will examine the metabolism of SKA-41 and the 'best' SKA-41 derivative in future studies. 4) SKA-41 and its derivatives may be toxic. Although we did not observe any untoward effects of SKA-41 at 10-30 mg/kg, we will carefully test for toxicity once the 'best' SKA-41 derivatives and effective doses are identified. 5) It has been reported that Glu transmission persists independently of the Glu-Gln cycle [113]: The studies reported in the Kam and Nicoll article used immature neuronal cultures (DIV8-10) and rats as young as P12. We show that activity-regulated Gln/MeAIB transport is very low in immature hippocampal neurons [81]. Furthermore, many studies [76-79, 112, 119] support the premise that Glu-Gln cycling sustains synaptic Glu release under high neural activity.

Aim 2: Validate that Novel Riluzole-Derivatives that Preferentially Block Activity-Stimulated Gln Transport in Synapses Reduce Amyloid β Pathology and Improve Learning and Memory in a Transgenic Mouse Model of Early-Onset AD.

Preliminary Data for Aim 2: Our preliminary data show that the novel, brain-penetrant riluzole-derivative SKA-41 that potently inhibits activity-regulated Gln transport prevents neuronal damage in two models of excitotoxic injury relevant to cerebral ischemia and epilepsy, an in vitro model of oxygen-glucose deprivation (OGD) and the kainic acid (KA) seizure in vivo model. Both of these models require excessive synaptic Glu release from pyramidal neurons.

Figure 18:
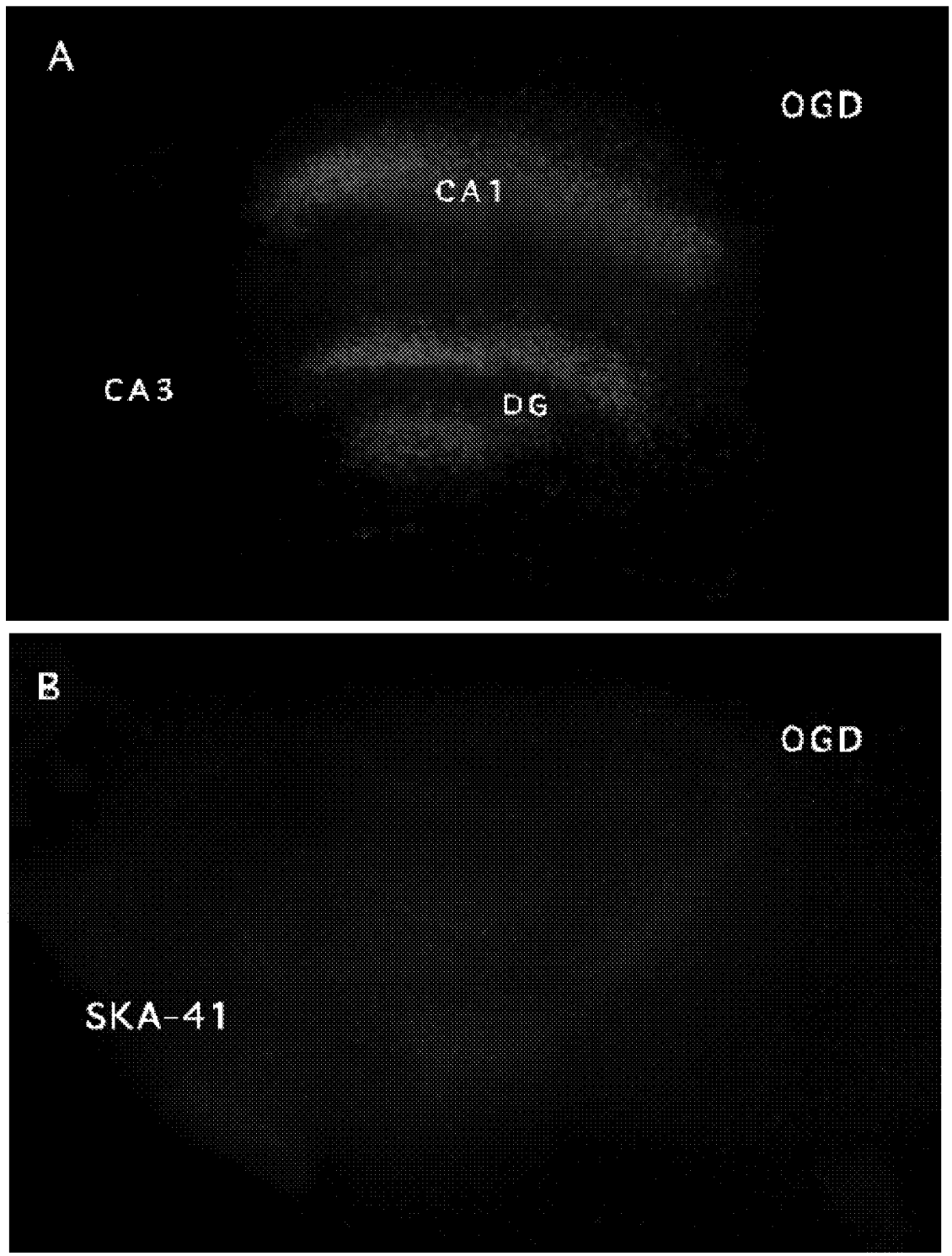
FIG. 18 provides representative images showing that SKA-41 (30 µM) prevents OGD-induced neural injury in organotypic hippocampal slice cultures.

OGD is an in vitro model for transient cerebral ischemia. In preliminary studies, we prepared hippocampal slice cultures from P7-8 rat pups. Experiments were performed at 14 DIV, when presynaptic Glu function is maximal [82, 83] and synapse formation and NMDAR subunit expression have reached a developmental stage sufficient to sensitize the slice to excitotoxic injury [129]. Propidium iodide (PI), which binds to DNA in a nonspecific manner by penetrating damaged phospholipoid bilayers, was used to assess neural injury 24 h after OGD. We observed obvious PI staining of both area CA1 and the DG following a 20 min period of OGD (FIG. 18). We observed that SKA-41 completely prevents PI staining indicating neuronal protection. SKA-41 was present 30 min prior to OGD, during OGD and during the 24 h recovery period. Similar results were obtained using MK-801 (20 µM), riluzole (30 µM), and NBQX (10 µM)/AP5 (50 µM) (not shown).

Various benzothiazoles including riluzole and riluzole derivatives (e.g., SKA-19) are potent anti-convulsants [61, 62, 128, 130]. Systemic administration of the glutamate analog, kainic acid (KA), to rats produces progressive limbic seizures culminating in status epilepticus that results in neuronal loss within limbic structures [131] in a pattern similar to that observed in human temporal lobe epilepsy [132, 133]. We injected a group of control rats and a group of rats that were pre-treated with SKA-41 (30 mg/kg; 30 min; n=5) with KA (8 mg/kg) (i.p.). The behavior of rats in the control group was as expected with an initial catatonic posture with staring behavior that lasted for more than an hour. Myoclonic twitching was observed within 30 min of treatment, which at a later stage resulted in generalized clonic-tonic convulsions involving the whole body. Four of the 5 control rats exhibited frequent rearing and falling over to one side, and hemorrhagic foam was observed coming from the mouth. In contrast, clonic-tonic convulsions were not observed in any of the rats pretreated with SKA-41. All five experimental rats treated with SKA-41 displayed staring behavior and twitching of the head and face but these signs disappeared within 2 h after KA injection.

Excessive and sustained release of Glu from pyramidal neurons triggers Glu-induced, NMDAR-dependent excitotoxicity in global cerebral ischemia, epilepsy and AD [16-18, 20, 28, 120-126]. Riluzole prevents damage to CA1 hippocampal neurons that occurs following global cerebral ischemia in rodents in vivo [53, 54, 57], [59, 64], is an anti-convulsant [61, 62, 127, 128], and prevents cognitive impairment in aging and in animal models of AD [17, 48-52, 73]. Without wishing to be bound by theory, the more brain penetrant SKA-41 will also be neuroprotective in models of AD.

a. Rationale. Those at risk for AD often exhibit hippocampal hyperexcitability in the years preceding diagnosis [18, 20-22]. Work with the tau mouse model of AD (rTg4510) suggests that this increase in hyperexcitability is likely mediated by an increase in depolarization-evoked Glu release from synapses [49, 50]. Excessive Glu release from the presynaptic terminals has also been suggested as a mechanism for increased amyloid production via NMDA receptor-mediated $Ca^{2+}$ influx [25-27, 134, 135]. Soluble β-amyloid peptide fragments also stimulate Glu release from hippocampal synapses [136-139]. The close apposition of glutamatergic terminals containing VGLUT1 to the APP-positive neurons in the hippocampus provide an anatomical basis to suggest a role of endogenously derived amyloid β peptides in the presynaptic regulation of Glu release from selected brain regions [28]. Hence, pharmacologic exploitation of means to reduce excessive synaptic Glu release could prevent NMDAR-induced excitotoxicity and excessive production of β amyloid peptides. The 5×FAD model of AD develops severe amyloid pathology. These mice accumulate high levels of intraneuronal Aβ42 beginning around 1.5 months of age with amyloid deposition rapidly following around two months, first in the subiculum and layer 5 of the cortex and increasing rapidly with age. Plaques spread throughout the hippocampus and cortex by six months of age. Synapse degeneration, neuronal loss and deficits in spatial memory in the Y-maze are observed at approximately four to five months [140]. Riluzole treatment (10 mg/kg) greatly reduces β-amyloid accumulation and rescues cognitive impairment in 5×FAD mice [52].

b. Design. We will validate that the brain penetrant SKA-41 and the 'best' SKA-41 derivative prevent cognitive impairment and AP disposition in the brains of 5×FAD mice, compared to riluzole. The strategy to select the 'best' SKA-41 derivative will be based upon efficiency (Exp. 1A), selectivity (Exp. 1B) and pharmacokinetics (Exp. 1C). Mice will receive daily injections (i.p.) of drug (10 or 2 mg/kg) from 1 to 6 months of age. A control group of 5×FAD mice and the wild-type (wt) littermates will receive vehicle (Migyol 812 alone).

The Y-maze will be used to test short-term spatial memory retention as described [52]. One day before Y-maze testing, mice will be habituated to an open field in the same room where the test will take place. On the day of testing, mice will be placed in the 'start' arm and allowed to explore the 'start' and 'familiar' arm for 10 min while the 'novel' arm is blocked. After one hour, the mice will be placed back into the 'start' arm for a 10-min trial and allowed to explore all three arms. The start, familiar, and novel arms will be changed for each mouse. Cues of different sizes and patterns will be placed on the curtain surrounding the maze to aid the mice in spatial orientation. Time in each arm, as well as frequency of entries, distance, and velocity will be automatically recorded and tracked by Noldus Ethovision video tracking system. The ratios of start/(start+familiar) for acquisition and novel/(novel+familiar) for trial will be calculated using the time spent in those arms. The rationale for the test is that a mouse with intact memory will spend a higher percentage of time in the novel arm during the trial phase due to their tendency to explore novel environments. n=10 per group, 2 groups; 2 drugs; 2 doses; both sexes=240 mice. Controls n=10 per group, 2 groups, both sexes=40 mice. Total=280 mice.

Without wishing to be bound by theory, the riluzole derivative SKA-41 and the 'best' SKA-41 derivative will rescue the cognitive impairment and reduce AP pathology in 5×FAD mice following a single/daily administration, and at lower doses compared to riluzole. SKA-41 and active SKA-41 derivatives are as potent as riluzole to block activity stimulated Gln/MeAIB transport in neurons, yet riluzole is not very brain penetrant, has high first pass hepatic metabolism and a short half life, and therefore must be continuously administered.

Other Considerations. 1) 5×FAD mice do not correctly model AD [141, 142] We will use rTg4510 and rTg3696AB mice [143, 144] that include another biological sign of AD—neurofibrillary tangles made of tau protein—in future studies. Recent studies indicate that riluzole rescues glutamate alterations, cognitive deficits and tau pathology in the hippocampus of rTg4510 mice [49, 50]. Initially, we will use 5×FAD mice because these mice exhibit robust AP accumulation, rapidly display cognitive deficits and riluzole (10 mg/kg) has recently been shown to reduce Aβ accumulation and cognitive deficits in these mice [52]. Without wishing to be bound by theory, our brain penetrant riluzole derivatives will prevent AP accumulation and cognitive deficits at a lower dose than riluzole. 2) Repeated i.p. injections may be stressful: We have injected 5×FAD mice and control littermates (i.p.) for up to 4 months without any adverse effects [71, 72]. 3) In humans, riluzole is administered orally (twice daily): Treatment of animals orally may be a suitable alternative although lipophilic SKA-41 derivatives may have limited solubility in drinking water. We can try gavage to assess oral availability and then the compounds could be added into the diet (Research Diets; New Brunswick, N.J.) 145. 4) Use-dependent NMDAR antagonists (e.g., memantine) together with cholinesterase inhibitors (e.g., donepezil) are already FDA approved in the symptomatic treatment of AD [146, 147]. Riluzole derivatives that selectively block activity-regulated Gln transport into axon terminals may offer a complementary presynaptic glutamatergic therapeutic approach to early stage AD to prevent excessive Glu release from synapses. 5) Very early time window in which Glu excitotoxicity must be targeted in AD: The development of biomarkers and cognitive tests for preclinical AD that indicate neuronal hyperactivity and increased functional connectivity [18, 19, 21, 22, 24] will allow for early therapeutic intervention. The development of more specific drugs to reduce synaptic Glu synthesis and excitotoxic Glu release that do not affect normal Glu transmission may delay/prevent cognitive dysfunction and neural injury for more successful aging. 6) The neuroprotective property of riluzole in AD models may occur by increasing the activity/levels of EAAT2/GLT1 in astrocytes [108, 148-151]: We will assess whether GLT-1 is down regulated at 5 months in 5×fad mice by quantitative Western blots and qPCR [152]. We will also determine if levels of GLT-1 are increased by SKA-41 in control mice. 7) Gln is also a precursor for GABA synthesis Riluzole has no effect on SNAT1 Gln transporter that is expressed in GABAergic interneurons or SNAT2, which is expressed in the cell soma of Glu neurons. The molecular identity of the activity-stimulated Gln transporter expressed in synapses is not known. 8) SKA-41 is not currently FDA approved: 9) Riluzole can be used for neuroprotection in humans instead because it is effective in transgenic animal models of AD: The effectiveness of riluzole as a therapeutic agent is limited in humans because riluzole has multiple targets that lead to various side-effects, it is not very brain penetrant and it has a short half-life. Recently efforts to increase the half-life and brain penetrance of riluzole have been reported [64, 65].

Without wishing to be bound by theory, the studies discussed herein can be useful for 1) establishing the safety, efficacy and potential side-effects of potent and brain penetrant SKA-41 riluzolederivatives, 2) testing active SKA-41 derivatives to prevent other neurodegenerative diseases such global cerebral ischemia and traumatic brain injury-induced epileptogenesis and 3) molecularly identifying the activity-regulated Gln/MeAIB transporter in hippocampal neurons and establish that SKA-41 blocks its activity and reduces activity-stimulated Glu release from synapses.

References Included in this Example, Each of Which Are Incorporated by Reference Herein in Each of Their Entireties 1. Price, J. L. & Morris J. C. Tangles and plaques in nondemented aging and "preclinical" Alzheimer's disease. *Ann. Neurol.* 45, 358-368 (1999).
2. Danysz, W., Parsons, C. G., Stoffler, H.-J. & G., Q. Neuroprotective and symptomological action of memantine relevant for Alzheimer's disease—a unified glutamatergic hypothesis on mechanism of action. *Neurotoxicity Res.* 2, 85-97 (2000).
3. Small, G. W. Early diagnosis of Alzheimer's disease: update on combining genetic and brain-imaging measures. *Dialogues Clin. Neurosci.* 2, 241-246 (2000).
4. Citon, M. Alzheimer's disease: strategies for disease modification. *Nat. Rev. Drug Discov.* 9, 387-398 (2010).
5. Cummings, J. L. Biomarkers in Alzheimer's disease drug development. *Alzheimer's & Dementia* 7, e13-e44 (2011).
6. Dickerson, B. C., Wolk, D. A. & Initiative, A.s.D.N. MRI cortical thickness biomarker predicts AD-like CSF and cognitive decline in normal adults. *Neurology* 78, 84-90 (2012).
7. Handoko, M., et al. Correlation of specific amyloid-β oligomers with tau in cerebrospinal fluid from cognitively normal older adults. *JAMA Neurol.* 70, 594-599 (2013).
8. Zahs, K. R. & Ashe, K. H. β-amyloid oligomers in aging and Alzheimer's disease. *Front. Aging Neurosci.* 5, 28 (2013).
9. Jack, C. R. J. & Holtzman, D. M. Biomarker modeling of Alzheimer's disease. *Neuron* 80, 1347-1358 (2013).
10. Edmonds, E. C., Delano-Wood, L., Galasko, D. R., Salmon, D. P. & Bondi, M. W. Subtle cognitive decline and biomarker staging in preclinical Alzheimer's disease. *J Alzheimers Dis.* 47, 231-242 (2015).
11. Lista, S., et al. Evolving evidence for the value of neuroimaging methods and biological markers in subjects categorized with subjective cognitive decline. *J Alzheimers Dis* 48, Suppl 1:S171-191 (2015).
12. Schaffer, C., et al. Biomarkers in the diagnosis and prognosis of Alzheimer's disease. *JALA* 20, 589-600 (2015).
13. Cacciamani, F., et al. Low cognitive awareness, but not complaint, is a good marker of preclinical Alzheimer's disease. *J. Alzheimers Dis* 59, 753-762 (2017).
14. Huynh, R. A. & Mohan, C. Alzheimer's Disease: biomarkers in the genome, blood, and cerebrospinal fluid. *Front. Neurol.* 8, 102 (2017).
15. Wang, M. J., et al. Oligomeric forms of amyloid-β protein in plasma as a potential blood-based biomarker for Alzheimer's disease. *Alzheimer's Res & Ther.* 9, 98 (2017).
16. Bell, K. F. S., Bennett, D. A. & Cuello, A. C. Paradoxical upregulation of glutamatergic presynaptic boutons during mild cognitive impairment. *J. Neurosci.* 27, 10810-10817 (2007).
17. Hunsberger, H. C., Rudy, C. C., Batten, S. R., Gerhardt, G. A. & Reed, M. N. P301L tau expression affects glutamate release and clearance in the hippocampal tri-synaptic pathway. *J. Neurochem.* 132, 169-182 (2014).
18. Busche, M. A. & Konnerth, A. Neuronal hyperactivity—A key defect in Alzheimer's disease? *BioEssays* 37, 624-632 (2015).
19. Maestu, F., et al. A multicenter study of the early detection of synaptic dysfunction in Mild Cognitive Impairment using Magnetoencephalography-derived functional connectivity. *Neuroimage Clin.* 9, 103-109 (2015).
20. Dickerson, B. C., et al. Increased hippocampal activation in mild cognitive impairment compared to normal aging and AD. *Neurology* 65, 404-411 (2005).
21. Sperling, R. A., et al. Funtional alterations in memory networks in early Alzheimer's Disease. *Neuromolecular Med.* 12, 27-43 (2010).
22. Celone, K. A., et al. Alterations in memory networks in mild cognitive impairment and Alzheimer's disease: an independent component analysis *J. Neurosci.* 26, 10222-10231 (2006).
23. Jones, D. T., et al. Cascading network failure across the Alzheimer's disease spectrum. *Brain* 139, 547-562 (2016).
24. de Haan, W., van Straaten, E. C. W., Gouw, A. A. & Stam, C. J. Altering neuronal excitability to preserve network connectivity in a computational model of Alzheimer's disease. *PLoS Comput. Biol.* 13, e1005707 (2017).
25. Cirrito, J. R., et al. Synaptic activity regulates interstitial fluid amyloid-beta levels in vivo. *Neuron* 48, 913-922 (2005).
26. Bordji, K., Becerril-Ortega, J. & Buisson, A. Synapses, NMDA receptor activity and neuronal Aβ production in Alzheimer's disease. *Rev. Neurosci.* 22, 285-294 (2011).
27. Bero, A. W., et al. Neuronal activity regulates the regional vulnerability to amyloid-beta deposition. *Nat. Neurosci.* 14, 750-756 (2011).
28. Revett, T. J., Baker, G. B., Jhamandas, J. & Kar, S. Glutamate system, amyloid θ peptides and tau protein: functional interrelationships and relevance to Alzheimer disease pathology. *J. Psychiatry Neurosci.* 38, 6-23 (2013).
29. Parsons, M. P. & Raymond, L. A. Extrasynaptic NMDA receptor involvement in central nervous system disorders. *Neuron* 82, 279-293 (2014).
30. Mota, S. I., Ferreira, I. L. & Rego, A. C. Dysfunctional synapse in Alzheimer's disease—A focus on NMDA receptors. *Neuropharmacology* 76, 16-26 (2014).
31. Tampellini, D. Synaptic activity and Alzheimer's disease: a critical update. *Front. Neurosci.* 9, Article 9 (2015).
32. Rudy, C. C., Hunsberger, H. C., Weitzner, D. S. & Reed, M. N. The role of the tripartite glutamatergic synapse in the pathophysiology of Alzheimer's disease. *Aging Dis* 6, 131-148 (2015).

33. Pallo, S. P., DiMaio, J., Cook, A., Nilsson, B. & Johnson, G. V. W. Mechanisms of tau and Aβ-induced excitotoxocity. *Brain Res.* 1634, 119-131 (2016).
34. Wang, R. & Reddy, P. H. Role of glutamate and NMDA receptors in Alzheimer's disease. *J. Alzheimers Dis* 57, 1041-1048 (2017).
35. Frankiewicz, T. & Parson, C. G. Memantine restores long term potentiation impaired by tonic Nmethyl-D-aspartate (NMDA) receptor activation following reduction of Mg2+ in hippocampal slices. *Neuropharmacology* 38, 1253-1259 (1999).
36. Parsons, C. G., Danysz, W. & Quack, G. Memantine is a clinically well tolerated N-methyl-Daspartate (NMDA) receptor antagonist—a review of preclinical data. *Neuropharmacology* 38, 735-767 (1999).
37. Winblad, B. & Poritis N. Memantine in severe dementia: results of the 9M-best study (benefit and efficacy in severly demented patients during treatment with memantine). *Int. J. Geriat. Psychiatry* 14, 135-146 (1999).
38. Miguel-Hidalgo, J. J., Alvarez, X. A., Cacabelos, R. & Quack, G. Neuroprotection by memantine against neurodegeneration induced by beta-amyloid(1-40). *Brain Res.* 958, 210-221 (2002).
39. Lipton, S. A. Failures and successes of NMDA receptor antagonists: molecular basis for the use of open-channel blockers like memantine in the treatment of acute and chronic neurologic insults. *NeuroRx* 1, 101-110 (2004).
40. Folch, J., et al. Memantine for the treatment of dementia: a review on its current and future applications. *J. Alzheimers Dis* 62, 1223-1240 (2018).
41. Minkeviciene, R., Benerjee, P. & Tanila, H. Memantine improves spatial learning in a transgenic mouse model of Alzheimer's disease. *J. Pharmacol. Exp. Ther.* 311, 677-682 (2004).
42. Martinez-Coria, H., et al. Memantine improves cognition and reduces Alzheimer's-like neuropathology in transgenic mice. *Am. J. Pathol.* 176, 870-880 (2010).
43. Nagakura, A., Shitaka, Y., Yarimizu, J. & Matsuoka, N. Characterization of cognitive deficits in a transgenic mouse model of Alzheimer's disease and effects of donepezil and memantine. *Eur. J. Pharmacol.* 703, 53-61 (2013).
44. Devi, L. & Ohno, M. Cognitive benefits of memantine in Alzheimer's 5xFAD model mice decline during advanced disease stages. *Pharmacol. Biochem. Behav.* 144, 60-66 (2016).
45. Godyn, J., Jonczyk, J., Panek, D. & Malawska, B. Therapeutic strategies for Alzheimer's disease in clinical trials. *Pharmacol. Rep.* 68, 127-138 (2016).
46. Hung, S. Y. & Fu, W. M. Drug canditates in clinical trials for Alzheimer's disease. *J. Biomed. Sci.* 24, 47 (2017).
47. Lao, K., et al. Drug development for Alzheimer's disease: review. *J. Drug Target* 20, 1-10 (2018).
48. Pereira, A. C., et al. Glutamatergic regulation prevents hippocampal-dependent age-related cognitive decline through dendritic spine clustering. *Proc. Natl. Acad. Sci.* 111, 18733-18738 (2014).
49. Hunsberger, H. C., et al. Riluzole rescues glutamate alterations, cognitive deficits, and tau pathology associated with P301L tau expression. *J. Neurochem.* 135, 381-394 (2015).
50. Hunsberger, H. C., Kickman, J. E. & Reed, M. N. Riluzole rescues alterations in rapid glutamate transients in the hippocampus of rTg4510 mice. *Metab. Brain Dis* 31, 711-715 (2016).
51. Mokhtari, Z., Baluchnejadmojarad, T., Nikbakht, F., Mansouri, M. & Roghani, M. Riluzole ameliorates learning and memory deficits in Aβ25-35-induced rat model of Alzheimer's disease and is independent of cholinoceptor activation. *Biomed. Pharmacother.* 87, 135-144 (2016).
52. Okamoto, M., et al. Riluzole reduces amyloid beta pathology, improves memory, and restores gene expression changes in a transgenic mouse model of early-onset Alzheimer's disease. *Translational Psychiatry* 8, 153 (2018).
53. Malgouris C., et al. Riluzole, a novel antiglutamate, prevents memory loss and hippocampal neuronal damage in ischemic gerbils. *J. Neurosci.* 9, 3720-3727 (1989).
54. Pratt, J., et al. Neuroprotective actions of riluzole in rodent models of global and focal cerebral ischaemia. *Neurosci. Lett.* 140, 225-230 (1992).
55. McIntosh, T. K., Smith, D. H., Voddi, M., Perri, B. R. & Stutzmann, J. M. Riluzole, a novel neuroprotective agent, attenuates both neurologic motor and cognitive dysfunction following experimental brain injury in the rat. *J. Neurotrauma* 13, 767-780 (1996).
56. Stuzmann, J. M., et al. Neuroprotective profile of riluzole in in vivo models of acute neurodegenerative diseases. *CNS Drug Rev.* 3, 83-101 (1997).
57. Bae, H.-J., et al. Neuroprotective effect of low dose riluzole in gerbil model of transient global ischemia. *Neurosci. Lett.* 294, 29-32 (2000).
58. Ruel, J., et al. Neuroprotective effect of riluzole in acute noise-induced hearing loss. *NeuroReport* 16, 1087-1090 (2005).
59. Heurteaux, C., Laigle, C., Blondeau, N., Jarretou, G. & Lazdunski, M. Alpha-linolenic acid and riluzole treatment confer cerebral protection and improve survival after focal brain ischemia. *Neuroscience* 137, 241-251 (2006).
60. Weng, Y. C. & Kriz, J. Differential neuroprotective effects of a minocycline-based drug cocktail in transient and permanent focal cerebral ischemia. *Exp. Neurol.* 204, 433-442 (2007).
61. Coleman, N., et al. The riluzole derivative 2-amino-6-trifuoromethylthio-benzothiazole (SKA-19), a mixed KCa2 activator and NaV blocker, is a potent novel anticonvulsant. *Neurotherapeutics* 12, 234-249 (2015).
62. Ugale, V. G., et al. Quinazolino-benzothiazoles: fused pharmacophores as anticonvulsant agents. *Eur. J. Med. Chem.* 53, 107-113 (2012).
63. McDonnell, M. E., et al. Riluzole prodrugs for melanoma and ALS: design, synthesis and in vitro metabolic profiling. *Bioorg. Med. Chem.* 20, 5642-5648 (2012).
64. Verma, S. K., Arora, I., Javed, K., Akhtar, M. & Samim, M. Enhancement in the neuroprotective power of riluzole against cerebral ischemia using a brain targeted drug delivery vehicle. *ACS Appl. Mater. Interfaces* 8, 19716-19723 (2016).
65. Pelletier, J. C., et al. Dipeptide prodrugs of the glutamate modulator riluzole. *ACS Med. Chem. Lett.* 9, 752-756 (2018).
66. Doble, A. The pharmacology and mechanism of action of riluzole. *Neurology* 47, S233-S241 (1996).
67. Pittenger, C., et al. Riluzole in the treatment of mood and anxiety disorders. *CNS Drugs* 22, 761-786 (2008).
68. Falcao de Campos, C. & de Carvalho, M. Riluzole-induced recurrent pancreatitis *J. Clin. Neurosci.* 45, 153-154 (2017).
69. Takeshima, S., et al. Riluzole-induced interstitial pneumonia in a case with amyotrophic lateral sclerosis *Rinsho Shinkeigaku* 55, 840-843 (2015).
70. Festing, M. F. & Altman, D. G. Guidelines for the design and statistical analysis of experiments using laboratory animals. *ILAR J.* 43, 244-258 (2002).

71. Chen, R., et al. Monoacylglycerol lipase is a therapeutic target for Alzheimer's disease. *Cell Rep.* 2, 1329-1339 (2012).
72. Zhang, J., Hu, M., Teng, Z., Tang, Y.-P. & Chen, C. Synaptic and cognitive improvements by inhibition of 2-AG metabolism are through upregulation of microRNA-188-3p in a muse model of Alzheimer's disease. *J. Neurosci.* 34, 14919-14933 (2014).
73. Pereira, A. C., et al. Age and Alzheimer's disease gene expression profiles reversed by the glutamate modulator riluzole. *Mol. Psychiatry* 22, 296-305 (2017).
74. Colie, S., et al. Neuronal p38a mediates synaptic and cognitive dysfunction in an Alzheimer's mouse mdel by controlling β-amyloid production. *Sci. Rep.* 7, 45306 (2017).
75. Boza-Serrano, A., Yang, Y., Paulus, A. & Deieborg, R. Innate immune alterations are elicited in microglial cells before plaque deposition in the Alzheimer's disease mouse model 5×FAD. *Sci. Rep.* 8, 1550 (2018).
76. Bacci, M., et al. Block of glutamate-glutamine cycle between astrocytes and neurons inhibits epileptiform activity in hippocampus. *J. Neurophysol.* 88, 2302-2310 (2002).
77. Tani, H., et al. Modulation of epileptoform activity by glutamine and system A transport in a model of posttraumatic epilepsy. *Neurobiol. Dis* 25, 230-238 (2007).
78. Tani, H., Dulla, C. G., Huguenard, J. R. & Reimer, R. J. Glutamine is required for persistent epileptiform activity in the disinhibited neocortical brain slice. *J. Neurosci.* 30, 1288-1300 (2010).
79. Kanamori, K. & Ross, B. D. Electrographic seizures are significantly reduced by in vivo inhibition of neuronal uptake of extracellular glutamine in rat hippocampus. *Epilepsy Res.* 107, 20-36 (2013).
80. Christensen, H. N. Role of amino acid transport and countertransport in nutrition and metabolism. *Physiol. Rev.* 70, 43-77 (1990).
81. Erickson, J. D. Functional identification of activity-regulated, high-affinity glutamine transport in hippocampal neurons inhibited by riluzole. *J. Neurochem.* 142, 29-40 (2017).
82. Chowdhury, G. M., Patel, A. B., Mason, G. F., Rothman, D. L. & Behar, K. L. Glutamatergic and GABAergic neurotransmitter cycling and energy metabolism in rat cerebral cortex during postnatal development. *J. Cereb. Blood Flow Metab.* 27, 1895-1907 (2007).
83. Hertz, L. The glutamate-glutamine (GABA) cycle: Importance of late postnatal development and potential reciprocal interactions between biosynthesis and degradation. *Front. Endocrinol.* 4, Article 59 (2013).
84. Bolshakov, V. Y. & Siegelbaum, S. A. Regulation of hippocampal transmitter release during development and long-term potentiation. *Science* 269, 1730-1734 (1995).
85. Wasling, P., Hanse, E. & Gustafsson, B. Developmental changes in release properties of the CA3-CA1 glutamate synapse in rat hippocampus. *J. Neurophysiol.* 92, 2714-2724 (2004).
86. De Gois S., et al. Homeostatic scaling of vesicular glutamate and GABA transporter expression in rat neocortical circuits. *J. Neurosci.* 25, 7121-7133 (2005).
87. Wilson, N. R., et al. Presynaptic regulation of quantal size by the vesicular glutamate transporter VGLUT1. *J. Neurosci.* 25, 6221-6234 (2005).
88. Sankaranarayanan, A., et al. Naphtho[1,2-d]thiazol-2-ylamine (SKA-31), a new activator of KCa2 and KCa3.1 potassium channels, potentiates the endothelium-derived hyperpolarizing factor response and lowers blood pressure. *Mol. Pharmacol.* 75, 281-295 (2009).
89. Colovic, M., Zennaro, E. & Caccia, S. Liquid chromatographic assay for riluzole in mouse plasma and central nervous system tissues. *J. Chromatography B* 803, 305-309 (2004).
90. Milane, A., et al. Minocycline and riluzole brain disposition: interactions with p-glycoprotein at the blood-brain barrier. *J. Neurochem.* 103, 164-173 (2007).
91. Martin, D., Thompson, M. A. & Nadler, J. V. The neuroprotective agent riluzole inhibits release of glutamate and aspartate from slices of hippocampal area CA1. *Eur. J. Pharmacol.* 250, 473-476 (1993).
92. Kretschmer, B. D., Kratzer, U. & Schmidt, W. J. Riluzole, a glutamate release inhibitor, and motor behavior. Nauyn *Schmiedebergs Arch. Pharmacol.* 358, 181-190 (1998).
93. Lingamaneni, R. & Hemmings, H. C. J. Effects of anticonvulsants on veratridine- and KCl-evoked glutamate release from rat cortical synaptosomes. *Neurosci. Lett.* 276, 127-130 (1999).
94. Wang, S. J., Wang, K. Y. & Wang, W. C. Mechanisms underlying the riluzole inhibition of glutamate release from rat cerebral cortex nerve terminals synaptosomes). *Neuroscience* 125, 191-201 (2004).
95. Ates, O., et al. Do sodium channel blockers have neuroprotective effect after onset of ischemic insult? *Neurolog. Res.* 29, 317-323 (2013).
96. Salameh, J. S., Brown, R. H. J. & Berry, J. D. Amyotrophic lateral sclerosis review. *Semin. Neurol.* 35, 469-476 (2015).
97. Bellingham, M. C. A review of the neural mechanisms of action and clinical efficiency of riluzole in treating amyotrophic lateral sclerosis what have we learned in the last decade? CNS *Neurosci. Ther.* 17, 4-31 (2011).
98. Benoit, E. & Escande, D. Riluzole specifically blocks inactivated Na channels in myelinated nerve fiber. *Pflugers Arch.* 419, 603-609 (1991).
99. Herbert, T., Drapeau, P., Pradier, L. & Dunn, R. J. Block of the rat brain IIA sodium channel alpha subunit by the neuroprotective drug riluzole. *Mol. Pharmacol.* 45, 1055-1060 (1994).
100. Song, J. H., Huang, C. S., Nagata, K., Yeh, J. Z. & Narahashi, T. Differential action of riluzole on tetrodotoxin-sensitive and tetrodotoxin-resistant sodium channels. *J. Pharmacol. Exp. Ther.* 282, 707-714 (1997).
101. Stefani, A., Spadoni, F. & Bernardi, G. Differential inhibition by riluzole, lamotrigine, and phenytoin of sodium and calcium currents in cortical neurons: implications for neuroprotective strategies. *Exp. Neurol.* 147, 115-122 (1997).
102. Prakriya, M. & Mennerick, S. Selective depression of low release probability excitatory synapses by sodium channel blockers. Neuron 26, 671-682 (2000).
103. Spadoni, F., et al. Lamotrigine derivatives and riluzole inhibit INa2P in cortical neurons. *NeuroReport* 13, 1167-1170 (2002).
104. Grunnet, M., et al. Pharmacological modulation of SK3 channels. *Neuropharmacology* 40, 879-887 (2001).
105. Duprat, F., et al. The neuroprotective agent riluzole activates the two P domain K(+) channels TREK-1 and TRAAK. *Mol. Pharmacol.* 57, 906-912 (2000).
106. Huang, C. S., Song, J. H., Nagata, K., Yeh, J. Z. & Narahashi, T. Effects of the neuroprotective agent riluzole on the high voltage-activated calcium channels of rat dorsal root ganglion neurons. *J. Pharmacol. Exp. Ther.* 282, 1280-1290 (1997).

107. Noh, K. M., Hwang, J. Y., Shin, H. C. & Koh, J. Y. A novel neuroprotective mechanism of riluzole: direct inhibition of protein kinase C. *Neurobiol. Dis* 7, 375-383 (2000).

108. Fumagalli, E., Funicello, M., Rauen, T., Gobbi, M. & Mennini, T. Riluzole enhances the activity of glutamate transporters GLAST, GLT1 and EAAC1. *Eur. J. Pharmacol.* 578, 171-176 (2008).

109. Priyanka, S. N. K. & Jha, K. K. Benzothiazole; the molecule of diverse biological activities. *Int. J. Curr. Pharm. Res.* 2, 1-6 (2010).

110. Sharma, P. C., Sinhmar, A., Sharma, A., Rajak, H. & Pathak, D. P. Medicinal significance of benzothiazole scaffold: an insight view. *J. Enz. Inhib. Med. Chem.* 28, 240-266 (2012).

111. Hassel, B. & Brathe, A. Neuronal pyruvate carboxylation supports formation of transmitter glutamate. *J. Neurosci.* 20, 1342-1347 (2000).

112. Masson, J., et al. Mice lacking brain/kidney phosphate-activated glutaminase (GLS1) have impaired glutamatergic synaptic transmission, altered breathing, disorganized goal-directed behavior and die shortly after birth. *J. Neurosci.* 26, 4660-4671 (2006).

113. Kam, K. & Nicoll, R. Excitatory synaptic transmission persists independently of the glutamate-glutamine cycle. *J. Neurosci.* 27, 9192-9200 (2007).

114. Takeda, K., Ishida, A., Takahashi, K. & Ueda, T. Synaptic vesicles are capable of synthesizing the VGLUT substrate glutamate from a-ketoglutarate for vesicular loading. *J. Neurochem.* 121, 184-196 (2012).

115. Groeneveld, G. J., et al. Inter- and intraindividual variability of riluzole serum concentrations in patients with ALS. *J. Neurol. Sci.* 191, 121-125 (2001).

116. Groeneveld, G. J., et al. Riluzole serum concentrations in patients with ALS: associations with side effects and symptoms. *Neurology* 61, 1141-1143 (2003).

117. van Kan, H. J., et al. Association between CYP1A2 activity and riluzole clearance in patients with amyotrophic lateral sclerosis *Br. J. Clin. Pharmacol.* 59, 310-313 (2005).

118. Sanderink, G. J., Bournique, B., Stevens, J., Petry, M. & Martinet, M. Involvement of human CYP1A isoenzymes in the metabolism and drug interactions of riluzole in vitro. *J. Pharmacol. Exp. Ther.* 282, 1465-1472 (1997).

119. Tani, H., et al. A local glutamate-glutamine cycle sustains synaptic excitatory transmitter release. *Neuron* 81, 888-900 (2014).

120. Bittigau, P. & Ikonomidou, C. Glutamate in neurologic diseases. *J. Child Neurol.* 12, 471-485 (1997).

121. Benveniste, H., Drejer, J., Schousboe, A. & Diemer, N. H. Elevation of the extracellular concentrations of glutamate and aspartate in rat hippocampus during transient cerebral ischemia monitored by intracerebral microdialysis *J. Neurochem.* 43, 1369-1374 (1984).

122. Holmes, G. L. Seizure-induced neuronal injury: animal data. Neurology 59, S3-6 (2002).

123. Fujimoto, S., Katsuki, H., Kume, T., Kaneko, S. & Akaike, A. Mechanisms of oxygen glucose deprivation-induced glutamate release from cerebrocortical slice cultures. *Neurosci. Res.* 50, 179-187 (2004).

124. Dudek, F. E. & Sutula, T. P. Epileptogenesis in the dentate gyrus: a critical perspective. *Prog. Brain Res.* 163, 755-773 (2007).

125. Kostandy, B. B. The role of glutamate in neuronal ischemic injury: the role of spark in fire. *Neurol. Sci.* 33, 223-237 (2012).

126. Stargardt, A., Swaab, D. F. & Bossers, K. The storm before the quiet: neuronal hyperactivity and Aβ in the presymptomatic stages of Alzheimer's disease. *Neurobiol. Aging* 36, 1-11 (2015).

127. Ali, R. & Siddiqui, N. Biological aspects of emerging benzothiazoles: a short review. *J. Chem.* Article ID 345198, 12 pages (2013).

128. Gagoria, J., Verma, P. K. & Khatkar, A. Anticonvulsant and neurological profile of benzothiazoles: a mini-review. *CNS Agents in Med. Chem.* 15, 11-16 (2015).

129. Ahlgren, H., Henjm, K., Ottersen, O. & Ruden-Pran, E. Validation of organotypical hippocampal slice cultures as an ex vivo model of brain ischemia: different roles of NMDA receptors in cell death signalling after exposure to NMDA or oxygen and glucose deprivation. *Cell & Tiss. Res.* 345, 329-341 (2011).

130. Ammir, M. & Hassan, M. Z. Functional roles of benzothiazole motif in antiepileptic drug research. *Mini Rev. Med. Chem.* 13, 2060-2075 (2013).

131. Nadler, J. V. & Cuthbertson, G. J. Kainic acid neurotoxicity toward hippocampal formation: dependence on specific excitatory pathways. *Brain Res.* 195, 47-56 (1980).

132. Nadler, J. V. Minireview. Kainic acid as a tool for the study of temporal lobe epilepsy. *Life Sci.* 29, 2031-2042 (1981).

133. Ben-Ari, Y. Limbic seizure and brain damage produced by kainic acid: mechanisms and relevance to human temporal lobe epilepsy. *Neuroscience* 14, 375-403 (1985).

134. Lesne, S., et al. NMDA receptor activation inhibits alpha-secretase and promotes neuronal amyloid-beta production. *J. Neurosci.* 25, 9367-9377 (2005).

135. Kim, S. H., et al. Group II metabotropic glutamate receptor stimulation triggers production and release of Alzheimer's amyloid (342 from isolated intact nerve erminals. *J. Neurosci.* 30, 3870-3875 (2010).

136. Arias, C., Arrieta, I. & Tapia, R. β-amyloid peptide fragment 25-35 potentiates the calcium-dependent release of excitatory amino acids from depolarized hippocampal slices. *J. Neurosci. Res.* 41, 561-566 (1995).

137. Chin, J. H., Ma, L., MacTavish, D. & Jhamandas, J. H. Amyloid beta protein modulates glutamate-mediated neurotransmission in the rat basal forebrain: involvement of presynaptic neuronal nicotinic acetylcholine and metabotropic glutamate receptors. *J. Neurosci.* 27, 9262-9269 (2007).

138. Kabogo, D., Rauw, G., Amritraj, A., Baker, G. & Kar, S. β-amyloid-related peptides potentiate K+-evoked glutamate release from adult rat hippocampal slices. *Neurobiol. Aging* 31, 1164-1172 (2010).

139. Hascup, K. N. & Hascup, E. R. Soluble amyloid-β42 stimulates glutamate release through activation of the α7 nicotinic acetylcholine receptor. *J. Alzheimers Dis* 53, 337-347 (2016).

140. Oakley, H., et al. Intraneuronal beta-amyloid aggregates, neurodegeneration, and neuron loss in transgenic mice with five familial Alzheimer's disease mutations: potential factors in amyloid plaque formation. *J. Neurosci.* 26, 10129-10140 (2006).

141. Ashe, K. H. & Zahs, K. R. Probing the biology of Alzheimer's disease in mice. *Neuron* 66, 631-645 (2010).

142. Webster, S., Bachstetter, A. D., Nelson, P. T., Schmitt, F. A. & Van Eldik, L. J. Using mice to model Alzheimer's dementia: an overview of the clinical disease and the preclinical behavioral changes in 10 mouse models. *Fron. Genet.* 5, 88 (2014).

143. SantaCruz, K., et al. Tau suppression in a neurodegenerative mouse model improves memory function. *Science,* 476-481 (2005).
144. Paulson, J. B., et al. Amyloid plaque and neurofibrillary tangle pathology in a regulatable mouse model of Alzheimer's disease. *Am. J. Pathol.* 173, 762-772 (2008).
145. Kazim, S. F., et al. Disease modifying effect of chronic oral treatment with a neurotrophic peptidergic compound in a triple transgenic mouse model of Alzheimer's disease. *Neurobiol. Dis.* 71, 110-130 (2014).
146. Parsons, C. G., Danysz, W., Dekundy, A. & Pulte, I. Memantine and cholinesterase inhibitors: complementary mechanisms in the treatment of Alzheimer's disease. *Neurotox. Res.* 24, 358-369 (2013).
147. Francis P. T., Parson, C. G. & Jones, R. W. Rationale for combining glutamatergic and cholinergic approaches in the symptomatic treatment of Alzheimer's disease. *Expert Rev. Neurotherapeutics* 12, 1351-1365 (2014).
148. Carbone, M., Duty, S. & Rattray, M. Riluzole elevates GLT-1 activity and levels in striatal astrocytes. *Neurochem. Int.* 60, 31-38 (2012).
149. Lin, C.-L. G., Kong, Q., Cuny, G. D. & Glicksman, M. A. Glutamate transporter EAAT2: a new target for the treatment of neurodegenerative diseases. *Future Med. Chem.* 4, 1689-1700 (2012).
150. Brothers, H. M., et al. Riluzole partially rescues age-associated, but not LPS-induced, loss of glutamate transporters and spatial memory. *J. Neuroimmune Pharmacol.* 8, 1098-1105 (2013).
151. Takahashi, K., et al. Restored glial glutamate transporter EAAT2 function as a potential therapeutic approach for Alzheimer's disease. *J. Exp. Med.* 212, 319-332 (2015).
152. Rothstein, J. D., et al. Localization of neuronal and glial glutamate transporters. *Neuron* 13, 713-725 (1994).

Example 10

Synthesis of SKA-41, SKA-190, SKA-219 and SKA-220 and will validate plasma protein binding with rat plasma using equilibrium dialysis so that we can validate protein binding.

We will also validate formulations, for example formulations specifically for KA seizure/neuronal injury model.

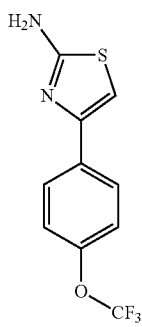

SKA-41

$C_{10}H_7F_3N_2OS$
MW: 260.23

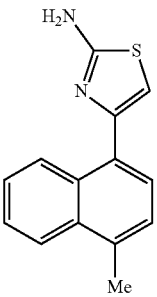

SKA-190

$C_{14}H_{12}F_3N_2S$
MW: 240.32

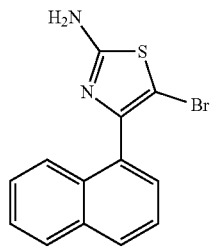

SKA-219

$C_{13}H_9BrN_2S$
MW: 305.19

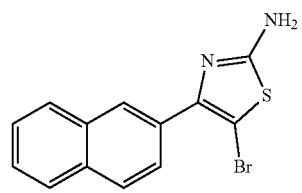

SKA-220

$C_{13}H_9BrN_2S$
MW: 305.19

New Derivative of SKA-41

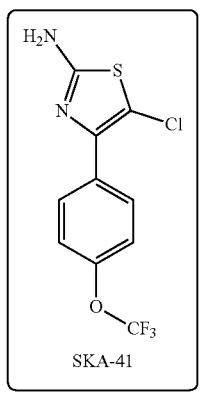

SKA-41

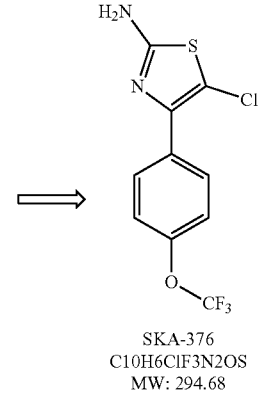

SKA-376
C10H6ClF3N2OS
MW: 294.68

Without wishing to be bound by theory, embodiments herein will to increase the brain penetration and the potency of SKA-41 without getting too bulky.

New Derivative of SKA-190

New Derivatives of SKA-75

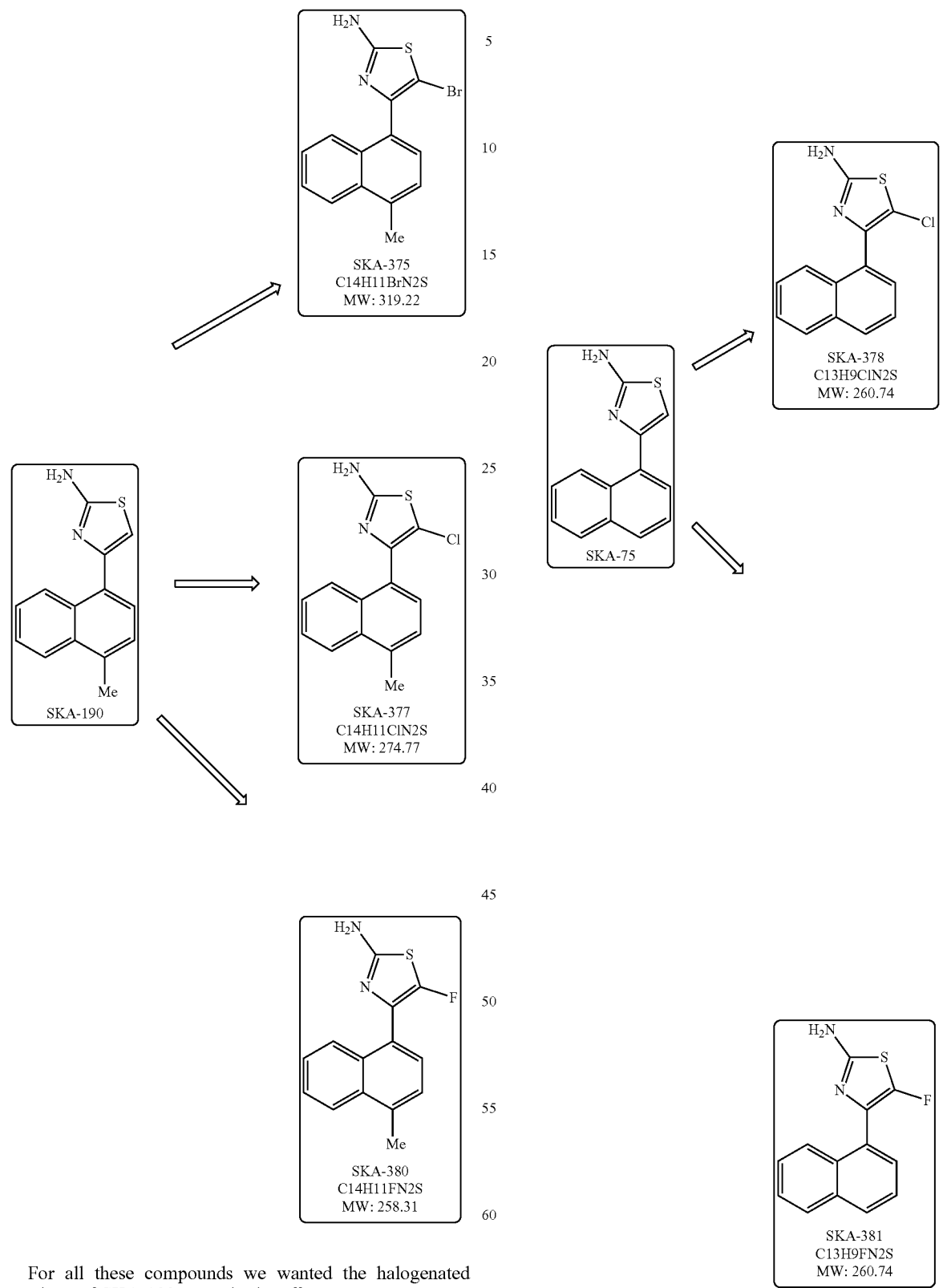

For all these compounds we wanted the halogenated versions of SKA-190 to study the effect on potency.

Without wishing to be bound by theory, the bromine substitute molecule can be poorly soluble, such as badly soluble as SKA-220, but can be more potent.

Without wishing to be bound by theory, these compounds can be more brain penetrable and can be more potent.

New Derivatives of SKA-76/SKA-220

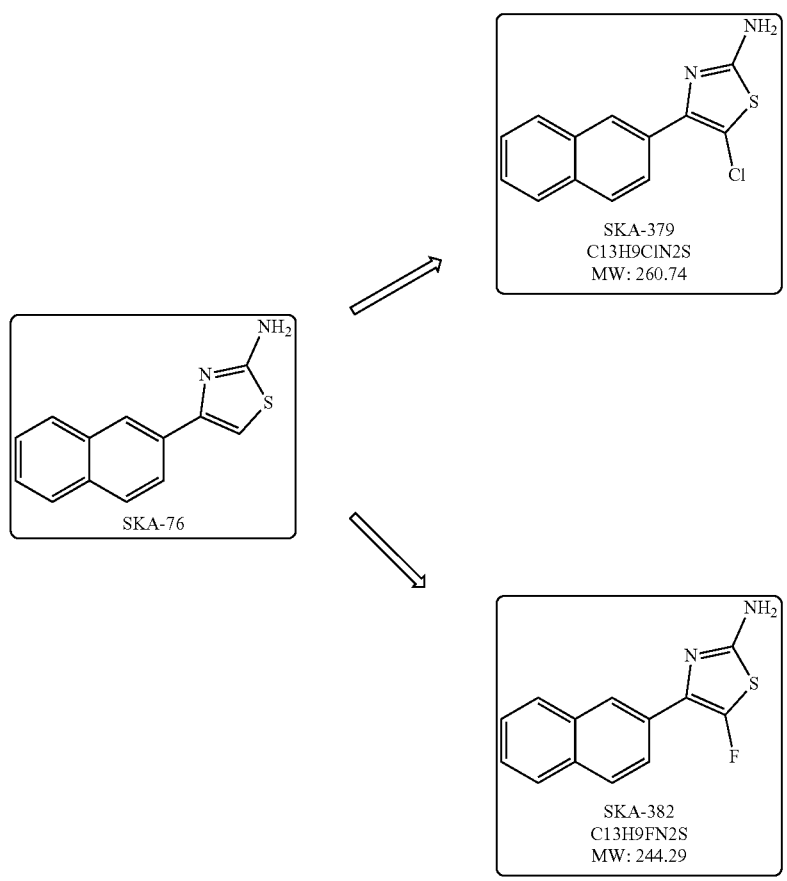

Without wishing to be bound by theory, these derivatives can be as potent as SKA-220 and can be more brain penetrable and have better solubility.

Example 11

SKA Compound Results for Inhibition of Activity-Regulated MeAIB Transport in Hippocampal Neurons Transport activity is measured on embryonic primary rat hippocampal neurons as 4-AP-stimulated (=depolarization; DIV16) and spontaneous (DIV 19) [$^{14}$C]-MeAIB uptake.

Log S; calculated unit stripped logarithm (base 10) of the solubility measured in mol/liter. Most drugs have a log S greater than −4 tPSA=topological polar surface area.

What I have done here is annotated the compounds that are currently being tested or still being synthesized as to whether they would be covered by the general structure, which was very narrow in claiming R groups.

| Compound | SNAT Activity IC$_{50}$ | ADME ChemBio | Plasma Protein | Selectivity IC$_{50}$ |
|---|---|---|---|---|
| 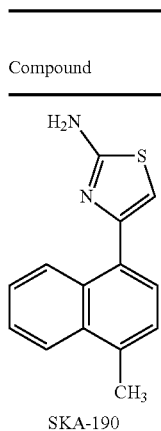 SKA-190 | Spont: 2.6 ± 0.25 µM (3) 4-AP: 11.7 ± 0.9 µM (4) 4.5x | LogP: 4.53 CLogP: 4.0 LogS: −4.452 tPSA: 38.38 Å$^2$ | | |

-continued

| Compound | SNAT Activity IC$_{50}$ | ADME ChemBio | Plasma Protein | Selectivity IC$_{50}$ |
|---|---|---|---|---|
| 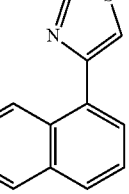 SKA-193 | Spont: ND<br>4-AP: ND | LogP: 4.53<br>CLogP: 4.0<br>LogS: −4.452<br>tPSA: 38.38 Å$^2$ | | |
| 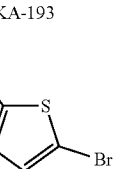 SKA-219 | Spont: 1.8 ± 0.2 µM (3)<br>4-AP: 5.1 ± 0.4 µM (5)<br>2.8x | LogP: 4.76<br>CLogP: 4.11<br>LogS: −4.65<br>tPSA: 38.38 Å$^2$ | > 98% | Nav1.2: 29.99 µM |
| 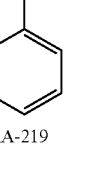 SKA-220 | Spont: 4.4 ± 0.5 µM (4)<br>4-AP: 6.8 ± 0.6 µM (5)<br>1.5x | LogP: 4.76<br>CLogP: 4.11<br>LogS: −4.65<br>tPSA: 38.38 Å$^2$ | > 98% | |
| 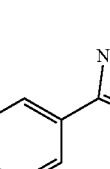 SKA-375 | Spont: 1.0 µM (1)<br>4-AP: 4.4 ± 0.3 µM (4)<br>4.4x | LogP: 5.24<br>CLogP: 4.60<br>LogS: −5.017<br>tPSA: 38.38 Å$^2$ | | |
| 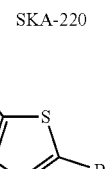 SKA-376 | Spont: 4.6 ± 0.2 µM (3)<br>4-AP: 7.4 ± 0.6 µM (6)<br>1.6x | LogP: 4.53<br>CLogP: 4.0<br>LogS: −4.452<br>tPSA: 38.38 Å$^2$ | | |

-continued
| Compound | SNAT Activity IC$_{50}$ | ADME ChemBio | Plasma Protein | Selectivity IC$_{50}$ |
|---|---|---|---|---|
| 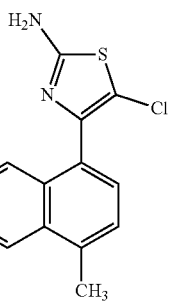 SKA-377 | Spont: 1.4 ± 0.1 μM (3) 4-AP: 7.4 ± 1.0 μM (6) 5.2x | LogP: 4.91 CLogP: 4.50 LogS: −4.896 tPSA: 38.38 Å$^2$ | | |
| 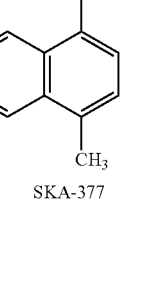 SKA-378 | Spont: 1.2 ± 0.15 μM (3) 4-AP: 5.2 ± 0.3 μM (5) 4.3x | LogP: 4.20 CLogP: 4.00 LogS: −4.524 tPSA: 38.38 Å$^2$ | | |
| 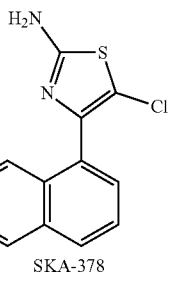 SKA-379 | Spont: 6.2 ± 0.6 μM (4) 4-AP: 9.3 ± 1.2 μM (5) 1.5x | LogP: 4.42 CLogP: 4.00 LogS: −4.562 tPSA: 38.38 Å$^2$ | | |
| 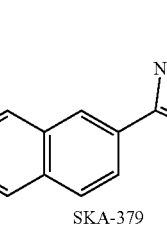 SKA-381 | Spont: 4-AP: | LogP: 4.14 CLogP: 3.68 LogS: −4.026 tPSA: 38.38 Å$^2$ | | |
| 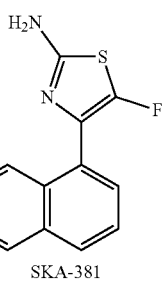 SKA-382 | Spont: 13.3 ± 1.8 μM (3) 4-AP: 17.9 ± 1.6 μM (3) 1.3x | LogP: 4.14 CLogP: 3.68 LogS: −4.022 tPSA: 38.38 Å$^2$ | | |

-continued
| Compound | SNAT Activity IC$_{50}$ | ADME ChemBio | Plasma Protein | Selectivity IC$_{50}$ |
|---|---|---|---|---|
| 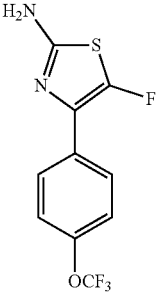 SKA-383 | Spont: 4-AP: | LogP: 4.67<br>CLogP: 3.63<br>LogS: −4.014<br>tPSA: 47.61 Å$^2$ | | |
| 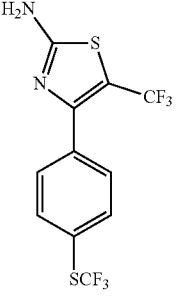 SKA-388 | Spont: 4-AP: | LogP: 6.12<br>CLogP: 5.04<br>LogS: −5.358<br>tPSA: 38.38 Å$^2$ | | |
| 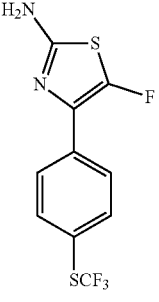 SKA-384 | Spont: 4-AP: | LogP: 5.24<br>CLogP: 4.21<br>LogS: −4.583<br>tPSA: 38.38 Å$^2$ | | |
| 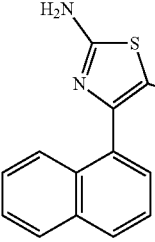 SKA-385 | Spont: 4-AP: | LogP: 5.02<br>CLogP: 4.52<br>LogS: −4.816<br>tPSA: 38.38 Å$^2$ | | |
| 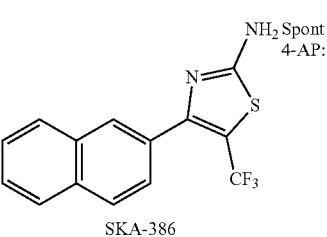 SKA-386 | Spont: 4-AP: | LogP: 5.02<br>CLogP: 4.52<br>LogS: −4.815<br>tPSA: 38.38 Å$^2$ | | |

| Compound | SNAT Activity IC$_{50}$ | ADME ChemBio | Plasma Protein | Selectivity IC$_{50}$ |
|---|---|---|---|---|
| 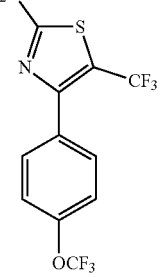 SKA-387 | Spont: 4-AP: | LogP: 5.55 CLogP: 4.47 LogS: −4.792 tPSA: 47.61 Å$^2$ | | |

Example 12

Experimental

All reactions were performed in flame-dried glassware under nitrogen unless otherwise noted. Tetrahydrofuran and diethyl ether were distilled from sodium/benzophenone ketyl under nitrogen. Dichloromethane and triethylamine were distilled from calcium hydride under nitrogen. Melting points were determined using a Büchi® B-540 melting point apparatus and are uncorrected. For HRMS analysis samples were analyzed by flow-injection analysis into a Thermo Fisher Scientific LTQ Orbitrap XL (San Jose, Calif.) operated in profile mode. Source parameters were 5 kV spray voltage, capillary temperature of 275° C. and sheath gas setting of 20. Spectral data were acquired at a resolution setting of 100,000 FWHM with the lockmass feature which typically results in a mass accuracy <2 ppm. $^1$H NMR, $^{19}$F NMR and proton decoupled $^{13}$C NMR ($^{13}$C NMR{$^1$H}) spectra were recorded on a Bruker 800 MHz and a 600 MHz Avance III Spectrometer equipped with cryoprobe and a 500 MHz Bruker Avance DRX Spectrometer (University of California, Davis) with the mentioned solvents. Chemical shifts are reported in parts per million (ppm) on the δ scale and were referenced to the appropriate solvent peaks (CDCl$_3$ referenced at $^1$H=7.26 ppm; DMSO-d$_6$ referenced at δ$_H$=2.54 ppm). NMR signals multiplicities are designated as follows: s (singlet), br (broad) d (doublet), t (triplet), septet (septet), m (multiplet). Thin-layer chromatography (TLC) was performed on Merck silica gel 60F$_{254}$ coated aluminum-backed plates and visualized with UV light (254 nm) and other common stains. Chromatographic separation was performed by using silica gel (Acros, 35-70 μm) or aluminum oxide (Sigma-Aldrich activated, neutral, Brockmann I).

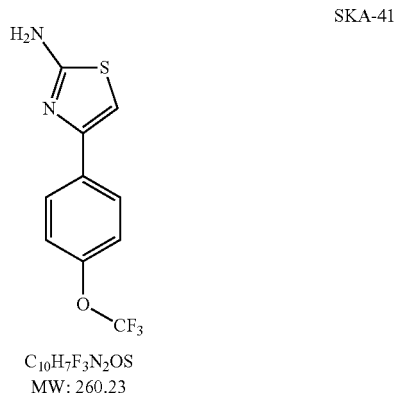 [SMILES: Nc1nc(-c2ccc(OC(F)(F)F)cc2)cs1]

SKA-41

C$_{10}$H$_7$F$_3$N$_2$OS
MW: 260.23

4-(4-(Trifluoromethoxy)phenyl)thiazol-2-amine (SKA-41)

SKA-41 was initially purchased in mg quantities from Oakwood Chemical (CAS no. 436151-95-0). It was later synthesized in house on gram scale according to the following procedure:

Step-1. Synthesis of 2-Bromo-1-(4-(trifluoromethoxy)phenyl)ethan-1-one

To a solution of 1-(4-(trifluoromethoxy)phenyl)ethanone (2.04 g, 10 mmol) in 30 mL diethyl ether was added a solution of bromine (0.5 mL, 10 mmol) dissolved in 10 mL diethyl ether, over a period of 10 min at RT. The resulting mixture was allowed to stir at RT for 12 hrs. The reaction mixture was then washed successively with saturated aqueous NaHCO$_3$ and Na$_2$S$_2$O$_3$ solutions. The organic phase was separated, dried over anhydrous Na$_2$SO$_4$ and evaporated under vacuum which furnished 2-bromo-1-(4-(trifluoromethoxy)phenyl)ethan-1-one as a light yellow thick liquid; yield: 2.51 g (90%). The crude bromo ketone, thus obtained, was immediately used for the next step without further purification.

Step-2. Synthesis of 4-(4-(Trifluoromethoxy)phenyl)thiazol-2-amine (SKA-41)

To a solution of 2-bromo-1-(4-(trifluoromethoxy)phenyl)ethan-1-one (1.42 g, 5 mmol) in 50 mL ethanol was added thiourea (381 mg, 5 mmol) and the resulting mixture was refluxed for 3 hours after which the solvent was evaporated and 50 mL chloroform was added to the residue. The resulting suspension was treated with saturated aqueous NaHCO$_3$. The organic phase was separated, dried over anhydrous Na$_2$SO$_4$ and evaporated under vacuum which furnished SKA-41 as a light-yellow solid. The crude product was purified by flash-chromatography using ethyl acetate/petroleum ether (2:8 v/v); yield: 1.045 g (80%), m.p. 118-119° C. $^1$H NMR (600 MHz, DMSO) δ 7.94-7.92 (m, 2H), 7.37 (d, J=8.1 Hz, 2H), 7.14 (brs, 2H), 7.10 (s, 1H). $^{13}$C NMR (150 MHz, DMSO) δ 168.4, 148.3, 147.2 (q, J=1.7 Hz), 134.1, 127.2, 121.0, 120.0 (q, J=256 Hz), 102.5.

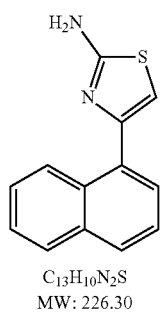

4-(Naphthalen-1-yl)thiazol-2-amine (SKA-75)

SKA-75 was initially purchased from Alfa Aesar (CAS no. 56503-96-9) and later synthesized in house on gram scale according to the following procedure.

Step-1. Synthesis of 2-Bromo-1-(naphthalen-1-yl)ethan-1-one

To a solution of 1-acetonaphthone (1.702 g, 10 mmol) in 30 mL diethyl ether was added a solution of bromine (0.5 mL, 10 mmol) dissolved in 10 mL diethyl ether, over a period of 10 min at RT. The resulting mixture was allowed to stir at RT for 12 hrs. The reaction mixture was then washed successively with saturated aqueous $NaHCO_3$ and $Na_2S_2O_3$ solutions. The organic phase was separated, dried over anhydrous $Na_2SO_4$ and evaporated under vacuum which furnished 2-bromo-1-(naphthalen-1-yl)ethan-1-one as a light yellow thick liquid; yield: 2.25 g (90%). The crude bromo ketone, thus obtained, was immediately used for the next step without further purification.

Step-2. Synthesis of 4-(Naphthalen-1-yl)thiazol-2-amine (SKA-75)

To a solution of 2-bromo-1-(naphthalen-1-yl)ethan-1-one (1.25 g, 5 mmol) in 50 mL ethanol was added thiourea (381 mg, 5 mmol) and the resulting mixture was refluxed for 3 hours after which the solvent was evaporated and 50 mL chloroform was added to the residue. The resulting suspension was treated with saturated aq. $NaHCO_3$. The organic phase was separated, dried over anhydrous $Na_2SO_4$ and evaporated under vacuum which furnished SKA-75 as a light-yellow solid. The crude product was purified by flash-chromatography using ethyl acetate/petroleum ether (2:8 v/v); yield: 0.795 g (70%), m.p. 154-155.5° C.

$^1$H NMR (800 MHz, DMSO) δ 8.50 (d, J=8.0 Hz, 1H), 7.98 (d, J=7.2 Hz, 1H), 7.93 (d, J=8.0 Hz, 1H), 7.68 (d, J=7.2 Hz, 1H), 7.56-7.53 (m, 3H), 7.16 (brs, 2H), 6.81 (s, 1H). $^{13}$C NMR (201 MHz, DMSO) δ 167.9, 150.0, 133.4, 133.4, 130.7, 128.1, 127.8, 126.5, 126.2, 125.8, 125.7, 125.3, 104.9.

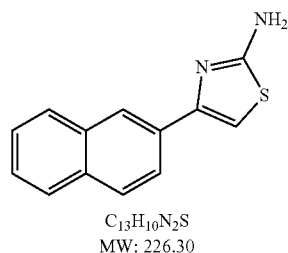

4-(Naphthalen-2-yl)thiazol-2-amine (SKA-76)

SKA-76 was initially purchased from Alfa Aesar (CAS no. 21331-43-1) and later synthesized in house on gram scale according to the following procedure.

Step-1. Synthesis of 2-Bromo-1-(naphthalen-2-yl)ethan-1-one

To a solution of 2-acetonaphthone (1.702 g, 10 mmol) in 30 mL diethyl ether was added a solution of bromine (0.5 mL, 10 mmol) dissolved in 10 mL diethyl ether, over a period of 10 min at RT. The resulting mixture was allowed to stir at RT for 12 hrs. The reaction mixture was then washed successively with saturated aqueous $NaHCO_3$ and $Na_2S_2O_3$ solutions. The organic phase was separated, dried over anhydrous $Na_2SO_4$ and evaporated under vacuum which furnished 2-bromo-1-(naphthalen-1-yl)ethan-1-one as a light yellow thick liquid; yield: 2.25 g (90%). The crude bromo ketone, thus obtained, was immediately used for the next step without further purification.

Step-2. Synthesis of 4-(Naphthalen-2-yl)thiazol-2-amine (SKA-76)

To a solution of 2-bromo-1-(naphthalen-1-yl)ethan-1-one (1.25 g, 5 mmol) in 50 mL ethanol was added thiourea (381 mg, 5 mmol) and the resulting mixture was refluxed for 3 hours after which the solvent was evaporated and 50 mL chloroform was added to the residue. The resulting suspension was treated with saturated aq. $NaHCO_3$. The organic phase was separated, dried over anhydrous $Na_2SO_4$ and evaporated under vacuum which furnished SKA-76 as a light-yellow solid. The crude product was purified by flash-chromatography using ethyl acetate/petroleum ether (2:8 v/v); yield: 0.850 g (75%), m.p. 144-146.5° C.

$^1$H NMR (600 MHz, DMSO) δ 8.35 (s, 1H), 7.99 (dd, J1=8.6, J2=1.8 Hz, 1H), 7.95 (d, J=8.0 Hz, 1H), 7.92-7.91 (m, 2H), 7.55-7.49 (m, 2H), 7.20 (s, 1H), 7.15 (brs, 2H). $^{13}$C NMR (150 MHz, DMSO) δ 168.2, 149.7, 133.1, 132.3, 132.2, 128.0, 127.8, 127.5, 126.3, 125.7, 124.0, 123.9, 102.3.

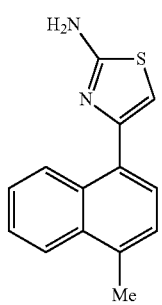

SKA-190

C₁₄H₁₂N₂S
MW: 240.32

4-(4-Methylnaphthalen-1-yl)thiazol-2-amine (SKA-190), (CAS no. 332064-25-2) was synthesized on gram scale according to the following procedure.

Step-1. Synthesis of 2-Bromo-1-(4-methylnaphthalen-1-yl)ethan-1-one

To a solution of 1-acetyl-4-methylnaphthalene (1.84 g, 10 mmol) in 30 mL diethyl ether was added a solution of bromine (0.5 mL, 10 mmol) dissolved in 10 mL diethyl ether, over a period of 10 min at RT. The resulting mixture was allowed to stir at RT for 12 hrs. The reaction mixture. was then washed successively with saturated aqueous $NaHCO_3$ and $Na_2S_2O_3$ solutions. The organic phase was separated, dried over anhydrous $Na_2SO_4$ and evaporated under vacuum which furnished 2-bromo-1-(4-methylnaphthalen-1-yl)ethan-1-one as a light yellow thick liquid; yield: 2.25 g (90%). The crude bromo ketone, thus obtained, was immediately used for the next step without further purification.

Step-2. Synthesis of 4-(4-Methylnaphthalen-1-yl)thiazol-2-amine (SKA-190)

To a solution of 2-bromo-1-(4-methylnaphthalen-1-yl)ethan-1-one (1.32 g, 5 mmol) in 50 mL ethanol was added thiourea (381 mg, 5 mmol) and the resulting mixture was refluxed for 3 hours after which the solvent was evaporated and 50 mL chloroform was added to the residue. The resulting suspension was treated with saturated aqueous $NaHCO_3$. The organic phase was separated, dried over anhydrous $Na_2SO_4$ and evaporated under vacuum which furnished SKA-190 as a light-yellow solid. The crude product was purified by flash-chromatography using ethyl acetate/petroleum ether (2:8 v/v); yield: 1.081 g (90%), m.p. 163.5-165.5° C.

¹H NMR (800 MHz, DMSO) δ 8.50 (d, J=8.0 Hz, 1H), 8.07 (d, J=8.0 Hz, 1H), 7.59 (t, J=8.0 Hz, 1H), 7.55-7.53 (m, 2H), 7.39 (d, J=7.2 Hz, 1H), 7.14 (brs, 2H), 6.73 (s, 1H), 2.69 (s, 3H).

¹³C NMR (201 MHz, DMSO) δ 167.8, 150.3, 133.8, 132.3, 132.0, 130.8, 126.8, 126.2, 126.1, 125.7, 125.5, 124.2, 104.5, 19.1.

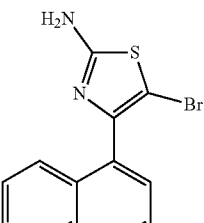

SKA-219

C₁₃H₉BrN₂S
MW: 305.19

5-Bromo-4-(naphthalen-1-yl)thiazol-2-amine (SKA-219)

2.0 mL of a 1M bromine solution in chloroform was added over a period of 5 min to a solution of 4-(naphthalen-1-yl)thiazol-2-amine (SKA-75) (453 mg, 2.0 mmol) in chloroform (30 mL). The resulting mixture was stirred at RT for 15 min. Then 1 mL of 1N aqueous NaOH was added to it followed by addition of 1.2 mL of a 1M bromine solution. After 30 more minutes of stirring, 2 mL NaOH (1N in water) was added, the organic phase was separated, and the aqueous phase was extracted using chloroform (1×15 mL). The combined organic phase was dried over anhydrous $Na_2SO_4$ and evaporated under vacuum and the residue was purified by column chromatography on silica using a gradient of ethyl acetate in hexane (10%-40%), which afforded (SKA-219) as a light yellow solid; yield: 427 mg (70%), m.p. 166° C. (decomposed)

¹H NMR (600 MHz, DMSO) δ 8.01 (d, J=7.8 Hz, 2H), 7.87 (d, J=7.8 Hz, 1H), 7.61-7.53 (m, 4H), 7.38 (brs, 2H).
¹³C NMR (201 MHz, DMSO) δ 167.7, 148.7, 133.7, 131.9, 131.5, 129.0, 128.6, 128.4, 126.6, 126.4, 125.6, 90.5.

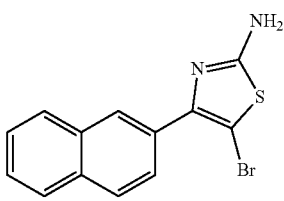

SKA-220

C₁₃H₉BrN₂S
MW: 305.19

5-Bromo-4-(naphthalen-2-yl)thiazol-2-amine (SKA-220)

2.0 mL of a 1M bromine solution in chloroform was added over a period of 5 min to a solution of 4-(naphthalen-2-yl)thiazol-2-amine (SKA-76) (453 mg, 2.0 mmol) in chloroform (30 mL). The resulting mixture was stirred at RT for 15 min. Then 1 mL of 1N aqueous NaOH was added to it followed by 1.2 mL of 1M bromine solution. After 30 more minutes of stirring, another 2 mL NaOH (1N in water) was added, the organic phase was separated, and the aqueous phase was extracted using chloroform (1×15 mL). The combined organic phase was dried over anhydrous Na₂SO₄ and evaporated under vacuum and the residue was purified by column chromatography on silica using a gradient of ethyl acetate in hexane (10%-40%), which afforded (SKA-220) as a light yellow solid; yield: 428 mg (70%), m.p. 137° C. (decomposed).

$^1$H NMR (600 MHz, DMSO) δ 8.38 (s, 1H), 8.01-7.95 (m, 4H), 7.58-7.56 (m, 2H), 7.40 (brs, 2H). $^{13}$C NMR (201 MHz, DMSO) δ 167.4, 147.5, 133.0, 132.7, 131.7, 128.6, 128.0, 127.9, 127.5, 126.96, 126.92, 126.1, 88.0.

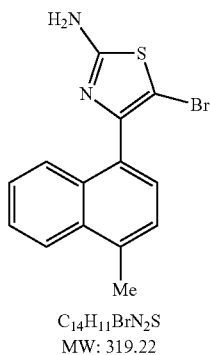

SKA-375

C₁₄H₁₁BrN₂S
MW: 319.22

5-Bromo-4-(4-methylnaphthalen-1-yl)thiazol-2-amine (SKA-375)

1.0 mL of a 1M bromine solution in chloroform was added over a period of 5 min to a solution of 4-(4-methylnaphthalen-1-yl)thiazol-2-amine (SKA-190) (240 mg, 1.0 mmol) in chloroform (20 mL). The resulting mixture was stirred at RT for 15 min. Then 0.5 mL of 1N aqueous NaOH was added to it followed by addition of 0.5 mL of a 1M bromine solution. After 30 more minutes of stirring, another 1.0 mL NaOH (1N in water) was added, the organic phase was separated, and the aqueous phase was extracted using chloroform (1×15 mL). The combined organic phase was dried over anhydrous Na₂SO₄ and evaporated under vacuum and the residue was purified by column chromatography on silica using a gradient of ethyl acetate in hexane (10%-40%), which afforded (SKA-375) as a light yellow solid; yield: 208 mg (65%), m.p. 181° C. (decomposed).

$^1$H NMR (600 MHz, DMSO) δ 8.10 (d, J=8.1 Hz, 1H), 7.76 (d, J=8.1 Hz, 1H), 7.61 (dt, $J_1$=7.4, $J_2$=1.2 Hz, 1H), 7.55 (dt, $J_1$=7.4, $J_2$=1.2 Hz, 1H), 7.44 (s, 2H), 7.36 (brs, 2H), 2.72 (s, 3H). $^{13}$C NMR (150 MHz, DMSO) δ 167.1, 148.6, 134.7, 132.2, 131.1, 129.8, 127.5, 126.5, 125.85, 125.84, 125.7, 124.3, 89.9, 19.1.

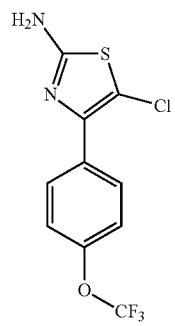

SKA-376

C₁₀H₆ClF₃N₂OS
MW: 294.68

5-Chloro-4-(4-(trifluoromethoxy)phenyl)thiazol-2-amine (SKA-376)

A solution of 4-(4-(Trifluoromethoxy)phenyl)thiazol-2-amine (SKA-41) (130 mg, 0.5 mmol) and 2-chloro-1,3-bis(methoxycarbonyl)guanidine (Palau'Chlor®) (120 mg, 0.55 mmol) in chloroform (20 mL) was stirred at RT for 12 h. 10 mL NaOH (1M in water) was then added to it and the heterogenous mixture was stirred for 1 h. The organic phase was separated, and the aqueous phase was extracted using chloroform (1×10 mL). The combined organic phase was dried over anhydrous Na₂SO₄, evaporated under vacuum and the residue was purified by column chromatography on silica using a gradient of ethyl acetate in hexane (5%-45%), which afforded (SKA-376) as a brown solid; yield: 74 mg (50%), m.p. 86° C. (decomposed).

$^1$H NMR (800 MHz, DMSO) δ 7.98-7.96 (m, 2H), 7.47 (d, J=8.2 Hz, 2H), 7.37 (brs, 2H). $^{13}$C NMR (201 MHz, DMSO) δ 164.3, 147.5, 143.1, 132.2, 129.5, 120.8, 120.0 (q, J=256 Hz), 104.7.

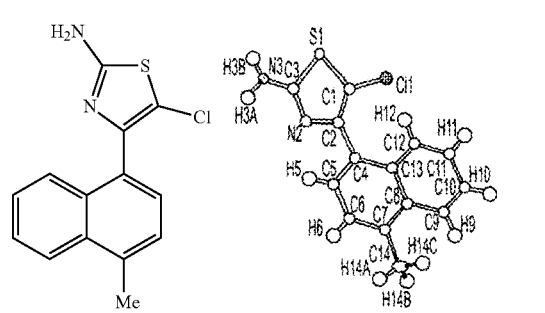

SKA-377

C₁₄H₁₁ClN₂S
MW: 274.77

5-Chloro-4-(4-methylnaphthalen-1-yl)thiazol-2-amine (SKA-377)

A solution of 4-(4-methylnaphthalen-1-yl)thiazol-2-amine (SKA-190) (120 mg, 0.5 mmol) and 2-chloro-1,3-bis(methoxycarbonyl)guanidine (Palau'Chlor®) (120 mg, 0.55 mmol) in chloroform (20 mL) was stirred at RT for 12 h. 10 mL NaOH (1M in water) was then added to it and the heterogenous mixture was stirred for 1 h. The organic phase was separated, and the aqueous phase was extracted using chloroform (1×10 mL). The combined organic phase was dried over anhydrous $Na_2SO_4$, evaporated under vacuum and the residue was purified by column chromatography on silica using a gradient of ethyl acetate in hexane (5%-45%), which afforded (SKA-377) as a brown solid; yield: 49 mg (36%). mp 206° C. (decomposed).

$^1$H NMR (600 MHz, DMSO) δ 8.10 (d, J=8.0 Hz, 1H), 7.91 (d, J=8.0 Hz, 1H), 7.61 (dt, $J_1$=7.5, $J_2$=1.3 Hz, 1H), 7.56 (dt, $J_1$=7.5, $J_2$=1.3 Hz, 1H), 7.45 (s, 2H), 7.34 (brs, 2H), 2.72 (s, 3H). $^{13}$C NMR (150 MHz, DMSO) δ 164.5, 145.9, 134.8, 132.2, 131.1, 128.9, 127.5, 126.4, 125.87, 125.80, 124.3, 105.8, 19.1. The structure of SKA-377 was further confirmed by single crystal X-ray diffraction method.

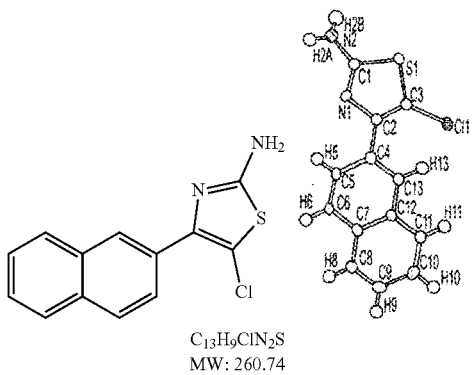

SKA-379

$C_{13}H_9ClN_2S$
MW: 260.74

5-Chloro-4-(naphthalen-2-yl)thiazol-2-amine (SKA-379)

A solution of 4-(naphthalen-2-yl)thiazol-2-amine (SKA-76) (114 mg, 0.5 mmol) and 2-chloro-1,3-bis(methoxycarbonyl)guanidine (Palau'Chlor®) (121 mg, 0.55 mmol) in chloroform (20 mL) was stirred at RT for 12 h. 10 mL NaOH (1M in water) was then added to it and the heterogenous mixture was stirred for 1 h. The organic phase was separated, and the aqueous phase was extracted using chloroform (1×10 mL). The combined organic phase was dried over anhydrous $Na_2SO_4$, evaporated under vacuum and the residue was purified by column chromatography on silica using a gradient of ethyl acetate in hexane (5%-45%), which afforded (SKA-379) as a brown solid; yield: 51 mg (40%), m.p. 150° C. (decomposed).

$^1$H NMR (600 MHz, DMSO) δ 8.389 (s, 1H), 8.02-7.98 (m, 3H), 7.96-7.95 (m, 1H), 7.58-7.56 (m, 2H), 7.39 (brs, 2H). $^{13}$C NMR (201 MHz, CDCl$_3$) δ 164.2, 144.4, 132.6, 132.2, 130.6, 128.2, 127.6, 127.4, 126.8, 126.47, 126.42, 125.4, 104.4. The structure of SKA-379 was further confirmed by single crystal X-ray diffraction method.

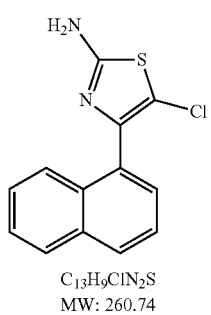

SKA-378

$C_{13}H_9ClN_2S$
MW: 260.74

5-Chloro-4-(naphthalen-1-yl)thiazol-2-amine (SKA-378)

A solution of 4-(naphthalen-1-yl)thiazol-2-amine (SKA-75) (115 mg, 0.5 mmol) and 2-chloro-1,3-bis(methoxycarbonyl)guanidine (Palau'Chlor®) (121 mg, 0.55 mmol) in chloroform (20 mL) was stirred at RT for 12 h. 10 mL NaOH (1M in water) was then added to it and the heterogenous mixture was stirred for 1 h. The organic phase was separated, and the aqueous phase was extracted using chloroform (1×10 mL). The combined organic phase was dried over anhydrous $Na_2SO_4$, evaporated under vacuum and the residue was purified by column chromatography on silica using a gradient of ethyl acetate in hexane (5%-45%), which afforded (SKA-378) as a brown solid; yield: 53 mg (40%), m.p. 182° C. (decomposed)

$^1$H NMR (800 MHz, DMSO) δ 8.01 (d, J=8.4 Hz, 2H), 7.91 (d, J=8.4 Hz, 1H), 7.61-7.55 (m, 4H), 7.36 (brs, 2H). $^{13}$C NMR (201 MHz, DMSO) δ 164.7, 145.6, 133.2, 131.0, 130.6, 128.6, 128.1, 127.8, 126.1, 125.9, 125.8, 125.2, 106.0.

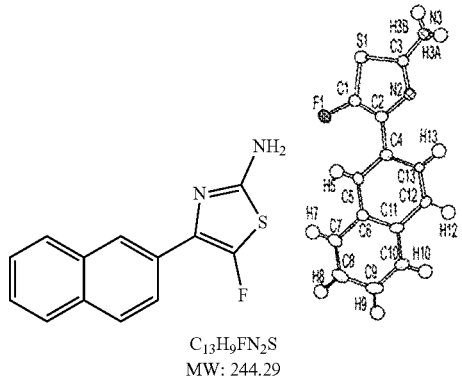

SKA-382

$C_{13}H_9FN_2S$
MW: 244.29

5-Fluoro-4-(naphthalen-2-yl)thiazol-2-amine (SKA-382)

A solution of 4-(naphthalen-2-yl)thiazol-2-amine (SKA-76) (114 mg, 0.5 mmol) and 1-chloromethyl-4-fluoro-1,4-diazoniabicyclo[2.2.2]octane bis(tetrafluoroborate) (Selectfluor®) (190 mg, 0.48 mmol) in acetonitrile (20 mL) was stirred at 0° C. for 5 h. The reaction mix was concentrated to 5 mL and the residue was purified by column chromatography on silica using a gradient of ethyl acetate in hexane (5%-45%), which afforded (SKA-382) as a brown solid; yield: 22 mg (18%).

$^1$H NMR (600 MHz, DMSO) δ 8.27 (s, 1H), 7.93 (d, J=8.7 Hz, 1H), 7.88-7.82 (m, 2H), 7.82-7.80 (m, 1H), 7.49-7.45 (m, 2H), 4.76 (brs, 2H). $^{13}$C NMR (150 MHz, CDCl$_3$) δ 155.0 (d, J=11.1 Hz), 149.8, 147.8, 133.6, 132.8 (d, J=1.2 Hz), 129.6 (d, J=6.0 Hz), 128.5, 128.3, 127.8, 126.4, 126.2, 126.0 (m), 124.6 (d, J=6.5 Hz). $^{19}$F NMR (170 MHz, CDCl$_3$) δ −152.40 (s, 1F).

The structure of SKA-382 was further confirmed by single crystal X-ray diffraction method.

SKA-377-XRD Data

TABLE 1

Crystal data and structure refinement for [C$_{14}$H$_{11}$N$_2$SCl].

| | |
|---|---|
| Identification code | JF2933AFMI |
| Empirical formula | C14 H11 Cl N2 S |
| Formula weight | 274.76 |
| Temperature | 90(2) K |
| Wavelength | 0.71073 Å |
| Crystal system | Monoclinic |
| Space group | P2$_{1/c}$ |
| Unit cell dimensions | a = 10.8062(3) Å  α = 90° |
| | b = 10.8522(3) Å  β = 91.9710(13)° |
| | c = 10.6814(3) Å  γ = 90° |
| Volume | 1251.88(6) Å$^3$ |
| Z | 4 |
| Density (calculated) | 1.458 Mg/m$^3$ |
| Absorption coefficient | 0.453 mm$^{-1}$ |
| F(000) | 568 |
| Crystal size | 0.273 × 0.139 × 0.124 mm$^3$ |
| Crystal color and habit | Orange Block |
| Diffractometer | Bruker APEX-II CCD |
| Theta range for data collection | 1.886 to 30.050°. |
| Index ranges | −15 <= h <= 15, −5 <= k <= 15, −15 <= l <= 15 |

TABLE 1-continued

Crystal data and structure refinement for [C$_{14}$H$_{11}$N$_2$SCl].

| | |
|---|---|
| Reflections collected | 11796 |
| Independent reflections | 3672 [R(int) = 0.0213] |
| Observed reflections (I > 2sigma(I)) | 3271 |
| Completeness to theta = 25.242° | 100.0 % |
| Absorption correction | Semi-empirical from equivalents |
| Max. and min. transmission | 0.9418 and 0.8638 |
| Solution method | SHELXT (Sheldrick, 2014) |
| Refinement method | SHELXL-2018/3 (Sheldrick, 2018) Full-matrix least-squares on F$^2$ |
| Data/restraints/parameters | 3672/0/207 |
| Goodness-of-fit on F$^2$ | 1.046 |
| Final R indices [I > 2sigma(I)] | R1 = 0.0356, wR2 = 0.0864 |
| R indices (all data) | R1 = 0.0404, wR2 = 0.0895 |
| Largest diff. peak and hole | 0.564 and −0.430 e.Å$^{-3}$ |

TABLE 2

Atomic coordinates (×10$^4$) and equivalent isotropic displacement parameters (Å$^2$ × 10$^3$) for JF2933AFMI. U(eq) is defined as one third of the trace of the orthogonalized U$^{ij}$ tensor.

| | x | y | z | U(eq) |
|---|---|---|---|---|
| Cl(1) | 3098(1) | 8071(1) | 6032(1) | 23(1) |
| S(1) | 5194(1) | 7880(1) | 7933(1) | 18(1) |
| C(1) | 3906(1) | 7244(1) | 7152(1) | 17(1) |
| C(2) | 3649(1) | 6100(1) | 7590(1) | 15(1) |
| N(2) | 4447(1) | 5701(1) | 8558(1) | 15(1) |
| C(3) | 5284(1) | 6542(1) | 8840(1) | 15(1) |
| N(3) | 6191(1) | 6388(1) | 9738(1) | 20(1) |
| C(4) | 2581(1) | 5302(1) | 7214(1) | 16(1) |
| C(5) | 1726(1) | 4999(1) | 8099(1) | 19(1) |
| C(6) | 690(1) | 4263(1) | 7787(2) | 22(1) |
| C(7) | 488(1) | 3796(1) | 6600(1) | 21(1) |
| C(8) | 1369(1) | 4069(1) | 5668(1) | 18(1) |
| C(9) | 1230(1) | 3600(1) | 4424(1) | 22(1) |
| C(10) | 2090(2) | 3835(1) | 3542(1) | 24(1) |
| C(11) | 3141(1) | 4565(1) | 3852(1) | 22(1) |
| C(12) | 3299(1) | 5054(1) | 5037(1) | 18(1) |
| C(13) | 2422(1) | 4827(1) | 5969(1) | 16(1) |
| C(14) | −619(2) | 3004(2) | 6293(2) | 28(1) |

TABLE 3

Bond lengths [Å] and angles [°] for JF2933AFMI.

| | | | |
|---|---|---|---|
| Cl(1)—C(1) | 1.7110(14) | C(2)—C(1)—S(1) | 111.51(10) |
| S(1)—C(1) | 1.7402(14) | Cl(1)—C(1)—S(1) | 120.49(8) |
| S(1)—C(3) | 1.7462(14) | C(1)—C(2)—N(2) | 114.28(12) |
| C(1)—C(2) | 1.3590(19) | C(1)—C(2)—C(4) | 127.21(12) |
| C(2)—N(2) | 1.3911(16) | N(2)—C(2)—C(4) | 118.34(12) |
| C(2)—C(4) | 1.4872(18) | C(3)—N(2)—C(2) | 111.03(11) |
| N(2)—C(3) | 1.3127(17) | N(2)—C(3)—N(3) | 123.47(12) |
| C(3)—N(3) | 1.3579(17) | N(2)—C(3)—S(1) | 115.19(10) |
| N(3)—H(3A) | 0.87(2) | N(3)—C(3)—S(1) | 121.30(10) |
| N(3)—H(3B) | 0.83(2) | C(3)—N(3)—H(3A) | 115.6(14) |
| C(4)—C(5) | 1.3841(19) | C(3)—N(3)—H(3B) | 120.7(14) |
| C(4)—C(13) | 1.4310(18) | H(3A)—N(3)—H(3B) | 116.4(19) |
| C(5)—C(6) | 1.406(2) | C(5)—C(4)—C(13) | 119.18(12) |
| C(5)—H(5) | 0.943(18) | C(5)—C(4)—C(2) | 118.95(12) |
| C(6)—C(7) | 1.376(2) | C(13)—C(4)—C(2) | 121.87(12) |
| C(6)—H(6) | 0.976(18) | C(4)—C(5)—C(6) | 121.19(13) |
| C(7)—C(8) | 1.433(2) | C(4)—C(5)—H(5) | 119.7(11) |
| C(7)—C(14) | 1.500(2) | C(6)—C(5)—H(5) | 119.1(11) |
| C(8)—C(9) | 1.426(2) | C(7)—C(6)—C(5) | 121.83(14) |
| C(8)—C(13) | 1.4315(18) | C(7)—C(6)—H(6) | 121.4(11) |
| C(9)—C(10) | 1.371(2) | C(5)—C(6)—H(6) | 116.7(11) |
| C(9)—H(9) | 0.977(19) | C(6)—C(7)—C(8) | 118.44(13) |
| C(10)—C(11) | 1.414(2) | C(6)—C(7)—C(14) | 120.85(14) |
| C(10)—H(10) | 0.99(2) | C(8)—C(7)—C(14) | 120.71(14) |
| C(11)—C(12) | 1.3782(19) | C(9)—C(8)—C(13) | 118.20(13) |

TABLE 3-continued

Bond lengths [Å] and angles [°] for JF2933AFMI.

| | | | |
|---|---|---|---|
| C(11)—H(11) | 1.01(2) | C(9)—C(8)—C(7) | 121.48(13) |
| C(12)—C(13) | 1.4195(19) | C(13)—C(8)—C(7) | 120.32(13) |
| C(12)—H(12) | 0.952(18) | C(10)—C(9)—C(8) | 121.46(13) |
| C(14)—H(14A) | 1.01(2) | C(10)—C(9)—H(9) | 117.2(11) |
| C(14)—H(14B) | 0.98(2) | C(8)—C(9)—H(9) | 121.3(11) |
| C(14)—H(14C) | 0.99(2) | C(9)—C(10)—C(11) | 120.08(14) |
| | | C(9)—C(10)—H(10) | 120.2(13) |
| C(1)—S(1)—C(3) | 87.97(6) | C(11)—C(10)—H(10) | 119.7(13) |
| C(2)—C(1)—Cl(1) | 127.95(11) | C(12)—C(11)—C(10) | 120.28(14) |
| C(12)—C(11)—H(11) | 118.6(11) | C(4)—C(13)—C(8) | 119.01(12) |
| C(10)—C(11)—H(11) | 121.1(11) | C(7)—C(14)—H(14A) | 106.6(14) |
| C(11)—C(12)—C(13) | 120.85(13) | C(7)—C(14)—H(14B) | 111.5(13) |
| C(11)—C(12)—H(12) | 120.0(11) | H(14A)—C(14)—H(14B) | 109.5(19) |
| C(13)—C(12)—H(12) | 119.1(11) | C(7)—C(14)—H(14C) | 109.4(14) |
| C(12)—C(13)—C(4) | 121.85(12) | H(14A)—C(14)—H(14C) | 111.8(19) |
| C(12)—C(13)—C(8) | 119.11(12) | H(14B)—C(14)—H(14C) | 108.1(18) |

Symmetry transformations used to generate equivalent atoms:

TABLE 4

Anisotropic displacement parameters (Å$^2$ × 10$^3$) for JF2933AFMI. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| Cl(1) | 25(1) | 23(1) | 20(1) | 7(1) | −4(1) | 0(1) |
| S(1) | 20(1) | 16(1) | 17(1) | 2(1) | −1(1) | −4(1) |
| C(1) | 17(1) | 19(1) | 14(1) | 1(1) | −1(1) | 0(1) |
| C(2) | 16(1) | 16(1) | 13(1) | −3(1) | −1(1) | 1(1) |
| N(2) | 17(1) | 15(1) | 14(1) | −1(1) | −2(1) | 0(1) |
| C(3) | 18(1) | 15(1) | 13(1) | −1(1) | 1(1) | −1(1) |
| N(3) | 23(1) | 19(1) | 18(1) | 1(1) | −6(1) | −5(1) |
| C(4) | 17(1) | 14(1) | 17(1) | 0(1) | −1(1) | 1(1) |
| C(5) | 19(1) | 18(1) | 18(1) | 1(1) | 2(1) | 1(1) |
| C(6) | 19(1) | 22(1) | 26(1) | 4(1) | 4(1) | −1(1) |
| C(7) | 17(1) | 17(1) | 27(1) | 3(1) | −1(1) | 1(1) |
| C(8) | 15(1) | 14(1) | 24(1) | 0(1) | −3(1) | 0(1) |
| C(9) | 21(1) | 20(1) | 26(1) | −3(1) | −5(1) | −1(1) |
| C(10) | 26(1) | 23(1) | 21(1) | −6(1) | −4(1) | 0(1) |
| C(11) | 22(1) | 23(1) | 20(1) | −3(1) | 1(1) | 0(1) |
| C(12) | 15(1) | 19(1) | 19(1) | 0(1) | 0(1) | 0(1) |
| C(13) | 15(1) | 15(1) | 17(1) | −1(1) | −2(1) | 2(1) |
| C(14) | 21(1) | 27(1) | 37(1) | 1(1) | −1(1) | −8(1) |

TABLE 5

Hydrogen coordinates (×10$^4$) and isotropic displacement parameters (Å$^2$ × 10$^3$) for JF2933 AFMI.

| | x | y | z | U(eq) |
|---|---|---|---|---|
| H(3A) | 6068(19) | 5800(20) | 10270(20) | 29(5) |
| H(3B) | 6609(19) | 6984(19) | 9996(19) | 28(5) |
| H(5) | 1828(16) | 5303(17) | 8924(17) | 18(4) |
| H(6) | 95(16) | 4136(17) | 8442(17) | 18(4) |
| H(9) | 509(18) | 3108(17) | 4162(18) | 22(5) |
| H(10) | 1970(20) | 3520(20) | 2680(20) | 39(6) |
| H(11) | 3788(18) | 4738(18) | 3217(18) | 26(5) |
| H(12) | 4002(17) | 5553(17) | 5239(17) | 21(4) |
| H(14A) | −1090(20) | 2920(20) | 7090(20) | 48(7) |
| H(14B) | −370(20) | 2180(20) | 6000(20) | 36(6) |
| H(14C) | −1130(20) | 3400(20) | 5620(20) | 42(6) |

TABLE 6

Torsion angles [°] for JF2933 AFMI.

| | |
|---|---|
| C(3)—S(1)—C(1)—C(2) | −1.11(11) |
| C(3)—S(1)—C(1)—Cl(1) | 176.39(9) |
| Cl(1)—C(1)—C(2)—N(2) | −176.55(10) |

TABLE 6-continued

Torsion angles [°] for JF2933 AFMI.

| | |
|---|---|
| S(1)—C(1)—C(2)—N(2) | 0.70(15) |
| Cl(1)—C(1)—C(2)—C(4) | −1.4(2) |
| S(1)—C(1)—C(2)—C(4) | 175.90(11) |
| C(1)—C(2)—N(2)—C(3) | 0.31(16) |
| C(4)—C(2)—N(2)—C(3) | −175.34(11) |
| C(2)—N(2)—C(3)—N(3) | −178.92(12) |
| C(2)—N(2)—C(3)—S(1) | −1.21(14) |
| C(1)—S(1)—C(3)—N(2) | 1.35(11) |
| C(1)—S(1)—C(3)—N(3) | 179.12(12) |
| C(1)—C(2)—C(4)—C(5) | −116.26(16) |
| N(2)—C(2)—C(4)—C(5) | 58.76(17) |
| C(1)—C(2)—C(4)—C(13) | 64.47(19) |
| N(2)—C(2)—C(4)—C(13) | −120.51(14) |
| C(13)—C(4)—C(5)—C(6) | −1.6(2) |
| C(2)—C(4)—C(5)—C(6) | 179.07(13) |
| C(4)—C(5)—C(6)—C(7) | 0.9(2) |
| C(5)—C(6)—C(7)—C(8) | 0.4(2) |
| C(5)—C(6)—C(7)—C(14) | 179.53(14) |
| C(6)—C(7)—C(8)—C(9) | 178.98(14) |
| C(14)—C(7)—C(8)—C(9) | −0.2(2) |
| C(6)—C(7)—C(8)—C(13) | −0.9(2) |
| C(14)—C(7)—C(8)—C(13) | 179.91(13) |
| C(13)—C(8)—C(9)—C(10) | 1.7(2) |
| C(7)—C(8)—C(9)—C(10) | −178.20(14) |
| C(8)—C(9)—C(10)—C(11) | −0.5(2) |
| C(9)—C(10)—C(11)—C(12) | −0.6(2) |
| C(10)—C(11)—C(12)—C(13) | 0.6(2) |
| C(11)—C(12)—C(13)—C(4) | 178.54(13) |
| C(11)—C(12)—C(13)—C(8) | 0.6(2) |
| C(5)—C(4)—C(13)—C(12) | −176.85(13) |
| C(2)—C(4)—C(13)—C(12) | 2.4(2) |
| C(5)—C(4)—C(13)—C(8) | 1.06(19) |
| C(2)—C(4)—C(13)—C(8) | −179.68(12) |
| C(9)—C(8)—C(13)—C(12) | −1.72(2) |
| C(7)—C(8)—C(13)—C(12) | 178.19(12) |
| C(9)—C(8)—C(13)—C(4) | −179.69(12) |
| C(7)—C(8)—C(13)—C(4) | 0.22(19) |

Symmetry transformations used to generate equivalent atoms:

TABLE 7

Hydrogen bonds for JF2933 AFMI [Å and °].

| D-H...A | d(D-H) | d(H...A) | d(D...A) | <(DHA) |
|---|---|---|---|---|
| N(3)-H(3A)...N(2)#1 | 0.87(2) | 2.14(2) | 3.0031(17) | 172.4(19) |
| N(3)-H(3A)...N(2)#1 | 0.87(2) | 2.14(2) | 3.0031(17) | 172.4(19) |

Symmetry transformations used to generate equivalent atoms:
1 −x + 1, −y + 1, −z + 2

SKA-379-XRD Data

TABLE 1

Crystal data and structure refinement for [C$_{13}$H$_9$ N$_2$SCl].

| | |
|---|---|
| Identification code | JF2926FMI (Cl-SKA-76) |
| Empirical formula | C13 H9 Cl N2 S |
| Formula weight | 260.73 |
| Temperature | 90(2) K |
| Wavelength | 0.71073 Å |
| Crystal system | Monoclinic |
| Space group | P2$_{1/c}$ |
| Unit cell dimensions | a = 4.0950(8) Å    α = 90°. |
| | b = 22.559(5) Å    β = 92.929(3)°. |
| | c = 12.279(3) Å    γ = 90°. |
| Volume | 1132.9(4) Å$^3$ |
| Z | 4 |
| Density (calculated) | 1.529 Mg/m$^3$ |
| Absorption coefficient | 0.496 mm$^{-1}$ |
| F(000) | 536 |
| Crystal size | 0.509 × 0.101 × 0.078 mm$^3$ |
| Crystal color and habit | Orange Rod |
| Diffractometer | Bruker APEX-II CCD |
| Theta range for data collection | 2.453 to 27.641°. |
| Index ranges | −5 <= h <= 5, −29 <= k <= 29, −15 <= l <= 15 |
| Reflections collected | 9906 |
| Independent reflections | 2630 [R(int) = 0.0395] |
| Observed reflections (I > 2sigma(I)) | 2294 |
| Completeness to theta = 25.242° | 99.9 % |
| Absorption correction | Semi-empirical from equivalents |
| Max. and min. transmission | 0.9182 and 0.6120 |
| Solution method | SHELXT (Sheldrick, 2014) |
| Refinement method | SHELXL-2018/3 (Sheldrick, 2018) Full-matrix least-squares on F$^2$ |
| Data /restraints/parameters | 2630/0/190 |
| Goodness-of-fit on F$^2$ | 1.072 |
| Final R indices [I > 2sigma(I)] | R1 = 0.0316, wR2 = 0.0778 |
| R indices (all data) | R1 = 0.0380, wR2 = 0.0814 |
| Largest diff. peak and hole | 0.489 and −0.235 e.Å$^{-3}$ |

TABLE 2

Atomic coordinates (×10$^4$) and equivalent isotropic displacement parameters (Å$^2$ × 10$^3$) for JF2926FMI. U(eq) is defined as one third of the trace of the orthogonalized U$^{ij}$ tensor.

| | x | y | z | U(eq) |
|---|---|---|---|---|
| S(1) | 7477(1) | 5204(1) | 3067(1) | 21(1) |
| Cl(1) | 6032(1) | 4193(1) | 4527(1) | 24(1) |
| C(1) | 6606(4) | 5125(1) | 1660(1) | 23(1) |
| N(1) | 5244(3) | 4620(1) | 1367(1) | 22(1) |
| C(2) | 4822(4) | 4250(1) | 2267(1) | 19(1) |
| N(2) | 7168(5) | 5575(1) | 961(1) | 33(1) |
| C(3) | 5877(4) | 4496(1) | 3236(1) | 20(1) |
| C(4) | 3560(4) | 3645(1) | 2057(1) | 19(1) |
| C(5) | 4330(4) | 3358(1) | 1065(1) | 20(1) |
| C(6) | 3324(4) | 2790(1) | 844(1) | 20(1) |
| C(7) | 1472(4) | 2467(1) | 1593(1) | 19(1) |
| C(8) | 400(4) | 1876(1) | 1394(1) | 22(1) |
| C(9) | −1418(4) | 1583(1) | 2132(1) | 24(1) |
| C(10) | −2220(4) | 1865(1) | 3118(1) | 24(1) |
| C(11) | −1208(4) | 2435(1) | 3335(1) | 22(1) |
| C(12) | 661(4) | 2752(1) | 2582(1) | 19(1) |
| C(13) | 1727(4) | 3342(1) | 2792(1) | 19(1) |

TABLE 3

Bond lengths [Å] and angles [°] for JF2926FMI.

| | | | | |
|---|---|---|---|---|
| S(1)—C(3) | 1.7418(17) | C(3)—C(2)—N(1) | 113.51(14) |
| S(1)—C(1) | 1.7547(16) | C(3)—C(2)—C(4) | 128.36(14) |
| Cl(1)—C(3) | 1.7245(15) | N(1)—C(2)—C(4) | 117.97(13) |
| C(1)—N(1) | 1.310(2) | C(1)—N(2)—H(2A) | 117.0(16) |
| C(1)—N(2) | 1.357(2) | C(1)—N(2)—H(2B) | 119.5(17) |
| N(1)—C(2) | 1.4027(19) | H(2A)—N(2)—H(2B) | 120(2) |
| C(2)—C(3) | 1.363(2) | C(2)—C(3)—Cl(1) | 129.53(13) |
| C(2)—C(4) | 1.477(2) | C(2)—C(3)—S(1) | 111.94(11) |
| N(2)—H(2A) | 0.90(3) | Cl(1)—C(3)—S(1) | 118.42(9) |
| N(2)—H(2B) | 0.82(3) | C(13)—C(4)—C(5) | 118.82(14) |
| C(4)—C(13) | 1.384(2) | C(13)—C(4)—C(2) | 122.66(13) |
| C(4)—C(5) | 1.429(2) | C(5)—C(4)—C(2) | 118.50(14) |
| C(5)—C(6) | 1.370(2) | C(6)—C(5)—C(4) | 121.10(14) |
| C(5)—H(5) | 0.960(18) | C(6)—C(5)—H(5) | 120.3(11) |
| C(6)—C(7) | 1.421(2) | C(4)—C(5)—H(5) | 118.6(11) |
| C(6)—H(6) | 0.984(19) | C(5)—C(6)—C(7) | 121.07(14) |
| C(7)—C(8) | 1.422(2) | C(5)—C(6)—H(6) | 121.6(11) |
| C(7)—C(12) | 1.428(2) | C(7)—C(6)—H(6) | 117.2(11) |
| C(8)—C(9) | 1.372(2) | C(6)—C(7)—C(8) | 122.63(14) |
| C(8)—H(8) | 0.941(19) | C(6)—C(7)—C(12) | 118.36(14) |
| C(9)—C(10) | 1.421(2) | C(8)—C(7)—C(12) | 119.01(14) |
| C(9)—H(9) | 0.93(2) | C(9)—C(8)—C(7) | 120.74(15) |
| C(10)—C(11) | 1.371(2) | C(9)—C(8)—H(8) | 120.2(12) |
| C(10)—H(10) | 0.96(2) | C(7)—C(8)—H(8) | 119.0(12) |
| C(11)—C(12) | 1.423(2) | C(8)—C(9)—C(10) | 120.27(15) |
| C(11)—H(11) | 0.97(2) | C(8)—C(9)—H(9) | 120.8(12) |
| C(12)—C(13) | 1.422(2) | C(10)—C(9)—H(9) | 118.9(12) |
| C(13)—H(13) | 0.966(18) | C(11)—C(10)—C(9) | 120.31(15) |
| | | C(11)—C(10)—H(10) | 120.6(13) |
| C(3)—S(1)—C(1) | 88.02(7) | C(9)—C(10)—H(10) | 119.1(13) |
| N(1)—C(1)—N(2) | 124.04(15) | C(10)—C(11)—C(12) | 120.76(15) |
| N(1)—C(1)—S(1) | 114.90(12) | C(10)—C(11)—H(11) | 120.2(12) |
| N(2)—C(1)—S(1) | 120.96(13) | C(12)—C(11)—H(11) | 119.0(12) |
| C(1)—N(1)—C(2) | 111.63(13) | C(13)—C(12)—C(11) | 121.53(14) |
| | | C(4)—C(13)—H(13) | 118.5(11) |
| C(13)—C(12)—C(7) | 119.56(14) | | |
| C(11)—C(12)—C(7) | 118.91(14) | C(12)—C(13)—H(13) | 120.4(11) |
| C(4)—C(13)—C(12) | 121.08(14) | | |

Symmetry transformations used to generate equivalent atoms:

TABLE 4

Anisotropic displacement parameters (Å$^2$ × 10$^3$) for JF2926FMI. The anisotropic displacement factor exponent takes the form: $-2\pi^2[h^2 a^{*2}U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| S(1) | 31(1) | 19(1) | 14(1) | −2(1) | −2(1) | 0(1) |
| Cl(1) | 36(1) | 26(1) | 11(1) | 0(1) | 1(1) | 0(1) |
| C(1) | 31(1) | 22(1) | 15(1) | 1(1) | −3(1) | 1(1) |
| N(1) | 30(1) | 19(1) | 15(1) | 2(1) | −2(1) | −1(1) |
| C(2) | 23(1) | 19(1) | 14(1) | 1(1) | 1(1) | 4(1) |
| N(2) | 56(1) | 23(1) | 18(1) | 3(1) | −8(1) | −12(1) |
| C(3) | 26(1) | 19(1) | 15(1) | 1(1) | 1(1) | 3(1) |
| C(4) | 22(1) | 20(1) | 14(1) | 0(1) | −2(1) | 4(1) |
| C(5) | 24(1) | 23(1) | 13(1) | 2(1) | 1(1) | 1(1) |
| C(6) | 24(1) | 24(1) | 13(1) | −3(1) | 0(1) | 4(1) |
| C(7) | 21(1) | 21(1) | 15(1) | −1(1) | −2(1) | 3(1) |
| C(8) | 24(1) | 22(1) | 20(1) | −3(1) | −2(1) | 3(1) |
| C(9) | 25(1) | 19(1) | 26(1) | 0(1) | −4(1) | 1(1) |
| C(10) | 25(1) | 27(1) | 21(1) | 5(1) | 0(1) | 0(1) |
| C(11) | 24(1) | 26(1) | 15(1) | 2(1) | 0(1) | 2(1) |
| C(12) | 20(1) | 22(1) | 14(1) | 0(1) | −2(1) | 4(1) |
| C(13) | 24(1) | 21(1) | 14(1) | −2(1) | 1(1) | 4(1) |

TABLE 5

Hydrogen coordinates (×10$^4$) and isotropic displacement parameters (Å$^2$ × 10$^3$) for JF2926FMI.

| | x | y | z | U(eq) |
|---|---|---|---|---|
| H(2A) | 6740(60) | 5506(11) | 250(20) | 46(6) |
| H(2B) | 8410(60) | 5844(11) | 1160(20) | 41(6) |
| H(5) | 5650(40) | 3566(8) | 566(15) | 19(4) |
| H(6) | 3930(40) | 2582(9) | 180(15) | 24(5) |

TABLE 5-continued

Hydrogen coordinates (×10⁴) and isotropic displacement parameters ($Å^2 \times 10^3$) for JF2926FMI.

|       | x       | y       | z        | U(eq)  |
|-------|---------|---------|----------|--------|
| H(8)  | 940(50) | 1687(9) | 744(16)  | 24(5)  |
| H(9)  | −2160(50)| 1199(9) | 1996(16) | 27(5)  |
| H(10) | −3520(50)| 1655(10)| 3623(17) | 32(5)  |
| H(11) | −1770(50)| 2627(9) | 4003(16) | 27(5)  |
| H(13) | 1200(40)| 3540(8) | 3458(15) | 18(4)  |

TABLE 6

Torsion angles [°] for JF2926FMI.

| | |
|---|---|
| C(3)—S(1)—C(1)—N(1) | 0.36(14) |
| C(3)—S(1)—C(1)—N(2) | 176.90(16) |
| N(2)—C(1)—N(1)—C(2) | −177.04(16) |
| S(1)—C(1)—N(1)—C(2) | −0.61(18) |
| C(1)—N(1)—C(2)—C(3) | 0.6(2) |
| C(1)—N(1)—C(2)—C(4) | −175.13(14) |
| N(1)—C(2)—C(3)—Cl(1) | −176.35(12) |
| C(4)—C(2)—C(3)—Cl(1) | −1.1(3) |
| N(1)—C(2)—C(3)—S(1) | −0.34(18) |
| C(4)—C(2)—C(3)—S(1) | 174.87(13) |
| C(1)—S(1)—C(3)—C(2) | 0.01(13) |
| C(1)—S(1)—C(3)—Cl(1) | 176.51(10) |
| C(3)—C(2)—C(4)—C(13) | 34.4(2) |
| N(1)—C(2)—C(4)—C(13) | −150.59(15) |
| C(3)—C(2)—C(4)—C(5) | −144.16(17) |
| N(1)—C(2)—C(4)—C(5) | 30.9(2) |
| C(13)—C(4)—C(5)—C(6) | −0.9(2) |
| C(2)—C(4)—C(5)—C(6) | 177.70(14) |
| C(4)—C(5)—C(6)—C(7) | 0.2(2) |
| C(5)—C(6)—C(7)—C(8) | −179.69(14) |
| C(5)—C(6)—C(7)—C(12) | 0.4(2) |
| C(6)—C(7)—C(8)—C(9) | −179.20(15) |
| C(12)—C(7)—C(8)—C(9) | 0.7(2) |
| C(7)—C(8)—C(9)—C(10) | −0.8(2) |
| C(8)—C(9)—C(10)—C(11) | 0.5(2) |
| C(9)—C(10)—C(11)—C(12) | −0.1(2) |
| C(10)—C(11)—C(12)—C(13) | 179.91(14) |
| C(10)—C(11)—C(12)—C(7) | −0.1(2) |
| C(6)—C(7)—C(12)—C(13) | −0.3(2) |
| C(8)—C(7)—C(12)—C(13) | 179.80(14) |
| C(6)—C(7)—C(12)—C(11) | 179.67(14) |
| C(8)—C(7)—C(12)—C(11) | −0.2(2) |
| C(5)—C(4)—C(13)—C(12) | 1.0(2) |
| C(2)—C(4)—C(13)—C(12) | −177.53(14) |
| C(11)—C(12)—C(13)—C(4) | 179.60(14) |
| C(7)—C(12)—C(13)—C(4) | −0.4(2) |

Symmetry transformations used to generate equivalent atoms:

TABLE 7

Hydrogen bonds for JF2926FMI [Å and °].

| D-H...A | d(D-H) | d(H...A) | d(D...A) | <(DHA) |
|---|---|---|---|---|
| N(2)—H(2A)...N(1)#1 | 0.90(3) | 2.13(3) | 3.009(2) | 169(2) |

Symmetry transformations used to generate equivalent atoms:
1 −x + 1, −y + 1, −z

SKA-382-XRD Data

TABLE 1

Crystal data and structure refinement for [$C_{13}H_9N_2FS$].

| | |
|---|---|
| Identification code | JF2934AFMI (F-SKA-76) |
| Empirical formula | C13 H9 F N2 S |
| Formula weight | 244.28 |
| Temperature | 90(2) K |
| Wavelength | 0.71073 Å |
| Crystal system | Monoclinic |
| Space group | I2/a |
| Unit cell dimensions | a = 14.8104(7) Å  α = 90°. |
|  | b = 6.6204(3) Å  β = 96.857(3)°. |
|  | c = 22.2519(10) Å γ = 90°. |
| Volume | 2166.21(17) Å3 |
| Z | 8 |
| Density (calculated) | 1.498 Mg/m³ |
| Absorption coefficient | 0.287 mm⁻¹ |
| F(000) | 1008 |
| Crystal size | 0.135 × 0.131 × 0.100 mm³ |
| Crystal color and habit | Orange Block |
| Diffractometer | Bruker APEX-II CCD |
| Theta range for data collection | 1.844 to 27.579° |
| Index ranges | −19 <= h <= 18, −8 <= k <= 8, −28 <= l <= 28 |
| Reflections collected | 8186 |
| Independent reflections | 2507 [R(int) = 0.0387] |
| Observed reflections (I > 2sigma(I)) | 1987 |
| Completeness to theta = 25.242° | 99.9% |
| Absorption correction | Semi-empirical from equivalents |
| Max. and min. transmission | 0.9679 and 0.8833 |
| Solution method | SHELXT (Sheldrick, 2014) |
| Refinement method | SHELXL-2018/3 (Sheldrick, 2018) Full-matrix least-squares on F2 |
| Data/restraints/parameters | 2507/0/190 |
| Goodness-of-fit on $F^2$ | 1.039 |
| Final R indices [I > 2sigma(I)] | R1 = 0.0389, wR2 = 0.0880 |
| R indices (all data) | R1 = 0.0544, wR2 = 0.0978 |
| Largest diff. peak and hole | 0.285 and −0.247 e.Å⁻³ |

TABLE 2

Atomic coordinates (×10⁴) and equivalent isotropic displacement parameters ($Å^2 \times 10^3$) for JF2934AFMI. U(eq) is defined as one third of the trace of the orthogonalized $U^{ij}$ tensor.

|       | x       | y        | z        | U(eq) |
|-------|---------|----------|----------|-------|
| S(1)  | 2669(1) | 1754(1)  | 4209(1)  | 24(1) |
| C(1)  | 3375(1) | 3845(3)  | 4263(1)  | 23(1) |
| F(1)  | 3812(1) | 4330(2)  | 4811(1)  | 34(1) |
| C(2)  | 3387(1) | 4848(3)  | 3737(1)  | 20(1) |
| N(2)  | 2830(1) | 3935(2)  | 3257(1)  | 20(1) |
| C(3)  | 2417(1) | 2348(3)  | 3440(1)  | 19(1) |
| N(3)  | 1815(1) | 1211(3)  | 3072(1)  | 23(1) |
| C(4)  | 3864(1) | 6751(3)  | 3630(1)  | 20(1) |
| C(5)  | 4524(1) | 7571(3)  | 4050(1)  | 21(1) |
| C(6)  | 4948(1) | 9432(3)  | 3938(1)  | 21(1) |
| C(7)  | 5635(1) | 10302(3) | 4361(1)  | 26(1) |
| C(8)  | 6044(1) | 12078(3) | 4236(1)  | 29(1) |
| C(9)  | 5787(1) | 13107(3) | 3686(1)  | 29(1) |
| C(10) | 5122(1) | 12328(3) | 3273(1)  | 26(1) |
| C(11) | 4690(1) | 10468(3) | 3383(1)  | 21(1) |
| C(12) | 4018(1) | 9592(3)  | 2959(1)  | 23(1) |
| C(13) | 3624(1) | 7792(3)  | 3076(1)  | 22(1) |

TABLE 3

Bond lengths [Å] and angles [°] for JF2934AFMI.

| | | | |
|---|---|---|---|
| S(1)—C(1) | 1.7305(19) | C(1)—C(2)—C(4) | 128.08(16) |
| S(1)—C(3) | 1.7524(18) | N(2)—C(2)—C(4) | 119.50(15) |
| C(1)—C(2) | 1.346(2) | C(3)—N(2)—C(2) | 111.38(15) |
| C(1)—F(1) | 1.350(2) | N(2)—C(3)—N(3) | 123.8(16) |
| C(2)—N(2) | 1.406(2) | N(2)—C(3)—S(1) | 115.56(13) |
| C(2)—C(4) | 1.477(2) | N(3)—C(3)—S(1) | 120.63(14) |
| N(2)—C(3) | 1.304(2) | C(3)—N(3)—H(3A) | 116.3(14) |
| C(3)—N(3) | 1.362(2) | C(3)—N(3)—H(3B) | 117.3(14) |

TABLE 3-continued

Bond lengths [Å] and angles [°] for JF2934AFMI.

| | | | |
|---|---|---|---|
| N(3)—H(3A) | 0.86(2) | H(3A)—N(3)—H(3B) | 118(2) |
| N(3)—H(3B) | 0.88(2) | C(5)—C(4)—C(13) | 118.67(17) |
| C(4)—C(5) | 1.380(3) | C(5)—C(4)—C(2) | 122.71(16) |
| C(4)—C(13) | 1.421(2) | C(13)—C(4)—C(2) | 118.61(16) |
| C(5)—C(6) | 1.418(3) | C(4)—C(5)—C(6) | 121.05(17) |
| C(5)—H(5) | 0.915(19) | C(4)—C(5)—H(5) | 120.4(12) |
| C(6)—C(11) | 1.424(3) | C(6)—C(5)—H(5) | 118.6(12) |
| C(6)—C(7) | 1.424(3) | C(5)—C(6)—C(11) | 119.54(16) |
| C(7)—C(8) | 1.367(3) | C(5)—C(6)—C(7) | 122.06(17) |
| C(7)—H(7) | 0.94(2) | C(11)—C(6)—C(7) | 118.40(17) |
| C(8)—C(9) | 1.413(3) | C(8)—C(7)—C(6) | 120.81(19) |
| C(8)—H(8) | 0.95(2) | C(8)—C(7)—H(7) | 122.0(13) |
| C(9)—C(10) | 1.367(3) | C(6)—C(7)—H(7) | 117.2(13) |
| C(9)—H(9) | 0.99(2) | C(7)—C(8)—C(9) | 120.74(19) |
| C(10)—C(11) | 1.422(3) | C(7)—C(8)—H(8) | 119.4(14) |
| C(10)—H(10) | 0.913(19) | C(9)—C(8)—H(8) | 119.9(14) |
| C(11)—C(12) | 1.413(3) | C(10)—C(9)—C(8) | 119.96(19) |
| C(12)—C(13) | 1.366(3) | C(10)—C(9)—H(9) | 121.6(12) |
| C(12)—H(12) | 0.96(2) | C(8)—C(9)—H(9) | 118.5(12) |
| C(13)—H(13) | 0.97(2) | C(9)—C(10)—C(11) | 120.87(19) |
| | | C(9)—C(10)—H(10) | 122.1(12) |
| C(1)—S(1)—C(3) | 86.81(8) | C(11)—C(10)—H(10) | 117.0(12) |
| C(2)—C(1)—F(1) | 127.75(17) | C(12)—C(11)—C(10) | 122.41(17) |
| C(2)—C(1)—S(1) | 113.90(14) | C(12)—C(11)—C(6) | 118.39(17) |
| F(1)—C(1)—S(1) | 118.30(13) | C(10)—C(11)—C(6) | 119.20(17) |
| C(1)—C(2)—N(2) | 112.34(16) | C(13)—C(12)—C(11) | 120.93(17) |
| C(13)—C(12)—H(12) | 121.8(12) | C(12)—C(13)—H(13) | 119.2(13) |
| C(11)—C(12)—H(12) | 117.2(12) | C(4)—C(13)—H(13) | 119.3(13) |
| C(12)—C(13)—C(4) | 121.41(17) | | |

Symmetry transformations used to generate equivalent atoms:

TABLE 4

Anisotropic displacement parameters (Å² × 10³) for JF2934AFMI.
The anisotropic displacement factor exponent takes the form:
$-2\pi^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| S(1) | 31(1) | 23(1) | 20(1) | 1(1) | 3(1) | −6(1) |
| C(1) | 27(1) | 23(1) | 19(1) | −3(1) | 1(1) | −4(1) |
| F(1) | 48(1) | 32(1) | 19(1) | −1(1) | −4(1) | −14(1) |
| C(2) | 20(1) | 18(1) | 21(1) | −3(1) | 2(1) | 1(1) |
| N(2) | 20(1) | 18(1) | 21(1) | −1(1) | 2(1) | −1(1) |
| C(3) | 20(1) | 18(1) | 19(1) | −2(1) | 4(1) | 2(1) |
| N(3) | 26(1) | 22(1) | 21(1) | 0(1) | 3(1) | −6(1) |
| C(4) | 22(1) | 17(1) | 21(1) | −2(1) | 4(1) | 2(1) |
| C(5) | 22(1) | 22(1) | 20(1) | −1(1) | 3(1) | 1(1) |
| C(6) | 20(1) | 20(1) | 23(1) | −3(1) | 5(1) | 2(1) |
| C(7) | 26(1) | 26(1) | 27(1) | −4(1) | 4(1) | 0(1) |
| C(8) | 23(1) | 29(1) | 35(1) | −10(1) | 6(1) | −4(1) |
| C(9) | 27(1) | 19(1) | 44(1) | −4(1) | 13(1) | −3(1) |
| C(10) | 27(1) | 20(1) | 33(1) | 2(1) | 10(1) | 2(1) |
| C(11) | 20(1) | 18(1) | 27(1) | −2(1) | 7(1) | 2(1) |
| C(12) | 27(1) | 19(1) | 23(1) | 3(1) | 4(1) | 4(1) |
| C(13) | 22(1) | 21(1) | 21(1) | −2(1) | 0(1) | 2(1) |

TABLE 5

Hydrogen coordinates (×10⁴) and isotropic displacement
parameters (Å² × 10³) for JF2934AFMI.

| | x | y | z | U(eq) |
|---|---|---|---|---|
| H(3A) | 1885(14) | 1210(30) | 2693(10) | 28(6) |
| H(3B) | 1612(15) | 110(40) | 3226(10) | 33(6) |
| H(5) | 4704(12) | 6910(30) | 4405(8) | 16(5) |
| H(7) | 5795(14) | 9590(30) | 4726(10) | 27(5) |
| H(8) | 6508(16) | 12620(40) | 4524(10) | 39(6) |
| H(9) | 6095(14) | 14400(30) | 3613(9) | 34(6) |
| H(10) | 4937(13) | 12960(30) | 2914(9) | 17(5) |
| H(12) | 3852(13) | 10310(30) | 2589(9) | 23(5) |
| H(13) | 3156(14) | 7230(30) | 2780(10) | 33(6) |

TABLE 6

Torsion angles [°] for JF2934AFMI.

| | |
|---|---|
| C(3)—S(1)—C(1)—C(2) | 0.49(15) |
| C(3)—S(1)—C(1)—F(1) | 178.02(16) |
| F(1)—C(1)—C(2)—N(2) | −178.35(17) |
| S(1)—C(1)—C(2)—N(2) | −1.1(2) |
| F(1)—C(1)—C(2)—C(4) | −1.5(3) |
| S(1)—C(1)—C(2)—C(4) | 175.73(15) |
| C(1)—C(2)—N(2)—C(3) | 1.3(2) |
| C(4)—C(2)—N(2)—C(3) | −175.84(15) |
| C(2)—N(2)—C(3)—N(3) | 177.96(17) |
| C(2)—N(2)—C(3)—S(1) | −0.9(2) |
| C(1)—S(1)—C(3)—N(2) | 0.29(14) |
| C(1)—S(1)—C(3)—N(3) | −178.66(16) |
| C(1)—C(2)—C(4)—C(5) | 13.4(3) |
| N(2)—C(2)—C(4)—C(5) | −169.98(17) |
| C(1)—C(2)—C(4)—C(13) | −165.76(19) |
| N(2)—C(2)—C(4)—C(13) | 10.9(2) |
| C(13)—C(4)—C(5)—C(6) | 1.0(3) |
| C(2)—C(4)—C(5)—C(6) | −178.19(16) |
| C(4)—C(5)—C(6)—C(11) | −0.2(3) |
| C(4)—C(5)—C(6)—C(7) | −179.57(17) |
| C(5)—C(6)—C(7)—C(8) | 178.79(18) |
| C(11)—C(6)—C(7)—C(8) | −0.6(3) |
| C(6)—C(7)—C(8)—C(9) | 0.7(3) |
| C(7)—C(8)—C(9)—C(10) | 0.2(3) |
| C(8)—C(9)—C(10)—C(11) | −1.1(3) |
| C(9)—C(10)—C(11)—C(12) | −178.25(18) |
| C(9)—C(10)—C(11)—C(6) | 1.1(3) |
| C(5)—C(6)—C(11)—C(12) | −0.3(3) |
| C(7)—C(6)—C(11)—C(12) | 179.15(17) |
| C(5)—C(6)—C(11)—C(10) | −179.71(16) |
| C(7)—C(6)—C(11)—C(10) | −0.3(3) |
| C(10)—C(11)—C(12)—C(13) | 179.31(18) |
| C(6)—C(11)—C(12)—C(13) | −0.1(3) |
| C(11)—C(12)—C(13)—C(4) | 0.9(3) |

Symmetry transformations used to generate equivalent atoms:

TABLE 7

Hydrogen bonds for JF2934AFMI [Å and °].

| D-H...A | d(D-H) | d(H...A) | d(D...A) | <(DHA) |
|---|---|---|---|---|
| N(3)-H(3A)...N(2)#1 | 0.86(2) | 2.21(2) | 3.068(2) | 175(2) |

Symmetry transformations used to generate equivalent atoms:
1 −x + ½, −y + ½, −z + ½

Example 13

Without wishing to be bound by theory, an activity-stimulated glutamine (Gln)/methylaminoisobutyric acid (MeAIB) transporter in hippocampal excitatory synapses supports excessive glutamate (Glu) neurotransmission under seizure conditions to facilitate NMDAR-dependent neurodegeneration.

Figure 19:
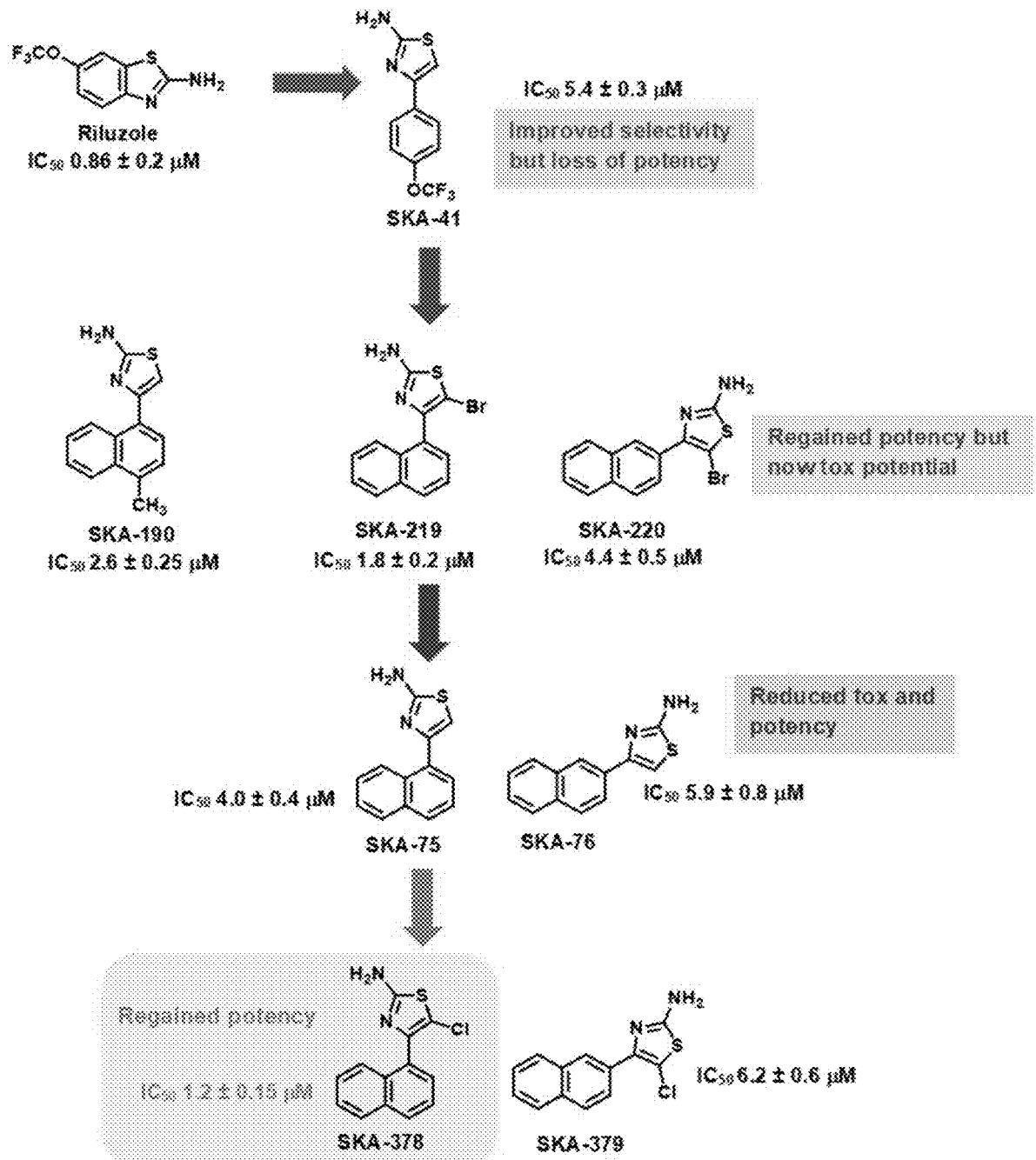
FIG. 19 shows a scheme of riluzole derivatives.

Aim 1 will to identify brain penetrant riluzole-derivatives that preferentially block activity-stimulated Gln transport into hippocampal neurons and Glu release from synapses. We have recently reported the functional identification of an activity-regulated, high-affinity ($K_m$~35 μM) Gln/MeAIB transport system in mature hippocampal neurons that is inhibited by riluzole, an anti-glutamatergic drug (Erickson, 2017). Without wishing to be bound by theory, we will validate a collection of riluzole derivatives to determine if they preferentially inhibit activity-regulated Gln transport over $Na^+$ channel blockade, which is a known target of riluzole. Initial screens were based on the ability of these compounds to block spontaneous activity-regulated $^{14}C$-MeAIB transport, which is dependent on the presence of external $Ca^{2+}$ ions and can be blocked by verapamil (a $Ca^{2+}$-channel blocker), tetrodotoxin (a $Na^+$-channel blocker), and high concentrations (2 mM) of GABA that suppress excitatory transmission. MeAIB is more stable than Gln and has been used to identify low affinity system A subtypes of Gln transporters in the past. We now show that high-affinity $^{14}C$-MeAIB transport is stimulated by treating neurons with 4-aminopyridine (4-AP), which is a $K^+$ channel blocker that prevents repolarization of neurons, thereby prolonging depolarization. Such $K^+$ stimulated transport using 4-AP is more physiological than our original method using 60 mM KCl to depolarize axon terminals. We find that maximal stimulation (~2×) occurs with 200 µM 4-AP, which is blocked by riluzole and all active SKA-41 derivatives. Our original screens shown in FIG. 2 of the grant application uncovered the novel riluzole derivative SKA-41, which unlike riluzole is not a benzothiazole with a fused heterocylic ring system; several other active compounds were identified that do have this fused structure (SKA-3, SKA-7, SKA-11, SKA-19, SKA-51), like riluzole. Without wishing to be bound by theory, these compounds may exhibit all (or many) of the adverse effects of riluzole as a specific therapy for excitotoxic disease. Also, the solubility/brain penetration (e.g., SKA-7) and activation of potassium activated calcium ($K_{Ca}2.2$, SK2) channels (Sankaranarayanan, 2009) or sodium channels (e.g., NaV) Coleman, 2014) are also like riluzole. Fortunately, we synthesized 20 derivatives of SKA-41 for testing. We found that several of those (SKA-190, SKA-193, SKA-219, SKA-220, and SKA-247) blocked spontaneous transport activity, like SKA-41 and riluzole. SKA-219 and SKA-220 were as potent as riluzole but they have a bromine substitution on the imidazole ring. Heavy halogens like bromine and iodine in drugs have been associated with phototoxicity, photoreactivity, reactive metabolite formation, etc. that can lead to safety issues. Brominated compounds are also typically poorly soluble that makes administration to individuals more complicated (Heike, 2020). We therefore re-examined the unsubstituted 'parent' compounds of SKA-219 and SKA-220 (i.e., SKA-75 and SKA-76) that were in the original SKA-41 derivative screen in my assay (but where much less potent than riluzole, so we did not focus on them), and show that they are indeed less potent (FIG. 19). $IC_{50}$ values confirm that while these two compounds (SKA-75 and SKA-76) are active they are much less potent than riluzole to block both spontaneous or 4-AP stimulated transport than any of the previously announced active compounds (i.e., SKA-3, SKA-7, SKA-11, SKA-19, SKA-47, SKA-51), including riluzole. So, the chlorinated substituted derivatives of SKA-75 and SKA-76 (instead of Br) have been synthesized to produce the chemical identities (NCI) SKA-378 and SKA-379 (and others), and they are as active as SKA-219 and SKA-220, respectively (FIG. 19).

The potency of riluzole and all the active SKA-41 derivatives to block 4-AP stimulated transport is ~3-fold less than the potency of these compounds to block spontaneous transport, reasons for which are currently under investigation. SKA-378 (and other active chlorine-substituted active derivatives described) are candidates for validation in vitro and in vivo. An objective is to evaluate the SKA-41 derivatives based upon potency to inhibit activity-regulated Gln/MeAIB transport and selectivity over blockade of $Na^+$ channels and obtain a compound(s) that has less sedative properties than riluzole and better pharmacokinetic and brain penetrating properties than riluzole.

Aim 2 tests if there is a single activity-stimulated Gln transporter expressed in hippocampal excitatory synapses. Without wishing to be bound by theory, we will determine whether any of the known Gln transporters that can transport MeAIB (SNAT1, SNAT2, SNAT8, NTT4/Rxt1, PAT2, or SNAT6 which is an orphan that is expressed in excitatory synapses) represent the activity-regulated Gln/MeAIB transporter that we have described in hippocampal neurons. Without wishing to be bound by theory, we will transduce dissociated neurons with lentiviral shRNA expression plasmids for these transporters and then assess their ability to block high-affinity, $K^+$-stimulated and spontaneous activity-regulated Gln/MeAIB transport. Our recent data indicates that we can also include another transporter in these experiments that can be involved in this activity, based on recent pharmacological results. Many neurotransmitter transporters are known to recycle between intracellular pools and the plasma membrane in a $Ca^{2+}$-regulated manner. Without wishing to be bound by theory, the activity-regulated Gln/MeAIB transporter described (Erickson, 2017) behaves in a similar manner. Indeed, we now report that the phorbal myristate acetate (PMA) treatment (10 min) prior to KCl (60 mM) depolarization stimulates $^{14}C$-MeAIB transport ~two-fold. PMA stimulation of $^{14}C$-MeAIB transport is dose related (maximal at ~20 nM) and is abolished by the general protein kinase inhibitor staurosporine (200 nM). PMA regulation of neurotransmitter transporter cycling between intracellular compartments (i.e., vesicles) and the plasma membrane, in general, is well described for many neural transporters for activity-dependent regulation presynaptic release of neurotransmitters. We showed that several neutral amino acids (alanine, proline, sarcosine, Gln, histidine, and glycine block (~90%) $^{14}C$-MeAIB transport activity when present at 2 mM concentration (Erickson, 2017). Assessing the potency of these amino acids in our in vitro assay in more detail and revealing now a surprising discovery. The relative affinities of these amino acids for the PMA-induced $K^+$-activity-stimulated Gln/MeAIB transport activity are: sarcosine (~8 µM), proline (~9 µM), alanine (~25 µM), MeAIB (~35 µM), histidine (~48 µM), Gln (~97 µM) and glycine ('100 µM). Without wishing to be bound by theory the high affinity, activity-regulated Gln/MeAiB transporter that we have identified in hippocampal neurons may be the L-proline transporter (PROT: Km~9 µM) expressed on synaptic vesicles in a subset of excitatory synaptic terminals (esp. in the hippocampus and cortical-synaptic connected regions), which recycles between vesicles and the plasma membrane (see Fremeau et al., 1992). The transport system can be dependent on both sodium and chloride ions; which it is (high-affinity $^{14}C$-MeAIB transport is 0 and 22% of control activity in choline-Cl and Na-gluconate containing buffers, respectively. System A transporters are only sodium dependent co-transporters, so it is that high-affinity, activity-regulated Gln/MeAIB transport in hippocampal neurons is not mediated by system A, which is a low affinity transport system anyway. In the early studies of transport specificity, MeAIB was never examined as a substrate (Fremeau et al., 1992). Interestingly, in the rare genetic conditions that cause hyperprolinemia in which the enzyme proline oxidase (PRODH) or 1-pyrroline-5-carboxylate dehydrogenase (ALDH4A1) is inactivated, serum proline levels increase.

Patients with either Type I (or Type II) hyperprolinemia mostly suffer from epilepsy often presenting with different types of seizures; the disorder is also associated with mild to moderate mental retardation (Afenjar et al., 2007; Reulecke and Denecke, 2009). In addition, recent work indicates that sarcosine suppresses epileptogenesis in rats by a mechanism that can rely on the glycine transporter GlyT1 (Shen et al. 2020). However, while GlyT1 is inhibited by sarcosine, it is does not recognize alanine or MeAIB (Guastella et al., 1992) so it cannot be the transporter described by us (Erickson, 2017). Our recent data provoke attention towards activity-regulated transport of proline, in addition to Gln, in the regulation of glutamatergic transmission that may be involved in Glu-induced excitoxocity; esp. after seizure conditions. Without wishing to be bound by theory, the activity-regulated Gln/MeAIB transporter that we have described, and will identify, is critical for epileptogenesis. In addition, the ability of our compounds to suppress epileptogenesis following seizure activity can be independent of their anti-convulsant properties.

Figure 20:
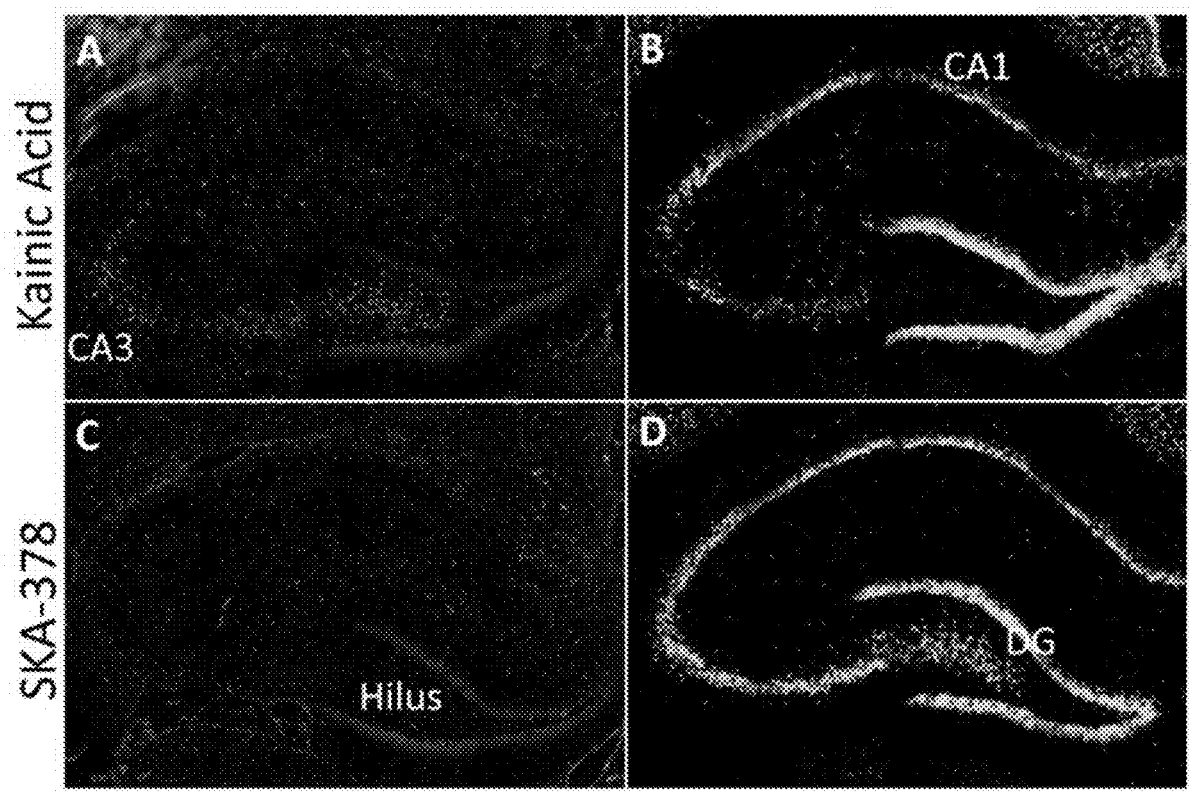
FIG. 20 shows panels A, B, C, and D immunohistochemistry images.

In Aim 3, we treat male and female rats with the 'best' SKA-41 derivatives before and after injection of kainic acid (KA). The KA-induced status epilepticus (SE) model is a well-validated model of temporal lobe epilepsy (TLE), the major form of human epilepsy. The model allows studying the different stages between SE and the development of TLE including SE, the acute and latent stages of epileptogenesis and chronic epilepsy. The excitotoxin KA causes excessive Glu release in the hippocampus and selective destruction of inhibitory SOM interneurons in the hilus region of the dentate gyrus (DG) and loss of pyramidal neurons in the CA3 (esp), and also CA1 regions. We scaled up synthesis of SKA-41, 219, and SKA-378. The identity of the compounds was confirmed by $^1$H- and $^{13}$C-NMR and high-resolution mass spectrometry. Compound purity is determined by HPLC and no compounds with less then 98% purity were used. We give injections of Migyol 812 (solvent) or riluzole derivative (30 mg/kg) to rats 30 min prior to KA (5 mg/kg/hr×2 hr; i.p.), and 30 min after the first KA injection. All rats pretreated with solvent only (controls) exhibited stage 4 seizures (SE) by 2 hr that last up to 4 hr. Rats were processed for immunohistochemistry 3 days after KA administration. As expected, we find that KA treatment induces significant neural damage (green cells) in the CA3 pyramidal neuron subfield and in neurons in the hilus (FIG. 20 Panel A), which are SOM containing GABAergic interneurons (not shown). Fluoro jade B is a high affinity fluorescent marker used for the localization of neuronal degeneration. Likewise, NeuN immunohistochemistry reveals disorganized neuronal distribution in pyramidal neurons in the CA3 region and loss of neurons in the hilus of the dentate gyrus (FIG. 20 Panel B). We find that pretreatment with SKA-378 prevents fluoro-jade B staining in all regions of the hippocampus (FIG. 20 Panel C). SKA-378 pretreatment also prevents the disorganization and cell loss in pyramidal neurons in the CA3 regions based in NeuN staining and also in inhibitory neuron loss in the hilus of the hippocampus (FIG. 20 Panel D). Prevention of the destruction of these neurons is critical to control the progression of epileptogenesis We have obtained similar results with SKA-41 and with SKA-219 (the bromine derivative of SKA-75). In studies, we have also administered SKA-378 (30 mg/kg) one hr after the onset of stage IV seizures (SE), followed by another injection at 4 hr post SE and then once each day for 3 days. We find that SKA-378 is also neuroprotective under these conditions. Our recent results indicate that SKA-41, SKA-378 and SKA-219 are neuroprotective against Glu-induced excitotoxicity in the KA model of TLE, and therefore are can be candidates that prevent seizure-induced epileptogenesis.

Example 14

As described herein, an activity-stimulated glutamine (Gln)/methylaminoisobutyric acid (MeAIB) transporter in hippocampal excitatory synapses supports excessive glutamate (Glu) neurotransmission under seizure conditions to facilitate NMDAR-dependent neurodegeneration. We have three aims as described herein.

Figure 21:
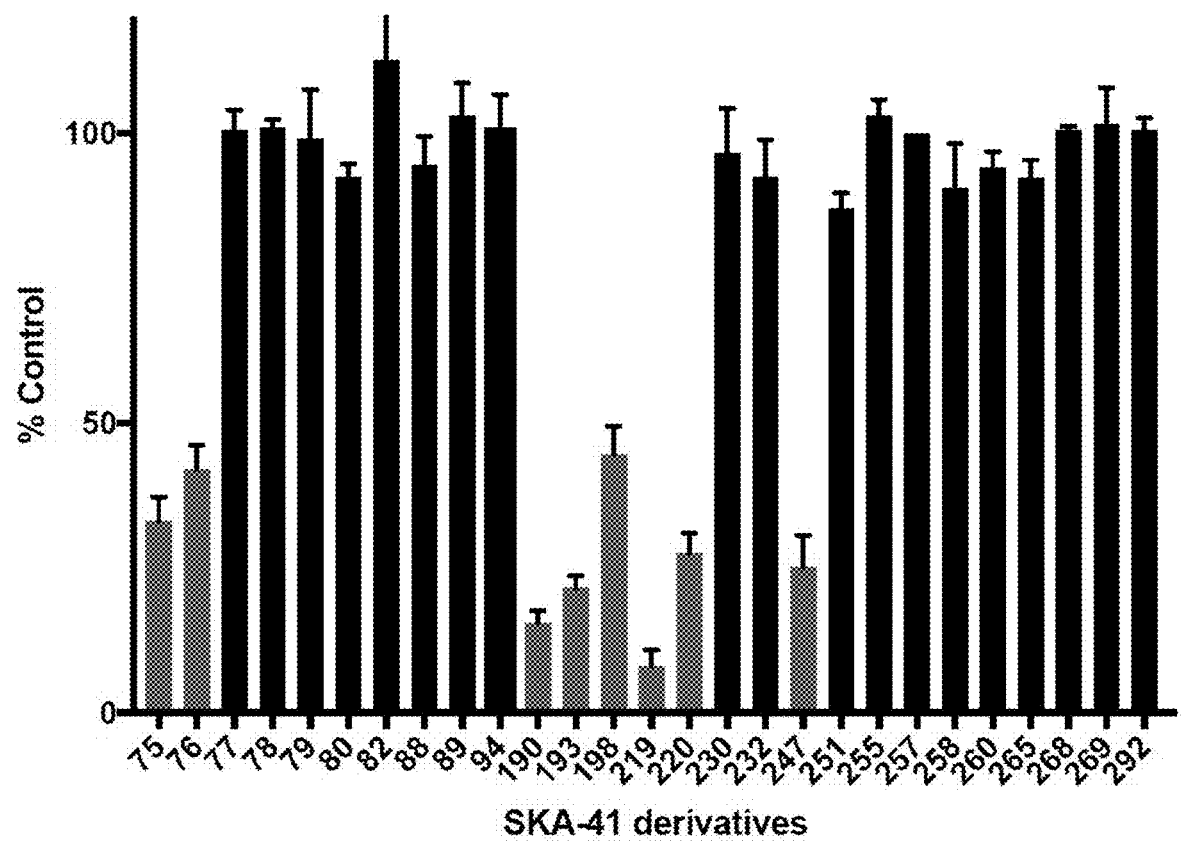
FIG. 21 shows a graph of transport activity of SKA-41 derivatives.
Figure 22:
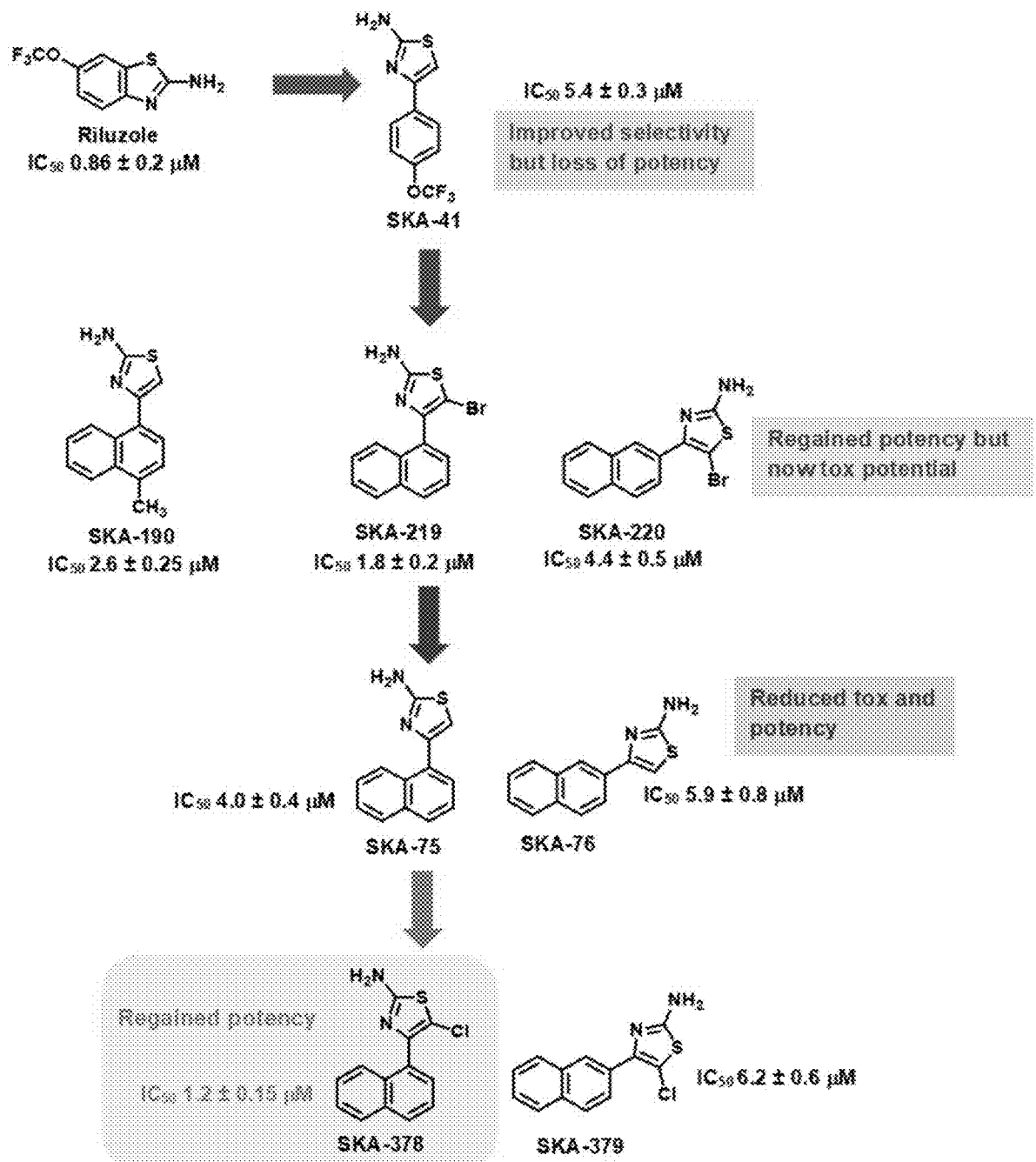
FIG. 22 shows a scheme of riluzole derivatives.

Aim 1 seeks to identify brain penetrant riluzole-derivatives that preferentially block activity-stimulated Gln/MeAIB transport into hippocampal neurons and Glu release from synapses. We have reported the functional identification of an activity-regulated, high affinity (Km~35 μM) Gln/MeAIB transport system in mature hippocampal neurons that is inhibited by riluzole, an anti-glutamatergic drug (Erickson, 2017). We examined a collection of riluzole derivatives to determine if they preferentially inhibit activity-regulated Gln transport over Na$^+$ channel blockade, which is a known target of riluzole. Initial screens were based on the ability of these compounds to block spontaneous activity-regulated $^{14}$C-MeAIB transport, which is dependent on the presence of external Ca$^{2+}$ ions and can be blocked by verapamil (a Ca$^{2+}$-channel blocker), tetrodotoxin (a Na$^+$-channel blocker), and high concentrations (2 mM) of GABA that suppress excitatory transmission. MeAIB is more stable than Gln and has been used to identify low affinity system A subtypes of Gln transporters in the past. We now show that high-affinity $^{14}$C-MeAIB transport is stimulated by treating neurons with 4-aminopyridine (4-AP), which is a K$^+$ channel blocker that prevents repolarization of neurons, thereby prolonging depolarization. Such K$^+$-stimulated transport using 4-AP is more physiological than our original method using 60 mM KCl to depolarize axon terminals. We find that maximal stimulation (~2×) occurs with 200 μM 4-AP, which is blocked by riluzole and all active SKA-41 derivatives. Our original screens (shown in FIG. 22) uncovered the riluzole derivative SKA-41, which unlike riluzole is not a benzothiazole with a fused heterocylic ring system; several other active compounds were identified that do have this fused structure (SKA-3, SKA-7, SKA-11, SKA-19, SKA-51), like riluzole. These compounds may exhibit all (or many) of the adverse effects of riluzole if used as a specific therapy for excitotoxic disease. Also, the solubility/brain penetration (e.g., SKA-7) and activation of potassium activated calcium (K$_{Ca}$2.2, SK2) channels (Sankaranarayanan, 2009) or sodium channels (e.g., NaV) (Coleman, 2014) are also like riluzole. We had 27 derivatives of SKA-41 for testing. We found that several of those (SKA-75, SKA-76, SKA-190, SKA-193, SKA-198, SKA-219, SKA-220, and SKA-247) inhibited spontaneous transport activity at 10 μM (FIG. 21), like SKA-41 and riluzole. SKA-219 was as potent as riluzole but it has a bromine substitution on the imidazole ring. SKA-219 is the brominated derivative of SKA-75. Heavy halogens like bromine and iodine in drugs have been associated with phototoxicity, photoreactivity, reactive metabolite formation, etc. that can lead to safety issues. Brominated compounds are also typically poorly soluble that makes administration to individuals more complicated (Heike, 2020). So, we have now synthesized the chlorinated substituted derivatives of SKA-75 and SKA-76 (instead of Br) to produce the new chemical identities (NCI) SKA-378 and SKA-379 (and others), and they are as active as SKA-219 and SKA-220, respectively (FIG. 22).

The potency of riluzole and all the active SKA-41 derivatives to block 4-AP stimulated transport is ~3-fold less than the potency of these compounds to block spontaneous transport. SKA-378 (and other active chlorine-substituted active derivatives described) are candidates for further testing in vitro and in vivo. An objective is to identify the SKA-41 derivative based upon its potency to inhibit activity-regulated Gln/MeAIB transport and selectivity over blockade of Na$^+$ channels and obtain a compound that has less sedative properties than riluzole and better pharmacokinetic and brain penetrating properties than riluzole.

Aim 2 tests whether there is a single activity stimulated Gln transporter expressed in hippocampal excitatory synapses. Without wishing to be bound by theory, we will determine whether any of the known Gln transporters that are capable of transporting MeAIB (SNAT8, NTT4/Rxt1, PAT2, or SNAT6; an orphan that supposedly is expressed in excitatory synapses) represent the activity regulated Gln/MeAIB transporter that we have described in hippocampal neurons. This also included SNAT1 and SNAT2, which we were the first to functionally identify 20 years ago (Varoqui et al., 2000; Yao et al., 2000). We will transduce dissociated neurons with lentiviral shRNA expression plasmids for these transporters and then assess their ability to block high affinity, K$^+$-stimulated and spontaneous activity-regulated Gln/MeAIB transport. Our recent data indicates that we can also include another transporter in these experiments that can be involved in this activity, based on recent pharmacological results. Many neurotransmitter transporters are known to recycle between intracellular pools and the plasma membrane in a Ca$^{2+}$-regulated manner. Without wishing to be bound by theory, the activity-regulated Gln/MeAIB transporter described (Erickson, 2017) behaves in a similar manner. Indeed, we report that the phorbal myristate acetate (PMA) treatment (10 min) prior to KCl (60 mM) depolarization stimulates 14C-MeAIB transport ~two-fold. PMA stimulation of 14C-MeAIB transport is dose related (maximal at ~20 nM) and is abolished by the general protein kinase inhibitor staurosporine (200 nM). PMA regulation of neurotransmitter transporter cycling between intracellular compartments (i.e., vesicles) and the plasma membrane, in general, is well described for many neural transporters for activity-dependent regulation presynaptic release of neurotransmitters. We showed that several neutral amino acids (alanine, proline, sarcosine, Gln, histidine, and glycine block (~90%) 14C-MeAIB transport activity when present at 2 mM concentration (Erickson, 2017). Assessing the potency of these amino acids in my in vitro assay in more detail we reveal now a surprising discovery. The relative affinities of these amino acids for the PMA-induced K+-activity-stimulated Gln/MeAIB transport activity are: sarcosine (~8 µM), proline (~9 µM), alanine (~25 µM), MeAIB (~35 µM), histidine (~48 µM), Gln (~97 µM) and glycine (~100 µM). Without wishing to be bound by theory, the high affinity, activity-regulated Gln/MeAiB transporter that we have identified in hippocampal neurons can be the high-affinity L-proline transporter (PROT: Km~9 µM) expressed on synaptic vesicles in a subset of excitatory synaptic terminals (esp. in the hippocampus and cortical-synaptic connected regions), which recycles between vesicles and the plasma membrane (see Fremeau et al., 1992). Without wishing to be bound by theory, the transport system should be dependent on both sodium and chloride ions; which we now know it is (high affinity 14C-MeAIB transport is 0 and 22% of control activity in choline-Cl and Na-gluconate containing buffers, respectively). System A transporters are only sodium dependent cotransporters, so without wishing to be bound by theory, high-affinity, activity-regulated Gln/MeAIB transport in hippocampal neurons is not mediated by system A, which is a low affinity transport system anyway. In the early studies of transport specificity, MeAIB was never examined as a substrate (Fremeau et al., 1992). Interestingly, in the rare genetic conditions that cause hyperprolinemia in which the enzyme proline oxidase (PRODH) or 1-pyrroline-5-carboxylate dehydrogenase (ALDH4A1) is inactivated, serum proline levels increase dramatically. Patients with either Type I (or Type II) hyperprolinemia mostly suffer from epilepsy often presenting with different types of seizures; the disorder is also associated with mild to moderate mental retardation (Afenjar et al., 2007; Reulecke and Denecke, 2009). In addition, recent work indicates that sarcosine suppresses epileptogenesis in rats by a mechanism that might rely on the glycine transporter GlyT1 (Shen et al. 2020). However, while GlyT1 is inhibited by sarcosine, it is does not recognize alanine or MeAIB (Guastella et al., 1992) so it cannot be the transporter described by my lab (Erickson, 2017). Our recent data provoke attention towards activity-regulated transport of proline, in addition to Gln, in the regulation of glutamatergic transmission that may be involved in Glu-induced excitoxocity; esp. after seizure conditions. Without wishing to be bound by theory, the activity-regulated Gln/MeAIB transporter that we have described is critical for epileptogenesis. In addition, the ability of our compounds to suppress epileptogenesis following seizure activity can be independent of their anticonvulsant properties.

Figure 23:
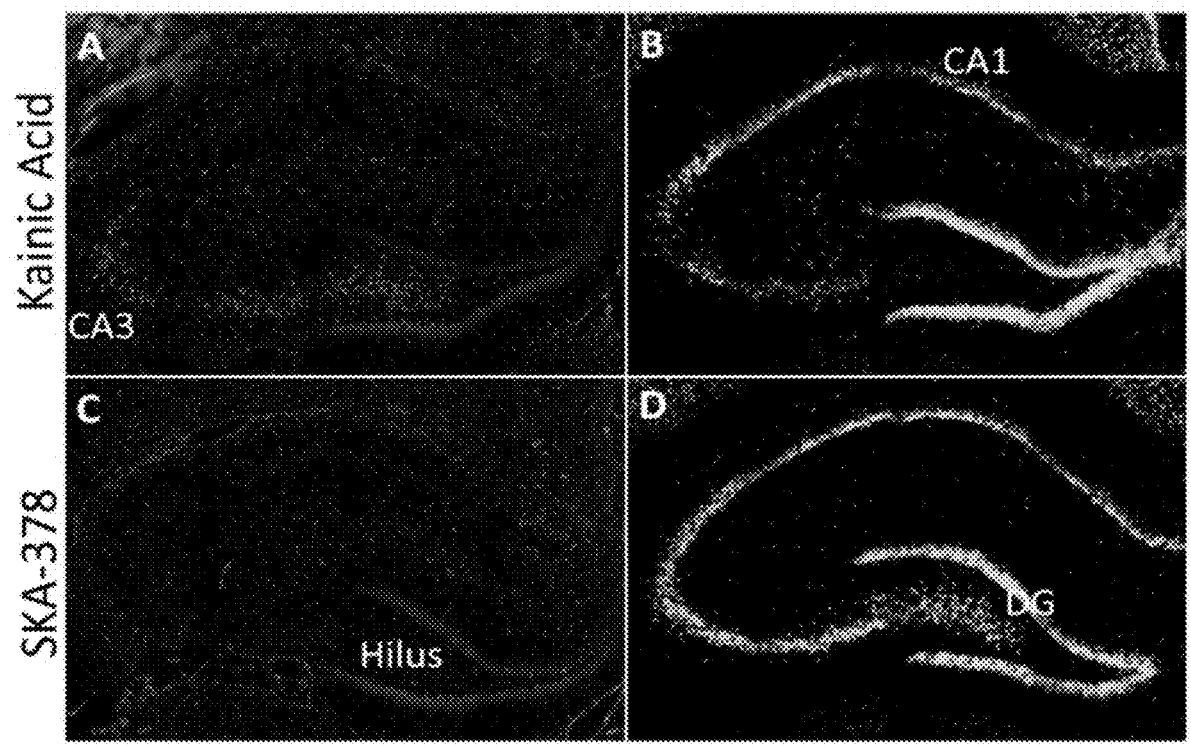
FIG. 23. shows immunohistochemistry images. Neural Protection by SKA-378 Following KA-induced SE in Rats. Notice, selective neural damage (green cells) in the CA3 region and hilus of the DG by fluorojade B labeling (Panel A) and loss of these same neurons as shown by NeuN IHC (Panel B). Neurodegeneration is not observed in the CA3 region nor in the hilar region in KA-treated rats given SKA-378 (Panel B and Panel C). This is a representative figure from the anterior portion of the hippocampus (Bregma −2.80).

In Aim 3, we treat male and female rats with SKA-41 derivatives before and after injection of kainic acid (KA). The KA-induced status epilepticus (SE) model is a well-validated model of temporal lobe epilepsy (TLE), the major form of human epilepsy. The model allows studying the different stages between SE and the development of TLE including SE, the acute and latent stages of epileptogenesis and chronic epilepsy. The excitotoxin KA causes excessive Glu release in the hippocampus and selective destruction of inhibitory SOM interneurons in the hilus region of the dentate gyrus (DG) and loss of pyramidal neurons in the CA3 (esp) and also CA1 regions. We scaled up synthesis of SKA-41, 219, and SKA-378. The identity of the compounds were confirmed by $^1$H- and $^{13}$C-NMR and high-resolution mass spectrometry. Compound purity is determined by HPLC and no compounds with less then 98% purity were used. We give injections of Migyol 812 (solvent) or riluzole derivative (30 mg/kg) to rats 30 min prior to KA (5 mg/kg/hr×2 hr; i.p.), and 30 min after the first KA injection. All rats pretreated with solvent only (controls) exhibited stage 4 seizures (SE) by 2 hr that last up to 4 hr. Rats were processed for immunohistochemistry 3 days after KA administration. We find that KA treatment induces significant neural damage (green cells) in the CA3 pyramidal neuron subfield and in neurons in the hilus (FIG. 23 Panel A), which are SOM containing GABAergic interneurons (not shown). Fluorojade B is a high affinity fluorescent marker used for the localization of neuronal degeneration. Likewise, NeuN immunohistochemistry reveals disorganized neuronal distribution in pyramidal neurons in the CA3 region and loss of neurons in the hilus of the dentate gyrus (FIG. 23 Panel B). We find that pretreatment with SKA-378 prevents fluorojade B staining in all regions of the hippocampus (FIG. 23 Panel C). SKA-378 pretreatment also prevents the disorganization and cell loss in pyramidal neurons in the CA3 regions based in NeuN staining and also in inhibitory neuron loss in the hilus of the hippocampus (FIG. 23 Panel D). Prevention of the destruction of these neurons is critical to control the progression of epileptogenesis We have obtained similar results with SKA-219 (the bromine derivative of SKA-75). In studies, we have also administered SKA-378 (30 mg/kg) one hr after the onset of stage IV seizures (SE), followed by another injection at 4 hr post SE and then once each day for 3 days. We find that SKA-378 is also neuroprotective under these conditions. Our results indicate that SKA-378 and SKA-219 are neuroprotective against Glu-induced excitotoxicity in the KA model of TLE, and therefore are candidates that prevent seizure-induced epileptogenesis.

Example 15

Below we describe our experiments of how validating presynaptic agents to prevent neural injury might be important for SE induced epileptogenisis.

Aim 1 Seeks to Validate Brain Penetrant Riluzole-Derivatives that Preferentially Block Activity-Stimulated Gln Transport into Hippocampal Neurons and Glu Release from Synapses.

We have identified an important subgroup of neurochemicals, related to riluzole (and some of them are new chemical identities (NCI's)), that inhibit high-affinity, activity regulated/stimulated Gln/MeAIB transport in hippocampal neurons in vitro. Structurally, they differ from riluzole because they do not have the fused heterocyclic ring system in riluzole as most other active riluzole derivatives we have identified. We have now advanced our in vitro procedures of activity-regulated and activity-stimulated $^{14}$C-MeAIB transport by including 4-AP stimulated spontaneous transport and PMA-induced K+-stimulated transport, respectively, in our screening process. These new assays are important to compare these new inhibitors that affect our novel transport system potentially at multiple sites, which enables us to further evaluate the efficacy and potency of these active riluzole derivatives; esp. our NCI's. We are and will continue to work on the effect of these NCI's on Glu release under all of these conditions. We will generate final $IC_{50}$ values for the effects of our SKA-75 related (via SKA-41) chlorinated derivative SKA-378, which we have deemed to be our 'best' candidate to date. We will continue to finalize data on the differential potency of these compounds to affect spontaneous vs. 4-AP stimulated transport and to obtain potency curves against riluzole compared to all our active compounds to inhibit the PMA-stimulated, $K^+$ depolarization induced transport activity. We will continue to identify our 'best' compounds based upon our in vitro assays. We will evaluate the potency of our 'best' compounds to affect other targets of riluzole, like $Na_V$ channels in vitro and in vivo as described in the grant. Without wishing to be bound by theory, the synthesis of the compounds will allow their incorporation into the food for long-term administration. We can monitor plasma/brain levels during time after their administration because we developed the chemical synthesis of these compounds and the methods used for their detection in the blood and brain.

Aim 2 Tests that there is a Single Activity-Stimulated Gln Transporter Expressed in Hippocampal Excitatory Synapses.

We are basing our assessment of our NCI's upon their differential potency to inhibit spontaneous, activity regulated $^{14}$C-MeAIB transport and 4-AP (depolarizing agent) stimulated transport. SKA-378 is our most potent riluzole derivative in both assays. We will now focus to determine if these compounds affect PMA (phorbol ester) stimulation of $K^+$ (60 mM) depolarization induced transport activity that results in increased exocytosis of synaptic vesicles to expose our transporter to the plasma membrane. We will continue to evaluate the pharmacology and biochemical determinants of this high affinity MeAIB/Gln transporter expressed in hippocampal neurons to ascertain if such activity is mediated by a specific neuronal transporter or by multiple ones. We will continue our pharmacological assessment of the nature of this activity using our in vitro assay, which is the fundamental basis that led to all these discoveries. We have experience in identifying transporters in neurotransmission and have data to support the identification of the transporter that is involved in this activity that can be involved in presynaptic prevention of neural injury. We have experience with molecular techniques involving cDNA cloning and using heterologous systems to characterize neurotransmitter transporter proteins.

Aim 3 Tests that Inhibition of Activity Regulated Gln/MeAIB Transport by the 'Best' SKA-41 Derivative is Neuroprotective.

We will validate which SKA-41 derivative would prevent hippocampal neural degeneration by kainic acid treatment in male and female rats. The KA-induced status epilepticus (SE) model is a well-validated model of temporal lobe epilepsy (TLE), the major form of human epilepsy. The model allows studying the different stages between SE and the development of TLE including SE, the acute and latent stages of epileptogenesis and chronic epilepsy. We will to finalize the quantification of results of fluorojade B labeling of injured pyramidal neurons in the CA3 region and in the inhibitory SOM-containing neurons in the hilus of the dentate gyrus in the KA treated rats and their protection by SKA-378 (30 mg/kg) when given prophylactically. We will assess the dose dependence of this effect in vivo using a lower dose; 5 mg/kg. We also include NeuN and SOM immunohistochemistry to quantitate cell numbers and to evaluate disorganized pyramidal neuronal fields. Without wishing to be bound by theory, we also include other chlorinated active derivatives pending further in vitro experiments to assess their potency and selectivity, and pharmacokinetics that include brain permeation.

Prevention of the destruction of pyramidal excitatory neurons in the CA3 region and the SOM-containing inhibitory neurons in the dentate hilar region of the dentate gyrus (DG) is critical to control the progression of epileptogenesis Without wishing to be bound by theory, it is also important to avoid damage to CA1 neurons, which are important for learning and memory. Pyramidal neurons in the CA2 region and DG neurons are not affected by KA treatment. We will therefore also test the prediction that administration of SKA-378 (and other derivatives) after KA-induced SE is also neuroprotective against Glu-induced excitotoxicity. We will administer SKA-378 (30 mg/kg) 1 hr after the rats reach stage IV seizure activity (SE) and then at 4 hr post-SE followed by a single injection each day for three days before sacrifice and analysis. This would model the clinical situation in human subjects that have a seizure and then are seen by EM first-responders or in the clinic. TLE is difficult to manage because the mechanisms involved in the process of epileptogenesis that leads to epilepsy are not well understood. Thus, the anti-convulsants that are used for epilepsy treatment may only manage the seizures, but do not necessarily prevent the development of disease following the initial traumatic event (i.e., SE). We will incorporate SKA-378 into lab chow, feed rats for several weeks and then measure plasma and brain levels to compare these levels to those observed after i.p. injection, for example. This will enable us to treat rats long term (months) after SE activity and thus may enable us to expand this project to test our NCIs as candidates to prevent seizure-induced epileptogenesis in rats.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

---

What is claimed:

1. A neuroprotective compound of formula (I):

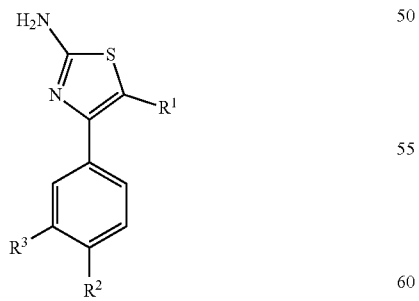

wherein: $R^1$ is $CH_3$, H, Br, Cl, F, I, D, $NH_2$, $OCH_3$, $CH_2CH_3$, $CH_2CH_2CH_3$, $CF_3$, alkyl group, or alkoxy group; $R^2$ is H, $CH_3$, $CF_3$, Cl, F, $OCF_3$, Br, I, $NH_2$, $OCH_3$, $CH_2CH_3$, $CH_2CH_2CH_3$, alkyl group, alkoxy group, or $SCF_3$; and $R^3$ is H, benzene, pyridine, imidazole, pyrrole, pyrimidine, pyridine, pyridazine, pyrimidine, pyrazine, a quinolone, an isoquinoline or methyl-benzene; or a pharmaceutically acceptable salt thereof.

2. A neuroprotective compound of formula (II):

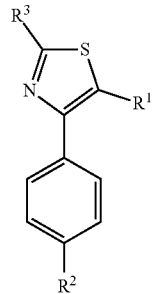

wherein $R^1$ is $CH_3$, H, Br, Cl, F, I, D, $NH_2$, $OCH_3$, $CH_2CH_3$, $CH_2CH_2CH_3$, alkyl group, alkoxy group, or CF$_3$; R$^2$ is H, CH$_3$ CF$_3$, Cl, F, OCF$_3$, pyridine, imidazole, pyrrole, pyrimidine, pyridine, pyridazine, pyrimidine, pyrazine, a quinolone, an isoquinoline, or SCF$_3$; and R$^3$ is NH$_2$, C$_6$H$_6$N, C$_7$H$_5$F$_3$N, C$_5$H$_5$N$_2$, C$_6$H$_4$Cl$_2$N; or a pharmaceutically acceptable salt thereof.

3. A neuroprotective compound of formula (III):

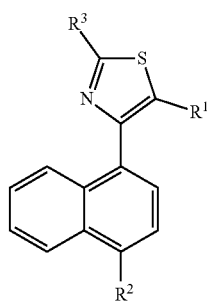

wherein R$^1$ is CH$_3$, H, Br, Cl, F, I, D, NH$_2$, OCH$_3$, CH$_2$CH$_3$, CH$_2$CH$_2$CH$_3$, alkyl group, alkoxy group or CF$_3$; R$^2$ is H, CH$_3$ CF$_3$, Cl, F, OCF$_3$, pyridine, imidazole, pyrrole, pyrimidine, pyridine, pyridazine, pyrimidine, pyrazine, a quinolone, an isoquinoline, or SCF$_3$; and R$^3$ is NH$_2$, C$_6$H$_6$N, C$_7$H$_5$F$_3$N, C$_5$H$_5$N$_2$, C$_6$H$_4$Cl$_2$N; or a pharmaceutically acceptable salt thereof.

4. A neuroprotective compound of formula (IV):

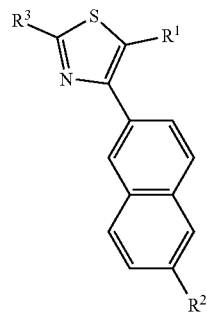

wherein R$^1$ is CH$_3$, H, Br, Cl, F, I, D, NH$_2$, OCH$_3$, CH$_2$CH$_3$, CH$_2$CH$_2$CH$_3$, alkyl group, alkoxy group, or CF$_3$; R$^2$ is H, CH$_3$ CF$_3$, Cl, F, OCF$_3$, pyridine, imidazole, pyrrole, pyrimidine, pyridine, pyridazine, pyrimidine, pyrazine, a quinolone, an isoquinoline, or SCF$_3$; and R$^3$ is NH$_2$, C$_6$H$_6$N, C$_7$H$_5$F$_3$N, C$_5$H$_5$N$_2$, C$_6$H$_4$Cl$_2$N; or a pharmaceutically acceptable salt thereof.

5. The neuroprotective compound of claim 2, wherein R$^1$ is Cl, R$^2$ is OCF$_3$, and R$^3$ is NH$_2$.

6. The neuroprotective compound of claim 3, wherein R$^1$ is Cl, R$^2$ is CH$_3$, and R$^3$ is NH$_2$.

7. The neuroprotective compound of claim 3, wherein R$^1$ is Cl, R$^2$ is H, and R$^3$ is NH$_2$.

8. The neuroprotective compound of claim 4, wherein R$^1$ is Cl, R$^2$ is H, and R$^3$ is NH$_2$.

9. A neuroprotective compound having the chemical structure according to any one of the following compounds:

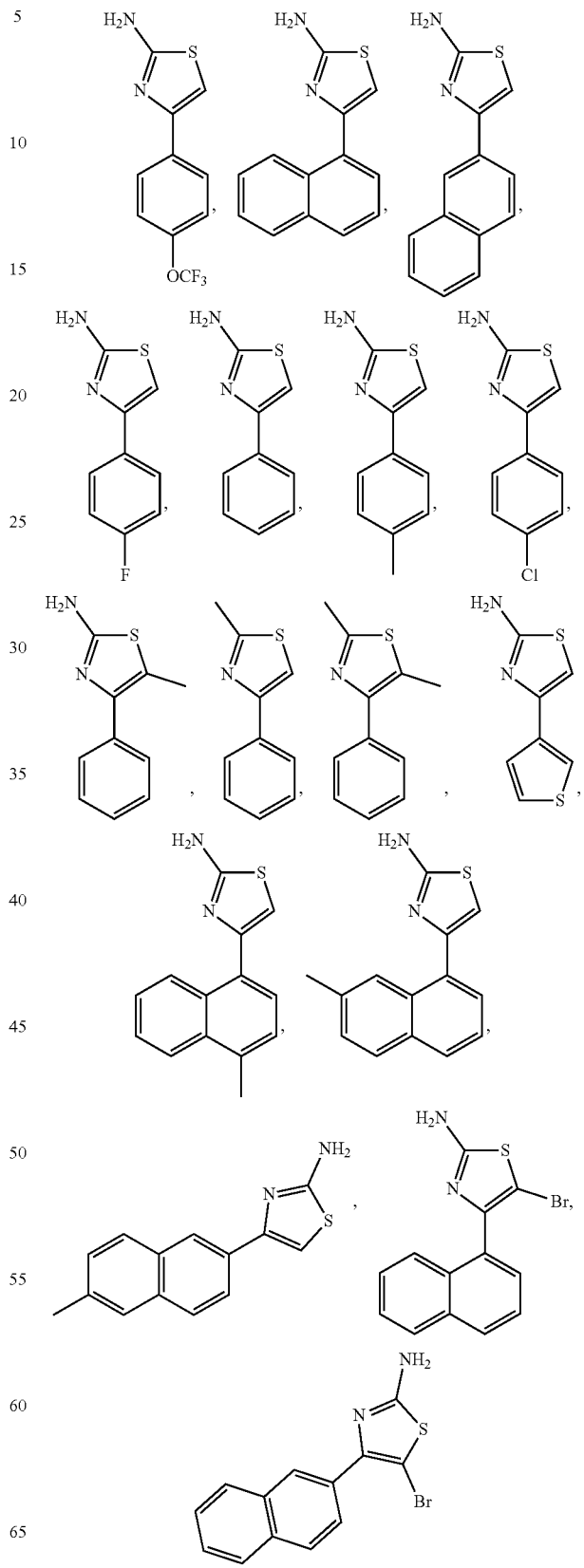

-continued
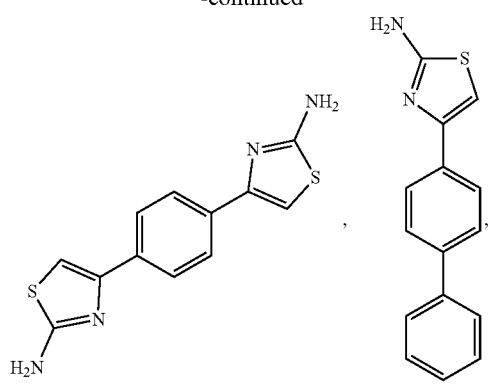
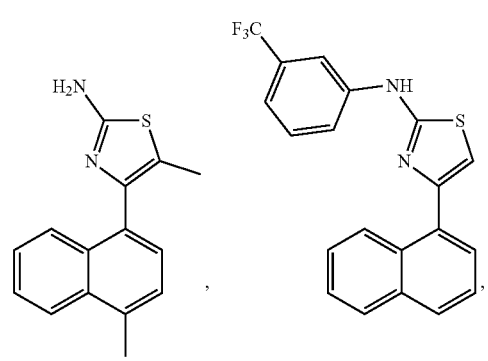
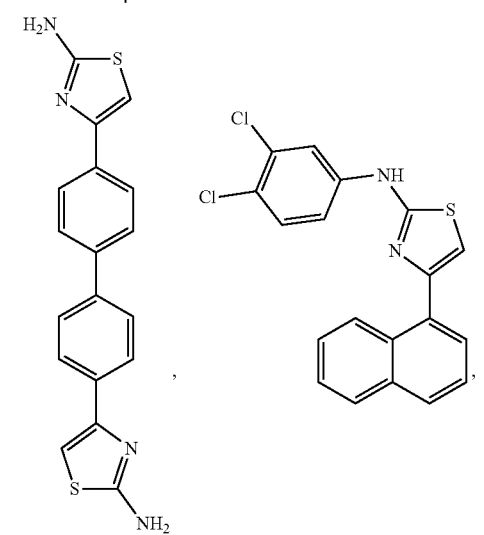
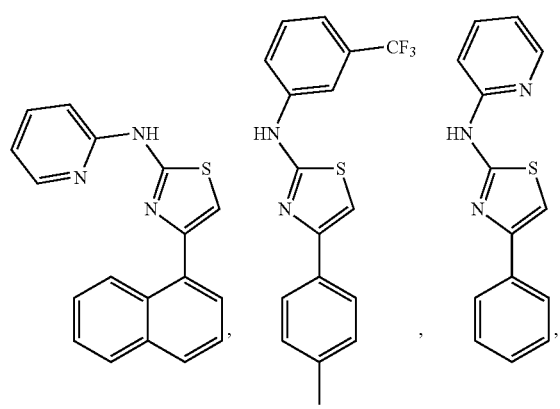
-continued
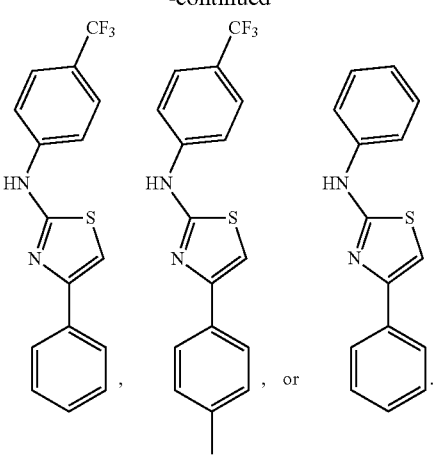
10. The neuroprotective compound of claim 2, wherein the compound is selected from the group consisting of SKA-41, SKA-376, SKA-383, SKA-384, SKA-387, and SKA-388:
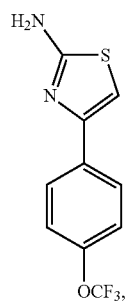
SKA-41
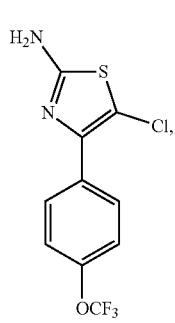
SKA-376
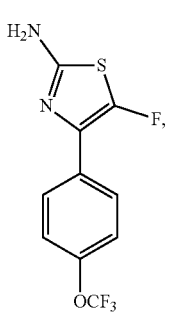
SKA-383

-continued
SKA-384
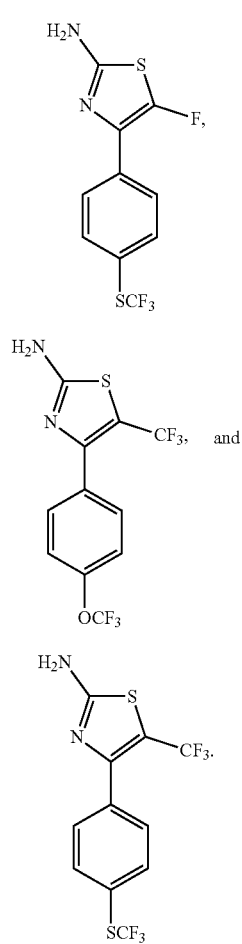
SKA-387
and
SKA-388
11. The neuroprotective compound of claim 3, wherein the compound is selected from the group consisting of SKA-190, SKA-219, SKA-247, SKA-375, SKA-377, SKA-378, SKA-380, SKA-381, and SKA-385:
SKA-190
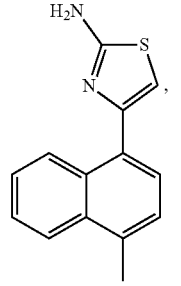
SKA-219
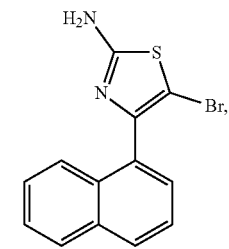
-continued
SKA-247
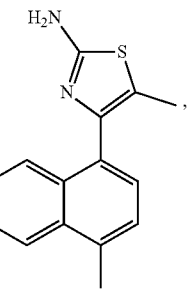
SKA-375
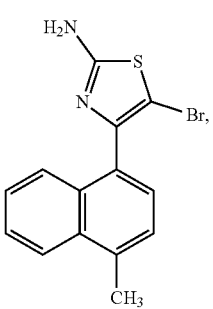
SKA-377
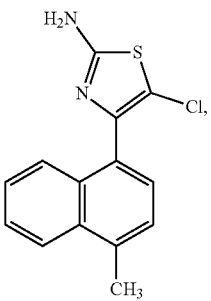
SKA-378
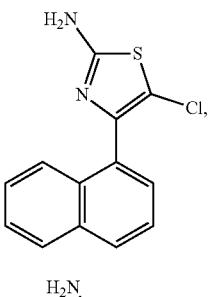
SKA-380
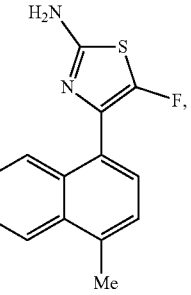

-continued

SKA-381

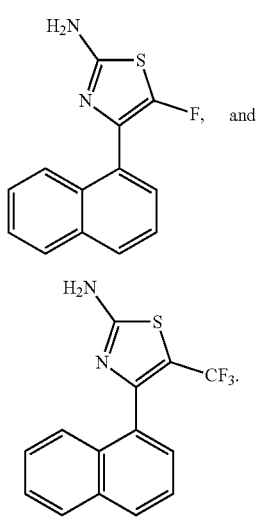

SKA-385

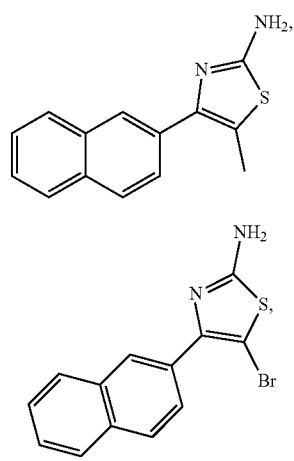

12. The neuroprotective compound of claim 4, wherein the compound is selected from the group consisting of SKA-379, SKA-220, SKA-386 and SKA-382:

SKA-379

SKA-220

-continued

SKA-386

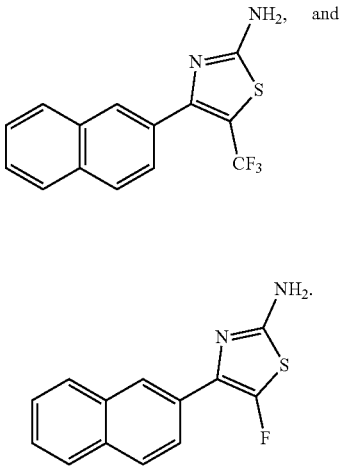

SKA-382

13. The neuroprotective compound of any one of claim 1-4 or 9, wherein said compound has an $EC_{50}$ value of 1-3 micromolar in vitro.

14. The neuroprotective compound of any one of claim 1-4 or 9, wherein said compound decreases glutamate-induced excitotoxicity.

15. The neuroprotective compound of any one of claim 1-4 or 9, wherein glutamine-derived excessive glutamate release from synapses is reduced and excitotoxicity is decreased without interrupting basal glutamatergic synaptic transmission.

16. The neuroprotective compound of any one of claim 1-4 or 9, wherein said compound modulates glutamine import into glutamatergic synapses and glutamate/glutamine cycling between astrocytes and neurons.

17. The neuroprotective compound of any one of claim 1-4 or 9, wherein said compound is provided in an acceptable pharmaceutical form for administration to a subject.

18. A pharmaceutical composition comprising a neuroprotective compound according to any one of claim 1-4 or 9 and a pharmaceutically acceptable carrier.

* * * * *